United States Patent
Altenbach et al.

(10) Patent No.: US 6,645,968 B2
(45) Date of Patent: Nov. 11, 2003

(54) POTASSIUM CHANNEL OPENERS

(75) Inventors: Robert J. Altenbach, Chicago, IL (US); Hao Bai, San Diego, CA (US); Jorge D. Brioni, Vernon Hills, IL (US); William A. Carroll, Evanston, IL (US); Murali Gopalakrishnan, Libertyville, IL (US); Robert J. Gregg, Libertyville, IL (US); Mark W. Holladay, Tucson, AZ (US); Peggy P. Huang, Lake Bluff, IL (US); John F. Kincaid, Newbury Park, CA (US); Michael E. Kort, Lake Bluff, IL (US); Philip R. Kym, Grayslake, IL (US); John K. Lynch, Kenosha, WI (US); Arturo Perez-Medrano, Grayslake, IL (US); Henry Q. Zhang, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 74 days.

(21) Appl. No.: 09/777,217

(22) Filed: Feb. 5, 2001

(65) Prior Publication Data

US 2002/0028836 A1 Mar. 7, 2002

Related U.S. Application Data

(63) Continuation-in-part of application No. 09/621,154, filed on Jul. 21, 2000, now abandoned.
(60) Provisional application No. 60/146,967, filed on Aug. 3, 1999.

(51) Int. Cl.[7] .................. A61K 31/4406; A61K 31/47; A61K 31/505; C07D 237/20
(52) U.S. Cl. .................. 514/256; 514/275; 514/311; 514/313; 514/353; 544/322; 544/327; 544/329; 544/332; 546/162; 546/172; 546/305; 546/306
(58) Field of Search .................. 544/322, 327, 544/329, 332; 546/162, 172, 305, 306; 514/256, 275, 311, 313, 353

(56) References Cited

U.S. PATENT DOCUMENTS

| | | | |
|---|---|---|---|
| 3,636,105 A | 1/1972 | Fest et al. | 260/553 R |
| 4,057,636 A | 11/1977 | Petersen | 424/263 |
| 4,146,646 A | 3/1979 | Percival et al. | 424/324 |
| 5,140,031 A | 8/1992 | Atwal et al. | 514/302 |
| 5,278,169 A | 1/1994 | Atwal et al. | 514/302 |
| 5,378,729 A | 1/1995 | Kohn et al. | 514/231.2 |
| 5,470,816 A | 11/1995 | Satake et al. | 503/201 |
| 5,547,966 A | 8/1996 | Atwal et al. | 514/352 |
| 5,612,279 A | 3/1997 | Satake et al. | 503/201 |
| 5,654,301 A | 8/1997 | Kohn et al. | 514/231.2 |

FOREIGN PATENT DOCUMENTS

| | | |
|---|---|---|
| EP | 0381504 | 8/1990 |
| EP | 0503627 A | 9/1992 |
| EP | 0501797a1 | 6/1996 |
| FR | 2023940 | 11/1969 |
| FR | 2340927 | 2/1977 |
| WO | 99/32495 | 1/1989 |
| WO | 92/04045 | 3/1992 |
| WO | 97/14417 | 4/1997 |
| WO | 98/57940 | 12/1998 |
| WO | 99/28291 | 6/1999 |
| ZA | 695324 | 7/1969 |

OTHER PUBLICATIONS

Ali et al., Chemical Abstracts, vol. 136:263163, 2002.*
Andersson, Pharmacological Reviews 45:253 (1993).
Andersson, Prostate 30:202–215 (1997).
Andersson, Urology, 50(Suppl 6A): 74–84 (1997).
Asano, Anesth. Analg. 90(5):1146–51 (2000).
Atwal et al., J. Med. Chem. 41:271 (1998).
Berge, S.M. et al., J. Pharmaceutical Sciences 66:1–19 (1977).
Bosch, BJU International 83(suppl 2): 7–9 (1999).
Buchheit, Pulmonary Pharmacology & Therapeutics 12:103 (1999).
Burger, J.Fluorine Chem. 20:813 (1982).
Creemer et al., Synth. Comm. 18:1103 (1988).
DeLean et al., Am. J. Physiol, 235:E97 (1980).
Fairfall and Peak, J. Chem. Soc. 796 (1955).
Farina et al., J. Org. Chem. 55:5833 (1990).
Freedman, et al., The Neuroscientist, 2:145–152 (1996).
Fujita, A. et al., "Molecular aspects of ATP–sensitive K+ channels in the cardiovascular systems and K+ channel openers." Pharmacology & Thera peutics 85:39–53 (2000).
Garlid, Circ. Res. 81(6):1072–82 (1997).
Gehlert, et al., Prog. Neuro –Psychopharmacol & Bio. Psychiat., v18:1093–1102 (1994).
Goldstein and Berman., *Vasculogenic female sexual dysfunction: vaginal engorgement and clitoral erectile insufficiency* syndromes, Int. J. Impotence Res., 10:S84–S90 (1998).
Gopalakrishnan et al., Drug Development Research, 28:95–127 (1993).
Grover, J Mol Cell Cardio. 32:677 (2000).
Hampel, Urology 50(Suppl 6A):4–14 (1997).

(List continued on next page.)

Primary Examiner—Richard L. Raymond
(74) Attorney, Agent, or Firm—Michael J. Ward; Portia Chen

(57) ABSTRACT

Compounds of formula I:

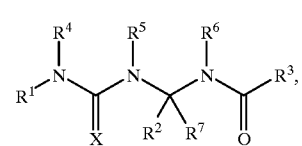

are useful in treating diseases prevented by or ameliorated with potassium channel openers. Also disclosed are potassium channel opening compositions and a method of opening potassium channels in a mammal.

78 Claims, No Drawings

OTHER PUBLICATIONS

Hendriksen, Acta Chem. Scand. 50:432 (1990).
Howe et al., J. Pharmacol. Exp. Ther., 274:884–890 (1995).
IUPAC 1974 Recommendations for Section E, Fundamental Stereochemistry, Pure Appl. Chem. 45:13–30 (1976).
Jones et al., J. Heterocyclic Chem. 31:1681 (1994).
Katritzky et al., J. Org. Che. 55:2206 (1990).
Katritzky, Chem. Rev. 98:409 (1998).
Katritzky, J. Heterocyclic chem.. 33:1935 (1996).
Klockner, U. et al., Pflugers Arch. 405:329–339 (1985).
Kostrzewska, Acta Obstet. Gynecol. Scand. 75(10), 886–91 (1996).
Lawson, Pharmacol. Ther., v70:39–63 (1996).
Lee, Int. J. Impot. Res. 11(4):179–188 (1999).
Loudon et al., 49:4277 (1984).
Loudon et al., J. Org. Chem. 49:4272 (1984).
Morrison, Am. J. obstet. Gynecol, 169(5):1277–85 (1993).
Nurse et al., Br. J. Urol., 68:27–31 (1991).
Pandita, The J. of Urology 162:943 (1999).
Poindexter et al., J. Org. Chem. 57:6257 (1992).
Prescott, Ed., Methods in Cell Biology, Academic Press, New York, NY v14:33 et seq (1976).
Quast et al., Mol. Pharmacol. 43:474–481 (1993).
Resnick, The Lancet 346:94–99 (1995).
Roche, E.B., Bioreversible Carriers inDrug Design: Theory and Application, Pergamon Press, New York, p14–21 (1987).
Rodrigues, Br. J. Pharmacol 129(1):110–4 (2000).
Sanborn, Semin. Perinatol. 19:31–40 (1995).
Scharpenberg, Chem. Ber. 106:1881 (1973).
Schroeder, K.S. et al., J. Biomed. Screen, 1:75–81 (1996).
Soliman, J. Med. Chem. 22:321 (1979).
Spanswick et al., Nature 390:521–25 (Dec. 4, 1997).
Steglich, chem.. Ber. 107:1488 (1974).
Tilley et all, Helv. Chim. Acta. 63:841 (1980).
Ulrich, Tetrahedron 22:1565 (1966).
Vergoni, Life Sci. 50(16):PL135–8 (1992).
Wallis and Lane, Org. React. 3:267–306 (1946).
Feng, et al., *Selective fluorescence derivatization and capillary electrophoretic separation of amidated amino acids*, Journal of Chromatography A, 832 (1999) 211–224.
Chemical Abstract, Eyada, H.A.: *Synthesis of some benzoxazole, benzimidazole, benzoxazine, and carbamate moieties*, Al–Azhar J. Pharm. Sci. (1994), 13, 93–103. Database accession No. 124:289398; XP002151933.
Chemical Abstract, Mohamed, Y.A.; *Synthesis and reactions of some new 5,6–dichlorophthalimidoacetic acid derivatives*, J. Serb. Chem. Soc. (1992), 57(9), 555–62; Database accession No. 118:38720; XP002151934.
Chemical Abstract, Ammar, Y.V. et al., *Some reactions with retrieved from STN*, J. Serb. Chem. Soc. (1992), 57(7), 407–13. Database accession No. 117:131520; XP002151935.
Chemical Abstract, Essawy, S. A. et al., *Synthesis and reactions of phthalimido aliphatic acid azides*, Pol. J. Chem. (1991), 65(7–8), 1243–50, Database accession No. 116:173943; XP002151936.
Chemical Abstract, Vinogradova, T.K. et al., *Intramolecular cyclization and annulation in dehydrochlorination of products of addition of amines to carboxylic acid N–(1 –isothiocyanato–2, 2–dichloroethyl)amid es*, Dokl. Akad. Nauk UKR SSR, Ser. B: Geol., Khim. Biol. Nauki (1990), (5), 36–9, Database accession No. 114:61984, XP002151937.
Chemical Abstract, Boyer, J. H. et al., *Alkylation of nitrocyanamide. A new synthesis of isocyanates*, J. Chem. Soc., Perkin Trans. 1 (1998), (8), 2137–40. Database accession No. 110:94646, XP002151938.
Chemical Abstract, Aly, N. F. et al., *Acid azides: part phthalimidoacetic acid azide and its derivatives*, Indian J. Chem., Sect. B (1984), 23B(2), 121–4. Database accession No. 101:110675, XP002151939.
Chemical Abstract, Tiwari, S. S. et al., *Synthesis of possible antiparkinsonian compounds. WIII Synthesis of N1–(nicotinamidomethyl)–N3–arylureas and N1–'2–(o–methylbenzimidazolyl)salicylamidomethyl!–N3—arylureas*. J. Indian Chem. Soc. (1975), 52(5), 460–1. Database accession No. 84:17225, XP002151940.
Chemical Abstract, Boehme, H. et al ., *N–(.alpha.–Haloalkyl)carboxamides. 20.Imidomethyl thiocyanates and isothiocyanates*. Arch. Pharm. (Weinheim, Ger.) (1974), 307(10), 775–9. Accession No. 82:3924, XP002151941.
Chemical Abstract, Drach, B. S. et al., *Reaction of N–chlormethyl acid amides with silver isocyanate and potassium isothiocyanate*. ZH. Org. Khim. (1972), 8(9), 1825–7. Database accession No. 78:15735, XP002151942.
Chemical Abstract, Moffatt, J. G. et al., *Carbodiimide–Sulfoxide reactions. XI. Reactions of carboxylic acids, hydroxamic acids, and amides*. J. Org. Chem. (1971), 36(22), 3391–400. Database accession No. 76:3528, XP002151943.
Chemical Abstract, Drach, B. S. et al., *N–(1,2,2,2 –Tetrachloroethyl) a mides*, ZH. Obshch. Khim. (1970), 40(9), 1933–7. Database accession No. 75:63069, XP002151944.
Chemical Abstract, Fest, C. et al., *Pesticidal carbamic acid esters and ureas*, ZA 6 905 324 1 (Farbenfabriken Bayer A. G) Apr. 28, 1970. Database accession No. 73:130653, XP002151945.

* cited by examiner

POTASSIUM CHANNEL OPENERS

This application is a continuation-in-part of Ser. No. 09/621,154, filed Jul. 21, 2000, now abandoned, which claims benefit of Provisional Application No. 60/146,967, filed Aug. 3, 1999.

TECHNICAL FIELD

Novel aminal compounds and their derivatives can open potassium channels and are useful for treating a variety of medical conditions.

BACKGROUND OF INVENTION

Potassium channels play an important role in regulating cell membrane excitability. When the potassium channels open, changes in the electrical potential across the cell membrane occur and result in a more polarized state. A number of diseases or conditions may be treated with therapeutic agents that open potassium channels; see for example (Lawson, Pharmacol. Ther., v. 70, pp. 39–63 (1996)); (Gehlert et al., Prog. Neuro-Psychopharmacol & Biol. Psychiat., v. 18, pp. 1093–1102 (1994)); (Gopalakrishnan et al., Drug Development Research, v. 28, pp. 95–127 (1993)); (Freedman et al., The Neuroscientist, v. 2, pp. 145–152 (1996)); (Nurse et al., Br. J. Urol., v. 68 pp. 27–31 (1991)); (Howe et al., J. Pharmacol. Exp. Ther., v. 274 pp. 884–890 (1995)); (Spanswick et al., Nature, v. 390 pp. 521–25 (Dec. 4, 1997)); (Dompeling Vasa. Supplementum (1992) 3434); (WO9932495); (Grover, J Mol Cell Cardiol. (2000) 32, 677); and (Buchheit, Pulmonary Pharmacology & Therapeutics (1999) 12, 103). Such diseases or conditions include asthma, epilepsy, male sexual dysfunction female sexual dysfunction, pain, bladder overactivity, stroke, diseases associated with decreased skeletal blood flow such as Raynaud's phenomenon and intermittent claudication, eating disorders, functional bowel disorders, neurodegeneration, benign prostatic hyperplasia (BPH), dysmenorrhea, premature labor, alopecia, cardioprotection, coronary artery disease, angina and ischemia.

Bladder overactivity is a condition associated with the spontaneous, uncontrolled contractions of the bladder smooth muscle. Bladder overactivity thus is associated with sensations of urgency, urinary incontinence, pollakiuria, bladder instability, nocturia, bladder hyerreflexia, and enuresis (Resnick, The Lancet (1995) 346, 94–99; Hampel, Urology (1997) 50 (Suppl 6A), 4–14; Bosch, BJU International (1999) 83 (Suppl 2), 79). Potassium channel openers (KCOs) act as smooth muscle relaxants. Because bladder overactivity and urinary incontinence can result from the spontaneous, uncontrolled contractions of the smooth muscle of the bladder, the ability of potassium channel openers to hyperpolarize bladder cells and relax bladder smooth muscle may provide a method to ameliorate or prevent bladder overactivity, pollakiuria, bladder instability, nocturia, bladder hyperreflexia, urinary incontinence, and enuresis (Andersson, Urology (1997) 50 (Suppl 6A), 74–84; Lawson, Pharmacol. Ther., (1996) 70, 39–63; Nurse., Br. J. Urol., (1991) 68, 27–31; Howe, J. Pharmacol. Exp. Ther., (1995) 274, 884–890; Gopalakrishnan, Drug Development Research, (1993) 28, 95–127).

The irritative symptoms of BPH (urgency, frequency, nocturia and urge incontinence) have been shown to be correlated to bladder instability (Pandita, The J. of Urology (1999) 162, 943). Therefore the ability of potassium channel openers to hyperpolarize bladder cells and relax bladder smooth muscle may provide a method to ameliorate or prevent the symptoms associated with BPH. (Andersson, Prostate (1997) 30: 202–215).

The excitability of corpus cavernosum smooth muscle cells is important in the male erectile process. The relaxation of corporal smooth muscle cells allows arterial blood to build up under pressure in the erectile tissue of the penis leading to erection (Andersson, Pharmacological Reviews (1993) 45, 253). Potassium channels play a significant role in modulating human corporal smooth muscle tone, and thus, erectile capacity. By patch clamp technique, potassium channels have been characterized in human corporal smooth muscle cells (Lee, Int. J. Impot. Res. (1999) 11(4), 179–188). Potassium channel openers are smooth muscle relaxants and have been shown to relax corpus cavernosal smooth muscle and induce erections (Andersson, Pharmacological Reviews (1993) 45, 253; Lawson, Pharmacol. Ther., (1996) 70, 39–63, Vick, J. Urol. (2000) 163: 202). Potassium channel openers therefore may have utility in the treatment of male sexual dysfunctions such as male erectile dysfunction, impotence and premature ejaculation.

The sexual response in women is classified into four stages: excitement, plateau, orgasm and resolution. Sexual arousal and excitement increase blood flow to the genital area, and lubrication of the vagina as a result of plasma transudation. Topical application of KCOs like minoxidil and nicorandil have been shown to increase clitoral blood flow (Kim et al., J. Urol. (2000) 163 (4): 240). KCOs may be effective for the treatment of female sexual dysfunction including clitoral erectile insufficiency, vaginismus and vaginal engorgement (Goldstein and Berman., Int.J. Impotence Res. (1998) 10:S84–S90), as KCOs can increase blood flow to female sexual organs.

Potassium channel openers may have utility as tocolytic agents to inhibit uterine contractions to delay or prevent premature parturition in individuals or to slow or arrest delivery for brief periods to undertake other therapeutic measures (Sanborn, Semin. Perinatol. (1995) 19, 31–40; Morrison, Am. J. Obstet. Gynecol. (1993) 169(5), 1277–85). Potassium channel openers also inhibit contractile responses of human uterus and intrauterine vasculature. This combined effect would suggest the potential use of KCOs for dysmenhorrea (Kostrzewska, Acta Obstet. Gynecol. Scand. (1996) 75(10), 886–91). Potassium channel openers relax uterine smooth muscle and intrauterine vasculature and therefore may have utility in the treatment of premature labor and dysmenorrhoea (Lawson, Pharmacol. Ther., (1996) 70, 39–63).

Potassium channel openers relax gastrointestinal smooth tissues and therefore may be useful in the treatment of functional bowel disorders such as irritable bowel syndrome (Lawson, Pharmacol. Ther., (1996) 70, 39–63).

Potassium channel openers relax airway smooth muscle and induce bronchodilation. Therefore potassium channel openers may be useful in the treatment of asthma and airways hyperreactivity (Lawson, Pharmacol. Ther., (1996) 70, 39–63; Buchheit, Pulmonary Pharmacology & Therapeutics (1999) 12, 103; Gopalakrishnan, Drug Development Research, (1993) 28, 95–127).

Neuronal hyperpolarization can produce analgesic effects. The opening of potassium channels by potassium channel openers and resultant hyperpolarization in the membrane of target neurons is a key mechanism in the effect of opioids. The peripheral antinociceptive effect of morphine results from activation of ATP-sensitive potassium channels, which causes hyperpolarization of peripheral terminals of primary afferents, leading to a decrease in action potential generation (Rodrigues, Br J Pharmacol (2000) 129(1), 110–4). Opening of $K_{ATP}$ channels by potassium channel openers plays an important role in the antinociception mediated by alpha-2 adrenoceptors and mu opioid receptors. KCOs can potentiate the analgesic action of both morphine and dexmedetomidine via an activation of $K_{ATP}$ channels at the spinal cord level (Vergoni, Life Sci. (1992) 50(16), PL135–8; Asano, Anesth. Analg. (2000) 90(5), 1146–51). Thus, potassium channel openers can hyperpolarize neuronal cells and have shown analgesic effects. Potassium channel openers therefore may be useful as analgesics in the treatment of various pain states including but not limited to migraine and dyspareunia (Lawson, Pharmacol. Ther., (1996) 70, 39–63; Gopalakrishnan, Drug Development Research, (1993) 28, 95–127; Gehlert, Prog. Neuro-Psychopharmacol. & Biol. Psychiat., (1994) 18, 1093–1102).

Epilepsy results from the propagation of nonphysiologic electrical impulses. Potassium channel openers hyperpolarize neuronal cells and lead to a decrease in cellular excitability and have demonstrated antiepileptic effects. Therefore potassium channel openers may be useful in the treatment of epilepsy (Lawson, Pharmacol. Ther., (1996) 70, 39–63; Gopalakrishnan, Drug Development Research, (1993) 28, 95–127; Gehlert, Prog. Neuro-Psychopharmacol. & Biol. Psychiat., (1994) 18, 1093–1102).

Neuronal cell depolarization can lead to excitotoxicity and neuronal cell death. When this occurs as a result of acute ischemic conditions, it can lead to stroke. Long term neurodegeneration can bring about conditions such as Alzheimer's and Parkinson's diseases. Potassium channel openers can hyperpolarize neuronal cells and lead to a decrease in cellular excitability. Activation of potassium channels has been shown to enhance neuronal survival. Therefore potassium channel openers may have utility as neuroprotectants in the treatment of neurodegenerative conditions and diseases such as cerebral ischemia, stroke, Alzheimer's disease and Parkinson's disease (Lawson, Pharmacol. Ther., (1996) 70, 39–63; Gopalakrishnan, Drug Development Research, (1993) 28, 95–127; Gehlert, Prog. Neuro-Psychopharmacol & Biol. Psychiat., (1994) 18, 1093–1102; Freedman, The Neuroscientist (1996) 2, 145).

Potassium channel openers may have utility in the treatment of diseases or conditions associated with decreased skeletal muscle blood flow such as Raynaud's syndrome and intermittent claudication (Lawson, Pharmacol. Ther., (1996) 70, 39–63; Gopalakrishnan, Drug Development Research, (1993) 28, 95–127; Dompeling Vasa. Supplementum (1992) 3434; and WO9932495).

Potassium channel openers may be useful in the treatment of eating disorders such as obesity (Spanswick, Nature, (1997) 390, 521–25; Freedman, The Neuroscientist (1996) 2, 145).

Potassium channel openers have been shown to promote hair growth therefore potassium channel openers have utility in the treatment of hair loss and baldness also known as alopecia (Lawson, Pharmacol. Ther., (1996) 70, 39–63; Gopalakrishnan, Drug Development Research, (1993) 28, 95–127).

Potassium channel openers possess cardioprotective effects against myocardial injury during ischemia and reperfusion (Garlid, Circ. Res. (1997) 81(6), 1072–82). Therefore, potassium channel openers may be useful in the treatment of heart diseases (Lawson, Pharmacol. Ther., (1996) 70, 39–63; Grover, J. Mol. Cell Cardiol. (2000) 32, 677).

Potassium channel openers, by hyperpolarization of smooth muscle membranes, can exert vasodilation of the collateral circulation of the coronary vasculature leading to increase blood flow to ischemic areas and could be useful for the coronary artery disease (Lawson, Pharmacol. Ther., (1996) 70, 39–63, Gopalakrishnan, Drug Development Research, (1993) 28, 95–127).

U.S. Pat. No. 3,636,105 discloses a group of 1-fluoroacetylamino-2,2,2-trichloroethyl urea rodenticide agents. U.S. Pat. No. 4,146,646 discloses a group of bis-amide fungicide agents. U.S. Pat. No. 5,140,031 and U.S. Pat. No. 5,278,169 disclose a group of cyanoguanidine cardiovascular agents. U.S. Pat. No. 4,057,636 discloses a group of pyridylcyanoguanidine hypotensive agents. U.S. Pat. No. 5,547,966 discloses a group of urea, thiourea, and cyanoguanidine agents for treating ischemia. ZA 695324 discloses a group of thioureas useful as insecticide, acaricidal, and rodenticide agents. WO 92/04045 discloses a group of carbamate cholecystokinin receptor antagonists. WO 97/14417 discloses a group of peptide mimetic agents useful as fibrinogen receptor antagonists. WO 98/57940 discloses a group of oxazolidinone and imidazolidinone agents useful as $\alpha_{1A}$ receptor antagonists. WO 99/28291 discloses a group of bis(hydroxyureas) useful as inhibitors of 5-lipoxygenase.

Compounds of the present invention are novel, hyperpolarize cell membranes, open potassium channels, relax smooth muscle cells, inhibit bladder contractions and may be useful for treating diseases that can be ameliorated by opening potassium channels.

SUMMARY OF THE INVENTION

In its principal embodiment, the present invention discloses compounds having formula I:

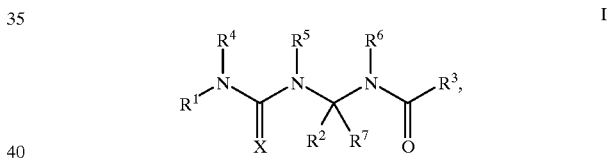

or a pharmaceutically acceptable salt, amide, ester or prodrug thereof wherein,

X is selected from O, S, CHCN, C(CN)$_2$, CHNO$_2$ and NR$^8$;

R$^8$ is selected from hydrogen, alkoxy, alkyl, alkylsulfonyl, arylalkoxy, aryloxy, arylsulfonyl, cyano, haloalkylsulfonyl, heterocyclealkoxy, heterocycleoxy, hydroxy, nitro, and sulfamyl;

R$^1$ is selected from aryl, arylalkyl, heterocycle, and heterocyclealkyl;

R$^2$ is selected from hydrogen, alkenyl, alkenyloxyalkyl, alkenyloxy(alkenyloxy)alkyl, alkoxyalkyl, alkoxycarbonyl, alkoxycarbonylalkyl, alkoxycarbonyl(halo)alkyl, alkoxy(halo)alkyl, alkyl, alkylcarbonyl, alkylcarbonylalkyl, alkylcarbonyl(halo)alkyl, alkylcarbonyloxyalkyl, alkylsulfinylalkyl, alkylsulfonylalkyl, alkylthioalkyl, alkynyl, amido, amidoalkyl, aryl, arylalkoxyalkyl, arylalkoxycarbonyl, arylalkoxycarbonylalkyl, arylalkyl, arylcarbonyl, arylcarbonylalkyl, arylcarbonyloxyalkyl, aryl(halo)alkyl, aryloxyalkyl, aryloxycarbonyl, aryloxycarbonylalkyl, arylalkylthioalkyl, arylsulfonylalkyl, carboxy, carboxyalkyl, carboxy(halo)alkyl, cyanoalkyl, cyano(halo)alkyl, cycloalkenyl, cycloalkenylalkyl, cycloalkyl, cycloalkylalkoxyalkyl, cycloalkylalkyl, cycloalkylcarbonyl, cycloalkyloxyalkyl, cycloalkylalkylthioalkyl, formyl, haloalkenyl, haloalkyl, haloalkylcarbonyl, haloalkynyl, heterocycle, heterocyclealkoxyalkyl, heterocyclealkyl, heterocyclecarbonyl, heterocycleoxyalkyl, heterocyclealkylthioalkyl, hydroxyalkyl, mercaptoalkyl, sulfamylalkyl, sulfamyl(halo)alkyl, and $(NR^9R^{10})$alkyl wherein $R^9$ and $R^{10}$ are independently selected from hydrogen, alkyl, akylcarbonyl, aryl, arylalkyl, arylcarbonyl, formyl, and $S(O)_2R^{11}$, wherein $R^{11}$ is selected from alkyl, aryl, and arylalkyl;

$R^3$ is selected from alkyl, aryl, arylalkyl, heterocycle, and heterocyclealkyl;

$R^4$ is hydrogen; or $R^4$ and $R^1$ taken together with the nitrogen atom to which they are attached, together form a heterocycle selected from benzimidazolyl, benzotriazolyl, indazolyl, indolyl, isoindolyl, indolinyl and isoindolinyl wherein benzimidazolyl, benzotriazolyl, indazolyl, indolyl, isoindolyl, indolinyl and isoindolinyl are optionally substituted with 1, 2, or 3 substituents independently selected from alkenyl, alkoxy, alkoxycarbonyl, alkyl, alkylcarbonyl, alkylsulfinyl, alkylsulfonyl, alkynyl, arylalkoxycarbonyl, cyano, halogen, haloalkyl, haloalkoxy, nitro, sulfamyl, and —$NR^AR^B$ wherein $R^A$ and $R^B$ are independently selected from hydrogen, alkyl, alkylcarbonyl and formyl;

$R^5$ is selected from hydrogen, alkyl and $OR^{12}$;

$R^{12}$ is selected from hydrogen, alkyl and arylalkyl; or $R^5$ and $R^4$ taken together form an alkylene bridge of 2–3 carbons;

$R^6$ is hydrogen; or $R^6$ and $R^5$ taken together form an alkylene bridge of 2–3 carbons; or $R^6$ taken together with the nitrogen atom to which it is attached and $R^3$ taken together with the carbon atom to which it is attached, together form a heterocycle selected from 1-isoindolinonyl and 1-isoquinolinonyl wherein 1-isoindolinonyl and 1-isoquinolinonyl are optionally substituted with 1, 2, or 3 substituents selected from alkenyl, alkoxy, alkoxycarbonyl, alkyl, alkylcarbonyl, alkylsulfinyl, alkylsulfonyl, alkynyl, arylalkoxycarbonyl, cyano, halogen, haloalkyl, haloalkoxy, nitro, oxo, sulfamyl, and —$NR^AR^B$ wherein $R^A$ and $R^B$ are independently selected from hydrogen, alkyl, alkylcarbonyl and formyl; and $R^7$ is selected from hydrogen, haloalkyl and lower alkyl; or $R^7$ and $R^2$ taken together with the carbon atom to which they are attached, together form a 5 or 6 membered carbocyclic ring wherein the 5 or 6 membered carbocyclic ring is optionally substituted with 1 or 2 substituents independently selected from alkenyl, alkoxy, alkyl, alkynyl, halogen, haloalkoxy, and haloalkyl;

provided that when X is O; $R^2$ is —$CCl_3$; $R^3$ is alkyl or phenyl; and $R^4$, $R^5$, $R^6$, and $R^7$ are hydrogen; then $R^1$ is other than phenyl.

DETAILED DESCRIPTION OF THE INVENTION

All patents, patent applications, and literature references cited in the specification are herein incorporated by reference in their entirety. In the case of inconsistencies, the present disclosure, including definitions, will prevail.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

In its principal embodiment, the present invention discloses compounds having formula I:

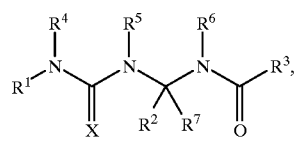

or a pharmaceutically acceptable salt, amide, ester or prodrug thereof wherein,

X is selected from O, S, CHCN, $C(CN)_2$, $CHNO_2$ and $NR^8$;

$R^8$ is selected from hydrogen, alkoxy, alkyl, alkylsulfonyl, arylalkoxy, aryloxy, arylsulfonyl, cyano, haloalkylsulfonyl, heterocyclealkoxy, heterocycleoxy, hydroxy, nitro, and sulfamyl;

$R^1$ is selected from aryl, arylalkyl, heterocycle, and heterocyclealkyl;

$R^2$ is selected from hydrogen, alkenyl, alkenyloxyalkyl, alkenyloxy(alkenyloxy)alkyl, alkoxyalkyl, alkoxycarbonyl, alkoxycarbonylalkyl, alkoxycarbonyl(halo)alkyl, alkoxy(halo)alkyl, alkyl, alkylcarbonyl, alkylcarbonylalkyl, alkylcarbonyl(halo)alkyl, alkylcarbonyloxyalkyl, alkylsulfinylalkyl, alkylsulfonylalkyl, alkylthioalkyl, alkynyl, amido, amidoalkyl, aryl, arylalkoxyalkyl, arylalkoxycarbonyl, arylalkoxycarbonylalkyl, arylalkyl, arylcarbonyl, arylcarbonylalkyl, arylcarbonyloxyalkyl, aryl(halo)alkyl, aryloxyalkyl, aryloxycarbonyl, aryloxycarbonylalkyl, arylalkylthioalkyl, arylsulfonylalkyl, carboxy, carboxyalkyl, carboxy(halo)alkyl, cyanoalkyl, cyano(halo)alkyl, cycloalkenyl, cycloalkenylalkyl, cycloalkyl, cycloalkylalkoxyalkyl, cycloalkylalkyl, cycloalkylcarbonyl, cycloalkyloxyalkyl, cycloalkylalkylthioalkyl, formyl, haloalkenyl, haloalkyl, haloalkylcarbonyl, haloalkynyl, heterocycle, heterocyclealkoxyalkyl, heterocyclealkyl, heterocyclecarbonyl, heterocycleoxyalkyl, heterocyclealkylthioalkyl, hydroxyalkyl, mercaptoalkyl, sulfamylalkyl, sulfamyl(halo)alkyl, and $(NR^9R^{10})$alkyl wherein $R^9$ and $R^{10}$ are independently selected from hydrogen, alkyl, alkylcarbonyl, aryl, arylalkyl, arylcarbonyl, formyl, and $S(O)_2R^{11}$, wherein $R^{11}$ is selected from alkyl, aryl, and arylalkyl;

$R^3$ is selected from alkyl, aryl, arylalkyl, heterocycle, and heterocyclealkyl;

$R^4$ is hydrogen; or $R^4$ and $R^1$ taken together with the nitrogen atom to which they are attached, together form a heterocycle selected from benzimidazolyl, benzotriazolyl, indazolyl, indolyl, isoindolyl, indolinyl and isoindolinyl wherein benzimidazolyl, benzotriazolyl, indazolyl, indolyl, isoindolyl, indolinyl and isoindolinyl are optionally substituted with 1, 2, or 3 substituents independently selected from alkenyl, alkoxy, alkoxycarbonyl, alkyl, alkylcarbonyl, alkylsulfinyl, alkylsulfonyl, alkynyl, arylalkoxycarbonyl, cyano, halogen, haloalkyl, haloalkoxy, nitro, sulfamyl, and —$NR^AR^B$ wherein $R^A$ and $R^B$ are independently selected from hydrogen, alkyl, alkylcarbonyl and formyl;

$R^5$ is selected from hydrogen, alkyl and $OR^{12}$;

$R^{12}$ is selected from hydrogen, alkyl and arylalkyl; or $R^5$ and $R^4$ taken together form an alkylene bridge of 2–3 carbons;

$R^6$ is hydrogen; or $R^6$ and $R^5$ taken together form an alkylene bridge of 2–3 carbons; or $R^6$ taken together with the nitrogen atom to which it is attached and $R^3$ taken together with the carbon atom to which it is attached, together form a heterocycle selected from 1-isoindolinonyl and 1-isoquinolinonyl wherein 1-isoindolinonyl and 1-isoquinolinonyl are optionally substituted with 1, 2, or 3 substituents selected from alkenyl, alkoxy, alkoxycarbonyl, alkyl, alkylcarbonyl, alkylsulfinyl, alkylsulfonyl, alkynyl, arylalkoxycarbonyl, cyano, halogen, haloalkyl, haloalkoxy, nitro, oxo, sulfamyl, and —$NR^AR^B$ wherein $R^A$ and $R^B$ are independently selected from hydrogen, alkyl, alkylcarbonyl and formyl; and $R^7$ is selected from hydrogen, haloalkyl and lower alkyl; or $R^7$ and $R^2$ taken together with the carbon atom to which they are attached, together form a 5 or 6 membered carbocyclic ring wherein the 5 or 6 membered carbocyclic ring is optionally substituted with 1 or 2 substituents independently selected from alkenyl, alkoxy, alkyl, alkynyl, halogen, haloalkoxy, and haloalkyl;

provided that when X is O; $R^2$ is —$CCl_3$; $R^3$ is alkyl or phenyl; and $R^4$, $R^5$, $R^6$, and $R^7$ are hydrogen; then $R^1$ is other than phenyl.

In another embodiment of the present invention, compounds have formula I wherein X is selected from O, S, CHCN, $C(CN)_2$, $CHNO_2$, and $NR^8$; $R^8$ is selected from alkoxy, alkylsulfonyl, arylalkoxy, arylsulfonyl, cyano, haloalkylsulfonyl, hydroxy, and nitro; $R^1$ is selected from the aryl, arylalkyl, heterocycle, and heterocyclealkyl; $R^2$ is selected from hydrogen, alkenyl, alkenyloxyalkyl, alkenyloxy(alkenyloxy)alkyl, alkoxyalkyl, alkoxycarbonylalkyl, alkyl, alkylcarbonyl, alkylsulfonylalkyl, alkylthioalkyl, aryl, arylalkyl, arylsulfonylalkyl, cyanoalkyl, cycloalkenyl, cycloalkenylalkyl, cycloalkyl, cycloalkylalkyl, haloalkyl, haloalkylcarbonyl, heterocycle, heterocyclealkyl, hydroxyalkyl, sulfamylalkyl, and ($NR^9R^{10}$)alkyl; $R^3$ is selected from aryl, arylalkyl, and heterocycle; $R^4$ is hydrogen; or $R^4$ and $R^1$ taken together with the nitrogen atom to which they are attached, together form a heterocycle selected from benzimidazolyl and indolyl wherein benzimidazolyl and indolyl are optionally substituted with 1 or 2 substituents independently selected from alkoxy, alkyl, halo, haloalkyl, and haloalkoxy; $R^5$ is selected from hydrogen and alkyl; or $R^5$ and $R^4$ taken together form an alkylene bridge of 2–3 carbons; $R^6$ is hydrogen; or $R^6$ and $R^5$ taken together form an alkylene bridge of 2–3 carbons; or $R^6$ taken together with the nitrogen atom to which it is attached and $R^3$ taken together with the carbon atom to which it is attached, together form a heterocycle selected from 1-isoindolinonyl and 1-isoquinolinonyl wherein 1-isoindolinonyl and 1-isoquinolinonyl are optionally substituted with 1 or 2 substituents selected from alkoxy, alkyl, halo, haloalkyl, and haloalkoxy; $R^7$ is selected from hydrogen, haloalkyl, and lower alkyl; or $R^7$ and $R^2$ taken together with the carbon atom to which they are attached, together form a 5 or 6 membered carbocyclic ring wherein the 5 or 6 membered carbocyclic ring is optionally substituted with 1 or 2 substituents independently selected from alkyl, halo, haloalkoxy, and haloalkyl; and $R^9$ and $R_{10}$ are as defined in formula I.

In another embodiment of the present invention, compounds have formula I wherein X is selected from O, S, CHCN, $C(CN)_2$, $CHNO_2$, and $NR^8$; $R^8$ is selected from alkoxy, alkylsulfonyl, haloalkylsulfonyl, cyano, hydroxy, nitro, arylalkoxy wherein the aryl portion of arylalkoxy is phenyl, and arylsulfonyl wherein the aryl portion of arylsulfonyl is phenyl; $R^1$ is selected from heterocycle and aryl wherein heterocycle is selected from pyridinyl, pyrimidinyl and quinolinyl wherein pyridinyl, pyrimidinyl and quinolinyl are optionally substituted with 1, 2, or 3 substituents independently selected from alkoxy, alkyl, halo, haloalkyl, nitro, phenylsulfonyl and sulfamyl, and wherein aryl is phenyl optionally substituted with 1, 2, or 3 substituents independently selected from alkoxy, alkyl, halo, haloalkyl, nitro, phenylsulfonyl, and sulfamyl; $R^2$ is selected from hydrogen, alkenyl, alkenyloxyalkyl, alkenyloxy(alkenyloxy)alkyl, alkoxyalkyl, alkoxycarbonylalkyl, alkyl, alkylcarbonyl, alkylsulfonylalkyl, aryl wherein aryl is phenyl, arylalkyl wherein the aryl portion of arylalkyl is phenyl, arylsulfonylalkyl wherein the aryl portion of arylsulfonylalkyl is phenyl, cyanoalkyl, cycloalkenylalkyl, cycloalkyl, haloalkyl, haloalkylcarbonyl, hydroxyalkyl, sulfamylalkyl, ($NR^9R^{10}$)alkyl and heterocycle wherein heterocycle is selected from 1,3-dioxanyl, pyrrolidinyl and thienyl; $R^3$ is selected from aryl wherein aryl is phenyl and arylalkyl wherein the aryl portion of arylalkyl is phenyl; $R^4$ is hydrogen; or $R^4$ and $R^1$ taken together with the nitrogen atom to which they are attached, together form a heterocycle selected from benzimidazolyl and indolyl wherein benzimidazolyl and indolyl are optionally substituted with 1 or 2 substituents independently selected from alkoxy, alkyl, halo, haloalkyl, and haloalkoxy; $R^5$ is hydrogen; or $R^5$ and $R^4$ taken together form an alkylene bridge of 2–3 carbons; $R^6$ is hydrogen; or $R^6$ and $R^5$ taken together form an alkylene bridge of 2–3 carbons; or $R^6$ taken together with the nitrogen atom to which it is attached and $R^3$ taken together with the carbon atom to which it is attached, together form a heterocycle selected from 1-isoindolinonyl and 1-isoquinolinonyl wherein 1-isoindolinonyl and 1-isoquinolinonyl are optionally substituted with 1 or 2 substituents selected from alkoxy, alkyl, halo, haloalkyl, and haloalkoxy; $R^7$ is selected from hydrogen, haloalkyl, and lower alkyl; or $R^7$ and $R^2$ taken together with the carbon atom to which they are attached, together form a 5 or 6 membered carbocyclic ring wherein the 5 or 6 membered carbocyclic ring is optionally substituted with 1 or 2 substituents independently selected from alkyl, halo, haloalkoxy, and haloalkyl; and $R^9$ and $R^{10}$ are as defined in formula I.

In another embodiment of the present invention, compounds have formula I wherein X is selected from O, S, $CHNO_2$, $C(CN)_2$, and $NR^8$; $R^8$ is selected from arylsulfonyl, cyano, haloalkylsulfonyl, nitro and sulfamyl; $R^1$ is selected from aryl, arylalkyl, heterocycle and heterocyclalkyl; $R^2$ is selected from hydrogen, alkenyl, alkenyloxyalkyl, alkenyloxy(alkenyloxy)alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and $(NR^9R^{10})$ alkyl; $R^3$ is selected from aryl and arylalkyl; $R^4$ is hydrogen; $R^5$ is selected from hydrogen and alkyl; or $R^5$ and $R^4$ taken together form an alkylene bridge of 2–3 carbons; $R^6$ is hydrogen; $R^7$ is hydrogen; and $R^9$ and $R^{10}$ are as defined in formula I.

In another embodiment of the present invention, compounds have formula I wherein X is selected from O, S, $CHNO_2$, $C(CN)_2$, and $NR^8$; $R^8$ is selected from arylsulfonyl wherein the aryl portion of arylsulfonyl is phenyl, cyano, haloalkylsulfonyl, nitro and sulfamyl; $R^1$ is selected from aryl wherein aryl is phenyl, arylalkyl wherein the aryl portion of arylalkyl is phenyl, heterocycle wherein heterocycle is selected from quinolinyl, pyridinyl and pyrimidinyl, and heterocyclalkyl wherein the heterocycle portion of heterocyclealkyl is pyridinyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from 1,3-dioxanyl, pyrrolidinyl and thienyl; $R^3$ is selected from aryl wherein aryl is phenyl and arylalkyl wherein the aryl portion of arylalkyl is phenyl; $R^4$ is hydrogen; $R^5$ is selected from hydrogen and alkyl; or $R^5$ and $R^4$ taken together form an alkylene bridge of 2–3 carbons; $R^6$ is hydrogen; $R^7$ is hydrogen; and $R^9$ and $R^{10}$ are as defined in formula I.

In another embodiment of the present invention, compounds have formula I wherein X is $NR^8$; $R^8$ is cyano; $R^1$ is selected from heterocycle and heterocyclealkyl; $R^3$ is selected from heterocycle and heterocyclealkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is $NR^8$; $R^8$ is cyano; $R^1$ is selected from heterocycle and heterocyclealkyl; $R^2$ is selected from hydrogen, alkenyl, alkenyloxyalkyl, alkenyloxy(alkenyloxy)alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and $(NR^9R^{10})$alkyl; $R^3$ is selected from heterocycle and heterocyclealkyl; $R^4$ is hydrogen; $R^5$ is hydrogen; $R^6$ is hydrogen; and $R^7$ is hydrogen.

In another embodiment of the present invention, compounds have formula I wherein X is $NR^8$; $R^8$ is cyano; $R^1$ is heterocycle wherein heterocycle is pyridinyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from the group consisting of 1,3-dioxanyl, pyrrolidinyl and thienyl; $R^3$ is heterocycle wherein heterocycle is selected from the group consisting of furanyl, pyrazinyl, pyridinyl, pyrimidinyl and quinolinyl; $R^4$ is hydrogen; $R^5$ is hydrogen; $R^6$ is hydrogen; and $R^7$ is hydrogen.

In another embodiment of the present invention, compounds have formula I wherein X is $NR^8$; $R^8$ is cyano; $R^1$ is selected from heterocycle and heterocyclealkyl; $R^3$ is selected from aryl and arylalkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is $NR^8$; $R^8$ is cyano; $R^1$ is selected from heterocycle and heterocyclealkyl; $R^2$ is selected from hydrogen, alkenyl, alkenyloxyalkyl, alkenyloxy(alkenyloxy)alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and $(NR^9R^{10})$alkyl; $R^3$ is selected from aryl and arylalkyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is $NR^8$; $R^8$ is cyano; $R^1$ is heterocyclealkyl wherein the heterocycle portion of heterocyclealkyl is pyridinyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; and $R^7$, $R^9$ and $R^{10}$ are as defined in formula I.

In another embodiment of the present invention, compounds have formula I wherein X is $NR^8$; $R^8$ is cyano; $R^1$ is heterocycle wherein the heterocycle is pyridinyl; $R^2$ is selected alkyl and haloalkyl; $R^3$ is aryl wherein aryl is phenyl; $R^4$ is hydrogen; $R^5$ is hydrogen; $R^6$ is hydrogen; and $R^7$ is hydrogen.

In another embodiment of the present invention, compounds have formula I wherein X is $NR^8$; $R^8$ is cyano; $R^1$ is heterocycle wherein the heterocycle is pyridinyl; $R^2$ is selected dichloroethyl; $R^3$ is aryl wherein aryl is phenyl; $R^4$ is hydrogen; $R^5$ is hydrogen; $R^6$ is hydrogen; and $R^7$ is hydrogen.

In another embodiment of the present invention, compounds have formula I wherein X is $NR^8$; $R^8$ is cyano; $R^1$ is heterocycle wherein the heterocycle pyridinyl which is optionally substituted with alkoxy, halo, and haloalkyl; $R^2$ is selected dichloroethyl; $R^3$ is aryl wherein aryl is phenyl which is optionally substituted with halo; $R^4$ is hydrogen; $R^5$ is hydrogen; $R^6$ is hydrogen; and $R^7$ is hydrogen.

In another embodiment of the present invention, compounds have formula I wherein X is $NR^8$; $R^8$ is cyano; $R^1$ is heterocycle wherein the heterocycle is pyridinyl; $R^2$ is selected alkyl and haloalkyl; $R^3$ is heterocycle wherein wherein the heterocycle is pyridinyl; $R^4$ is hydrogen; $R^5$ is hydrogen; $R^6$ is hydrogen; and $R^7$ is hydrogen.

In another embodiment of the present invention, compounds have formula I wherein X is $NR^8$; $R^8$ is cyano; $R^1$ is heterocycle wherein the heterocycle is pyridinyl; $R^2$ is selected dichloroethyl; $R^3$ is heterocycle wherein wherein the heterocycle is pyridinyl; $R^4$ is hydrogen; $R^5$ is hydrogen; $R^6$ is hydrogen; and $R^7$ is hydrogen.

In another embodiment of the present invention, compounds have formula I wherein X is $NR^8$; $R^8$ is cyano; $R^1$ is heterocycle wherein the heterocycle is pyridinyl which is optionally substituted with alkoxy, halo, and haloalkyl; $R^2$ is selected dichloroethyl; $R^3$ is heterocycle wherein wherein the heterocycle is pyridinyl which is optionally substituted with alkoxy, halo, and haloalkyl; $R^4$ is hydrogen; $R^5$ is hydrogen; $R^6$ is hydrogen; and $R^7$ is hydrogen.

In another embodiment of the present invention, compounds have formula I wherein X is $NR^8$; $R^8$ is cyano; $R^1$ is heterocycle wherein heterocycle is selected from quinolinyl and pyrimidinyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, ($NR^9R^{10}$)alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is $NR^8$; $R^8$ is cyano; $R^1$ is heterocycle wherein heterocycle is pyridinyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, ($NR^9R^{10}$)alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is $NR^8$; $R^8$ is cyano; $R^1$ is heterocycle; $R^2$ is haloalkyl; $R^3$ is aryl; $R^4$ is hydrogen; $R^5$ is hydrogen; $R^6$ is hydrogen; and $R^7$ is hydrogen.

In another embodiment of the present invention, compounds have formula I wherein X is $NR^8$; $R^8$ is cyano; $R^1$ is heterocycle wherein heterocycle is pyridinyl; $R^2$ is haloalkyl; $R^3$ is aryl wherein aryl is phenyl; $R^4$ is hydrogen; $R^5$ is hydrogen; $R^6$ is hydrogen; and $R^7$ is hydrogen.

In another embodiment of the present invention, compounds have formula I wherein X is $NR^8$; $R^8$ is cyano; $R^1$ is heterocycle wherein heterocycle is 6-chloro-3-pyridinyl; $R^2$ is haloalkyl; $R^3$ is aryl wherein aryl is phenyl; $R^4$ is hydrogen; $R^5$ is hydrogen; $R^6$ is hydrogen; and $R^7$ is hydrogen.

In another embodiment of the present invention, compounds have formula I wherein X is $NR^8$; $R^8$ is cyano; $R^1$ is heterocycle wherein heterocycle is 6-(trifluoromethyl)-3-pyridinyl; $R^2$ is haloalkyl; $R^3$ is aryl wherein aryl is phenyl; $R^4$ is hydrogen; $R^5$ is hydrogen; $R^6$ is hydrogen; and $R^7$ is hydrogen.

In another embodiment of the present invention, compounds have formula I wherein X is $NR^8$; $R^8$ is cyano; $R^1$ is heterocycle wherein heterocycle is selected from quinolinyl, pyridinyl and pyrimidinyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, ($NR^9R^{10}$)alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is alkyl; $R^6$ is hydrogen; $R^7$ is hydrogen; and $R^9$ and $R^{10}$ are as defined in formula I.

In another embodiment of the present invention, compounds have formula I wherein X is $NR^8$; $R^8$ is cyano; $R^1$ is selected from heterocycle and heterocyclealkyl; $R^3$ is alkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is $NR^8$; $R^8$ is cyano; $R^1$ is selected from aryl and arylalkyl; $R^3$ is selected from heterocycle and heterocyclealkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is $NR^8$; $R^8$ is cyano; $R^1$ is selected from aryl and arylalkyl; $R^3$ is selected from aryl and arylalkyl; $R^4$ is hydrogen; $R^5$ is hydrogen; and $R^6$ is hydrogen; and $R^2$ and $R^7$ are as defined in formula I.

In another embodiment of the present invention, compounds have formula I wherein X is $NR^8$; $R^8$ is cyano; $R^1$ is selected from aryl and arylalkyl; $R^2$ is selected from hydrogen, alkenyl, alkenyloxyalkyl, alkenyloxy(alkenyloxy)alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and ($NR^9R^{10}$)alkyl; $R^3$ is selected from aryl and arylalkyl; $R^4$ is hydrogen $R^5$ is hydrogen; $R^6$ is hydrogen; $R^7$ is hydrogen; and $R^9$ and $R^{10}$ are as defined in formula I.

In another embodiment of the present invention, compounds have formula I wherein X is $NR^8$; $R^8$ is cyano; $R^1$ is arylalkyl wherein the aryl portion of arylalkyl is phenyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, ($NR^9R^{10}$)alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is $NR^8$; $R^5$ is cyano; $R^1$ is aryl wherein aryl is phenyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, ($NR^9R^{10}$)alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is $NR^8$; $R^8$ is cyano; $R^1$ is selected from aryl and arylalkyl; $R^3$ is alkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is $NR^8$; $R^8$ is selected from hydrogen, alkoxy, alkyl, alkylsulfonyl, arylalkoxy, aryloxy, arylsulfonyl, haloalkylsulfonyl, heterocyclealkoxy, heterocycleoxy, hydroxy, nitro, and sulfamyl; $R^4$ is hydrogen; $R^5$ is hydrogen; $R^6$ is hydrogen; and $R^1$, $R^2$, $R^3$ and $R^7$ are as defined in formula I.

In another embodiment of the present invention, compounds have formula I wherein X is $NR^8$; $R^8$ is nitro; $R^4$ is hydrogen; $R^5$ is hydrogen; $R^6$ is hydrogen; and $R^1$, $R^2$, $R^3$ and $R^7$ are as defined in formula I.

In another embodiment of the present invention, compounds have formula I wherein X is $NR^8$; $R^8$ is nitro; $R^1$ is heterocycle wherein heterocycle is selected from quinolinyl, pyridinyl and pyrimidinyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, ($NR^9R^{10}$)alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; and $R^7$, $R^9$ and $R^{10}$ are as defined in formula I.

In another embodiment of the present invention, compounds have formula I wherein X is $NR^8$; $R^8$ is selected from arylsulfonyl, haloalkylsulfonyl and sulfamyl; $R^4$ is hydrogen; $R^5$ is hydrogen; $R^6$ is hydrogen; and $R^1$, $R^2$, $R^3$, and $R^7$ are as defined in formula I.

In another embodiment of the present invention, compounds have formula I wherein X is $NR^8$; $R^8$ is selected from arylsulfonyl wherein the aryl portion of arylsulfonyl is phenyl, haloalkylsulfonyl and sulfamyl; $R^1$ is heterocycle wherein heterocycle is selected from quinolinyl, pyridinyl and pyrimidinyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; and $R^7$, $R^9$ and $R^{10}$ are as defined in formula I.

In another embodiment of the present invention, compounds have formula I wherein X is S; $R^4$ is hydrogen; $R^5$ is hydrogen; $R^6$ is hydrogen; and $R^1$, $R^2$, $R^3$ and $R^7$ are as defined in formula I.

In another embodiment of the present invention, compounds have formula I wherein X is S; $R^1$ is selected from heterocycle and heterocyclealkyl; $R^3$ is selected from aryl and arylalkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is S; $R^1$ is selected from heterocycle and heterocyclealkyl; $R^2$ is selected from hydrogen, alkenyl, alkenyloxyalkyl, alkenyloxy(alkenyloxy)alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and $(NR^9R^{10})$alkyl; $R^3$ is selected from aryl and arylalkyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is S; $R^1$ is heterocycle wherein heterocycle is selected from quinolinyl, pyridinyl and pyrimidinyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, $(NR^9R^{10})$alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is S; $R^1$ is heterocycle; $R^2$ is haloalkyl; $R^3$ is aryl; $R^4$ is hydrogen; $R^5$ is hydrogen; $R^6$ is hydrogen; and $R^7$ is hydrogen.

In another embodiment of the present invention, compounds have formula I wherein X is S; $R^1$ is heterocycle wherein heterocycle is pyridinyl; $R^2$ is haloalkyl; $R^3$ is aryl wherein aryl is phenyl; $R^4$ is hydrogen; $R^5$ is hydrogen; $R^6$ is hydrogen; and $R^7$ is hydrogen.

In another embodiment of the present invention, compounds have formula I wherein X is S; $R^1$ is selected from aryl and arylalkyl; $R^3$ is selected from aryl and arylalkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is S; $R^1$ is selected from aryl and arylalkyl; $R^2$ is selected from hydrogen, alkenyl, alkenyloxyalkyl, alkenyloxy(alkenyloxy)alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and $(NR^9R^{10})$alkyl; $R^3$ is selected from aryl and arylalkyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is S; $R^1$ is aryl wherein aryl is phenyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is S; $R^1$ is aryl wherein aryl is phenyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is O; $R^1$ is selected from heterocycle and heterocyclealkyl; $R^3$ is selected from aryl and arylalkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is O; $R^1$ is selected from heterocycle and heterocyclealkyl; $R^2$ is selected from hydrogen, alkenyl, alkenyloxyalkyl, alkenyloxy(alkenyloxy)alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and $(NR^9R^{10})$alkyl; $R^3$ is selected from aryl and arylalkyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is O; $R^1$ is heterocycle wherein heterocycle is selected from quinolinyl, pyridinyl and pyrimidinyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, $(NR^9R^{10})$alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is O; $R^1$ is heterocycle; $R^2$ is haloalkyl; $R^3$ is aryl; $R^4$ is hydrogen; $R^5$ is hydrogen; $R^6$ is hydrogen; and $R^7$ is hydrogen.

In another embodiment of the present invention, compounds have formula I wherein X is O; $R^1$ is heterocycle wherein heterocycle is pyridinyl; $R^2$ is haloalkyl; $R^3$ is aryl wherein aryl is phenyl; $R^4$ is hydrogen; $R^5$ is hydrogen; $R^6$ is hydrogen; and $R^7$ is hydrogen.

In another embodiment of the present invention, compounds have formula I wherein X is O; $R^1$ is selected from heterocycle and heterocyclealkyl; $R^3$ is selected from heterocycle, and heterocyclealkyl; $R^4$ is hydrogen; $R^5$ is hydrogen; $R^6$ is hydrogen; and $R^2$ and $R^7$ are as defined in forumula I.

In another embodiment of the present invention, compounds have formula I wherein X is O; $R^1$ is selected from aryl and arylalkyl; $R^3$ is selected from aryl and arylalkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is O; $R^1$ is selected from aryl and arylalkyl; $R^2$ is selected from hydrogen, alkenyl, alkenyloxyalkyl, alkenyloxy(alkenyloxy)alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and $(NR^9R^{10})$alkyl; $R^3$ is selected from aryl and arylalkyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is O; $R^1$ is aryl wherein aryl is phenyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; and $R^7$, $R^9$ and $R^{10}$ are as defined in formula I.

In another embodiment of the present invention, compounds have formula I wherein X is selected from CHCN and $CHNO_2$; $R^1$ is selected from heterocycle and heterocyclealkyl; $R^3$ is selected from heterocycle and heterocyclealkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is selected from CHCN and $CHNO_2$; $R^1$ is selected from heterocycle and heterocyclealkyl; $R^3$ is selected from aryl and arylalkyl; $R^4$ is hydrogen; $R^5$ is hydrogen; $R^6$ is hydrogen; and $R^2$ and $R^7$ are as defined in formual I.

In another embodiment of the present invention, compounds have formula I wherein X is selected from CHCN and $CHNO_2$; $R^1$ is selected from heterocycle and heterocyclealkyl; $R^2$ is selected from hydrogen, alkenyl, alkenyloxyalkyl, alkenyloxy(alkenyloxy)alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and $(NR^9R^{10})$alkyl; $R^3$ is selected from aryl and arylalkyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is selected from CHCN and $CHNO_2$; $R^1$ is heterocycle wherein heterocycle is selected from quinolinyl, pyridinyl and pyrimidinyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is selected from CHCN and $CHNO_2$; $R^1$ is heterocycle wherein heterocycle is selected from quinolinyl, pyridinyl and pyrimidinyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, $(NR^9R^{10})$alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; $R^7$ is hydrogen; and $R^9$ and $R^{10}$ are as defined in formula I.

In another embodiment of the present invention, compounds have formula I wherein X is selected from CHCN and $CHNO_2$; $R^1$ is heterocycle; $R^2$ is haloalkyl; $R^3$ is aryl; $R^4$ is hydrogen; $R^5$ is hydrogen; $R^6$ is hydrogen; and $R^7$ is hydrogen.

In another embodiment of the present invention, compounds have formula I wherein X is selected from CHCN and $CHNO_2$; $R^1$ is heterocycle wherein heterocycle is pyridinyl; $R^2$ is haloalkyl; $R^3$ is aryl wherein aryl is phenyl; $R^4$ is hydrogen; $R^5$ is hydrogen; $R^6$ is hydrogen; and $R^7$ is hydrogen.

In another embodiment of the present invention, compounds have formula I wherein X is selected from CHCN and $CHNO_2$; $R^1$ is selected from heterocycle and heterocyclealkyl; $R^3$ is alkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is selected from CHCN and $CHNO_2$; $R^1$ is selected from aryl and arylalkyl; $R^3$ is selected from heterocycle and heterocyclealkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is selected from CHCN and $CHNO_2$; $R^1$ is selected from aryl and arylalkyl; $R^3$ is selected from aryl and arylalkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is selected from CHCN and $CHNO_2$; $R^1$ is selected from aryl and arylalkyl; $R^3$ is alkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is $C(CN)_2$; $R^1$ is selected from heterocycle and heterocyclealkyl; $R^3$ is selected from aryl and arylalkyl; $R^4$ is hydrogen; $R^5$ is hydrogen; $R^6$ is hydrogen; and $R^2$ and $R^7$ are as defined in formula I.

In another embodiment of the present invention, compounds have formula I wherein X is $C(CN)_2$; $R^1$ is heterocycle wherein heterocycle is selected from quinolinyl, pyridinyl and pyrimidinyl; $R^2$ is selected from hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from 1,3-dioxanyl, pyrrolidinyl and thienyl; $R^3$ is aryl wherein aryl is phenyl; $R^4$ is hydrogen; $R^5$ is hydrogen; $R^6$ is hydrogen; and $R^7$, $R^9$ and $R^{10}$ are as defined in formula I.

In another embodiment of the present invention, compounds have formula II:

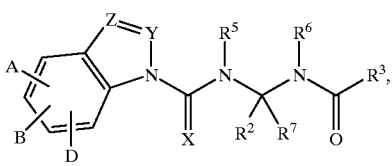

II or a pharmaceutically acceptable salt, amide, ester or prodrug thereof wherein Z and Y are independently selected from CH and N; A, B, and D are independently selected from hydrogen, alkenyl, alkoxy, alkoxycarbonyl, alkyl, alkylcarbonyl, alkylsulfinyl, alkylsulfonyl, alkynyl, arylalkoxycarbonyl, arylsulfonyl, cyano, halo, haloalkyl, haloalkoxy, nitro, sulfamyl, and —$NR^A R^B$; and X, $R^2$, $R^3$, $R^5$, $R^6$, $R^7$, $R^A$ and $R^B$ are as defined in formula I.

In another embodiment of the present invention, compounds have formula II wherein X is $NR^8$; $R^8$ is cyano; $R^5$ is hydrogen; $R^6$ is hydrogen; A, B, D, Z and Y are as defined in formula II; and $R^2$, $R^3$ and $R^7$ are as defined in formula I.

In another embodiment of the present invention, compounds have formula II wherein X is $NR^8$; $R^8$ is selected from hydrogen, alkoxy, alkyl, alkylsulfonyl, arylalkoxy, aryloxy, arylsulfonyl, haloalkylsulfonyl, heterocyclealkoxy, hydroxy, nitro, and sulfamyl; $R^5$ is hydrogen; $R^6$ is hydrogen; A, B, D, Z and Y are as defined in formula II; and $R^2$, $R^3$ and $R^7$ are as defined in formula I.

In another embodiment of the present invention, compounds have formula II wherein X is S; $R^5$ is hydrogen; $R^6$ is hydrogen; A, B, D, Z and Y are as defined in formula II; and $R^2$, $R^3$ and $R^7$ are as defined in formula I.

In another embodiment of the present invention, compounds have formula II wherein X is O; $R^5$ is hydrogen; $R^6$ is hydrogen; A, B, D, Z and Y are as defined in formula II; and $R^2$, $R^3$ and $R^7$ are as defined in formula I.

In another embodiment of the present invention, compounds have formula II wherein X is selected from CHCN and $CHNO_2$; $R^5$ is hydrogen; $R^6$ is hydrogen; A, B, D, Z and Y are as defined in formula II; and $R^2$, $R^3$ and $R^7$ are as defined in formula I.

In another embodiment of the present invention, compounds have formula III:

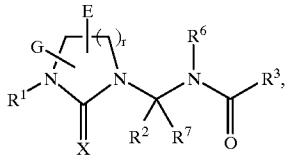

III or a pharmaceutically acceptable salt, amide, ester or prodrug thereof wherein r is an integer of 1–2; E and G are independently selected from hydrogen, alkyl and oxo; and X, $R^1$, $R^2$, $R^3$, $R^6$ and $R^7$ are as defined in formula I.

In another embodiment of the present invention, compounds have formula III wherein X is $NR^8$; $R^8$ is cyano; $R^6$ is hydrogen; r, E and G are as defined in formula III; and $R^1$, $R^2$, $R^3$ and $R^7$ are as defined in formula I.

In another embodiment of the present invention, compounds have formula III wherein X is $NR^8$; $R^8$ is selected from hydrogen, alkoxy, alkyl, alkylsulfonyl, arylalkoxy, aryloxy, arylsulfonyl, haloalkylsulfonyl, heterocyclealkoxy, hydroxy, nitro, and sulfamyl; $R^6$ is hydrogen; r, E and G are as defined in formula III; and $R^1$, $R^2$, $R^3$ and $R^7$ are as defined in formula I.

In another embodiment of the present invention, compounds have formula III wherein X is S; $R^6$ is hydrogen; r, E and G are as defined in formula III; and $R^1$, $R^2$, $R^3$ and $R^7$ are as defined in formula I.

In another embodiment of the present invention, compounds have formula III wherein $R^2$ is haloalkyl; $R^7$ is hydrogen; r, E and G are as defined in formula III; and X, $R^1$, $R^3$ and $R^6$ are as defined in formula I.

In another embodiment of the present invention, compounds have formula III wherein X is O; $R^6$ is hydrogen; r, E and G are as defined in formula III; and $R^1$, $R^2$, $R^3$ and $R^7$ are as defined in formula I.

In another embodiment of the present invention, compounds have formula III wherein X is selected from CHCN and $CHNO_2$; $R^6$ is hydrogen; r, E and G are as defined in formula III; and $R^1$, $R^2$, $R^3$ and $R^7$ are as defined in formula I.

In another embodiment of the present invention, compounds have formula IV:

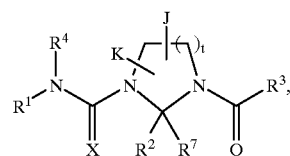

IV or a pharmaceutically acceptable salt, amide, ester or prodrug thereof wherein t is an integer of 1–2; J and K are independently selected from hydrogen, alkyl and oxo; and X, $R^1$, $R^2$, $R^3$, $R^4$ and $R^7$ are as defined in formula I.

In another embodiment of the present invention, compounds have formula IV wherein X is $NR^8$; $R^8$ is cyano; $R^4$ is hydrogen; t, J and K are as defined in formula IV; and $R^1$, $R^2$, $R^3$ and $R^7$ are as defined in formula I.

In another embodiment of the present invention, compounds have formula IV wherein X is $NR^8$; $R^8$ is selected from hydrogen, alkoxy, alkyl, alkylsulfonyl, arylalkoxy, aryloxy, arylsulfonyl, haloalkylsulfonyl, heterocyclealkoxy, hydroxy, nitro, and sulfamyl; $R^4$ is hydrogen; t, J and K are as defined in formula IV; and $R^1$, $R^2$, $R^3$ and $R^7$ are as defined in formula I.

In another embodiment of the present invention, compounds have formula IV wherein X is S; $R^4$ is hydrogen; t, J and K are as defined in formula IV; and $R^1$, $R^2$, $R^3$ and $R^7$ are as defined in formula I.

In another embodiment of the present invention, compounds have formula IV wherein X is O; $R^4$ is hydrogen; t, J and K are as defined in formula IV; and $R^1$, $R^2$, $R^3$ and $R^7$ are as defined in formula I.

In another embodiment of the present invention, compounds have formula IV wherein X is selected from CHCN and $CHNO_2$; $R^4$ is hydrogen; t, J and K are as defined in formula IV; and $R^1$, $R^2$, $R^3$ and $R^7$ are as defined in formula I.

In another embodiment of the present invention, compounds have formula V:

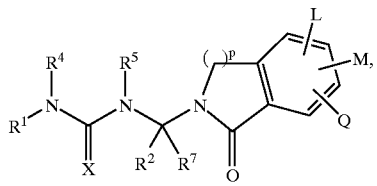

or a pharmaceutically acceptable salt, ester, amide, or prodrug thereof wherein p is an integer of 1–2; L, M and Q are independently selected from hydrogen, alkenyl, alkoxy, alkoxycarbonyl, alkyl, alkylcarbonyl, alkylsulfinyl, alkylsulfonyl, alkynyl, arylalkoxycarbonyl, arylsulfonyl, cyano, halo, haloalkyl, haloalkoxy, nitro, sulfamyl, and —$NR^AR^B$; and X, $R^1$, $R^2$, $R^4$, $R^5$, $R^7$, $R^A$ and $R^B$ are as defined in formula I.

In another embodiment of the present invention, compounds have formula V wherein X is $NR^8$; $R^8$ is cyano; $R^4$ is hydrogen; $R^5$ is hydrogen; p, L, M and Q are as defined in formula V; and $R^1$, $R^2$ and $R^7$ are as defined in formula I.

In another embodiment of the present invention, compounds have formula V wherein X is $NR^8$; $R^8$ is selected from hydrogen, alkoxy, alkyl, alkylsulfonyl, arylalkoxy, aryloxy, arylsulfonyl, haloalkylsulfonyl, heterocyclealkoxy, hydroxy, nitro, and sulfamyl; $R^4$ is hydrogen; $R^5$ is hydrogen; p, L, M and Q are as defined in formula V; and $R^1$, $R^2$ and $R^7$ are as defined in formula I.

In another embodiment of the present invention, compounds have formula V wherein X is S; $R^4$ is hydrogen; $R^5$ is hydrogen; p, L, M and Q are as defined in formula V; and $R^1$, $R^2$ and $R^7$ are as defined in formula I.

In another embodiment of the present invention, compounds have formula V wherein X is O; $R^4$ is hydrogen; $R^5$ is hydrogen; p, L, M and Q are as defined in formula V; and $R^1$, $R^2$ and $R^7$ are as defined in formula I.

In another embodiment of the present invention, compounds have formula V wherein X is selected from CHCN and $CHNO_2$; $R^4$ is hydrogen; $R^5$ is hydrogen; p, L, M and Q are as defined in formula V; and $R^1$, $R^2$ and $R^7$ are as defined in formula I.

In another embodiment of the present invention, compounds have formula VI:

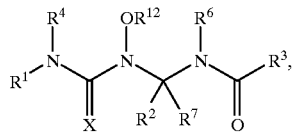

or a pharmaceutically acceptable salt, ester, amide, or prodrug thereof wherein X, $R^1$, $R^2$, $R^3$, $R^4$, $R^6$, $R^7$ and $R^{12}$ are as defined in formula I.

In another embodiment of the present invention, compounds have formula VI wherein X is $NR^8$; $R^8$ is cyano; $R^4$ is hydrogen; $R^6$ is hydrogen; $R^1$, $R^2$, $R^3$, $R^7$ and $R^{12}$ are as defined in formula I.

In another embodiment of the present invention, compounds have formula VI wherein X is $NR^8$; $R^8$ is selected from hydrogen, alkoxy, alkyl, alkylsulfonyl, arylalkoxy, aryloxy, arylsulfonyl, haloalkylsulfonyl, heterocyclealkoxy, hydroxy, nitro, and sulfamyl; $R^4$ is hydrogen; $R^6$ is hydrogen; and $R^1$, $R^2$, $R^3$, $R^7$ and $R^{12}$ are as defined in formula I.

In another embodiment of the present invention, compounds have formula VI wherein X is S; $R^4$ is hydrogen; $R^6$ is hydrogen; and $R^1$, $R^2$, $R^3$, $R^7$ and $R^{12}$ are as defined in formula I.

In another embodiment of the present invention, compounds have formula VI wherein X is O; $R^4$ is hydrogen; $R^6$ is hydrogen; and $R^1$, $R^2$, $R^3$, $R^7$ and $R^{12}$ are as defined in formula I.

In another embodiment of the present invention, compounds have formula VI wherein X is S; X is selected from CHCN and $CHNO_2$; $R^4$ is hydrogen; $R^6$ is hydrogen; and $R^1$, $R^2$, $R^3$, $R^7$ and $R^{12}$ are as defined in formula I.

Another embodiment of the invention relates to a method of treating a disease in a host mammal in need of such treatment comprising administering a therapeutically effective amount of a compound of formula VII:

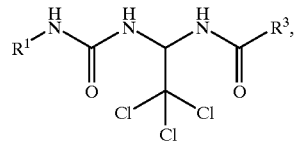

or a pharmaceutically acceptable salt, amide, ester or prodrug thereof wherein $R^1$ is phenyl; and $R^3$ is selected from alkyl and phenyl.

Another embodiment of the present invention relates to pharmaceutical compositions comprising a therapeutically effective amount of a compound of formula I–VII or a pharmaceutically acceptable salt, ester, amide, or prodrug thereof in combination with a pharmaceutically acceptable carrier.

Another embodiment of the invention relates to a method of treating urinary incontinence comprising administering a therapeutically effective amount of a compound of formula I–VII or a pharmaceutically acceptable salt, ester, amide, or prodrug thereof.

Another embodiment of the invention relates to a method of treating male sexual dysfunction including, but not limited to, male erectile dysfunction and premature ejaculation, comprising administering a therapeutically effective amount of a compound of formula I–VII or a pharmaceutically acceptable salt, ester, amide, or prodrug thereof.

Another embodiment of the invention relates to a method of treating female sexual dysfunction including, but not limited to, female anorgasmia, clitoral erectile insufficiency, vaginal engorgement, dyspareunia, and vaginismus comprising administering a therapeutically effective amount of a compound of formula I–VII or a pharmaceutically acceptable salt, ester, amide, or prodrug thereof.

Yet another embodiment of the invention relates to a method of treating asthma, epilepsy, Raynaud's syndrome, intermittent claudication, migraine, pain, bladder overactivity, pollakiuria, bladder instability, nocturia, bladder hyperreflexia, eating disorders, urinary incontinence, enuresis, functional bowel disorders, neurodegeneration, benign prostatic hyperplasia (BPH), dysmenorrhea, premature labor, alopecia, cardioprotection, and ischemia comprising administering a therapeutically effective amount of a compound of formula I–VII or a pharmaceutically acceptable salt, ester, amide, or prodrug thereof.

Definition of Terms

As used throughout this specification and the appended claims, the following terms have the following meanings.

The term "alkenyl," as used herein, refers to a straight or branched chain hydrocarbon containing from 2 to 10 carbons and containing at least one carbon—carbon double bond formed by the removal of two hydrogens. Representative examples of alkenyl include, but are not limited to, ethenyl, 2-propenyl, 2-methyl-2-propenyl, 3-butenyl, 1,1-dimethyl-3-butenyl, 4-pentenyl, 5-hexenyl, 2-heptenyl, 2-methyl-1-heptenyl, 3-decenyl and the like.

The term "alkenyloxy," as used herein, refers to an alkenyl group, as defined herein, appended to the parent molecular moiety through an oxy moiety, as defined herein. Representative examples of alkenyloxy include, but are not limited to, allyloxy, 2-butenyloxy, 3-butenyloxy and the like.

The term "alkenyloxyalkyl," as used herein, refers to a alkenyloxy group, as defined herein, appended to the parent molecular moiety through an alkyl group, as defined herein. Representative examples of alkenyloxyalkyl include, but are not limited to, (allyloxy)methyl, (2-butenyloxy)methyl and (3-butenyloxy)methyl.

The term "alkenyloxy(alkenyloxy)alkyl," as used herein, refers to 2 independent alkenyloxy groups, as defined herein, appended to the parent molecular moiety through an alkyl group, as defined herein. Representative examples of alkenyloxy(alkenyloxy)alkyl include, but are not limited to, 1,2-bis(allyloxy)ethyl and 1,1-bis[(allyloxy)methyl]propyl and the like.

The term "alkoxy," as used herein, refers to an alkyl group, as defined herein, appended to the parent molecular moiety through an oxy moiety, as defined herein. Representative examples of alkoxy include, but are not limited to, methoxy, ethoxy, propoxy, 2-propoxy, butoxy, tert-butoxy, and the like.

The term "alkoxyalkyl," as used herein, refers to an alkoxy group, as defied herein, appended to the parent molecular moiety through an alkyl group, as defined herein. Representative examples of alkoxyalkyl include, but are not limited to, tert-butoxymethyl, 2-ethoxyethyl, 2-methoxyethyl, methoxymethyl, 1,1-dimethyl-3-(methoxy)propyl, and the like.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, tert-butoxycarbonyl, and the like.

The term "alkoxycarbonylalkyl," as used herein, refers to an alkoxycarbonyl group, as defined herein, appended to the parent molecular moiety through an alkyl group, as defined herein. Representative examples of alkoxycarbonylalkyl include, but are not limited to, methoxycarbonylmethyl, ethoxycarbonylmethyl, tert-butoxycarbonylmethyl, 1,1-dimethyl-2-(methoxycarbonyl)ethyl and the like.

The term "alkoxycarbonyl(halo)alkyl," as used herein, refers to an alkoxycarbonyl group and at least one halogen, as defined herein, appended to the parent molecular moiety through an alkyl group, as defined herein. Representative examples of alkoxycarbonyl(halo)alkyl include, but are not limited to, 1,1-dichloro-2-methoxy-2-oxoethyl, 1,1-difluoro-2-methoxy-2-oxoethyl, 1,1-dichloro-3-methoxy-3-oxopropyl, 1,1-difluoro-3-methoxy-3-oxopropyl, and the like.

The term "alkoxy(halo)alkyl," as used herein, refers to an alkoxy group and at least one halogen, as defined herein, appended to the parent molecular moiety through an alkyl group, as defined herein. Representative examples of alkoxy(halo)alkyl include, but are not limited to, dichloro(methoxy)methyl, dichloro(ethoxy)methyl, dichloro(tert-butoxy)methyl, 1,1-dichloro-2-ethoxyethyl, 1,1-dichloro-2-methoxyethyl, 1,1-dichloro-3-methoxypropyl, 1,2-dichloro-3-methoxypropyl, and the like.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 3-methylhexyl, 1-ethylpropyl, 2,2-dimethylpentyl, 2,3-dimethylpentyl, n-heptyl, n-octyl, n-nonyl, n-decyl, and the like.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, 1-oxopentyl, and the like.

The term "alkylcarbonylalkyl," as used herein, refers to an alkylcarbonyl group, as defined herein, appended to the parent molecular moiety through an alkyl group, as defined herein. Representative examples of alkylcarbonylalkyl include, but are not limited to, 2-oxopropyl, 1,1-dimethyl-3-oxobutyl, 3-oxobutyl, 3-oxopentyl, and the like.

The term "alkylcarbonyl(halo)alkyl," as used herein, refers to an alkylcarbonyl group and at least one halogen, as defined herein, appended to the parent molecular moiety through an alkyl group, as defined herein. Representative examples of alkylcarbonyl(halo)alkyl include, but are not limited to, 1,1-dichloro-2-oxopropyl, 1,1-dichloro-3-oxobutyl, 1,1-difluoro-3-oxobutyl, 1,1-dichloro-3-oxopentyl, and the like.

The term "alkylcarbonyloxy," as used herein, refers to an alkylcarbonyl group, as defined herein, appended to the parent molecular moiety through an oxy moiety, as defined herein. Representative examples of alkylcarbonyloxy include, but are not limited to, acetyloxy, ethylcarbonyloxy, and the like.

The term "alkylcarbonyloxyalkyl," as used herein, refers to an alkylcarbonyloxy group, as defined herein, appended to the parent molecular moiety through an alkyl group, as defined herein. Representative examples of alkylcarbonyloxyalkyl include, but are not limited to, acetyloxymethyl, 2-(ethylcarbonyloxy)ethyl, and the like.

The term "alkylene" or "alkylene bridge" refers to a divalent group derived from a straight chain hydrocarbon of from 2 to 6 carbon atoms. The alkylene or alkylene bridge can be optionally substituted with 1 or 2 substituents selected from alkyl and oxo. Representative examples of alkylene or alkylene bridge include, but are not limited to, $-CH_2CH_2-$, $-C(O)CH_2-$, $-C(O)C(O)-$, $-CH_2CH_2CH_2-$, $-CH_2C(CH_3)_2CH_2-$, $-CH_2CH_2CH_2CH_2-$, $-CH_2CH_2CH_2CH_2CH_2-$ and the like.

The term "alkylsulfinyl," as used herein, refers to an alkyl group, as defined herein, appended to the parent molecular moiety through a sulfinyl group, as defined herein. Representative examples of alkylsulfinyl include, but are not limited to, methylsulfinyl, ethylsulfinyl, and the like.

The term "alkylsulfinylalkyl," as used herein, refers to an alkylsulfinyl group, as defined herein, appended to the parent molecular moiety through an alkyl group, as defined herein. Representative examples of alkylsulfinylalkyl include, but are not limited to, methylsulfinylmethyl, ethylsulfinylmethyl, and the like.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl, ethylsulfonyl, and the like.

The term "alkylsulfonylalkyl," as used herein, refers to an alkylsulfonyl group, as defined herein, appended to the parent molecular moiety through an alkyl group, as defined herein. Representative examples of alkylsulfonylalkyl include, but are not limited to, methylsulfonylmethyl, ethylsulfonylmethyl, and the like.

The term "alkylthio," as used herein, refers to an alkyl group, as defined herein, appended to the parent molecular moiety through a thio moiety, as defined herein. Representative examples of alkylthio include, but are not limited to, methylsulfanyl, ethylsulfanyl, propylsulfanyl, 2-propylsulfanyl, tert-butylsulfanyl, and the like.

The term "alkylthioalkyl," as used herein, refers to an alkylthio group, as defined herein, appended to the parent molecular moiety through an alkyl group, as defined herein. Representative examples of alkylthioalkyl include, but are not limited to, tert-butylsulfanylmethyl, 2-ethylsulfanylethyl, 2-methylsulfanylethyl, methylsulfanylmethyl, and the like.

The term "alkynyl," as used herein, refers to a straight or branched chain hydrocarbon group containing from 2 to 10 carbon atoms and containing at least one carbon—carbon triple bond. Representative examples of alkynyl include, but are not limited to, acetylenyl, 1-propynyl, 2-propynyl, 3-butynyl, 2-pentynyl, 1-butynyl, and the like.

The term "amido," as used herein, refers to a —NR$^9$R$^{10}$ group, as defined herein, appended to the parent molecular moiety through a carbonyl group, as defined herein. Representative examples of amido include, but are not limited to, aminocarbonyl, dimethylaminocarbonyl, ethylaminocarbonyl, benzylaminocarbonyl, and the like.

The term "amidoalkyl," as used herein, refers to an amido group, as defined herein, appended to the parent molecular moiety through an alkyl group, as defined herein. Representative examples of amidoalkyl include, but are not limited to, aminocarbonylmethyl, dimethylaminocarbonylmethyl, 2-(ethylaminocarbonyl)ethyl, 3-(benzylaminocarbonyl)propyl, and the like.

The term "aryl," as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like.

The aryl groups of this invention, including the representative examples listed above, can be optionally substituted with 1, 2, 3, 4, or 5 substituents independently selected from alkenyl, alkoxy, alkoxycarbonyl, alkoxycarbonylalkyl, alkyl, alkylcarbonyl, alkylcarbonyloxy, alkylcarbonyloxyalkyl, alkylsulfinyl, alkylsulfonyl, alkynyl, amido, amidoalkyl, arylalkoxycarbonyl, arylalkoxycarbonylalkyl, arylcarbonyloxy, arylcarbonyloxyalkyl, aryloxycarbonyl, aryloxycarbonylalkyl, arylsulfonyl, cyano, halo, haloalkyl, haloalkoxy, nitro, sulfamyl, sulfamylalkyl, —NR$^A$R$^B$, (NR$^A$R$^B$)alkyl, furyl, imidazolyl, isothiazolyl, isoxazolyl, naphthyl, oxadiazolyl, oxazolyl, phenyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothiadiazolyl, benzothienyl, benzoxadiazolyl, benzoxazolyl, benzofuranyl, cinnolinyl, indolyl, naphthyridinyl, isobenzofuranyl, isobenzothienyl, isoindolyl, isoquinolinyl, and quinolinyl, wherein said furyl, imidazolyl, isothiazolyl, isoxazolyl, naphthyl, oxadiazolyl, oxazolyl, phenyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothiadiazolyl, benzothienyl, benzoxadiazolyl, benzoxazolyl, benzofuranyl, cinnolinyl, indolyl, naphthyridinyl, isobenzofuranyl, isobenzothienyl, isoindolyl, isoquinolinyl, and quinolinyl may be substituted with 1 or 2 substituents independently selected from alkenyl, alkoxy, alkoxycarbonyl, alkoxycarbonylalkyl, alkyl, alkylcarbonyl, alkylcarbonyloxy, alkylcarbonyloxyalkyl, alkylsulfinyl, alkylsulfonyl, alkynyl, amido, amidoalkyl, arylalkoxycarbonyl, arylalkoxycarbonylalkyl, arylcarbonyloxy, arylcarbonyloxyalkyl, aryloxycarbonyl, aryloxycarbonylalkyl, arylsulfonyl, cyano, halo, haloalkyl, haloalkoxy, nitro, sulfamyl, sulfamylalkyl, —NR$^A$R$^B$, and (NR$^A$R$^B$)alkyl.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-naphth-2-ylpropoxy, 5-phenylpentyloxy, and the like.

The term "arylalkoxyalkyl," as used herein, refers to an arylalkoxy group, as defined herein, appended to the parent molecular moiety through an alkyl group, as defined herein. Representative examples of arylalkoxyalkyl include, but are not limited to, 2-phenylethoxymethyl, 2-(3-naphth-2-ylpropoxy)ethyl, 5-phenylpentyloxymethyl, and the like.

The term "arylalkoxycarbonyl," as used herein, refers to an arylalkoxy group, as defined herein, appended to the parent molecular moiety through a carbonyl group, as defined herein. Representative examples of arylalkoxycarbonyl include, but are not limited to, benzyloxycarbonyl, naphth2-ylmethyloxycarbonyl, and the like.

The term "arylalkoxycarbonylalkyl," as used herein, refers to an arylalkoxycarbonyl group, as defined herein, appended to the parent molecular moiety through an alkyl group, as defined herein. Representative examples of arylalkoxycarbonylalkyl include, but are not limited to, benzyloxycarbonylmethyl, 2-(benzyloxycarbonyl)ethyl, 2-(naphth-2-ylmethyloxycarbonyl)ethyl, and the like.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 1,1-dimethyl-2-phenylethyl, 3-phenylpropyl, 2-naphth-2-ylethyl, and the like.

The term "arylalkylthio," as used herein, refers to an arylalkyl group, as defined herein, appended to the parent molecular moiety through a thio moiety, as defined herein. Representative examples of arylalkylthio include, but are not limited to, 2-phenylethylthio, 3-naphth-2-ylpropylthio, 5-phenylpentylthio, and the like.

The term "arylalkylthioalkyl," as used herein, refers to an arylalkylthio group, as defined herein, appended to the parent molecular moiety through an alkyl group, as defined herein. Representative examples of arylalkylthioalkyl include, but are not limited to, 2-phenylethylsulfanylmethyl, 3-naphth-2-ylpropylsulfanylmethyl, 2-(5-phenylpentylsulfanyl)ethyl, and the like.

The term "arylcarbonyl," as used herein, refers to an aryl group, as defined herein, appended to the parent molecular moiety through a carbonyl group, as defined herein. Representative examples of arylcarbonyl include, but are not limited to, benzoyl, naphthoyl, and the like.

The term "arylcarbonylalkyl," as used herein, refers to an arylcarbonyl group, as defined herein, appended to the parent molecular moiety through an alkyl group, as defined herein. Representative examples of arylcarbonylalkyl include, but are not limited to, 2-oxo-3-phenylpropyl, 1,1-dimethyl-3-oxo-4-phenylbutyl, and the like.

The term "arylcarbonyloxy," as used herein, refers to an arylcarbonyl group, as defined herein, appended to the parent molecular moiety through an oxy moiety, as defined herein. Representative examples of arylcarbonyloxy include, but are not limited to, benzoyloxy, naphthoyloxy, and the like.

The term "arylcarbonyloxyalkyl," as used herein, refers to an arylcarbonyloxy group, as defined herein, appended to the parent molecular moiety through an alkyl group, as defined herein. Representative examples of arylcarbonyloxyalkyl include, but are not limited to, benzoyloxymethyl, 2-(benzoyloxy)ethyl, 2-(naphthoyloxy)ethyl, and the like.

The term "aryl(halo)alkyl," as used herein, refers to an aryl group and at least one halogen, as defined herein, appended to the parent molecular moiety through an alkyl group, as defined herein. Representative examples of aryl(halo)alkyl include, but are not limited to, dichloro(phenyl)methyl, 1,1-dichloro-2-phenylethyl, 1,1-difluoro-2-phenylethyl, 1,1-dichloro-3-phenylpropyl, 1,1-difluoro-3-phenylpropyl, and the like.

The term "aryloxy," as used herein, refers to an aryl group, as defined herein, appended to the parent molecular moiety through an oxy moiety, as defined herein. Representative examples of aryloxy include, but are not limited to, phenoxy, naphthyloxy, 3-bromophenoxy, 4-chlorophenoxy, 4-methylphenoxy, 3,5-dimethoxyphenoxy, and the like.

The term "aryloxyalkyl," as used herein, refers to an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl, 3-bromophenoxymethyl, and the like.

The term "aryloxycarbonyl," as used herein, refers to an aryloxy group, as defined herein, appended to the parent molecular moiety through an oxy moiety, as defined herein. Representative examples of aryloxycarbonyl include, but are not limited to, phenoxycarbonyl, naphthyloxycarbonyl, and the like.

The term "aryloxycarbonylalkyl," as used herein, refers to an aryloxycarbonyl group, as defined herein, appended to the parent molecular moiety through an alkyl group, as defined herein. Representative examples of aryloxycarbonylalkyl include, but are not limited to, phenoxycarbonylmethyl, 2-(phenoxycarbonyl)ethyl, naphthyloxycarbonyl, and the like.

The term "arylsulfonyl," as used herein, refers to an aryl group, as defined herein, appended to the parent molecular moiety through a sulfonyl group, as defined herein. Representative examples of arylsulfonyl include, but are not limited to, naphthylsulfonyl, phenylsulfonyl, 4-fluorophenylsulfonyl, and the like.

The term "arylsulfonylalkyl," as used herein, refers to an arylsulfonyl group, as defined herein, appended to the parent molecular moiety through an alkyl group, as defined herein. Representative examples of arylsulfonylalkyl include, but are not limited to, 1,1-dimethyl-3-(phenylsulfonyl)propyl, naphthylsulfonylmethyl, 2-(phenylsulfonyl)ethyl, phenylsulfonylmethyl, 4-fluorophenylsulfonylmethyl, and the like.

The term "arylthio," as used herein, refers to an aryl group, as defined herein, appended to the parent molecular moiety through a thio moiety, as defined herein. Representative examples of arylthio include, but are not limited to, phenylsulfanyl, naphth-2-ylsulfanyl, 5-phenylhexylsulfanyl, and the like.

The term "arylthioalkyl," as used herein, refers to an arylthio group, as defined herein, appended to the parent molecular moiety through an alkyl group, as defined herein. Representative examples of arylthioalkyl include, but are not limited to, phenylsulfanylmethyl, 2-naphth-2-ylsulfanylethyl, 5-phenylhexylsulfanylmethyl, and the like.

The term "carbonyl," as used herein, refers to a —C(O)— group.

The term "carboxy," as used herein, refers to a —CO$_2$H group.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, 3-carboxypropyl, 3-carboxy-1,1-dimethylpropyl and the like.

The term "carboxy(halo)alkyl," as used herein, refers to a carboxy group and at least one halogen, as defined herein, appended to the parent molecular moiety through an alkyl group, as defined herein. Representative examples of carboxy(halo)alkyl include, but are not limited to, carboxy(dichloro)methyl, carboxy(difluoro)methyl, 2-carboxy 1,1-dichloroethyl, 2-carboxy-1,1-difluoroethyl, and the like.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, 3-cyanopropyl, 3-cyano-1,1-dimethylpropyl, 3-cyano-1,1-diethylpropyl and the like.

The term "cyano(halo)alkyl," as used herein, refers to a cyano group and at least one halogen, as defined herein, appended to the parent molecular moiety through an alkyl group, as defined herein. Representative examples of cyano(halo)alkyl include, but are not limited to, 3-cyano-1,1-difluoropropyl, 1,1-dichloro-3-cyanopropyl, 3-cyano-1,1-bis(trifluoromethyl)propyl, and the like.

The term "cycloalkenyl," as used herein, refers to a cyclic hydrocarbon containing from 3 to 8 carbons and containing at least one carbon—carbon double bond formed by the removal of two hydrogens. Representative examples of cycloalkenyl include, but are not limited to, cyclohexene, 1-cyclohexen-2-yl, 3,3-dimethyl-1-cyclohexene, cyclopentene, cycloheptene, and the like.

The cycloalkenyl groups of this invention can be substituted with 1, 2, 3, 4, or 5 substituents independently selected from alkenyl, alkoxy, alkoxycarbonyl, alkoxycarbonylalkyl, alkyl, alkylcarbonyloxy, alkylcarbonyloxyalkyl, alkynyl, amido, amidoalkyl, arylalkoxycarbonyl, arylalkoxycarbonylalkyl, arylcarbonyloxy, arylcarbonyloxyalkyl, aryloxycarbonyl, aryloxycarbonylalkyl, halo, haloalkoxy, haloalkyl, hydroxy, hydroxyalkyl, sulfamylalkyl, —NR$^A$R$^B$, (NR$^A$R$^B$)alkyl.

The term "cycloalkenylalkyl," as used herein, refers to a cycloalkenyl group, as defined herein, appended to the parent molecular moiety through an alkyl group, as defined herein. Representative examples of cycloalkenylalkyl include, but are not limited to, (2,6,6-trimethyl-1- cyclohexen-1-yl)methyl, 1-cyclohexen-1-ylmethyl, 2-(2-cyclohepten-1-yl)ethyl, and the like.

The term "cycloalkyl," as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo [2.2.2]octane, bicyclo[3.2.2] nonane, bicyclo [3.3.1 ]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The cycloalkyl groups of this invention can be optionally substituted with 1, 2, 3, 4, or 5 substituents independently selected from alkenyl, alkoxy, alkoxycarbonyl, alkoxycarbonylalkyl, alkyl, alkylcarbonylalkyl, alkylcarbonyloxy, alkylcarbonyloxyalkyl, alkylsulfonylalkyl, alkynyl, alkylcarbonyloxy, amido, amidoalkyl, arylalkoxycarbonyl, arylalkoxycarbonylalkyl, arylalkyl, arylcarbonyloxy, arylcarbonyloxyalkyl, aryloxycarbonyl, aryloxycarbonylalkyl, arylsulfonylalkyl, cyanoalkyl, cycloalkylalkyl, halo, haloalkoxy, haloalkyl, heterocyclealkyl, hydroxy, hydroxyalkyl, sulfamylalkyl, —NR$^A$R$^B$, and (NR$^A$R$^B$)alkyl.

The term "cycloalkylalkoxy," as used herein, refers to a cycloalkyl group, as defined herein, appended to the parent molecular moiety through an alkoxy group, as defined herein. Representative examples of cycloalkylalkoxy include, but are not limited to, cyclopropylmethoxy, 2-cyclobutylethoxy, cyclopentylmethoxy, cyclohexylmethoxy, 4-cycloheptylbutoxy, and the like.

The term "cycloalkylalkoxyalkyl," as used herein, refers to a cycloalkylalkoxy group, as defined herein, appended to the parent molecular moiety through an alkyl group, as defined herein. Representative examples of cycloalkylalkoxyalkyl include, but are not limited to, cyclopropylmethoxymethyl, 2-cyclobutylethoxymethyl, cyclopentylmethoxymethyl, 2-cyclohexylethoxymethyl, 2-(4-cycloheptylbutoxy)ethyl, and the like.

The term "cycloalkylalkyl," as used herein, refers to a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl and 4-cycloheptylbutyl, and the like.

The term "cycloalkylcarbonyl," as used herein, refers to a cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, cyclohexylcarbonyl, and the like.

The term "cycloalkyloxy," as used herein, refers to a cycloalkyl group, as defined herein, appended to the parent molecular moiety through an oxy moiety, as defined herein. Representative examples of cycloalkyloxy include, but are not limited to, cyclohexyloxy, cyclopentyloxy, and the like.

The term "cycloalkyloxyalkyl," as used herein, refers to a cycloalkyloxy group, as defined herein, appended to the parent molecular moiety through an alkyl group, as defined herein. Representative examples of cycloalkyloxyalkyl include, but are not limited to, 4-(cyclohexyloxy)butyl, cyclohexyloxymethyl, and the like.

The term "cycloalkylalkylthio," as used herein, refers to a cycloalkylalkyl group, as defined herein, appended to the parent molecular moiety through a thio moiety, as defined herein. Representative examples of cycloalkylalkylthio include, but are not limited to, (2-cyclohexylethyl)sulfanyl, cyclohexylmethylsulfanyl, and the like.

The term "cycloalkylalkylthioalkyl," as used herein, refers to a cycloalkylalkylthio group, as defined herein, appended to the parent molecular moiety through an alkyl group, as defined herein. Representative examples of cycloalkylalkylthioalkyl include, but are not limited to, 2-[(2-cyclohexylethyl)sulfanyl]ethyl, (2-cyclohexylethyl)sulfanylmethyl, and the like.

The term "cycloalkylthio," as used herein, refers to a cycloalkyl group, as defined herein, appended to the parent molecular moiety through a thio moiety, as defined herein. Representative examples of cycloalkylthio include, but are not limited to, cyclohexylsulfanyl, cyclopentylsulfanyl, and the like.

The term "cycloalkylthioalkyl," as used herein, refers to a cycloalkylthio group, as defined herein, appended to the parent molecular moiety through an alkyl group, as defined herein. Representative examples of cycloalkylthioalkyl include, but are not limited to, 4-(cyclohexylsulfanyl)butyl, cyclohexylsulfanylmethyl, and the like.

The term "formyl," as used herein, refers to a —C(O)H group.

The term "halo" or "halogen," as used herein, refers to —Cl, —Br, —I or —F.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, 1,2-difluoroethoxy, trifluoromethoxy, pentafluoroethoxy, and the like.

The term "haloalkenyl," as used herein, refers to at least one halogen, as defined herein, appended to the parent molecular moiety through an alkenyl group, as defined herein. Representative examples of haloalkenyl include, but are not limited to, 2,2-dichloroethenyl, 2,2-difluoroethenyl, 5-chloropenten-2-yl, and the like.

The term "haloalkyl," as used herein, refers to at least one halogen, as defined herein, appended to the parent molecular moiety through an alkyl group, as defined herein. Representative examples of haloalkyl include, but are not limited to, chloromethyl, trichloromethyl, 1,1-dichloroethyl, 2-fluoroethyl, trifluoromethyl, 2,2,2-trifluoroethyl, 2,2,2-trifluoro-1-(trifluoromethyl)-1-(methyl)ethyl, pentafluoroethyl, 2-chloro-3-fluoropentyl, and the like.

The term "haloalkylcarbonyl," as used herein, refers to a haloalkylgroup, as defined herein, appended to the parent molecular moiety through a carbonyl group, as defined herein. Representative examples of haloalkylcarbonyl include, but are not limited to, chloromethylcarbonyl, trichloromethylcarbonyl, trifluoromethylcarbonyl, and the like.

The term "haloalkylsulfonyl," as used herein, refers to a haloalkyl group, as defined herein, appended to the parent molecular moiety through a sulfonyl group, as defined herein. Representative examples of haloalkylsulfonyl include, but are not limited to, chloromethylsulfonyl, trichloromethylsulfonyl, trifluoromethylsulfonyl, and the like.

The term "haloalkynyl," as used herein, refers to at least one halogen, as defined herein, appended to the parent molecular moiety through an alkynyl group, as defined herein. Representative examples of haloalkynyl include, but are not limited to, 4,4,4-trichlorobutyn-2-yl, and the like.

The term "heterocycle," as used herein, refers to a monocyclic or a bicyclic ring system. Monocyclic ring systems are exemplified by any 5 or 6 membered ring containing 1, 2, 3, or 4 heteroatoms independently selected from oxygen, nitrogen and sulfur. The 5-membered ring has from 0–2 double bonds and the 6-membered ring has from 0–3 double bonds. Representative examples of monocyclic ring systems include, but are not limited to, azetidinyl, azepanyl, aziridinyl, diazepanyl, 1,3-dioxolanyl, dioxanyl, 1,3-dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, thiomorpholine sulfone, thiopyranyl, triazinyl, triazolyl, trithianyl, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazolyl, benzothiazolyl, benzothiadiazolyl, benzothienyl, benzoxadiazolyl, benzoxazolyl, benzofuranyl, benzopyranyl, benzothiopyranyl, benzotriazolyl, benzodioxinyl, 1,3-benzodioxolyl, cinnolinyl, indazolyl, indolyl, indolinyl, indolizinyl, naphthyridinyl, isobenzofuranyl, isobenzothienyl, isoindolyl, isoindolinyl, 1-isoindolinonyl, isoquinolinyl, 1-isoquinolinonyl, phthalazinyl, pyranopyridinyl, quinolinyl, quinolizinyl, quinoxalinyl, quinazolinyl, tetrahydroisoquinolinyl, tetrahydroquinolinyl, and thiopyranopyridinyl.

The heterocycle groups of this invention, including the representative examples listed above, can be optionally substituted with 1, 2, or 3 substituents independently selected from alkenyl, alkoxy, alkoxycarbonyl, alkoxycarbonylalkyl, alkyl, alkylcarbonyl, alkylcarbonyloxy, alkylcarbonyloxyalkyl, alkylsulfinyl, alkylsulfonyl, alkynyl, amido, amidoalkyl, arylalkoxycarbonyl, arylalkoxycarbonylalkyl, arylcarbonyloxy, arylcarbonyloxyalkyl, aryloxycarbonyl, aryloxycarbonylalkyl, arylsulfonyl, cyano, halo, haloalkyl, haloalkoxy, nitro, oxo, sulfamyl, sulfamylalkyl, —NR$^A$R$^B$, (NR$^A$R$^B$)alkyl, furyl, imidazolyl, isothiazolyl, isoxazolyl, naphthyl, oxadiazolyl, oxazolyl, phenyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothiadiazolyl, benzothienyl, benzoxadiazolyl, benzoxazolyl, benzofuranyl, cinnolinyl, indolyl, naphthyridinyl, isobenzofuranyl, isobenzothienyl, isoindolyl, isoquinolinyl, and quinolinyl wherein said furyl, imidazolyl, isothiazolyl, isoxazolyl, naphthyl, oxadiazolyl, oxazolyl, phenyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothiadiazolyl, benzothienyl, benzoxadiazolyl, benzoxazolyl, benzofuranyl, cinnolinyl, indolyl, naphthyridinyl, isobenzofuranyl, isobenzothienyl, isoindolyl, isoquinolinyl, and quinolinyl may be substituted with 1 or 2 substituents independently selected from alkenyl, alkoxy, alkoxycarbonyl, alkoxycarbonylalkyl, alkyl, alkylcarbonyl, alkylcarbonyloxy, alkylcarbonyloxyalkyl, alkylsulfinyl, alkylsulfonyl, alkynyl, amido, amidoalkyl, arylalkoxycarbonyl, arylalkoxycarbonylalkyl, arylcarbonyloxy, arylcarbonyloxyalkyl, aryloxycarbonyl, aryloxycarbonylalkyl, arylsulfonyl, cyano, halo, haloalkyl, haloalkoxy, nitro, sulfamyl, sulfamylalkyl, —NR$^A$R$^B$, and (NR$^A$R$^B$)alkyl.

The term "heterocyclealkoxy," as used herein, refers to a heterocycle group, as defined herein, appended to the parent molecular moiety through an alkoxy group, as defined herein. Representative examples of heterocyclealkoxy include, but are not limited to, 2-pyrid-3-ylethoxy, 3-quinolin-3-ylpropoxy, 5-pyrid-4-ylpentyloxy, and the like.

The term "heterocyclealkoxyalkyl," as used herein, refers to a heterocyclealkoxy group, as defined herein, appended to the parent molecular moiety through an alkyl group, as defined herein. Representative examples of heterocyclealkoxyalkyl include, but are not limited to, 2-pyrid-3-ylethoxymethyl, 2-(3-quinolin-3-ylpropoxy)ethyl, 5-pyrid-4-ylpentyloxymethyl, and the like.

The term "heterocyclealkyl," as used herein, refers to a heterocycle, as defined herein, appended to the parent molecular moiety through an alkyl group, as defined herein. Representative examples of heterocyclealkyl include, but are not limited to, pyrid-3-ylmethyl, pyrimidin-5-ylmethyl, and the like.

The term "heterocyclealkylthio," as used herein, refers to a heterocyclealkyl group, as defined herein, appended to the parent molecular moiety through a thio moiety, as defined herein. Representative examples of heterocyclealkylthio include, but are not limited to, 2-pyrid-3-ylethysulfanyl, 3-quinolin-3-ylpropysulfanyl, 5-pyrid-4-ylpentylsulfanyl, and the like.

The term "heterocyclealkylthioalkyl," as used herein, refers to a heterocyclealkylthio group, as defined herein, appended to the parent molecular moiety through an alkyl group, as defined herein. Representative examples of heterocyclealkylthioalkyl include, but are not limited to, 2-pyrid-3-ylethysulfanylmethyl, 2-(3-quinolin-3-ylpropysulfanyl)ethyl, 5-pyrid-4-ylpentylsulfanylmethyl, and the like.

The term "heterocyclecarbonyl," as used herein, refers to a heterocycle, as defined herein, appended to the parent molecular moiety through a carbonyl group, as defined herein. Representative examples of heterocyclecarbonyl include, but are not limited to, pyrid-3-ylcarbonyl, quinolin-3-ylcarbonyl, thiophen-2-ylcarbonyl, and the like.

The term "heterocycleoxy," as used herein, refers to a heterocycle group, as defined herein, appended to the parent molecular moiety through an oxy moiety, as defined herein. Representative examples of heterocycleoxy include, but are not limited to, pyrid-3-yloxy, quinolin-3-yloxy, and the like.

The term "heterocycleoxyalkyl," as used herein, refers to a heterocycleoxy group, as defined herein, appended to the parent molecular moiety through an alkyl group, as defined herein. Representative examples of heterocycleoxyalkyl include, but are not limited to, pyrid-3-yloxymethyl, 2-quinolin-3-yloxyethyl, and the like.

The term "heterocyclethio," as used herein, refers to a heterocycle group, as defined herein, appended to the parent molecular moiety through a thio moiety, as defined herein. Representative examples of heterocyclethio include, but are not limited to, pyrid-3-ylsulfanyl, quinolin-3-ylsulfanyl, and the like.

The term "heterocyclethioalkyl," as used herein, refers to a heterocyclethio group, as defined herein, appended to the parent molecular moiety through an alkyl group, as defined herein. Representative examples of heterocyclethioalkyl include, but are not limited to, pyrid-3-ylsulfanylmethyl, 2-quinolin-3-ylsulfanylethyl, and the like.

The term "hydroxy," as used herein, refers to an —OH group.

The term "hydroxyalkyl," as used herein, refers to 1 or 2 hydroxy groups, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypropyl, 2-ethyl-4-hydroxyheptyl, 2-hydroxy-1,1-dimethylethyl, 3-hydroxy-1,1-dimethylpropyl, and the like.

The term "Lewis acid," as used herein, refers to a chemical species that has a vacant orbital or can accept an electron pair. Representative examples of Lewis acid include, but are not limited to, aluminum chloride, boron trifluoride, iron(II) chloride, iron(III) chloride, magnesium bromide, magnesium chloride, magnesium trifluoromethanesulfonate, manganese(II) chloride, titanium(IV) isopropoxide, zinc bromide, zinc chloride, zirconium(IV) chloride, and the like.

The term "lower alkyl," as used herein, is a subset of alkyl as defined herein and refers to a straight or branched chain hydrocarbon group containing from 1 to 6 carbon atoms. Representative examples of lower alkyl include, but are not limited to, methyl, ethyl, n-propyl, iso-propyl, n-butyl, iso-butyl, tert-butyl, and the like.

The term "mercapto," as used herein, refers to a —SH group.

The term "mercaptoalkyl," as used herein, refers to a mercapto group, as defined herein, appended to the parent molecular moiety through an alkyl group, as defined herein. Representative examples of mercaptoalkyl include, but are not limited to, 2-sulfanylethyl, 3-sulfanylpropyl, and the like.

The term "—NR$^9$R$^{10}$," as used herein, refers to two groups, R$^9$ and R$^{10}$, which are appended to the parent molecular moiety through a nitrogen atom. R$^9$ and R$^{10}$ are independently selected from hydrogen, alkyl, alkylcarbonyl, aryl, arylalkyl, arylcarbonyl, formyl, and S(O)$_2$R$^{11}$, as defined herein, wherein R$^{11}$ is selected from alkyl, aryl, and arylalkyl, as defined herein. Representative examples of —NR$^9$R$^{10}$ include, but are not limited to, acetylamino, amino, methylamino, (ethylcarbonyl)methylamino, ethylmethylamino, formylamino, methylsulfonylamino, phenylsulfonylamino, benzylsulfonylamino, and the like.

The term "(NR$^9$R$^{10}$)alkyl," as used herein, refers to a —NR$^9$R$^{10}$ group, as defined herein, appended to the parent molecular moiety through an alkyl group, as defined herein. Representative examples of (NR$^9$R$^{10}$)alkyl include, but are not limited to, acetylaminomethyl, aminomethyl, 2-aminoethyl, 2-(methylamino)ethyl, (ethylcarbonyl) methylaminomethyl, 3-(ethylmethylamino)propyl, 1,1-dimethyl-3-(dimethylamino)propyl, 2-(formylamino)ethyl, methylsulfonylaminomethyl, 2-(phenylsulfonylamino) ethyl, benzylsulfonylaminomethyl, and the like.

The term "—NR$^A$R$^B$," as used herein, refers to two groups, R$^A$ and R$^B$, which are appended to the parent molecular moiety through a nitrogen atom. R$^A$ and R$^B$ are independently selected from hydrogen, alkyl, alkylcarbonyl and formyl, as defined herein. Representative examples of —NR$^A$R$^B$ include, but are not limited to, acetylamino, amino, methylamino, (ethylcarbonyl)methylamino, dimethylamino, ethylmethylamino, formylamino, and the like.

The term "(NR$^A$R$^B$)alkyl," as used herein, refers to a —NR$^A$R$^B$ group, as defined herein, appended to the parent molecular moiety through an alkyl group, as defined herein. Representative examples of (NR$^A$R$^B$)alkyl include, but are not limited to, acetylaminomethyl, aminomethyl, 2-aminoethyl, 2-(methylamino)ethyl, (ethylcarbonyl) methylaminomethyl, 3-(ethylmethylamino)propyl, 1,1-dimethyl-3-(dimethylamino)propyl, 2-(formylamino)ethyl, and the like.

The term "nitro," as used herein, refers to a —NO$_2$ group.

The term "oxo," as used herein, refers to a (=O) moiety.

The term "oxy," as used herein, refers to a (—O—) moiety.

The term "sulfamyl," as used herein, refers to a —SO$_2$NR$^{94}$R$^{95}$ group, wherein R$^{94}$ and R$^{95}$ are independently selected from hydrogen, alkyl, aryl, and arylalkyl, as defined herein. Representative examples of sulfamyl include, but are not limited to, aminosulfonyl, methylaminosulfonyl, dimethylaminosulfonyl, phenylaminosulfonyl, benzylaminosulfonyl, and the like.

The term "sulfamylalkyl," as used herein, refers to a sulfamyl group, as defined herein, appended to the parent molecular moiety through an alkyl group, as defined herein. Representative examples of sulfamylalkyl include, but are not limited to, (aminosulfonyl)methyl, (dimethylaminosulfonyl)methyl, 2-(aminosulfonyl)ethyl, 3-(aminosulfonyl)propyl, 3-aminosulfonyl-1,1-dimethylpropyl, and the like.

The term "sulfamyl(halo)alkyl," as used herein, refers to a sulfamyl group and at least one halogen, as defined herein, appended to the parent molecular moiety through an alkyl group, as defined herein. Representative examples of sulfamyl(halo)alkyl include, but are not limited to, (aminosulfonyl)dichloromethyl, (aminosulfonyl) difluoromethyl, (dimethylaminosulfonyl)difluoromethyl, 2-(aminosulfonyl)-1,1-dichloroethyl, 3-(aminosulfonyl)-1,1-difluoropropyl, 3-aminosulfonyl-1,1-dichloropropyl, 3-(aminosulfonyl)-1,2-difluoropropyl, and the like.

The term "sulfinyl," as used herein, refers to a —S(O)— group.

The term "sulfonyl," as used herein, refers to a —SO$_2$— group.

The term "tautomer," as used herein, refers to a proton shift from one atom of a molecule to another atom of the same molecule.

The term "thio," as used herein, refers to a (—S—) moiety.

Compounds of the present invention may exist as stereoisomers wherein, asymmetric or chiral centers are present.

These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13–30. The present invention contemplates various stereoisomers and mixtures thereof and are specifically included within the scope of this invention. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Tautomers may exist in the compounds of the present invention and are specifically included within the scope of the present invention. The present invention contemplates tautomers due to proton shifts from one atom to another atom of the same molecule generating two or more compounds that are in equilibrium with each other. An example of tautomers of the present invention includes, but is not limited to,

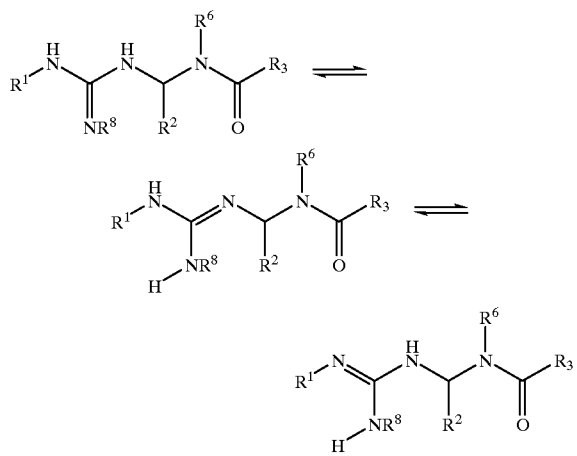

wherein $R^1$, $R^2$, $R^3$, $R^6$ and $R^8$ are as defined in formula I.

Syn and anti geometric isomers and mixtures thereof may also exist in the compounds of the present invention. Syn and anti geometric isomers and mixtures thereof are specifically included within the scope of this invention. An example of syn and anti geometric isomers of the present invention includes, but is not limited to,

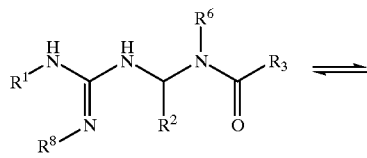

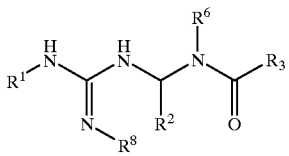

wherein $R^1$, $R^2$, $R^3$, $R^6$ and $R^8$ are as defined in formula I.
Preferred compounds of formula I include,
4-chloro-N-(1-{[(hydroxyimino)(3-pyridinylamino)methyl]amino}-2,2-dimethylpropyl)benzamide;
4-chloro-N-(1-{[(methoxyimino)(3-pyridinylamino)methyl]amino}-2,2-dimethylpropyl)benzamide;
4-chloro-N-(1-{[{[(4-fluorobenzyl)oxy]imino}(3-pyridinylamino)methyl]amino}-2,2-dimethylpropyl)benzamide;
4-chloro-N-(2,2-dimethyl-1-{[[(methylsulfonyl)imino](3-pyridinylamino)methyl]amino}propyl)benzamide;
4-chloro-N-(1-{[(cyanoimino)(6-fluoro-1H-indol-1-yl)methyl]amino}-2,2-dimethylpropyl)benzamide;
4-chloro-N-(1-{[(cyanoimino)(6-fluoro-1H-benzimidazol-1-yl)methyl]amino}-2,2-dimethylpropyl)benzamide;
3-(4-chlorophenyl)-N-(1-{[(cyanoimino)(3-pyridinylamino)methyl]amino}-2,2-dimethylpropyl)propanamide;
N-(1-{[(cyanoimino)(3-pyridinylamino)methyl]amino}-2,2-dimethylpropyl)-3-phenylpropanamide;
N-(1-{[(cyanoimino)(3-pyridinylamino)methyl]amino}-2,2-dimethylpropyl)-2-phenylacetamide;
N-[1-(5-chloro-1-oxo-1,3-dihydro-2H-isoindol-2-yl)-2,2-dimethylpropyl]-N''-cyano-N'-(3-pyridinyl)guanidine;
4-(aminosulfonyl)-N-(1-{[(cyanoimino)(3-pyridinylamino)methyl]amino}-2,2-dimethylpropyl)-2-fluorobenzamide;
4-chloro-N-[1-({(cyanoimino)[(4-ethyl-3-pyridinyl)amino]methyl}amino)-2,2-dimethylpropyl]benzamide;
N-(1-{[(cyanoimino)(3-pyridinylamino)methyl]amino}-2,2-dimethylpropyl)-4-(trifluoromethoxy)benzamide;
4-chloro-N-[1-({(cyanoimino)[(4-ethyl-3-pyridinyl)amino]methyl}amino)-2,2-dimethylpropyl]-2-fluorobenzamide;
4-chloro-N-(1-{[(cyanoimino)(5-pyrimidinylamino)methyl]amino}-2,2-dimethylpropyl)benzamide;
4-chloro-N-(1-{[(cyanoimino)(5-pyrimidinylamino)methyl]amino}-2,2-dimethylpropyl)-2-fluorobenzamide;
N-(1-{[[(4-bromo-3-pyridinyl)amino](cyanoimino)methyl]amino}-2,2-dimethylpropyl)-4-chlorobenzamide;
4-chloro-2-fluoro-N-[2,2,2-trichloro-1-({(cyanoimino)[(4-ethyl-3-pyridinyl)amino]methyl}amino)ethyl]benzamide;
4-chloro-N-(2,2,2-trichloro-1-{[(cyanoimino)(5-pyrimidinylamino)methyl]amino}ethyl)benzamide;
4-chloro-2-fluoro-N-(2,2,2-trichloro-1-{[(cyanoimino)(5-pyrimidinylamino)methyl]amino}ethyl)benzamide;
N-(1-{[[(4-bromo-3-pyridinyl)amino](cyanoimino)methyl]amino}-2,2,2-trichloroethyl)-4-chlorobenzamide;
N-(1-{[[(2-bromo-3-pyridinyl)amino](cyanoimino)methyl]amino}-2,2-dimethylpropyl)-4-chlorobenzamide;
4-chloro-N-[1-({(cyanoimino)[(2-ethyl-3-pyridinyl)amino]methyl}amino)-2,2-dimethylpropyl]benzamide;
N-(1-{[[(5-bromo-4-ethyl-3-pyridinyl)amino](cyanoimino)methyl]amino}-2,2-dimethylpropyl)-4-chlorobenzamide;
4-chloro-N-[1-({(cyanoimino)[(4,5-dibromo-3-pyridinyl)amino]methyl}amino)-2,2-dimethylpropyl]benzamide;
4-chloro-N-(1-{[[(5-chloro-3-pyridinyl)amino](cyanoimino)methyl]amino}-2,2-dimethylpropyl)benzamide;
N-(1-{[[(5-bromo-6-chloro-3-pyridinyl)amino](cyanoimino)methyl]amino}-2,2-dimethylpropyl)-4-chlorobenzamide;

N-(1-{[[(5-bromo-3-pyridinyl)amino](cyanoimino)methyl]amino}-2,2-dimethylpropyl)-4-chlorobenzamide;
N-(1-{[[(6-bromo-3-pyridinyl)amino](cyanoimino)methyl]amino}-2,2-dimethylpropyl)-4-chlorobenzamide;
4-chloro-N-(1-{[(cyanoimino)({5-[(4-fluorophenyl)sulfonyl]-3-pyridinyl}amino)methyl]amino}-2,2-dimethylpropyl)benzamide;
N-(1-{[({5-[(aminoperoxy)sulfanyl]-3-pyridinyl}amino)(cyanoimino)methyl]amino}-2,2-dimethylpropyl)-4-chlorobenzamide;
N-(1-{[[(6-bromo-4-fluoro-3-pyridinyl)amino](cyanoimino)methyl]amino}-2,2-dimethylpropyl)-4-chlorobenzamide;
4-chloro-N-[1-{[(cyanoimino)(3-pyridinylamino)methyl]amino}-2,2,2-trifluoro-1-(trifluoromethyl)ethyl]benzamide;
4-chloro-N-(1-{[(cyanoimino)(3-pyridinylamino)methyl]amino}cyclopentyl)benzamide;
4-chloro-N-(1-{[(cyanoimino)(3-pyridinylamino)methyl]amino}cyclohexyl)benzamide;
4-chloro-N-[{[(cyanoimino)(3-pyridinylamino)methyl]amino}(2,6-dimethylphenyl)methyl]benzamide;
4-chloro-N-[{[(cyanoimino)(3-pyridinylamino)methyl]amino}(3-pyridinyl)methyl]benzamide;
4-chloro-N-[{[(cyanoimino)(3-pyridinylamino)methyl]amino}(2-pyridinyl)methyl]benzamide;
4-chloro-N-(1-{[(cyanoimino)(3-pyridinylamino)methyl]amino}-2-methyl-2-phenylpropyl)benzamide;
4-chloro-N-(1-{[(cyanoimino)(3-pyridinylamino)methyl]amino}-3,3-dimethyl-2-oxobutyl)benzamide;
4-chloro-N-(1-{[(cyanoimino)(3-pyridinylamino)methyl]amino}-3,3,3-trifluoro-2-oxopropyl)benzamide;
4-chloro-N-[1-{[(cyanoimino)(3-pyridinylamino)methyl]amino}-3,3,3-trifluoro-2-methyl-2-(trifluoromethyl)propyl]benzamide;
methyl 4-[(4-chlorobenzoyl)amino]-4-{[(cyanoimino)(3-pyridinylamino)methyl]amino}-3,3-dimethylbutanoate;
4-chloro-N-[1-{[(cyanoimino)(3-pyridinylamino)methyl]amino}-4-(dimethylamino)-2,2-dimethylbutyl]benzamide;
4-chloro-N-(4-cyano-1-{[(cyanoimino)(3-pyridinylamino)methyl]amino}-2,2-dimethylbutyl)benzamide;
4-chloro-N-(1-{[(cyanoimino)(3-pyridinylamino)methyl]amino}-4-methoxy-2,2-dimethylbutyl)benzamide;
4-chloro-N-(1-{[(cyanoimino)(3-pyridinylamino)methyl]amino}-4-hydroxy-2,2-dimethylbutyl)benzamide;
N-(4-(aminosulfonyl)-1-{[(cyanoimino)(3-pyridinylamino)methyl]amino}-2,2-dimethylbutyl)-4-chlorobenzamide;
4-chloro-N-[1-{[(cyanoimino)(3-pyridinylamino)methyl]amino}-2,2-dimethyl-4-(phenylsulfonyl)butyl]benzamide;
4-chloro-N-(1-{[(cyanoimino)(3-pyridinylamino)methyl]amino}-3-hydroxy-2,2-dimethylpropyl)benzamide;
4-chloro-N-{2,2,2-trichloro-1-[2-(cyanoimino)-3-(3-pyridinyl)imidazolidinyl]ethyl}benzamide;
4-chloro-N-{1-[2-(cyanoimino)-3-(3-pyridinyl)imidazolidinyl]-2,2-dimethylpropyl}benzamide;
2-tert-butyl-3-(4-chlorobenzoyl)-N'-cyano-N-(3-pyridinyl)-1-imidazolidinecarboximidamide;
N-(4-(aminosulfonyl)-2,2-dichloro-1-{[(cyanoimino)(3-pyridinylamino)methyl]amino}butyl)-4-chlorobenzamide;
4-chloro-N-[4-cyano-1-{[(cyanoimino)(3-pyridinylamino)methyl]amino}-2,2-bis(trifluoromethyl)butyl]benzamide;
4-chloro-N-(1-{[(cyanoimino)(3-pyridinylamino)methyl]amino}-2,2-difluoro-4-oxopentyl)benzamide;
4-chloro-N-(1-{2-cyano-1-(3-pyridinylamino)ethenyl]amino}-2,2-dimethylpropyl)benzamide;
4-chloro-N-{1-[[(cyanoimino)(3-pyridinylamino)methyl](hydroxy)amino]-2,2-dimethylpropyl}benzamide;
4-chloro-N-(2,2,2-trichloro-1-{[2-nitro-1-(3-pyridinylamino)ethenyl]amino}ethyl)benzamide;
4-chloro-N-(2,2,2-trichloro-1-{[2-cyano-1-(3-pyridinylamino)ethenyl]amino}ethyl)benzamide and pharmaceutically acceptable salts, amides, esters, or prodrugs thereof.

More preferred compounds of formula I include,
4-methyl-N-(2,2,2-trifluoro-1-{[(3-pyridinylamino)carbothioyl]amino}ethyl)benzamide;
4-methyl-N-{2,2,2-trifluoro-1-[(2-toluidinocarbothioyl)amino]ethyl}benzamide;
4-methyl-N-(2,2,2-trifluoro-1-{[(4-fluoroanilino)carbothioyl]amino}ethyl)benzamide;
4-methyl-N-(2,2,2-trifluoro-1-{[(3-nitroanilino)carbothioyl]amino}ethyl)benzamide;
4-methyl-N-[2,2,2-trifluoro-1-({[2-fluoro-3-(trifluoromethyl)anilino]carbothioyl}amino)ethyl]benzamide;
4-methyl-N-(2,2,2-trifluoro-1-{[(4-methoxyanilino)carbothioyl]amino}ethyl)benzamide;
N-[1-({[(6-chloro-3-pyridinyl)amino]carbothioyl}amino)-2,2,2-trifluoroethyl]-4-methylbenzamide;
4-methyl-N-(2,2,2-trifluoro-1-{[(2-methoxyanilino)carbothioyl]amino}ethyl)benzamide;
N-{1-[(anilinocarbothioyl)amino]-2,2,2-trifluoroethyl}-4-methylbenzamide;
4-methyl-N-{2,2,2-trifluoro-1-[(4-toluidinocarbothioyl)amino]ethyl}benzamide;
4-methyl-N-(2,2,2-trifluoro-1-{[(2-fluoroanilino)carbothioyl]amino}ethyl)benzamide;
4-methyl-N-(2,2,2-trifluoro-1-{[(3-methoxyanilino)carbothioyl]amino}ethyl)benzamide;
4-methyl-N-(2,2,2-trifluoro-1-{[(3-fluoroanilino)carbothioyl]amino}ethyl)benzamide;
N-(1-{[(2,5-difluoroanilino)carbothioyl]amino}-2,2,2-trifluoroethyl)-4-methylbenzamide;
N-(1-{[(2,4-difluoroanilino)carbothioyl]amino}-2,2,2-trifluoroethyl)-4-methylbenzamide;
4-methyl-N-{2,2,2-trifluoro-1-[(3-toluidinocarbothioyl)amino]ethyl}benzamide;
N-(1-{[(2,6-difluoroanilino)carbothioyl]amino}-2,2,2-trifluoroethyl)-4-methylbenzamide;
N-(1-{[(2,3-difluoroanilino)carbothioyl]amino}-2,2,2-trifluoroethyl)-4-methylbenzamide;
4-chloro-N-(2,2,2-trifluoro-1-{[(3-pyridinylamino)carbothioyl]amino}ethyl)benzamide;
N-{1-[(anilinocarbothioyl)amino]-2,2,2-trifluoroethyl}-4-chlorobenzamide;
4-chloro-N-(2,2,2-trifluoro-1-{[(2-fluoroanilino)carbothioyl]amino}ethyl)benzamide;
N-(2,2-dimethyl-1-{[(3-pyridinylamino)carbothioyl]amino}propyl)-4-methylbenzamide;
N-((1R)-2,2-dimethyl-1-{[(3-pyridinylamino)carbothioyl]amino}propyl)-4-methylbenzamide;
N-((1S)-2,2-dimethyl-1-{[(3-pyridinylamino)carbothioyl]amino}propyl)-4-methylbenzamide;
N-(2,2-dimethyl-1-{[(3-nitroanilino)carbothioyl]amino}propyl)-4-methylbenzamide;
N-(2,2-dimethyl-1-{[(3-pyridinylamino)carbothioyl]amino}propyl)-2-methylbenzamide;
4-chloro-N-(2,2-dimethyl-1-{[(3-pyridinylamino)carbothioyl]amino}propyl)benzamide;
N-(2,2-dimethyl-1-{[(3-pyridinylamino)carbothioyl]amino}propyl)benzamide;
4-methyl-N-(1-{[(3-nitroanilino)carbothioyl]amino}ethyl)benzamide;

4-methyl-N-(1-{[(3-nitroanilino)carbothioyl]amino}-2-phenylethyl)benzamide;
N-((1R)-2-(tert-butoxy)-1-{[(3-nitroanilino)carbothioyl]amino)ethyl)-4-methylbenzamide;
N-(2-fluoro-1-{[(3-nitroanilino)carbothioyl]amino I ethyl)-4-methylbenzamide;
4-methyl-N-[{[(3-nitroanilino)carbothioyl]amino}(phenyl)methyl]benzamide;
4-methyl-N-(phenyl{[(3-pyridinylamino)carbothioyl]amino}methyl)benzamide;
4-methyl-N-(2-methyl-1-{[(3-pyridinylamino)carbothioyl]amino}propyl)benzamide;
4-methyl-N-((1R,2S)-2-methyl-1-{[(3-pyridinylamino)carbothioyl]amino}butyl)benzamide;
4-methyl-N-{2,2,2-trichloro-1-[3-(3-fluorophenyl)-2-thioxo-1-imidazolidinyl]ethyl}benzamide;
4-methyl-N-(2,2,2-trichloro-1-{[(3-pyridinylamino)carbonyl]amino}ethyl)benzamide;
2-methyl-N-(2,2,2-trichloro-1-{[(3-pyridinylamino)carbonyl]amino}ethyl)benzamide;
N-(2,2,2-trichloro-1-{[(3-pyridinylamino)carbonyl]amino}ethyl)benzamide;
4-chloro-N-(2,2,2-trichloro-1-{[(3-pyridinylamino)carbonyl]amino}ethyl)benzamide;
N-{1-[(anilinocarbonyl)amino]-2,2,2-trichloroethyl}-4-methylbenzamide;
4-methyl-N-(2,2,2-trichloro-1-{[(2-fluoroanilino)carbonyl]amino}ethyl)benzamide;
4-methyl-N-(2,2,2-trichloro-1-{[(cyanoimino)(3-pyridinylamino)methyl]amino}ethyl)benzamide;
4-chloro-N-(2,2,2-trichloro-1-{[(cyanoimino)(3-pyridinylamino)methyl]amino}ethyl)benzamide;
N-(1-{[anilino(cyanoimino)methyl]amino}-2,2,2-trichloroethyl)-4-methylbenzamide;
4-methyl-N-(2,2,2-trichloro-1-{[(cyanoimino)(2-fluoroanilino)methyl]amino}ethyl)benzamide;
4-methyl-N-(2,2,2-trichloro-1-{[(cyanoimino)(5-pyrimidinylamino)methyl]amino}ethyl)benzamide;
N-(2,2,2-trichloro-1-{[(cyanoimino)(3-pyridinylamino)methyl]amino}ethyl)benzamide;
2-methyl-N-(2,2,2-trichloro-1-{[(cyanoimino)(3-pyridinylamino)methyl]amino}ethyl)benzamide;
N-(1-{[(cyanoimino)(3-pyridinylamino)methyl]amino}-2,2-dimethylpropyl)-4-methylbenzamide;
4-chloro-N-(1-{[(cyanoimino)(3-pyridinylamino)methyl]amino}-2,2-dimethylpropyl)benzamide;
N-(1-{[(cyanoimino)(3-fluoroanilino)methyl]amino}-2,2-dimethylpropyl)-4-methylbenzamide;
4-chloro-N-[{[(cyanoimino)(3-pyridinylamino)methyl]amino}(cyclopropyl)methyl]benzamide;
N-(1-{[[(6-chloro-3-pyridinyl)amino](cyanoimino)methyl]amino}-2,2-dimethylpropyl)-4-methylbenzamide;
4-chloro-N-[{[(cyanoimino)(3-fluoroanilino)methyl]amino}(3-thienyl)methyl]benzamide;
(−) N-(1-{[(cyanoimino)(3-pyridinylamino)methyl]amino}-2,2-dimethylpropyl)-4-methylbenzamide;
(+) N-(1-{[(cyanoimino)(3-pyridinylamino)methyl]amino}-2,2-dimethylpropyl)-4-methylbenzamide;
4-chloro-N-(1-{[[(cyanoimino)(3-pyridinylamino)methyl]amino}-2-ethylbutyl)benzamide;
4-chloro-N-(1-{[(cyanoimino)(3-pyridinylamino)methyl]amino}-3-methylbutyl)benzamide;
4-chloro-N-[{[(cyanoimino)(3-pyridinylamino)methyl]amino}(cyclohexyl)methyl]benzamide;
4-chloro-N-(1-{[(cyanoimino)(3-pyridinylamino)methyl]amino}-3,3-dimethylbutyl)benzamide;
4-chloro-N-(1-{[(cyanoimino)(3-pyridinylamino)methyl]amino}-2-methylpropyl)benzamide;
4-chloro-N-(1-{[(cyanoimino)(3-pyridinylamino)methyl]amino}-2,2,2-trifluoroethyl)benzamide;
4-chloro-N-(4-cyano-1-{[(cyanoimino)(3-pyridinylamino)methyl]amino}-2,2-diethylbutyl)benzamide;
4-chloro-N-[1-{[(cyanoimino)(3-pyridinylamino)methyl]amino}-2-(2,6,6-trimethyl-1-cyclohexen-1-yl)ethyl]benzamide;
4-chloro-N-(1-{[(cyanoimino)(3-pyridinylamino)methyl]amino}-2,2-dimethyl-4-pentenyl)benzamide;
4-chloro-N-(2-ethyl-1-{[2-nitro-1-(3-pyridinylamino)ethenyl]amino}butyl)benzamide;
4-chloro-N-(1-{[(cyanoimino)(2-fluoroanilino)methyl]amino}-2,2-dimethylpropyl)benzamide;
4-chloro-N-(1-{[(cyanoimino)(3-fluoroanilino)methyl]amino}-2,2-dimethylpropyl)benzamide;
4-chloro-N-[1-({(cyanoimino)[3-(trifluoromethyl)anilino]methyl}amino)2,2-dimethylpropyl]benzamide;
4-chloro-N-(1-{[(cyanoimino)(3,5-difluoroanilino)methyl]amino}-2,2-dimethylpropyl)benzamide;
4-chloro-N-(1-{[(cyanoimino)(2,5-difluoroanilino)methyl]amino}-2,2-dimethylpropyl)benzamide;
4-chloro-N-(1-{[(cyanoimino)(2,6-difluoroanilino)methyl]amino}-2,2-dimethylpropyl)benzamide;
4-chloro-N-(1-{[(cyanoimino)(3-chloroanilino)methyl]amino}-2,2-dimethylpropyl)benzamide;
4-chloro-N-(1-{[(cyanoimino)(3-methoxyanilino)methyl]amino}-2,2-dimethylpropyl)benzamide;
4-chloro-N-(1-{[[(2-chlorobenzyl)amino](cyanoimino)methyl]amino}-2,2-dimethylpropyl)benzamide;
4-chloro-N-(1-{[[(3-chlorobenzyl)amino](cyanoimino)methyl]amino}-2,2-dimethylpropyl)benzamide;
4-chloro-N-(1-{[[(4-chlorobenzyl)amino](cyanoimino)methyl]amino}-2,2-dimethylpropyl)benzamide;
4-chloro-N-[1-({(cyanoimino)[(3-pyridinylmethyl)amino]methyl}amino)-2,2-dimethylpropyl]benzamide;
4-chloro-N-[1-({(cyanoimino)[(4-pyridinylmethyl)amino]methyl}amino)-2,2-dimethylpropyl]benzamide;
4-chloro-N-[1-({(cyanoimino)[(2-pyridinylmethyl)amino]methyl}amino)-2,2-dimethylpropyl]benzamide;
4-chloro-N-(1-{[(cyanoimino)(3-quinolinylamino)methyl]amino}-2,2-dimethylpropyl)benzamide;
4-chloro-N-(1-{[(cyanoimino)(3-pyridinylamino)methyl]amino}propyl)benzamide;
4-chloro-N-({[(cyanoimino)(3-pyridinylamino)methyl]amino}methyl)benzamide;
(−) 4-chloro-N-(4-cyano-1-{[(cyanoimino)(3-pyridinylamino)methyl]amino}-2,2-diethylbutyl)benzamide;
(+) 4-chloro-N-(4-cyano-1-{[(cyanoimino)(3-pyridinylamino)methyl]amino}-2,2-diethylbutyl)benzamide;
(+) 4-chloro-N-[1-{[(cyanoimino)(3-pyridinylamino)methyl]amino}-2-(2,6,6-trimethyl-1-cyclohexen-1-yl)ethyl]benzamide;
(−) 4-chloro-N-[1-{[(cyanoimino)(3-pyridinylamino)methyl]amino}-2-(2,6,6-trimethyl-1-cyclohexen-1-yl)ethyl]benzamide;
(−) 4-chloro-N-(1-{[(cyanoimino)(3-pyridinylamino)methyl]amino}-2,2-dimethyl-4-pentenyl)benzamide;
(+) 4-chloro-N-(1-{[(cyanoimino)(3-pyridinylamino)methyl]amino}-2,2-dimethyl-4-pentenyl)benzamide;
4-chloro-N-(1-{[(cyanoimino)(3-pyridinylamino)methyl]amino}-3,3-dimethyl-4-pentenyl)benzamide;
4-chloro-N-(1-{[(cyanoimino)(3-pyridinylamino)methyl]amino}-2-cyclohexyl-2-methylpropyl)benzamide;
4-chloro-N-(1-{[(cyanoimino)(3-pyridinylamino)methyl]amino}-2,2-dimethylhexyl)benzamide;

N-(2-(1-adamantyl)-1-{[(cyanoimino)(3-pyridinylamino)methyl]amino}ethyl)-4-chlorobenzamide;

N-(2,2-bis[(allyloxy)methyl]-1-{[(cyanoimino)(3-pyridinylamino)methyl]amino}butyl)-4-chlorobenzamide;

4-chloro-N-[1-{[(cyanoimino)(3-pyridinylamino)methyl]amino}-3-(dimethylamino)-2,2-dimethylpropyl]benzamide;

tert-butyl (2R)-2-((R)-[(4-chlorobenzoyl)amino]{[(cyanoimino)(3-pyridinylamino)methyl]amino}methyl)-1-pyrrolidinecarboxylate;

4-chloro-N-[1-{[(cyanoimino)(3-pyridinylamino)methyl]amino}-3-(methylsulfanyl)propyl]benzamide;

N-(1-adamantyl {[(cyanoimino)(3-pyridinylamino)methyl]amino}methyl)-4-chlorobenzamide;

4-chloro-N-[{[(cyanoimino)(3-pyridinylamino)methyl]amino}(5-ethyl-1,3-dioxan-5-yl)methyl]benzamide;

4-chloro-N-(1-{[(cyanoimino)(3-pyridinylamino)methyl]amino}-2,2-dimethyl-3-phenylpropyl)benzamide;

N-(1-{[(cyanoimino)(3-pyridinylamino)methyl]amino}-2,2-dimethylpropyl)-4-iodobenzamide;

N-(1-{[(cyanoimino)(3-pyridinylamino)methyl]amino}-2,2-dimethylpropyl)-4-(2-furyl)benzamide;

4-bromo-N-(1-{[(cyanoimino)(3-pyridinylamino)methyl]amino}-2,2-dimethylpropyl)benzamide;

4-chloro-N-(1-{[(cyanoimino)(3-pyridinylamino)methyl]amino}-2,2-dimethylpropyl)-2-fluorobenzamide;

N-(1-{[(cyanoimino)(3-pyridinylamino)methyl]amino}-2,2-dimethylpropyl)-4-fluorobenzamide;

N-(1-{[(cyanoimino)(3-pyridinylamino)methyl]amino}-2,2-dimethylpropyl)-3-methylbenzamide;

N-(1-{[(cyanoimino)(3-pyridinylamino)methyl]amino}-2,2-dimethylpropyl)-2-methylbenzamide;

N-(1-{[(cyanoimino)(3-pyridinylamino)methyl]amino}-2,2-dimethylpropyl)-3,5-difluorobenzamide;

4-chloro-N-{1-[[(cyanoimino)(3-pyridinylamino)methyl](methyl)amino]-2,2-dimethylpropyl}benzamide;

(−) 4-chloro-N-(2,2,2-trichloro-1-{[(cyanoimino)(3-pyridinylamino)methyl]amino}ethyl)benzamide;

(+) 4-chloro-N-(2,2,2-trichloro-1-{[(cyanoimino)(3-pyridinylamino)methyl]amino}ethyl)benzamide;

4-iodo-N-(2,2,2-trichloro-1-{[(cyanoimino)(3-pyridinylamino)methyl]amino}ethyl)benzamide;

4-chloro-N-(2,2-dichloro-1-{[(cyanoimino)(3-pyridinylamino)methyl]amino}pentyl)benzamide;

4-chloro-N-(2,2-dichloro-1-{[(cyanoimino)(3-pyridinylamino)methyl]amino}propyl)benzamide;

(−) 4-chloro-N-(2,2-dichloro-1-{[(cyanoimino)(3-pyridinylamino)methyl]amino}propyl)benzamide;

(+) 4-chloro-N-(2,2-dichloro-1-{[(cyanoimino)(3-pyridinylamino)methyl]amino}propyl)benzamide;

3-chloro-N-(2,2-dichloro-1-{[(cyanoimino)(3-pyridinylamino)methyl]amino)propyl)benzamide;

N-(2,2-dichloro-1-{[(cyanoimino)(3-pyridinylamino)methyl]amino propyl}-3,5-difluorobenzamide;

4-chloro-N-(1-{[(cyanoimino)(3-pyridinylamino)methyl]amino}-2,2,3,3,3-pentafluoropropyl)benzamide;

3-chloro-N-(1-{[(cyanoimino)(3-pyridinylamino)methyl]amino}-2,2,3,3,3-pentafluoropropyl)benzamide;

4-chloro-N-(1-{[(nitroimino)(3-pyridinylamino)methyl]amino}-2,2-dimethylpropyl)benzamide;

4-chloro-N-(1-{[(nitroimino)(3-pyridinylamino)methyl]amino}-3,3-dimethylbutyl)benzamide;

(+) 4-chloro-N-(1-{[(nitroimino)(3-pyridinylamino)methyl]amino}-3,3-dimethylbutyl)benzamide;

(−) 4-chloro-N-(1-{[(nitroimino)(3-pyridinylamino)methyl]amino}-3,3-dimethylbutyl)benzamide;

4-chloro-N-(1-{[(nitroimino)(3-pyridinylamino)methyl]amino}-2,2-dimethyl-4-pentenyl)benzamide;

4-chloro-N-(1-{[(nitroimino)(3-pyridinylamino)methyl]amino}-2,2-dimethyl-3-phenylpropyl)benzamide;

4-chloro-N-[1-{[(nitroimino)(3-pyridinylamino)methyl]amino}-2-(2,6,6-trimethyl-1-cyclohexen-1-yl)ethyl]benzamide;

4-chloro-N-(1-{[(nitroimino)(3-pyridinylamino)methyl]amino}-2-cyclohexyl-2-methylpropyl)benzamide;

N-(2,2-bis[(allyloxy)methyl]-1-{[(nitroimino)(3-pyridinylamino)methyl]amino}butyl)-4-chlorobenzamide;

4-chloro-N-(4-cyano-1-{[(nitroimino)(3-pyridinylamino)methyl]amino}-2,2-diethylbutyl)benzamide;

4-chloro-N-(1-{[(nitroimino)(3-pyridinylamino)methyl]amino}-3,3-dimethyl4-pentenyl)benzamide;

N-(2-(1-adamantyl)-1-{[(nitroimino)(3-pyridinylamino)methyl]amino}ethyl}4-chlorobenzamide;

N-(1-[(nitroimino)(3-pyridinylamino)methyl]amino-2,2-dimethylpropyl)-4-phenylbenzamide;

4-chloro-N-(2,2-dichloro-1-{[(nitroimino)(3-pyridinylamino)methyl]amino}pentyl)benzamide;

4-chloro-N-(2,2-dichloro-1-{[(nitroimino)(3-pyridinylamino)methyl]amino}propyl)benzamide;

3-chloro-N-(2,2-dichloro-1-{[(nitroimino)(3-pyridinylamino)methyl]amino}propyl)benzamide;

4-chloro-N-(2,2-dimethyl-1-{[[(phenylsulfonyl)imino](3-pyridinylamino)methyl]amino}propyl)benzamide;

4-chloro-N-(3,3-dimethyl-1-{[[(phenylsulfonyl)imino](3-pyridinylamino)methyl]amino}butyl)benzamide;

4-chloro-N-{2,2-dimethyl-1-[((3-pyridinylamino){[(trifluoromethyl)sulfonyl]imino}methyl)amino]propyl}benzamide;

4-chloro-N-{3,3-dimethyl-1-[((3-pyridinylamino){[(trifluoromethyl)sulfonyl]imino}methyl)amino]butyl}benzamide;

N-(1-{[[(aminosulfonyl)imino](3-pyridinylamino)methyl]amino}-2,2-dimethylpropyl)-4-chlorobenzamide;

N-(1-{[[(aminosulfonyl)imino](3-pyridinylamino)methyl]amino}-3,3-dimethylbutyl)-4-chlorobenzamide;

4-chloro-N-(1-{[{[(dimethylamino)sulfonyl]imino}(3-pyridinylamino)methyl]amino}-2,2-dimethylpropyl)benzamide;

4-chloro-N-(1-{[{[(dimethylamino)sulfonyl]imino}(3-pyridinylamino)methyl]amino}-3,3-dimethylbutyl)benzamide;

4-chloro-N-(1-{[(2-fluoroanilino)carbonyl]amino}-2,2-dimethylpropyl)benzamide;

4-iodo-N-(2,2,2-trichloro-1-{[(3-pyridinylamino)carbothioyl]amino}ethyl)benzamide;

3-phenyl-N-(2,2,2-trichloro-1-{[(3-nitroanilino)carbothioyl]amino}ethyl)propanamide;

4-chloro-N-(2,2-dimethyl-1-{[2-nitro-1-(3-pyridinylamino)ethenyl]amino}propyl)benzamide;

4-chloro-N-(2,2-dichloro-1-{[2-nitro-1-(3-pyridinylamino)ethenyl]amino}pentyl)benzamide;

4-chloro-N-(1-{[2,2-dicyano-1-(3-pyridinylamino)vinyl]amino}-2,2-dimethylpropyl)benzamide;

3-chloro-N-(2,2-dichloro-1-{[[(6-chloro-3-pyridinyl)amino](cyanoimino)methyl]amino}propyl)benzamide;

N-(2,2-dichloro-1-{[[(6-chloro-3-pyridinyl)amino](cyanoimino)methyl]amino}propyl)-4-methylbenzamide;

N-{2,2-dichloro-1-[((cyanoimino)){[6-(trifluoromethyl)-3-pyridinyl]amino}methyl)amino]propyl}-3,5-difluorobenzamide;

N-(2,2-dichloro-1-{[[(6-chloro-3-pyridinyl)amino](cyanoimino)methyl]amino}propyl)-3-fluorobenzamide;

N-[2,2-dichloro-1-({(cyanoimino)[(2-methoxy-3-pyridinyl)amino]methyl}amino)propyl]-3,5-difluorobenzamide;
4-chloro-N-{2,2-dichloro-1-[((cyanoimino){[6-(trifluoromethyl)-3-pyridinyl]amino}methyl)amino]propyl}benzamide;
3-chloro-N-{2,2-dichloro-1-[((cyanoimino){[6-(trifluoromethyl)-3-pyridinyl]amino}methyl)amino]propyl}benzamide;
4-chloro-N-(2,2-dichloro-1-{[[(6-chloro-3-pyridinyl)amino](cyanoimino)methyl]amino}propyl)benzamide;
(−) 4-chloro-N-(2,2-dichloro-1-{[[(6-chloro-3-pyridinyl)amino](cyanoimino)methyl]amino}propyl)benzamide;
(+) 4-chloro-N-(2,2-dichloro-1-{[[(6-chloro-3-pyridinyl)amino](cyanoimino)methyl]amino}propyl)benzamide;
4-bromo-N-(2,2-dichloro-1-{[[(6-chloro-3-pyridinyl)amino](cyanoimino)methyl]amino}propyl)benzamide;
3,5-dichloro-N-[2,2-dichloro-1-({(cyanoimino)[(2-methoxy-3-pyridinyl)amino]methyl}amino)propyl]benzamide;
3,5-dichloro-N-(2,2-dichloro-1-{[[(6-chloro-3-pyridinyl)amino](cyanoimino)methyl]amino}propyl)benzamide;
N-(2,2-dichloro-1-{[[(6-chloro-3-pyridinyl)amino](cyanoimino)methyl]amino}propyl)-3,5-difluorobenzamide;
4-bromo-N-(2,2-dichloro-1-{[[(6-chloro-3-pyridinyl)amino](cyanoimino)methyl]amino}propyl)benzamide;
4-chloro-N-(2,2-dichloro-1-{[[(2-chloro-3-pyridinyl)amino](cyanoimino)methyl]amino}propyl)benzamide;
3-chloro-N-(2,2-dichloro-1-{[(cyanoimino)(3-fluoroanilino)methyl]amino}propyl)benzamide;
N-(2,2-dichloro-1-{[[(6-chloro-3-pyridinyl)amino](cyanoimino)methyl]amino}propyl)-3-methylbenzamide;
N-(2,2-dichloro-1-{[[(6-chloro-3-pyridinyl)amino](cyanoimino)methyl]amino}propyl)-4-(trifluoromethyl)benzamide;
3-chloro-N-(2,2-dichloro-1-{[(cyanoimino)(2-fluoroanilino)methyl]amino}propyl)benzamide;
N-(2,2-dichloro-1-{[[(6-chloro-3-pyridinyl)amino](cyanoimino)methyl]amino}propyl)-4-fluorobenzamide;
3-chloro-N-[2,2-dichloro-1-({(cyanoimino)[(2-methoxy-3-pyridinyl)amino]methyl}amino)propyl]benzamide;
4-chloro-N-(2,2-dichloro-1-{[(cyanoimino)(2-fluoroanilino)methyl]amino}propyl)benzamide;
4-chloro-N-[2,2-dichloro-1-({(cyanoimino)[(2-methoxy-3-pyridinyl)amino]methyl}amino)propyl]benzamide;
3-chloro-N-[2,2-dichloro-1-({(cyanoimino)[(6-fluoro-3-pyridinyl)amino]methyl}amino)propyl]benzamide;
N-(2,2-dichloro-1-{[[(6-chloro-3-pyridinyl)amino](cyanoimino)methyl]amino}propyl)-3,5-dimethoxybenzamide;
N-(2,2-dichloro-1-{[(cyanoimino)(3-pyridinylamino)methyl]amino}propyl3-methylbenzamide;
4-chloro-N-[2,2-dichloro-1-({(cyanoimino)[(6-fluoro-3-pyridinyl)amino]methyl}amino)propyl]benzamide;
4-chloro-N-(2,2-dichloro-1-{[(cyanoimino)(2-methoxyanilino)methyl]amino}propyl)benzamide;
3-chloro-N-[2,2-dichloro-1-({(cyanoimino)[(6-methoxy-3-pyridinyl)amino]methyl}amino)propyl]benzamide;
N-{2,2-dichloro-1-[((cyanoimino){[6-(trifluoromethyl)-3-pyridinyl]amino}methyl)amino]propyl}-3,5-dimethoxybenzamide;
4-chloro-N-{2,2-dichloro-1-[((cyanoimino){[2-methyl-6-(trifluoromethyl)-3-pyridinyl]amino}methyl)amino]propyl}benzamide;
N-(1-{[(cyanoimino)(3-pyridinylamino)methyl]amino}-2,2-dimethylpropyl)-4-fluoro-3-(trifluoromethyl)benzamide;
(+) 4-chloro-N-{3,3-dimethyl-1-[((3-pyridinylamino){[(trifluoromethyl)sulfonyl]imino}methyl)amino]butyl}benzamide;
(−) 4-chloro-N-{3,3-dimethyl-1-[((3-pyridinylamino){[(trifluoromethyl)sulfonyl]imino}methyl)amino]butyl}benzamide;
4-bromo-N-{3,3-dimethyl-1-[((3-pyridinylamino){[(trifluoromethyl)sulfonyl]imino}methyl)amino]butyl}benzamide;
N-{3,3-dimethyl-1-[((3-pyridinylamino){[(trifluoromethyl)sulfonyl]imino}methyl)amino]butyl}-4-(trifluoromethyl)benzamide;
3,5-dichloro-N-{2,2-dichloro-1-[((3-pyridinylamino){[(trifluoromethyl)sulfonyl]imino}methyl)amino]propyl}benzamide;
N-{2,2-dichloro-1-[((3-pyridinylamino){[(trifluoromethyl)sulfonyl]imino}methyl)amino]propyl}4-(trifluoromethyl)benzamide;
N-(2,2-dichloro-1-{[[(6-chloro-3-pyridinyl)amino](cyanoimino)methyl]amino}propyl)-2-thiophenecarboxamide; and
N-(2,2-dichloro-1-{[[(6-chloro-3-pyridinyl)amino](cyanoimino)methyl]amino}propyl)nicotinamide and pharmaceutically acceptable salts, esters, amides, or prodrugs thereof.

Abbreviations

The following abbreviations are used: Ac for acetyl; (Boc)$_2$O for di-tert-butyl dicarbonate; DCC for dicyclohexylcarbodiimide; DMF for N,N-dimethylformamide; DMSO for dimethyl sulfoxide; EDCI for 1-ethyl-3-[3-(dimethylamino)propyl]carbodiimide hydrochloride; Et for ethyl; Et$_3$N for triethylamine; EtOH for ethanol; Me for methyl; MeOH for methanol; NaHMDS for sodium bis(trimethylsilyl)amide; i-Pr for isopropyl; pyr for pyridine; Tf for triflate or —OS(O)$_2$CF$_3$; THF for tetrahydrofuran; and p-TsOH for para-toluenesulfonic acid monohydrate.

Preparation of Compounds of the Invention

The compounds and processes of the present invention will be better understood in connection with the following synthetic schemes and methods which illustrate a means by which the compounds of the invention can be prepared.

The compounds of this invention may be prepared by a variety of synthetic routes. Representative procedures are shown in Schemes 1–25.

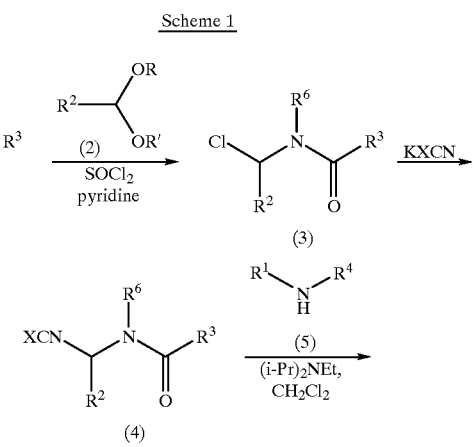

Scheme 1

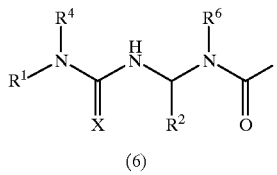

As shown in Scheme 1, urea and thiourea aminals of general formula (6), wherein $R^1$, $R^3$, $R^4$, and $R^6$ are as defined in formula I, $R^2$ is haloalkyl (such as $CCl_3$ or $CF_3$), and X is O or S, may be prepared using the strategy outlined above. Amides of general formula (1) may be treated with α-haloaldehyde hydrates or α-halohemiacetals of general formula (2), wherein R is H and R' is H or alkyl, such as 2,2,2-trichloro-1,1-ethanediol or 1-ethoxy-2,2,2-trifluoro-1-ethanol, followed by addition of a chlorinating agent such as thionyl chloride and a base such as pyridine to provide chloroamides of general formula (3). The chloroamides (3) may be treated with potassium cyanate or potassium thiocyanate to provide isocyanates or isothiocyanates respectively of general formula (4). The isocyanates or isothiocyanates (4) may be treated with amines of general formula (5) in the presence of a base such as diisopropylethylamine to provide urea and thiourea aminals of general formula (6).

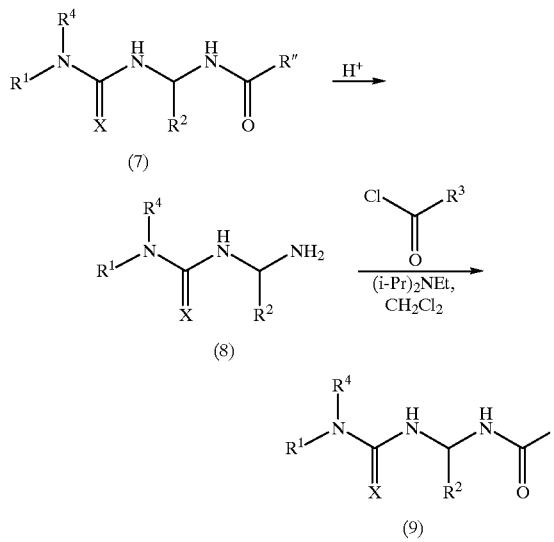

As shown in Scheme 2, urea and thiourea aminal derivatives of general formula (9), wherein $R^1$, $R^3$, and $R^4$, are as defined in formula I, $R^2$ is haloalkyl (such as $CCl_3$ or $CF_3$), and X is O or S, may be prepared using the above strategy. Urea and thiourea aminals of general formula (7), wherein R" is alkoxy, may be prepared following the strategy described in Scheme 1. Urea and thiourea aminals of general formula (7) may be treated with an acid such as hydrobromic acid to provide primary amines of general formula (8). Amines of general formula (8) may be treated with acid chlorides in the presence of a base such as diisopropylethylamine to provide urea and thiourea aminals of general formula (9).

Scheme 3

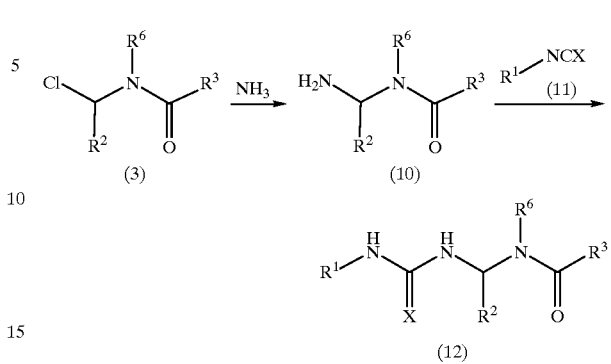

Urea and thiourea aminals of general formula (12), wherein $R^1$, $R^3$, and $R^6$ are as defined in formula I, $R^2$ is haloalkyl (such as $CCl_3$ or $CF_3$), and X is O or S, may be prepared as described in Scheme 3. Chloroamides of general formula (3) may be treated with ammonia to provide aminoamides of general formula (10). The aminoamides (10) may be treated with an isocyanate or an isothiocyanate of general formula (11), wherein X is O or S, to provide urea and thiourea aminals of general formula (12).

Scheme 4

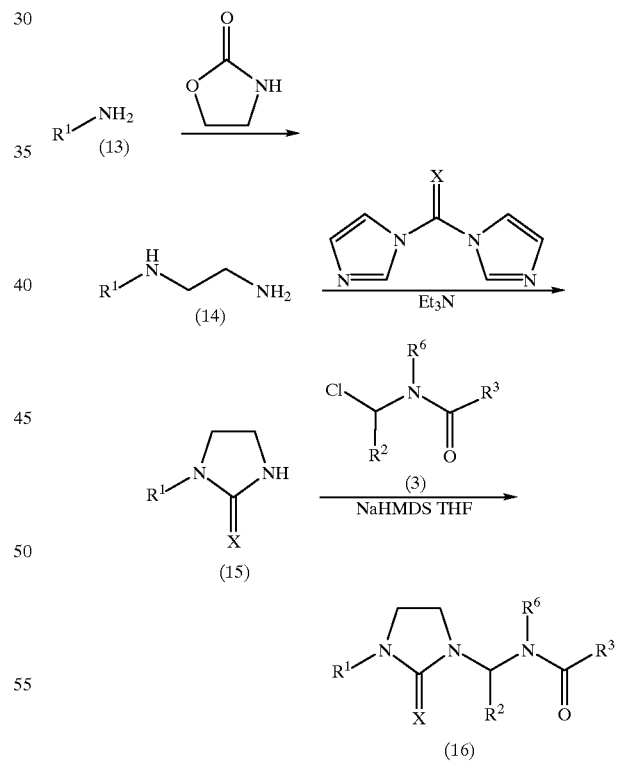

Urea and thiourea aminals of general formula (16) wherein $R^1$ and $R^3$ are as defined in formula I, $R^2$ is haloalkyl (such as $CCl_3$ or $CF_3$), and X is O or S, may be prepared as described in scheme 4. Amines of general formula (13) may be treated with 1,3-oxazolidin-2-one as described in (Poindexter et al., J. Org. Chem. (1992), 57, 6257) to provide primary amines of general formula (14) which may be cyclized to ureas or thioureas of general formula (15) with carbonyl or thiocarbonyl transfer reagents (such as carbonyldiimidazole or thiocarbonyldiimidazole) in the presence of a base such as triethylamine. Cyclic ureas or thioureas of general formula (15) may be treated with a strong base such as sodium bis(trimethylsilyl)amide (NaHMDS) followed by treatment with chloroamides of general formula (3) to provide urea and thiourea aminals of general formula (16).

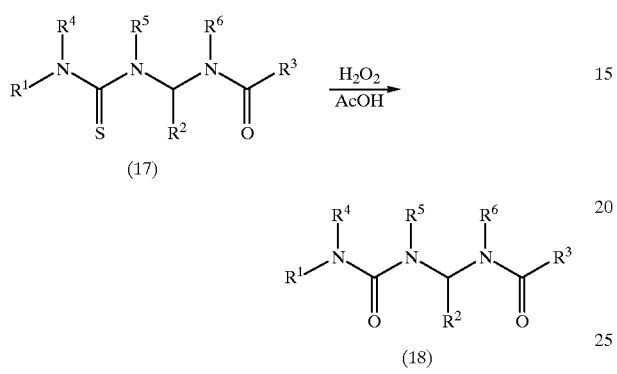

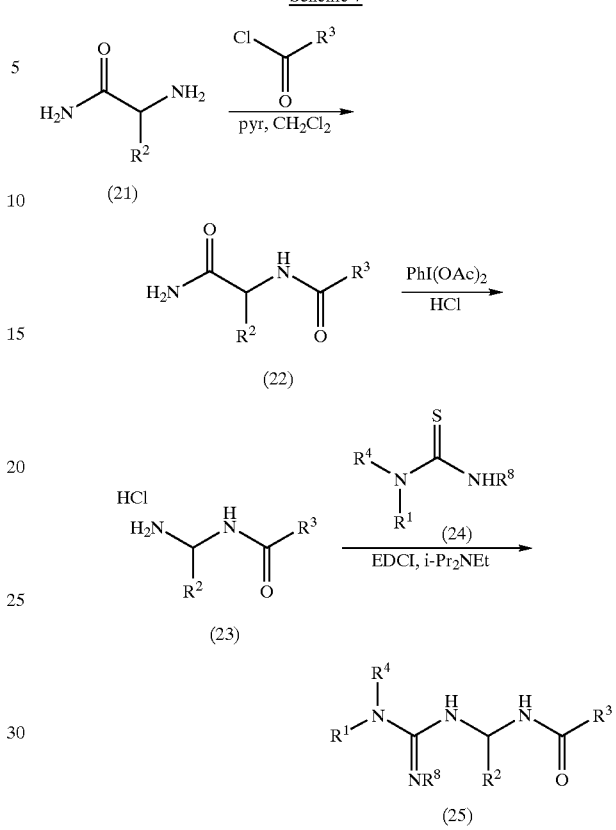

A general method for preparing urea aminals from thiourea aminals is described in Scheme 5. Thiourea aminals of general formula (17) may be treated with an oxidizing agent such as hydrogen peroxide in a protic solvent such as acetic acid to provide urea aminals of general formula (18) wherein $R^1$, $R^2$, $R^3$, $R^4$, $R^5$, and $R^6$ are as defined in formula I.

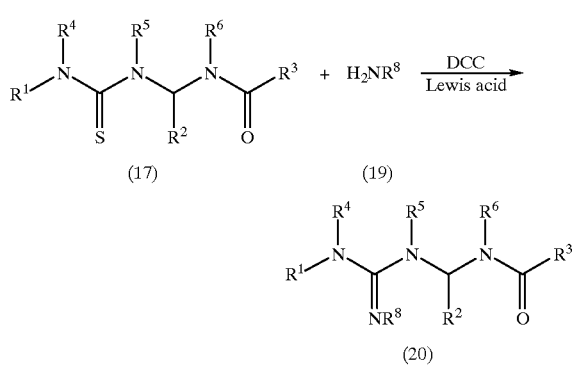

A general method for preparing guanidine aminals from thiourea aminals is described in Scheme 6. Thiourea aminals of general formula (17) may be treated with a dehydrating agent such as DCC followed by addition of amines of general formula (19), prepared as described in (Scharpenberg, Chem. Ber. (1973), 106, 1881), in the presence of a Lewis acid such as titanium isopropoxide to provide guanidine aminals of general formula (20) wherein $R^1$, $R^2$, $R^3$, $R^4$, $R^5$, $R^6$ and $R^8$ are as defined in formula I.

As shown in Scheme 7, guanidine aminals of general formula (25), wherein $R^1$, $R^2$, $R^3$, $R^4$, and $R^8$ are as defined in formula I, may be prepared by using the above strategy. Aminoacetamides of general formula (21) may be treated with acid chlorides in the presence of a base such as pyridine or triethylamine to provide the corresponding acylaminoamides of general formula (22). The acylaminoamides (22) may undergo a Hofmann rearrangement as described in (Wallis and Lane, Org. React. (1946), 3, 267–306, and references contained therein) with reagents such as iodosobenzene diacetate as described in (Loudon et al., J. Org. Chem. (1984), 49, 4272); (Loudon and Boutin J. Org. Chem. (1984), 49, 4277); (Chan et al., Synth. Commun. (1988), 53, 5158) to provide aminoamides of general formula (23), which may be typically isolated as their hydrochloride salts. The aminoamides (23) may be treated with thioureas of general formula (24), prepared as described in (Solimar, J.Med.Chem. (1979), 22, 321; and Ulrich, Tetrahedron (1966), 22, 1565) to provide guanidine aminals of general formula (25). An alternate approach for preparation of cyanoguanidine aminals of general formula (25), wherein $R^8$ is cyano, may be used. Aminoamides of general formula (23) may be treated with cyanothioureas of general formula (24), wherein $R^8$ is cyano, in the presence of a base such as diisopropylethylamine and a suitable activating agent such as EDCI to provide cyanoguanidine aminals of general formula (25).

Scheme 8

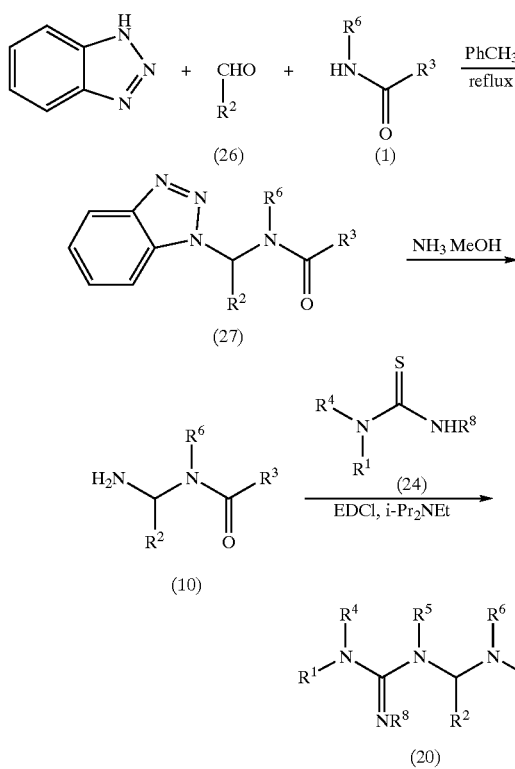

An alternate route to guanidine aminals of general formula (20), wherein $R^1$, $R^2$, $R^3$, $R^4$, $R^6$ and $R^8$ are as defined in formula I and $R^5$ is H, is shown in Scheme 8. A three-component condensation including benzotriazole, aldehydes of general formula (26), and amides of general formula (1) in the presence of an acid catalyst such as p-toluenesulfonic acid monohydrate as described in (Katritzky et al., J. Org. Chem. (1990), 55, 2206); (Katritzky; Chem. Rev. (1998), 98, 409); (Katritzky; J. Heterocyclic Chem. (1996), 33, 1935) provides benzotriazole adducts of general formula (27). Nucleophilic displacement of the benzotriazole moiety as described in (Katritzky et al., J. Org. Chem. (1990), 55, 2206); (Katritzky, Chem. Rev. (1998), 98, 409); (Katritzky, J. Heterocyclic Chem. (1996), 33, 1935) with ammonia in an alcoholic solvent such as methanol provides aminoamides of general formula (10). The aminoamides (10) may be treated with thioureas of general formula (24) in the presence of a base such as diisopropylethylamine and a suitable activating agent such as EDCl to provide guanidine aminals of general formula (20).

Scheme 9

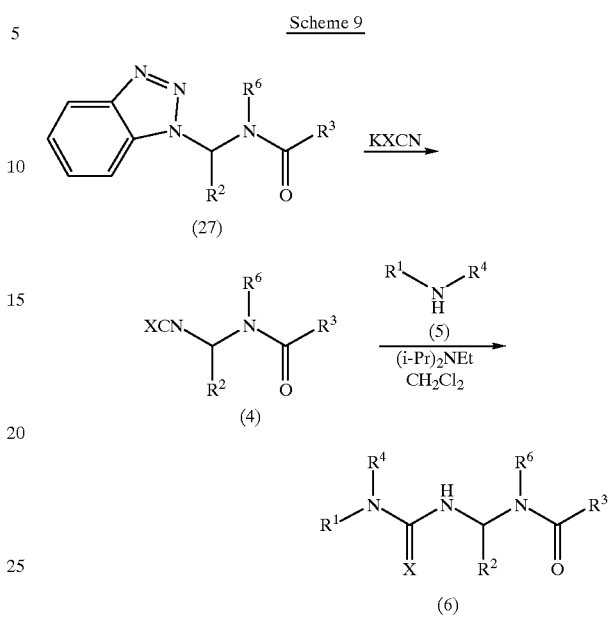

As shown in Scheme 9, urea and thiourea aminals of general formula (6), wherein $R^1$, $R^2$, $R^3$, $R^4$ and $R^6$ are as defined in formula I and X is O or S, may be prepared by treating benzotriazole adducts of general formula (27) with potassium cyanate or potassium thiocyanate to provide isocyanates or isothiocyantes of general formula (4). Isocyanates or isothiocyanates of general formula (4) may be treated with amines of general formula (5) in the presence of a base such as diisopropylethylamine to provide urea and thiourea aminals of general formula (6).

Scheme 10

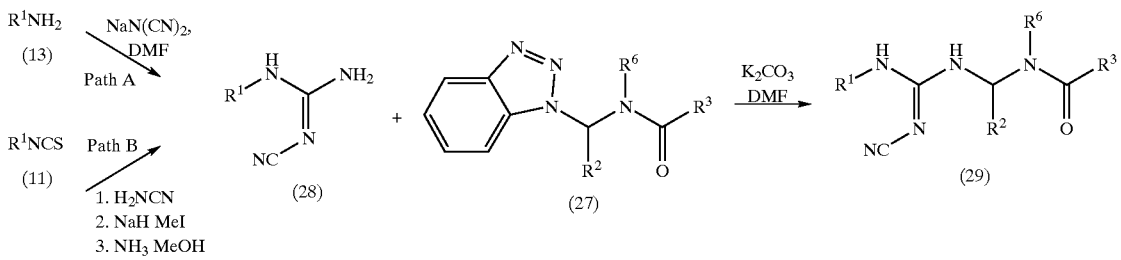

As shown in Scheme 10, cyanoguanidine aminals of general formula (29), wherein $R^1$, $R^2$, $R^3$ and $R^6$ are as defined in formula I, may be prepared by using a strategy that employs a two-step sequence. Cyanoguanidines of general formula (28) are first prepared either by Path A or Path B. In path A, amines of general formula (13) are treated with sodium dicyanamide as described in (Tilley et al., Helv. Chim. Acta. (1980), 63, 841); (Jones et al., J. Heterocyclic Chem. (1994), 31, 1681) to provide cyanoguanidines of general formula (28). In Path B, isothiocyanates of general formula (11) are treated in succession with cyanamide, a sodium base such as sodium hydride, an electrophile such as methyl iodide, and ammonia in a polar aprotic solvent such as methanol as described in (Fairfall and Peak; J. Chem. Soc. (1955), 796) to provide cyanoguanidines of general formula (28). The cyanoguanidines (28) are then treated with benzotriazole adducts of general formula (27) in the presence of a base such as potassium carbonate to provide cyanoguanidine aminals of general formula (29).

Scheme 11

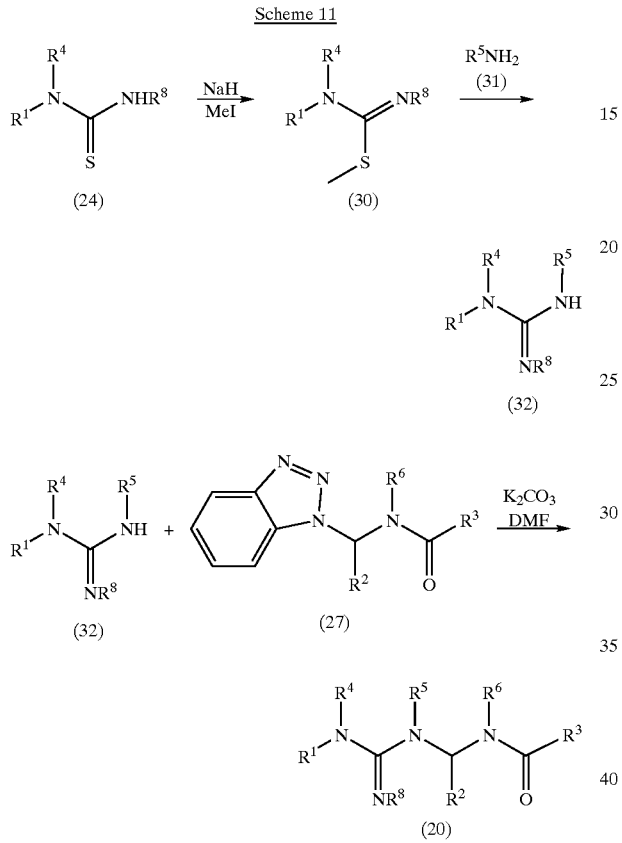

Functionality may be introduced onto the guanidine nitrogen ($R^5$) by the synthetic sequence described in Scheme 11. Thioureas of general formula (24) may be treated with a sodium base such as sodium hydride and then alkylated with electrophiles such as methyl iodide to provide methyl carbamimidothioates of general formula (30). Methyl carbamimidothioates (30) may be treated with amines of general formula (31) to provide guanidines of general formula (32) which are then further reacted with benzotriazole adducts of general formula (27) in the presence of a base such as potassium carbonate to provide guanidine aminals of general formula (20) wherein $R^1$, $R^2$, $R^3$, $R^4$, $R^5$, $R^6$, and $R^8$ are as defined in formula I.

Scheme 12

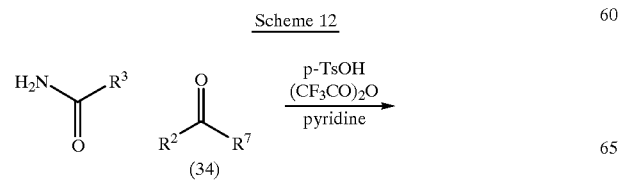

-continued

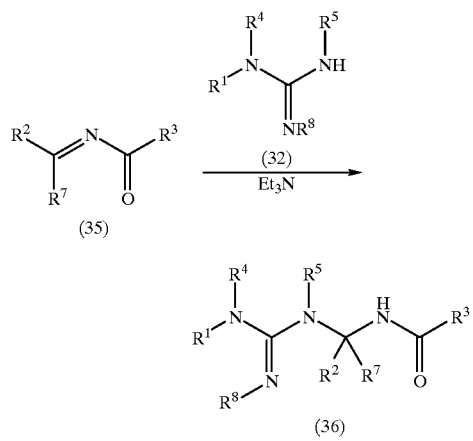

As shown in Scheme 12, geminally-substituted products of general formula (36) wherein $R^1$, $R^3$, $R^4$, $R^5$, $R^7$, and $R^8$ are as defined in formula I and $R^2$ is the same as $R^7$ or $R^2$ and $R^7$ taken together with the carbon atom to which they are attached, together form a 5 or 6 membered carbocyclic ring, may be prepared using the above strategy and as described in (Steglich, Chem. Ber. (1974), 107, 1488); (Burger, J. Fluorine Chem. (1982), 20, 813). Optionally substituted primary amides may be treated with symmetrical ketones of general formula (34) in the presence of a dehydrating agent such as trifluoroacetic anhydride and a base such as pyridine to provide symmetrical imines of general formula (35). The symmetrical imines (35) may be treated with guanidines of general formula (32) in the presence of a base such as triethylamine to provide geminally-substituted compounds of general formula (36).

Scheme 13

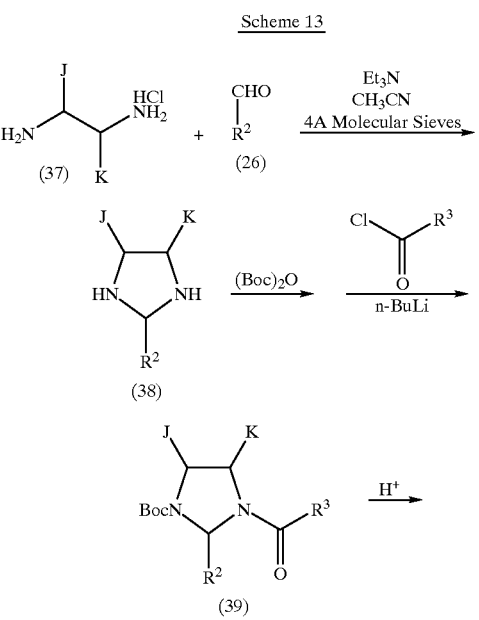

Scheme 15

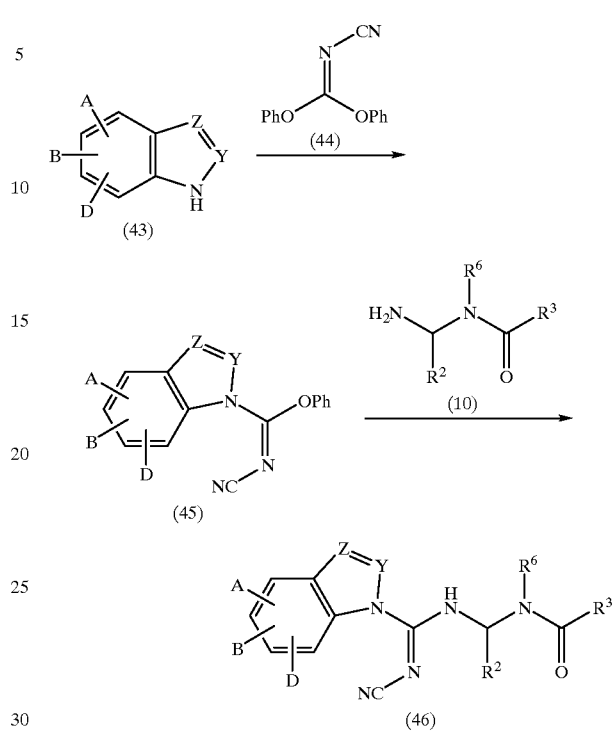

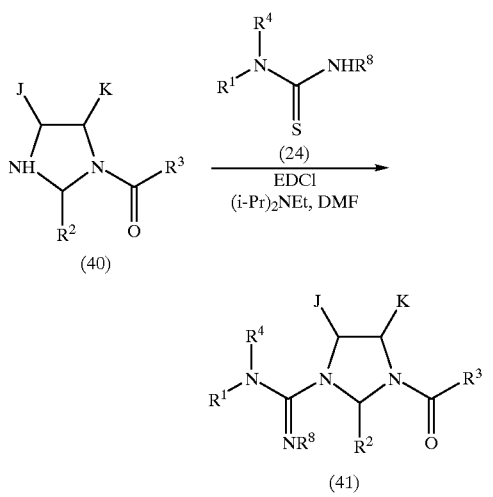

Guanidine aminals of general formula (41), wherein $R^1$, $R^2$, $R^3$, $R^4$, and $R^8$ are as defined in formula I and J and K are as defined in formula IV, may be prepared using the strategy described in Scheme 13. Diamino compounds of general formula (37), such as 1,2-ethanediamine, may be condensed with aldehydes of general formula (26) in the presence of molecular sieves to provide 2-substituted imidazolidines of general formula (38). Monoprotection, such as with di-tert-butyl dicarbonate, followed by acylation may provide 2-substituted imidazolidines of general formula (39). Removal of the protecting group provides secondary amines of general formula (40). The secondary amines (40) may be treated with thioureas (24) in the presence of a dehydrating agent such as EDCI to provide guanidine aminals of general formula (41).

As shown in Scheme 15, cyanoguanidines of general formula (46) wherein $R^2$, $R^3$, and $R^6$ are as defined in formula I, Y and Z are independently selected from CH and N, and A, B, and D are independently selected from hydrogen, alkenyl, alkoxy, alkoxycarbonyl, alkyl, alkylcarbonyl, alkylsulfinyl, alkylsulfonyl, alkynyl, arylalkoxycarbonyl, cyano, halogen, haloalkyl, haloalkoxy, nitro, sulfamyl, and $-NR^AR^B$ wherein $R^A$ and $R^B$ are as defined in formula I, may be prepared by treating heterocycles of general formula (43) with diphenyl cyanocarbonimidate (44) as described in (Atwal et al., J. Med. Chem. (1998), 41, 271) to provide cyanocarboximidates of general formula (45). The cyanocarboximidates (45) may be treated with amines of general formula (10) to provide cyanoguanidines of general formula (46).

Scheme 14

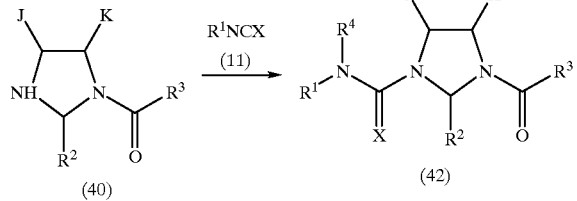

As shown in Scheme 14, ureas and thioureas of general formula (42) wherein $R^1$, $R^2$, $R^3$, and $R^4$ are as defined in formula I, X is O or S. and J and K are as defined in formula IV, may be prepared by treating amines of general formula (40) with an isocyanate or isothiocyanate of general formula (11).

Scheme 16

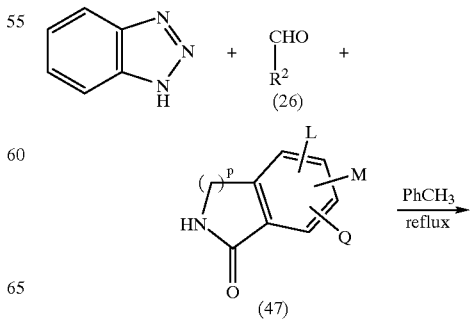

-continued

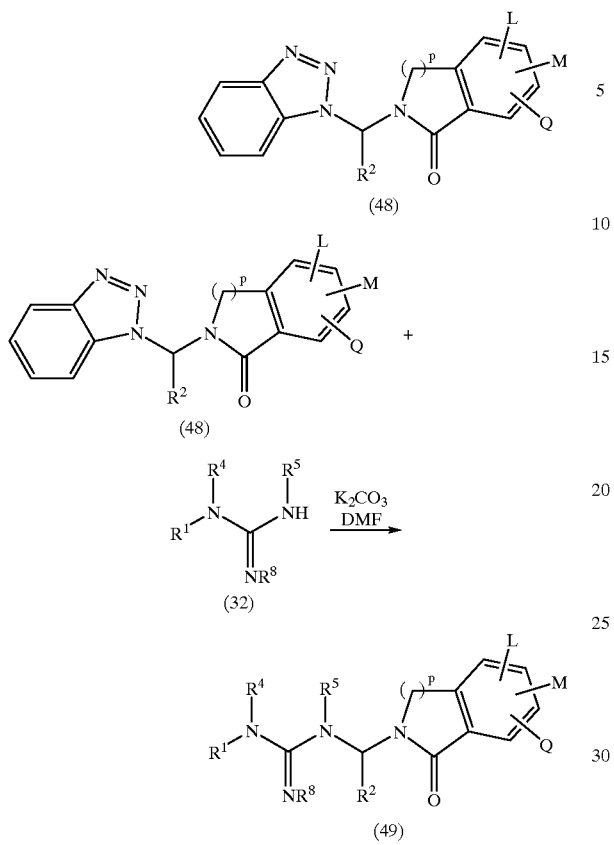

As shown in Scheme 16, guanidine aminals of general formula (49) wherein $R^1$, $R^2$, $R^4$, $R^5$, and $R^8$ are as defined in formula I, L, M, and Q are independently selected from hydrogen, alkenyl, alkoxy, alkoxycarbonyl, alkyl, alkylcarbonyl, alkylsulfinyl, alkylsulfonyl, alkynyl, arylalkoxycarbonyl, cyano, halogen, haloalkyl, haloalkoxy, nitro, sulfamyl, and —$NR^A R^B$ wherein $R^A$ and $R^B$ are as defined in formula I, and p is an integer of 1–2, may be prepared by treating heterocycles of general formula (47) with benzotriazole and aldehydes of general formula (26) in the presence of an acid catalyst such as p-toluenesulfonic acid monohydrate to provide benzotriazole adducts of general formula (48). Nucleophilic displacement of the benzotriazole moiety with guanidines of general formula (32) in a polar aprotic solvent such as N,N-dimethylformamide provides guanidine aminals of general formula (49).

Scheme 17

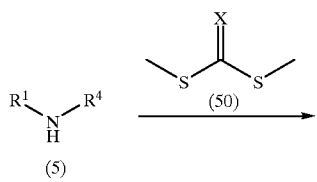

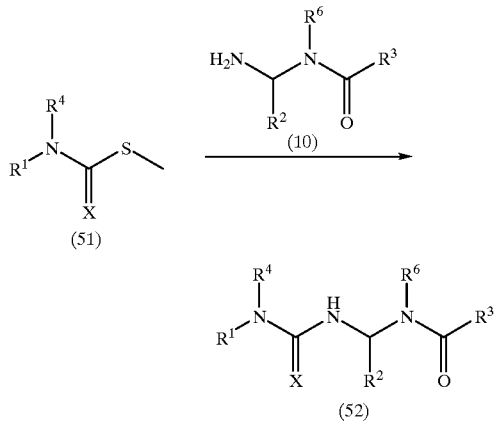

Aminals of general formula (52), wherein $R^1$, $R^2$, $R^3$, $R^4$, and $R^6$ are as defined in formula I and X is selected from NCN, $CHNO_2$, CHCN and $C(CN)_2$, may be prepared as illustrated in Scheme 17. Bis(methylthio) compounds of general formula (50) are commercially available when X is NCN, $CHNO_2$, or $C(CN)_2$ or may be prepared as described in (Hendriksen, Acta Chem. Scand. (1990), 50, 432 and Creemer et al., Synth. Comm. (1988), 18, 1103) when X is CHCN. Compounds of general formula (50) may be treated with amines of general formula (5) to provide methylthio compounds of general formula (51). Methylthio compounds of general formula (51) may be treated with amines of general formula (10) to provide aminals of general formula (52) wherein X is NCN, $CHNO_2$, CHCN, or $C(CN)_2$.

Scheme 18

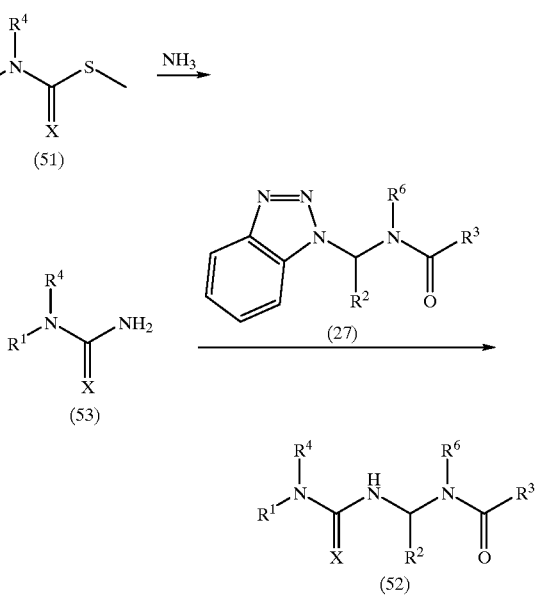

An alternate method of preparing aminals of general formula (52) wherein $R^1$, $R^2$, $R^3$, $R^4$, and $R^6$ are as defined in formula I and X is selected from NCN, $CHNO_2$, CHCN and $C(CN)_2$ is shown in Scheme 18. Methylthio compounds of general formula (51) may be treated with ammonia in an alcoholic solvent such as methanol to provide compounds of general formula (53). Compounds of general formula (53)

may be treated with benzotriazoles of general formula (27) to provide aminals of general formula (52) wherein X is NCN, CHNO$_2$, CHCN or C(CN)$_2$.

Scheme 19

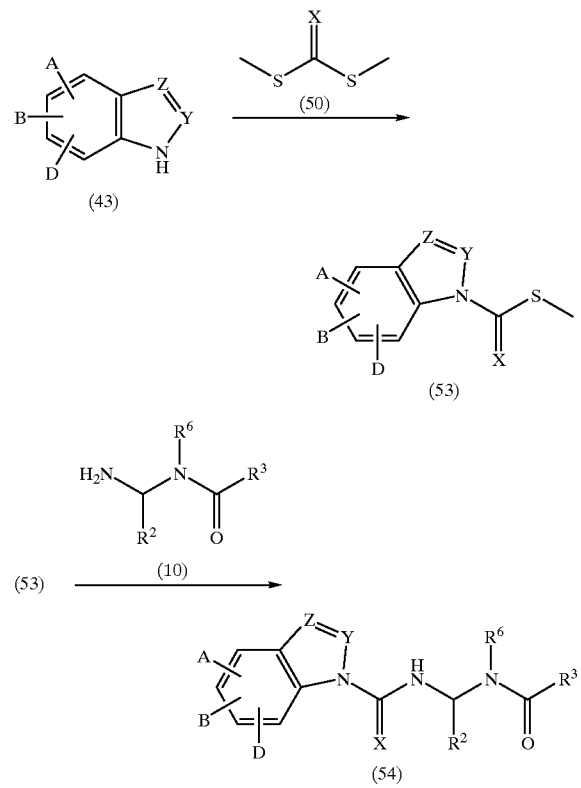

Aminals of general formula (54), wherein R$^2$, R$^3$, and R$^6$ are as defined in formula I and X is selected from NCN, CHNO$_2$, CHCN and C(CN)$_2$, may be prepared as illustrated in Scheme 19. Bis(methylthio) compounds of general formula (50) may be treated with heterocycles of general formula (43) to provide methylthio compounds of general formula (53). Methylthio compounds of general formula (53) may be treated with amines of general formula (10) to provide aminals of general formula (54) wherein X is NCN, CHNO$_2$, CHCN or C(CN)$_2$.

Scheme 20

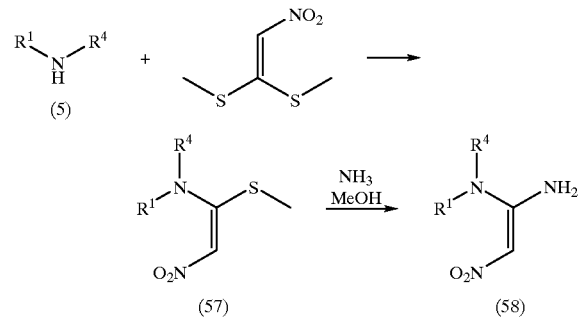

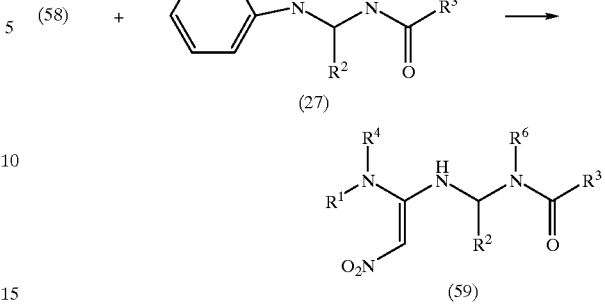

Aminals of general formula (59), wherein R$^1$, R$^2$, R$^3$, R$^4$ and R$^6$ are as defined in formula I, may be prepared as described in Scheme 20. Amines of general formula (5) may be treated with 1,1-bis(methylsulfanyl)-2-nitroethylene in a solvent such as isopropanol to provide nitroethenyl compounds of general formula (57). Nitroethenyl compounds of general formula (57) may be treated with ammonia and methanol to provide nitroethenediamines of general formula (58). Nitroethenediamines of general formula (58) may be treated with benzotriazole adducts of general formula (27) and a base such as potassium carbonate in a solvent such as DMF to provide aminals of general formula (59).

Scheme 21

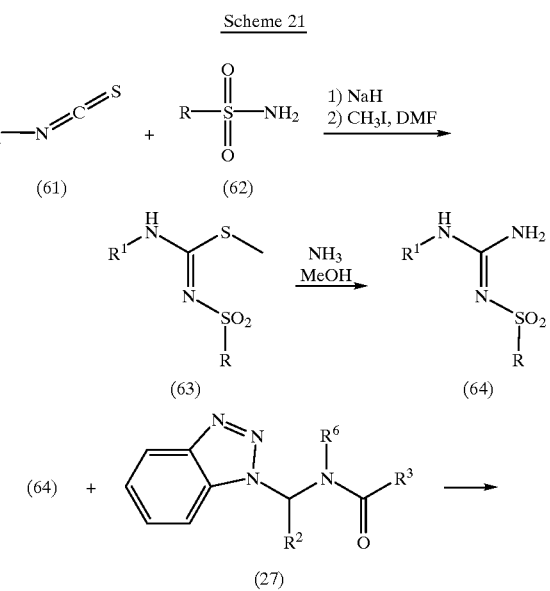

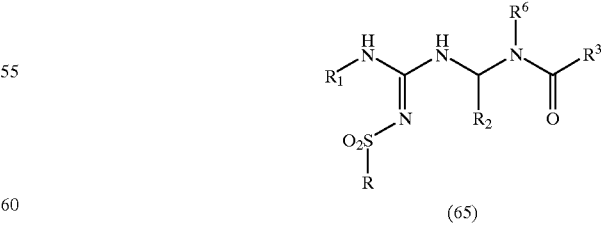

Aminals of general formula (65), wherein R$^1$, R$^2$, R$^3$ and R$^6$ are as defined in formula I and R is selected from alkyl, aryl, haloalkyl and NR$^{94}$R$^{95}$ wherein R$^{94}$ and R$^{95}$ are independently selected from hydrogen, alkyl, aryl, and arylalkyl, may be prepared as described in Scheme 21.

Isothiocyanates of general formula (61) may be treated with compounds of general formula (62) and sodium hydride followed by treatment with iodomethane in DMF to provide compounds of general formula (63). Compounds of general formula (63) may be treated with ammonia and methanol to provide guanidines of general formula (64). Guanidines of general formula (64) may be treated with benzotriazole adducts of general formula (27) and a base such as potassium carbonate in a solvent such as DMF to provide aminals of general formula (65).

Scheme 22

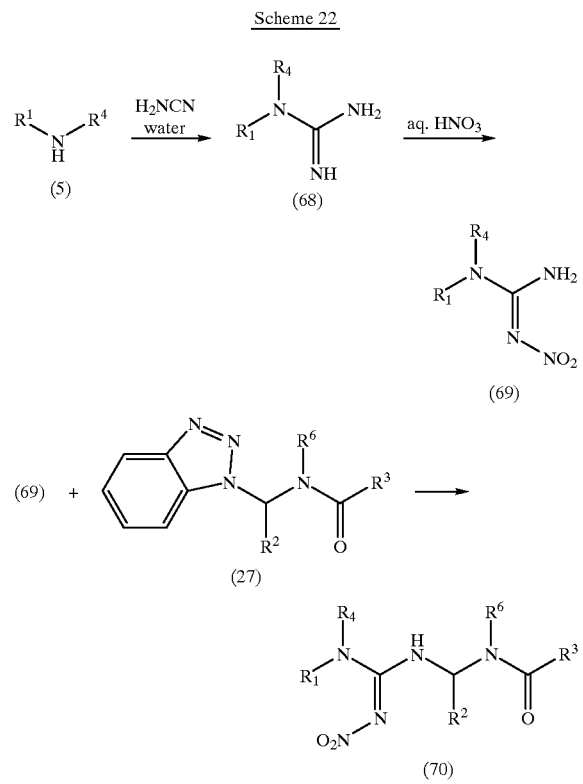

Aminals of general formula (70), wherein $R^1$, $R^2$, $R^3$, $R^4$ and $R^6$ are as defined in formula I, may be prepared as described in Scheme 22. Amines of general formula (5) may be treated with cyanamide in water in the presence of a protic acid such as HCl to provide guanidines of general formula (68). Guanidines of general formula (68) may be treated with aqueous nitric acid to provide nitroguanidines of general formula (69). Nitroguanidines of general formula (69) may be treated with benzotriazole adducts of general formula (27) and a base such as potassium carbonate in a solvent such as DMF to provide aminals of general formula (70).

Scheme 23

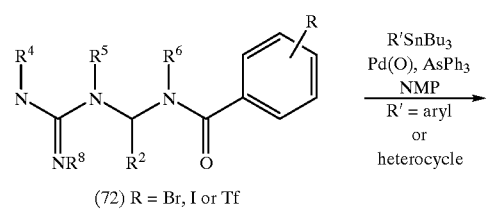

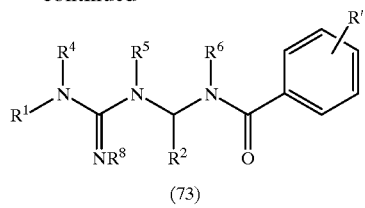

Aminals of general formula (73), wherein $R^1$, $R^2$, $R^4$, $R^5$, $R^6$ and $R^8$ are as defined in formula I and R' is selected from alkoxycarbonyl, aryl, carboxy, heterocycle and —$NR^A R^B$ wherein $R^A$ and $R^B$ are as defined in formula I, may be prepared as described in Scheme 23. Aminals of general formula (72), wherein R is Br, I or —$OS(O)_2CF_3$, may be treated with a palladium catalyst, a trialkyltin reagent and triphenylarsine in a solvent such as N-methylpyrrolidin-2-one to provide aminals of general formula (73). Alternatively, cross-coupling reactions (and carbonylations) may be done using Buchwald, Stille, Suzuki or Heck coupling reactions all of which are well known to those skilled in the art of organic chemistry.

Scheme 24

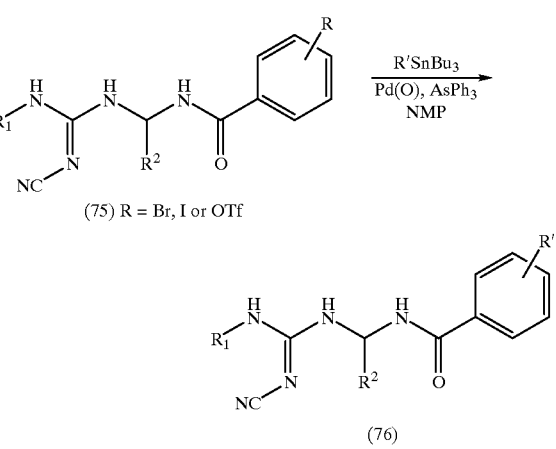

Aminals of general formula (76), wherein $R^1$ and $R^2$ are as defined in formula (I) and R' is selected from alkoxycarbonyl, aryl, carboxy, heterocycle and —$NR^A R^B$ wherein $R^A$ and $R^B$ are as defined in formula (I), may be prepared as described in Scheme 24. Aminals of general formula (75), wherein R is Br, I or —$OS(O)_2CF_3$, may be treated with a palladium catalyst, a trialkyltin reagent and triphenylarsine in a solvent such as N-methylpyrrolidin-2-one as described in Farina et al., J. Org. Chem. (1990), 55, 5833 to provide aminals of general formula (76). Alternatively, cross-coupling reactions and carbonylations may be done on aminals of general formula (75) using Buchwald, Stille, Suzuki or Heck coupling reaction conditions all of which are well known to those skilled in the art of organic chemistry.

Scheme 25

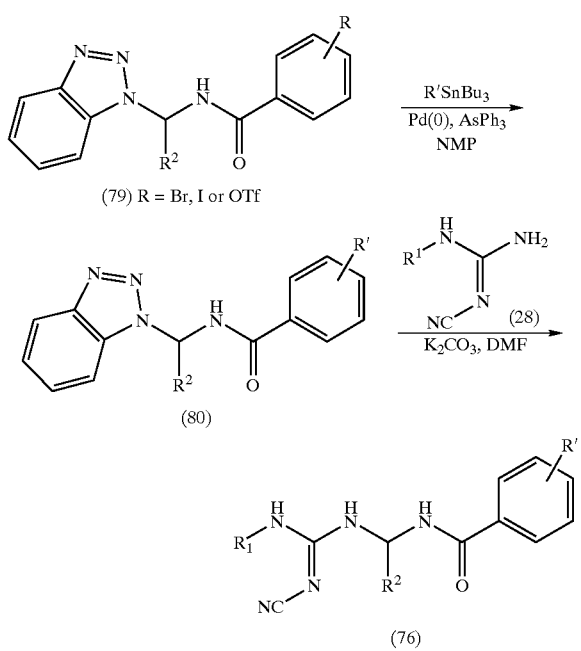

An alternative and more preferred method of preparing aminals of general formula (76), wherein $R^1$ and $R^2$ are as defined in formula (I) and R' is selected from alkoxycarbonyl, aryl, carboxy, heterocycle and —$NR^A R^B$ wherein $R^A$ and $R^B$ are as defined in formula (I), is described in Scheme 25. Benzotriazole compounds of general formula (79), wherein R is Br, I or —$OS(O)_2CF_3$, may be treated with a palladium catalyst, a trialkyltin reagent and triphenylarsine in a solvent such as N-methylpyrrolidin-2-one as described in Farina et al., J. Org. Chem. (1990), 55, 5833 to provide elaborated benzotriazoles general formula (80). Alternatively, cross-coupling reactions and carbonylations may be done on benzotriazoles of general formula (80) using Buchwald, Stille, Suzuki or Heck coupling reaction conditions all of which are well known to those skilled in the art of organic chemistry. Benzotriazoles of general formula (80) may be treated with cyanoguanidines of general formula (28) in a polar, aprotic solvent such as DMF in the presence of a base such as cesium carbonate to provide aminals of general formula (76).

The compounds and processes of the present invention will be better understood by reference to the following examples, which are intended as an illustration of and not a limitation upon the scope of the invention.

EXAMPLE 1

4-methyl-N-(2,2,2-trifluoro-1-{[(3-pyridinylamino)carbothioyl]amino}ethyl)benzamide

EXAMPLE 1A 4-methyl-N-(2,2,2-trifluoro-1-hydroxyethyl)benzamide

A 500 mL round-bottom flask was charged with trifluoroacetaldehyde ethyl hemiacetal (12.3 g, 85.0 mmol), p-toluamide (10.0 g, 74.0 mmol), and dioxane (150 mL). The thick white slurry was stirred at ambient temperature for 3 hours, then heated at reflux for 44 hours. The homogeneous solution was cooled and concentrated in vacuo to provide a white solid. The crude material was dissolved in ethyl acetate (50 mL), adsorbed onto silica gel (50 g), and eluted through a medium porosity fritted filter funnel (elution with 25% ethyl acetate/hexanes, then ethyl acetate) to provide 14.1 g of the desired product as a white solid.

MS (APCI+) m/z 215 $(M-H_2O)^+$.

EXAMPLE 1B

N-(1-chloro-2,2,2-trifluoroethyl)-4-methylbenzamide

A stirred solution of Example 1A (3.48 g, 15.0 mmol) in $CH_2Cl_2$ (60 mL) at 0° C. was treated with pyridine (1.20 mL). The reaction mixture was treated dropwise with thionyl chloride (1.10 mL, 15.0 mmol), and the reaction flask was equipped with a calcium chloride drying tube. The reaction mixture was stirred at 0° C. for 4 hours, the cooling bath was removed, and the solution was stirred at ambient temperature for an additional 12 hours. Concentration of the reaction mixture provided a white solid which was triturated with diethyl ether (2×200 mL) to provide 2.40 g of the desired product as a white solid.

MS (APCI+) m/z 252 $(M+H)^+$.

EXAMPLE 1C 4-methyl-N-(2,2,2-trifluoro-1-isothiocyanatoethyl)benzamide

A stirred solution of Example 1B (2.00 g, 8.00 mmol) in acetone (35 mL) at ambient temperature was treated with potassium thiocyanate (1.60 g, 16.0 mmol). The reaction mixture was stirred for 12 hours, concentrated, and the crude residue was purified by flash chromatography (elution with 40% ethyl acetate/hexanes) to provide 1.34 g of the desired product as an off-white solid.

MS (APCI+) m/z 275 $(M+H)^+$.

EXAMPLE 1D 4-methyl-N-(2,2,2-trifluoro-1-{[(3-pyridinylamino)carbothioyl]amino}ethyl)benzamide A solution of 3-aminopyridine (145 mg, 1.54 mmol) in benzene (8 mL) at ambient temperature was treated with a solution of Example 1C (500 mg, 1.54 mmol) in benzene (1.5 mL). The reaction mixture was stirred for 1.5 hours, then concentrated to a nominal volume. The white solids which precipitated from solution were collected by filtration and were washed with diethyl ether. Recrystallization from 25% ethyl acetate/hexanes provided the desired product as a white solid.

mp 185–186° C.;

MS (APCI+) m/z 369 $(M+H)^+$;

$^1$H NMR (DMSO-$d_6$) δ 10.43 (s, 1H), 9.25 (d, 1H, J=8 Hz), 8.61 (dd, 1H, J=3, 1 Hz), 8.39–8.35 (m, 2H), 8.04–8.00 (m, 1H), 7.79 (m, 2H), 7.43–7.38 (m, 1H), 7.35–7.23 (m, 3H), 2.38 (s, 3H);

Anal. calcd for $C_{16}H_{15}F_3N_4OS$: C, 52.17; H, 4.10; N, 15.21. Found: C, 52.2; H, 3.96; N, 15.16.

EXAMPLE 2

4-methyl-N-{2,2,2-trifluoro-1-[(2-toluidinocarbothioyl)amino]ethyl}benzamide

Example 1C and 2-methylaniline were processed as described in Example 1D to provide the desired product.

mp 210–211° C.;

MS (APCI+) m/z 382 (M+H)+;

$^1$H NMR (DMSO-d$_6$) δ 10.01 (br s, 1H), 9.09–8.96 (m, 1H), 7.74 (d, 2H, J=8 Hz), 7.39–7.22 (m, 7H), 2.37 (s, 3H);

Anal. calcd for $C_{18}H_{18}F_3N_3OS$: C, 56.68; H, 4.76; N, 11.02. Found: C, 56.66; H, 4.73; N, 10.84.

EXAMPLE 3

4-methyl-N-(2,2,2-trifluoro-1-{[(4-fluoroanilino)carbothioyl]amino}ethyl)benzamide Example 1C and 4-fluoroaniline were processed as described in Example 1D to provide the desired product.

mp 208–210° C.;

MS (APCI+) m/z 386 (M+H)+;

$^1$H NMR (DMSO-d$_6$) δ 10.30 (s, 1H), 9.19 (d, 1H, J=8 Hz), 8.11 (d, 1H, J=10 Hz), 7.77 (d, 2H, J=8 Hz), 7.47 (m, 2H), 7.34 (d, 2H, J=8 Hz), 7.30–7.19 (m, 3H), 2.37 (s, 3H);

Anal. calcd for $C_{17}H_{15}F_4N_3OS$: C, 52.98; H, 3.92; N, 10.90. Found: C, 53.08; H, 3.92; N, 10.91.

EXAMPLE 4

4-methyl-N-(2,2,2-trifluoro-1-{[(3-nitroanilino)carbothioyl]amino}ethyl)benzamide Example 1C and 3-nitroaniline were processed as described in Example 1D to provide the desired product.

mp 185–186° C.;

MS (APCI+) m/z 416 (M+H)+;

$^1$H NMR (DMSO-d$_6$) δ 10.72 (s, 1H), 9.32 (d, 1H, J=9 Hz), 8.69 (s, 1H), 8.48 (m, 1H), 8.04 (m, 1H), 7.90 (d, 1H, J=9 Hz), 7.80 (d, 2H, J=9 Hz), 7.65 (t, 1H, J=9 Hz), 7.35 (d, 2H, J=9 Hz), 7.29–7.17 (m, 1H), 2.38 (s, 3H);

Anal. calcd for $C_{17}H_{15}F_3N_4O_3S.0.2\ H_2O$: C, 49.08; H, 3.73; N, 13.47. Found: C, 48.96;

H, 3.54; N, 13.38.

EXAMPLE 5

4-methyl-N-[2,2,2-trifluoro-1-({[2-fluoro-3-(trifluoromethyl)anilino]carbothioyl}amino)ethyl]benzamide Example 1C and 2-fluoro-3-(trifluoromethyl)aniline were processed as described in Example 1D to provide the desired product.

mp 179–181° C.;

MS (APCI+) m/z 454 (M+H)+;

$^1$H NMR (DMSO-d$_6$) δ 10.23 (s, 1H), 9.28 (d, 1H, J=8 Hz), 8.62 (d, 1H, J=8 Hz), 8.05 (t, 1H, J=9 Hz), 7.80 (d, 2H, J=8 Hz), 7.67 (t, 1H, J=7 Hz), 7.42 (t, 1H, J=7 Hz), 7.34 (d, 2H, J=Hz), 7.30–7.18 (m, 1H), 2.38 (s, 3H);

Anal. calcd for $C_{18}H_{14}F_3N_3OS.0.5\ C_4H_8O$: C, 49.08; H, 3.71; N, 8.59. Found: C, 49.48; H, 3.75; N, 8.36.

EXAMPLE 6

4-methyl-N-(2,2,2-trifluoro-1-{[(4-methoxyanilino)carbothioyl]amino}ethyl)benzamide Example 1C and 4-methoxyaniline were processed as described in Example 1D to provide the desired product.

mp 193–194° C.;

MS (APCI+) m/z 398 (M+H)+;

$^1$H NMR (DMSO-d$_6$) δ 10.19 (s, 1H), 9.12 (br s, 1H), 7.8–7.9 (br s, 1H), 7.75 (d, 2H, J=8 Hz), 7.33 (d, 2H, J=8 Hz), 7.32–7.21 (m, 3H), 6.97 (d, 2H, J=9 Hz), 3.76 (s, 3H), 2.37 (s, 3H);

Anal. calcd for $C_{18}H_{18}F_3N_3O_2S$: C, 54.40; H, 4.57; N, 10.57. Found: C, 54.47; H, 4.49;

N, 10.44.

EXAMPLE 7

N-[1-({[(6-chloro-3-pyridinyl)amino]carbothioyl}amino)-2,2,2-trifluoroethyl]-4-methylbenzamide Example 1C and 5-amino-2-chloropyridine were processed as described in Example 1D to provide the desired product.

mp 199–200° C.;

MS (APCI+) m/z 403 (M+H)+;

$^1$H NMR (DMSO-d$_6$) δ 10.51 (s, 1H), 9.29 (d, 1H, J=8 Hz), 8.55–5.46 (m, 2H), 8.12 (dd, 1H, J=9, 3 Hz), 7.78 (d, 2H, J=8 Hz), 7.53 (d, 1H, J=9 Hz), 7.34 (d, 1H, J=8 Hz), 7.29–7.21 (m, 1H), 2.38 (s, 3H);

Anal. calcd for $C_{16}H_{14}F_3N_4OS$: C, 47.71; H, 3.50; N, 13.91. Found: C, 47.93; H, 3.53; N, 13.76.

EXAMPLE 8

4-methyl-N-(2,2,2-trifluoro-1-{[(2-methoxyanilino)carbothioyl]amino}ethyl)benzamide Example 1C and 2-methoxyaniline were processed as described in Example 1D to provide the desired product.

mp 212–214° C.;

MS (APCI+) m/z 396 (M+H)+;

$^1$H NMR (DMSO-d$_6$) δ 9.86 (s, 1H), 9.20–9.12 (m, 1H), 7.76 (d, 2H, J=8 Hz), 7.6 (br s, 1H), 7.33 (d, 2H, J=8 Hz), 7.26–7.20 (m, 1H), 7.09 (d, 1H, J=8 Hz), 6.95 (t, 1H, J=8 Hz), 2.37 (s, 3H);

Anal. calcd for $C_{18}H_{18}F_3N_3O_2S$: C, 54.40; H, 4.57; N, 10.57. Found: C, 54.49; H, 4.62;

N, 10.55.

EXAMPLE 9

N-{1-[(anilinocarbothioyl)amino]-2,2,2-trifluoroethyl}-4-methylbenzamide

Example 1C and aniline were processed as described in Example 1D to provide the desired product.

mp 205–206° C.;

MS (APCI+) m/z 368 (M+H)+;

$^1$H NMR (DMSO-d$_6$) δ 10.37 (s, 1H), 9.19 (d, 1H, J=8 Hz), 8.12 (d, 1H, J=10 Hz), 7.76 (d, 2H, J=8 Hz), 7.47–7.28 (m, 4H), 7.21 (t, 1H, J=7 Hz), 2.37 (s, 3H);

Anal. calcd for $C_{17}H_{16}F_3N_3OS.0.5\ H_2O$: C, 54.25; H, 4.55; N, 11.16. Found: C, 54.64; H, 4.08; N, 11.14.

EXAMPLE 10

4-methyl-N-{2,2,2-trifluoro-1-[(4-toluidinocarbothioyl)amino]ethyl}benzamide

Example 1C and p-toluidine were processed as described in Example 1D to provide the desired product.

mp 192–193° C.;

MS (APCI+) m/z 382 (M+H)+;

¹H NMR (DMSO-d₆) δ 10.28 (s, 1H), 9.18–9.12 (m, 1H), 8.10–7.92 (m, 1H), 7.76 (d, 2H, J=8 Hz), 7.34–7.28 (m, 5H), 7.20 (d, 2H, J=8 Hz), 2.37 (s, 3H), 2.30 (s, 3H);

Anal. calcd for $C_{18}H_{18}F_3N_3OS$: C, 56.68; H, 4.76; N, 11.02. Found: C, 56.95; H, 4.71; N, 10.87.

EXAMPLE 11

4-methyl-N-(2,2,2-trifluoro-1-{[(2-fluoroanilino)carbothioyl]amino}ethyl)benzamide Example 1C and 2-fluoroaniline were processed as described in Example 1D to provide the desired product.

mp 197–198° C.;

MS (APCI+) m/z 386 (M+H)⁺;

¹H NMR (DMSO-d₆) δ 10.11 (s, 1H), 9.22 (d, 1H, J=8 Hz), 8.34 (d, 1H, J=8 Hz), 7.78 (d, 2H, J=8 Hz), 7.69 (t, 1H, J=8 Hz), 7.19–7.35 (m, 6H), 2.38 (s, 3H);

Anal. calcd for $C_{17}H_{15}F_4N_3OS$: C, 52.98; H, 3.92; N, 10.90. Found: C, 52.89; H, 3.92; N, 10.83.

EXAMPLE 12

4-methyl-N-(2,2,2-trifluoro-1-{[(3-methoxyanilino)carbothioyl]amino}ethyl)benzamide Example 1C and 3-methoxyaniline were processed as described in Example 1D to provide the desired product.

mp 206–208° C.;

MS (APCI+) m/z 396 (M+H)⁺;

¹H NMR (DMSO-d₆) δ 10.39 (s, 1H), 9.16 (d, 1H, J=8 Hz), 8.12 (d, 1H, J=9 Hz), 7.76 (d, 2H, J=8 Hz), 7.33–7.21 (m, 4H), 7.14 (br s, 1H), 6.96 (d, 1H, J=8 Hz), 6.83–6.75 (m, 1H), 2.37 (s, 3H);

Anal. calcd for $C_{18}H_{18}F_3N_3O_2S$: C, 54.40; H, 4.57; N, 10.57. Found: C, 54.50; H, 4.44; N, 10.55.

EXAMPLE 13

4-methyl-N-(2,2,2-trifluoro-1-{[(3-fluoroanilino)carbothioyl]amino}ethyl)benzamide Example 1C and 3-fluoroaniline were processed as described in Example 1D to provide the desired product.

mp 205–206° C.;

MS (APCI+) m/z 386 (M+H)⁺;

¹H NMR (DMSO-d₆) δ 10.51 (s, 1H), 9.25 (d, 1H, J=8 Hz), 8.31 (d, 1H, J=9 Hz), 7.78 (d, 2H, J=8 Hz), 7.64–7.58 (m, 1H), 7.45–7.22 (m, 6H), 7.06–7.01 (m, 1H), 2.38 (s, 3H);

Anal. calcd for $C_{17}H_{15}F_4N_3OS$: C, 52.98; H, 3.92; N, 10.90. Found: C, 52.86; H, 3.88; N, 10.76.

EXAMPLE 14

N-(1-{[(2,5-difluoroanilino)carbothioyl]amino}-2,2,2-trifluoroethyl)-4-methylbenzamide Example 1C and 2,5-difluoroaniline were processed as described in Example 1D to provide the desired product.

mp 183–185° C.;

MS (APCI+) m/z 404 (M+H)⁺;

¹H NMR (DMSO-d₆) δ 10.21 (s, 1H), 9.29 (d, 1H, J=8 Hz), 8.65 (d, 1H, J=8 Hz), 7.89–7.82 (m, 1H), 7.79 (d, 2H, J=8 Hz), 7.40–7.32 (m, 3H), 7.30–7.25 (m, 1H), 7.17–7.12 (m, 1H), 2.38 (s, 3H);

Anal. calcd for $C_{17}H_{14}F_5N_3OS$: C, 50.62; H, 3.5; N. 10.42. Found: C, 50.58; H, 3.49; N, 10.25.

EXAMPLE 15

N-(1-{[(2,4-difluoroanilino)carbothioyl]amino}-2,2,2-trifluoroethyl)-4-methylbenzamide Example 1C and 2,4-difluoroaniline were processed as described in Example 1D to provide the desired product.

mp 202–204° C.;

MS (APCI+) m/z 404 (M+H)⁺;

¹H NMR (DMSO-d₆) δ 10.02 (s, 1H), 9.20 (br d, 1H, J=8 Hz), 8.40 (br d, 1H, J=8 Hz), 7.78 (d, 2H, J=9 Hz), 7.57–7.51 (m, 1H), 7.43–7.20 (m, 4H), 7.17–7.11 (m, 1H), 2.38 (s, 3H);

Anal. calcd for $C_{17}H_{14}F_5N_3OS$: C, 50.62; H, 3.50; N, 10.42. Found: C, 50.74; H, 3.41; N, 10.39.

EXAMPLE 16

4-methyl-N-{2,2,2-trifluoro-1-[(3-toluidinocarbothioyl)amino]ethyl}benzamide

Example 1C and m-toluidine were processed as described in Example 1D to provide the desired product.

mp 197–198° C.;

MS (APCI+) m/z 382 (M+H)⁺;

¹H NMR (DMSO-d₆) δ 10.31 (s, 1H), 9.16 (d, 1H, J=8 Hz), 8.07 (d, 1H, J=8 Hz), 7.76 (d, 2H, J=8 Hz), 7.34 (d, 2H, J=8 Hz), 7.30–7.21 (m, 4H), 7.03 (d, 1H, J=7 Hz), 2.37 (s, 3H), 2.30 (s, 3H);

Anal. calcd for $C_{18}H_{19}F_3N_3OS$: C, 56.68; H, 4.76; N, 11.02. Found: C, 56.72; H, 464; N, 10.85.

EXAMPLE 17

N-(1-{[(2,6-difluoroanilino)carbothioyl]amino}-2,2,2-trifluoroethyl)-4-methylbenzamide Example 1C and 2,6-difluoroaniline were processed as described in Example 1D to provide the desired product.

mp 185–186° C.;

MS (APCI+) m/z 404 (M+H)⁺;

¹H NMR (DMSO-d₆) δ 9.84 (s, 1H), 9.22 (br s, 1H), 8.40 (br s, 1H), 7.78 (d, 2H, J=8 Hz), 7.48–7.43 (m, 1H), 7.35 (d, 2H, J=8 Hz), 7.30–7.17 (m, 3H), 2.38 (s, 3H);

Anal. calcd for $C_{17}H_{14}F_5N_3OS$: C, 50.62; H, 3.5; N, 10.42. Found: C, 50.85; H, 3.41; N, 10.38.

EXAMPLE 18

N-(1-{[(2,3-difluoroanilino)carbothioyl]amino}-2,2,2-trifluoroethyl)-4-methylbenzamide Example 1C and 2,3-difluoroaniline were processed as described in Example 1D to provide the desired product.

mp 210–211° C.;

MS (APCI+) m/z 404 (M+H)⁺;

¹H NMR (DMSO-d₆) δ 10.20 (s, 1H), 9.23 (d, 1H, J=8 Hz), 8.48 (d, 1H, J=9 Hz), 7.79 (d, 2H, J=8 Hz), 7.53–7.49 (m, 1H), 7.46–7.16 (m, 4H), 2.38 (s, 3H);

Anal. calcd for $C_{17}H_{14}F_5N_3OS$: C, 50.62; H, 3.50; N, 10.42. Found: C, 50.83; H, 3.44; N, 10.18.

EXAMPLE 19

4-chloro-N-(2,2,2-trifluoro-1-{[(3-pyridinylamino)carbothioyl]amino}ethyl)benzamide

EXAMPLE 19A 4-chloro-N-(2,2,2-trifluoro-1-hydroxyethyl)benzamide

Trifluoroacetaldehyde ethyl hemiacetal and 4-chlorobenzamide were processed as described in Example 1A to provide the desired product.

MS (APCI+) m/z 237 (M−H₂O)⁺.

EXAMPLE 19B 4-chloro-N-(1-chloro-2,2,2-trifluoroethyl)benzamide

Example 19A, thionyl chloride, and pyridine were processed as described in Example 1B to provide the desired product.

MS (APCI+) m/z 271 (M+H)$^+$.

EXAMPLE 19C 4-chloro-N-(2,2,2-trifluoro-1-isothiocyanatoethyl) benzamide

Example 19B and potassium thiocyanate were processed as described in Example 1C to provide the desired product.

MS (APCI+) m/z 294 (M+H)$^+$.

EXAMPLE 19D 4-chloro-N-(2,2,2-trifluoro-1-{[(3-pyridinylamino) carbothioyl]amino}ethyl)benzamide Example 19C and 3-aminopyridine were processed as described in Example 1D to provide the desired product.

mp 147–149° C.;

MS (ESI+) m/z 389 (M+H)$^+$;

$^1$H NMR (DMSO-d$_6$) δ 10.42 (s, 1H), 9.49–9.46 (m, 1H), 8.60 (d, 1H, J=3 Hz), 8.50–8.41 (m, 2H), 8.06–8.01 (m, 1H), 7.92 (d, 2H, J=9 Hz), 7.65 (d, 2H, J=9 Hz), 7.42 (q, 1H, J=3 Hz), 7.29–7.25 (m, 1H);

Anal. calcd for $C_{15}H_{12}ClF_3N_4OS$: C, 46.34; H, 3.11; N, 14.41. Found: C, 46.32; H, 3.10; N, 14.50.

EXAMPLE 20

N-{1-[(anilinocarbothioyl)amino]-2,2,2-trifluoroethyl}-4-chlorobenzamide

Example 19C and aniline were processed as described in Example 1D to provide the desired product.

mp 198–201° C.;

MS (ESI+) m/z 357 (M+H)$^+$;

$^1$H NMR (DMSO-d$_6$) δ 10.37 (br s, 1H), 9.37 (d, 1H, J=8 Hz), 8.15 (d, 1H, J=9 Hz), 7.91–7.86 (m, 2H), 7.63–7.58 (m, 2H), 7.51–7.45 (m, 2H), 7.42–7.26 (m, 3H), 7.22–7.17 (m, 1H);

Anal. calcd for $C_{16}H_{13}ClF_3N_3OS$: C, 49.55; H, 3.38; N, 10.84. Found: C, 48.71; H, 3.33; N, 10.86.

EXAMPLE 21

4-chloro-N-(2,2,2-trifluoro-1-{[(2-fluoroanilino) carbothioyl]amino}ethyl)benzamide Example 19C and 2-fluoroaniline were processed as described in Example 1D to provide the desired product.

mp 197–200° C.;

MS (ESI+) m/z 357 (M+H)$^+$;

$^1$H NMR (DMSO-d$_6$) δ 10.04 (br s, 1H), 9.36 (d, 1H, J=8 Hz), 8.35 (br s, 1H), 7.87–7.82 (m, 2H), 7.59–7.55 (m, 2H), 7.29–7.13 (m, 5H);

Anal. calcd for $C_{16}H_{12}ClF_4N_3OS$: C, 47.36; H, 2.98; N, 10.35. Found: C, 47.58; H, 2.86; N, 10.43.

EXAMPLE 22

N-(2,2-dimethyl-1-{[(3-pyridinylamino)carbothioyl] amino}propyl)-4-methylbenzamide

EXAMPLE 22A 2-((tert-butoxycarbonyl)amino)-3,3-dimethylbutanoic acid

A stirred solution of racemic tert-butylglycine (2.15 g, 16.4 mmol), di-tert-butyl dicarbonate (4.65 g, 21.3 mmol) in dioxane (30 mL), and water (30 mL) at 5° C. was treated with N-methylmorpholine (2.07 mL, 24.6 mmol). The mixture was allowed to slowly warm to ambient temperature and stirred for 16 hours. The reaction mixture was poured into cold aqueous NaHCO$_3$ solution (50 mL) and extracted with ethyl acetate (3×50 mL). The aqueous layer was acidified to pH 1 (2M HCl) and extracted with ethyl acetate (3×30 mL). The organic fractions were combined, dried (MgSO$_4$), and filtered. Removal of solvent provided 2.47 g of the desired product as a white solid.

MS (APCI+) m/z 232 (M+H)$^+$.

EXAMPLE 22B

Tert-butyl 1-(aminocarbonyl)-2,2-dimethylpropylcarbamate

A stirred solution of Example 22A (1.81 g, 7.83 mmol) in THF (20 mL) at –40° C. was treated with isobutyl chloroformate (1.01 mL, 7.83 mmol) followed by N-methylmorpholine (0.860 mL, 7.83 mmol). After 15 minutes, the milky white reaction mixture was treated dropwise with ammonium hydroxide (6.0 mL of 30% reagent, 15.0 mmol), the reaction flask was warmed to –15° C., stirred for 45 minutes, treated with brine (20 mL), and the clear homogeneous mixture was extracted with ethyl acetate (2×40 mL). The organic portions were combined, washed with aqueous KHSO$_4$ solution (15 mL), aqueous NaHCO$_3$ solution (15 mL), and brine (15 mL), and dried (MgSO$_4$). Filtration and removal of solvent provided 1.68 g of the desired product as a white solid.

MS (APCI+) m/z 231 (M+H)$^+$.

EXAMPLE 22C 2-amino-3,3-dimethylbutanamide mono (trifluoroacetate)

Example 22B (1.49 g, 6.47 mmol) was dissolved in CH$_2$Cl$_2$ (20 mL), cooled to 0° C., treated with trifluoroacetic acid (5 mL), and the reaction was stirred for 3 hours at 0° C. Solvents were removed under reduced pressure, the residue was taken up in brine (10 mL), and extracted with ethyl acetate (25 mL). The aqueous layer was basified with 2M aqueous K$_2$CO$_3$ solution and extracted with 25% isopropanol/chloroform (3×20 mL). The organic portions were combined and solvents were removed to provide 516 mg of the analytically pure desired product as a white solid.

MS (APCI+) m/z 131 (M+H)$^+$.

EXAMPLE 22D

N-(1-(aminocarbonyl)-2,2-dimethylpropyl-4-methylbenzamide

A solution of Example 22C (489 mg, 3.76 mmol) and p-toluoyl chloride (0.560 mL, 4.14 mmol) in CH$_2$Cl$_2$ (8 mL) at 0° C. was treated with triethylamine (0.520 mL, 3.76 mmol). After 6 hours, the mixture was diluted with ethyl acetate (25 mL) and washed sequentially with 1M HCl (10 mL), saturated aqueous NaHCO$_3$ solution (10 mL), water (15 mL), and brine (10 mL). The organic portion was dried (Na$_2$SO$_4$), filtered, and concentrated to provide an oily residue which was purified by flash chromatography (elution with 50% ethyl acetate/hexanes) to provide 750 mg of the desired product as a sticky white solid.

MS (APCI+) m/z 249 (M+H)$^+$.

EXAMPLE 22E

N-(1-amino-2,2-dimethylpropyl)-4-methylbenzamide Hydrochloride

A solution of iodobenzene diacetate (1.50 g, 3.48 mmol) in 50% aqueous CH$_3$CN (6 mL) at ambient temperature was treated with Example 22D (721 mg, 2.90 mmol). After 16 hours, water (50 mL) and concentrated hydrochloric acid (5 mL) were added, and the mixture was extracted with ethyl acetate (2×40 mL). The aqueous layer was lyophilized leaving the hydrochloride salt which was triturated with diethyl ether to provide 422 mg of the desired product as a white solid.

MS (APCI+) m/z 221 (M+H)$^+$.

EXAMPLE 22F

N-(2,2-dimethyl-1-{[(3-pyridinylamino)carbothioyl]amino}propyl)-4-methylbenzamide A solution of Example 22E (152 mg, 0.592 mmol) and 3-pyridyl isothiocyanate (81 mg, 0.58 mmol) in THF (3 mL) at ambient temperature was treated with triethylamine (0.83 mL, 0.59 mmol). The mixture was stirred for 10 hours, diluted with ethyl acetate (20 mL), and washed sequentially with 1M HCl (5 mL), saturated aqueous NaHCO$_3$ solution (5 mL), water (10 mL), and brine (5 mL). The organic portion was dried (MgSO$_4$), filtered, and concentrated to provide an oily residue which was purified by flash chromatography (elution with 2% ethanol/ethyl acetate) to provide 126 mg of the desired product as an off-white solid.

mp 168–169° C.;

MS (APCI+) m/z 357 (M+H)$^+$;

$^1$H NMR (DMSO-d$_6$) δ 10.04 (s, 1H), 8.59 (d, 1H, J=9 Hz), 8.39–8.30 (m, 2H), 8.04 (d, 1H, J=9 Hz), 7.80 (d, 1H, J=9 Hz), 7.73 (d, 2H, J=9 Hz), 7.37 (dd, 1H, J=9, 3 Hz), 7.28 (d, 2H, J=9 Hz), 6.23 (br s, 1H), 2.35 (s, 3H), 1.00 (s, 9H);

Anal. calcd for C$_{19}$H$_{24}$N$_4$OS.0.2 C$_4$H$_8$O$_2$: C, 63.57; H, 6.90; N, 14.98. Found: C, 63.21; H, 6.80; N, 14.86.

EXAMPLE 23

N-((1R)-2,2-dimethyl-1-{[(3-pyridinylamino)carbothioyl]amino}propyl)-4-methylbenzamide Optically pure (R)-tert-butylglycine was processed as described in Example 22 to provide the desired product.

mp 168–170° C.;

MS (ESI+) m/z 357 (M+H)$^+$;

$^1$H NMR (DMSO-d$_6$) δ 10.05 (s, 1H), 8.59 (d, 1H, J=3 Hz), 8.39–8.31 (m, 2H), 8.05 (br d, 1H, J=9 Hz), 7.80 (br d, 1H, J=9 Hz), 7.78 (d, 2H, J=9 Hz), 7.38 (dd, 1H, J=9, 6 Hz), 7.28 (d, 2H, J=9 Hz), 6.25 (br s, 1H), 2.36 (s, 3H), 1.00 (s, 9H);

Anal. calcd for C$_{19}$H$_{24}$N$_4$OS: C, 64.02; H, 6.79; N, 15.72. Found: C, 64.01; H, 6.91; N, 15.55.

EXAMPLE 24

N-((1S)-2,2-dimethyl-1-{[(3-pyridinylamino)carbothioyl]amino}propyl)-4-methylbenzamide Optically pure (S)-tert-butylglycine was processed as described in Example 22 to provide the desired product.

mp 166–168° C.;

MS (ESI+) m/z 357 (M+H)$^+$;

$^1$H NMR (DMSO-d$_6$) δ 10.02 (s, 1H), 8.60 (s, 1H), 8.39–8.31 (m, 2H), 8.05 (br d, 1H, J=9 Hz), 7.82 (d, 1H, J=9 Hz), 7.75 (d, 2H, J=9 Hz), 7.38 (dd, 1H, J=9, 6 Hz), 7.28 (d, 2H, J=9 Hz), 6.25 (br s, 1H), 2.36 (s, 3H), 1.00 (s, 9H);

Anal. calcd for C$_{19}$H$_{24}$N$_4$OS: C, 64.02; H, 6.79; N, 15.72. Found: C, 64.09; H, 6.82; N, 15.44.

EXAMPLE 25

N-(2,2-dimethyl-1-{[(3-nitroanilino)carbothioyl]amino}propyl)-4-methylbenzamide

Example 22E and 3-nitrophenyl isothiocyanate were processed as described in Example 22F to provide the desired product.

mp 181–182° C.;

MS (APCI+) m/z 401 (M+H)$^+$;

$^1$H NMR (DMSO-d$_6$) δ 10.35 (s, 1H); 8.72 (s, 1H), 8.38–8.32 (m, 1H), 7.92 (q, 3H, J=9 Hz), 7.75 (d, 2H, J=9 Hz), 7.62 (t, 1H, J=9 Hz), 7.29 (d, 2H, J=9 Hz), 6.24 (br s, 1H), 2.35 (s, 3H), 1.00 (s, 9H);

Anal. calcd for C$_{20}$H$_{24}$N$_4$O$_3$S: C, 59.98; H, 6.04; N, 13.99. Found: C, 5983; H, 6.10; N, 13.97.

EXAMPLE 26

N-(2,2-dimethyl-1-{[(3-pyridinylamino)carbothioyl]amino}propyl)-2-methylbenzamide

EXAMPLE 26A 3,3-dimethyl-2-((2-methylbenzoyl)amino)butanoic acid

Racemic tert-butylglycine (502 mg, 3.83 mmol) was dissolved in water (10 mL) containing NaOH (153 mg, 3.83 mmol). This solution was cooled to 5° C. and treated with o-toluoyl chloride (0.501 mL, 3.83 mmol) followed by additional NaOH (153 mg, 3.83 mmol). The mixture was warmed to ambient temperature, stirred for 1.5 hours, recooled to 5° C., and treated with 1M HCl (pH 3). The thick precipitate that formed was collected by filtration and washed with cold water to provide 550 mg of the desired product as a white solid.

MS (APCI+) m/z 250 (M+H)$^+$.

EXAMPLE 26B

N-(1-(aminocarbonyl)-2,2-dimethylpropyl)-2-methylbenzamide

A stirred solution of Example 26A (458 mg, 1.84 mmol) in THF (10 mL) at −15° C. was treated with isobutyl chloroformate (0.240 mL, 1.84 mmol) followed by N-methylmorpholine (0.200 mL, 1.84 mmol). After 15 minutes, the milky white reaction mixture was treated dropwise with ammonium hydroxide (4.2 mL of 30% reagent, 15.0 mmol). The reaction flask was warmed to −15° C., stirred for 45 minutes, treated with brine (20 mL), and the clear homogeneous mixture was extracted with ethyl acetate (2×40 mL). The organic portions were combined, washed with aqueous KHSO$_4$ solution (15 mL), aqueous NaHCO$_3$ solution (15 mL), and brine (15 mL), and dried (MgSO$_4$). Filtration and removal of solvent provided 232 mg of the desired product a white solid.

MS (APCI+) m/z 249 (M+H)$^+$.

EXAMPLE 26C

N-(1-amino-2,2-dimethylpropyl)-2-methylbenzamide hydrochloride

Example 26B and iodobenzene diacetate were processed as described in Example 22E to provide the desired product.

MS (APCI+) m/z 221 (M+H)$^+$.

EXAMPLE 26D

N-(2,2-dimethyl-1-{[(3-pyridinylamino)carbothioyl]amino}propyl)-2-methylbenzamide Example 26C and 3-pyridyl isothiocyanate were processed as described in Example 22F to provide the desired product.

mp 186–187° C.;

MS (APCI+) m/z 357 (M+H)$^+$;

$^1$H NMR (DMSO-d$_6$) δ 10.00 (s, 1H), 8.61 (d, 1H, J=3 Hz), 8.39–8.28 (m, 2H), 8.14 (d, 1H, J=9 Hz), 7.77 (d, 1H, J=9 Hz), 7.40–7.18 (m, 5H), 6.07 (br s, 1H), 2.34 (s, 3H), 1.02 (s, 9H);

Anal. calcd for C$_{19}$H$_{24}$N$_4$OS: C, 64.02; H, 6.79; N, 15.72. Found: C, 63.83; H, 6.69; N, 15.64.

EXAMPLE 27

4-chloro-N-(2,2-dimethyl-1-{[(3-pyridinylamino)carbothioyl]amino}propyl)benzamide

EXAMPLE 27A 2-((4-chlorobenzoyl)amino)-3,3-dimethylbutanoic Acid

Racemic tert-butylglycine and 4-chlorobenzoyl chloride were processed as described in Example 26A to provide the desired product.

MS (APCI+) m/z 270 (M+H)$^+$.

EXAMPLE 27B

N-(1-(aminocarbonyl)-2,2-dimethylpropyl)-4-chlorobenzamide

Example 27A, isobutyl chloroformate, and ammonium hydroxide were processed as described in Example 26B to provide the desired product.

MS (APCI+) m/z 269 (M+H)$^+$.

EXAMPLE 27C

N-(1-amino-2,2-dimethylpropyl)-4-chlorobenzamide hydrochloride

Example 27B and iodobenzene diacetate were processed as described in Example 22E to provide the desired product.

MS (APCI+) m/z 241 (M+H)$^+$.

EXAMPLE 27D 4-chloro-N-(2,2-dimethyl-1-{[(3-pyridinylamino)carbothioyl]amino}propyl)benzamide Example 27C and 3-pyridyl isothiocyanate were processed as described in Example 22F to provide the desired product.

mp 164–167° C.;

MS (APCI+) m/z 377 (M+H)$^+$;

$^1$H NMR (DMSO-d$_6$) δ 10.04 (s, 1H), 8.60 (d, 1H, J=3 Hz), 8.49 (d, 1H, J=9 Hz), 8.31 (dd, 1H, J=9, 3 Hz), 8.07 (br d, 1H, J=9 Hz), 7.88–7.76 (m, 3H), 7.55 (d, 1H, J=9 Hz), 7.36 (dd, 2H, J=9, 6 Hz), 6.18 (br s, 1H), 1.00 (s, 9H);

Anal. calcd for C$_{18}$H$_{21}$ClN$_4$OS: C, 57.36; H, 5.62; N, 14.87. Found: C, 57.19; H, 5.50; N, 14.73.

EXAMPLE 28

N-(2,2-dimethyl-1-{[(3-pyridinylamino)carbothioyl]amino}propyl)benzamide

EXAMPLE 28A 2-(benzoylamino)-3,3-dimethylbutanoic Acid

Racemic tert-butylglycine and benzoyl chloride were processed as described in Example 26A to provide the desired product.

MS (APCI+) m/z 236 (M+H)$^+$.

EXAMPLE 28B

N-(1-(aminocarbonyl)-2,2-dimethylpropyl)benzamide

Example 28A, isobutyl chloroformate, and ammonium hydroxide were processed as described in Example 26B to provide the desired product.

MS (APCI+) m/z 236 (M+H)$^+$.

EXAMPLE 28C

N-(1-amino-2,2-dimethylpropyl)benzamide Hydrochloride

Example 28B and iodobenzene diacetate were processed as described in Example 22E to provide the desired product.

MS (APCI+) m/z 207 (M+H)$^+$.

EXAMPLE 28D

N-(2,2-dimethyl-1-{[(3-pyridinylamino)carbothioyl]amino}propyl)benzamide

Example 28C and 3-pyridyl isothiocyanate were processed as described in Example 22E to provide the desired product.

mp 193–194° C.;

MS (APCI+) m/z 343 (M+H)$^+$;

$^1$H NMR (DMSO-d$_6$) δ 10.05 (s, 1H), 8.60 (d, 1H, J33 Hz), 8.41 (d, 1H, J=9 Hz), 8.31 (dd, 1H, J=9, 3 Hz), 8.06 (br d, 1H, J=9 Hz), 7.85–7.78 (m, 3H), 7.57–7.42 (m, 3H), 7.36 (dd, 2H, J=9, 6 Hz), 6.22 (br s, 1H), 1.00 (s, 9H);

Anal. calcd for C$_{18}$H$_{22}$N$_4$OS: C, 63.13; H, 6.48; N, 16.36. Found: C, 62.99; H, 6.30; N, 16.24.

EXAMPLE 29

4-methyl-N-(1-{[(3-nitroanilino)carbothioyl]amino}ethyl)benzamide

EXAMPLE 29A

N-(4-methylbenzoyl)alanine

Racemic alanine and p-toluoyl chloride were processed as described in Example 26A to provide the desired product.

MS (APCI+) m/z 208 (M+H)$^+$.

EXAMPLE 29B

Benzyl 1-((4-methylbenzoyl)amino)ethylcarbamate

Example 29A (511 mg, 2.46 mmol) was suspended in benzyl alcohol (5 mL) at ambient temperature and treated with diisopropylethylamine (0.470 mL, 2.71 mmol). The homogeneous solution was treated with diphenyl phosphorylazide (0.580 mL, 2.71 mmol), stirred at ambient temperature for 30 minutes, then stirred at 90° C. for 12 hours. The reaction was cooled, and benzyl alcohol was removed in vacuo. The resulting residue was dissolved in ethyl acetate (30 mL) and washed sequentially with 10% aqueous citric acid (10 mL), saturated aqueous NaHCO$_3$ (10 mL), water (10 mL), and brine (5 mL). Removal of solvent left an oily residue that was recrystallized from hot ethyl acetate/hexanes to provide a white precipitate which was collected by filtration and washed with hexanes to provide 77 mg of the desired product as a white solid.

MS (APCI+) m/z 313 (M+H)$^+$.

EXAMPLE 29C

N-(1-aminoethyl)-4-methylbenzamide Hydrochloride

A suspension of Example 29B (66 mg, 0.21 mmol) in methanol (9 mL) at ambient temperature was treated with 10% Pd/C (20 mg) aid sufficient 1M HCl to solubilize the substrate (ca. 0.20 mL). The system was equipped with a hydrogen balloon and stirred for 4 hours at ambient temperature. The reaction mixture was purged with nitrogen, filtered through diatomaceous earth (Celite®), rinsed with methanol and water, and the aqueous filtrate was washed with diethyl ether (2×15 mL). The aqueous layer was lyophilized providing 38 mg of the desired product as a white solid.

MS (APCI+) m/z 179 (M+H)$^+$.

EXAMPLE 29D

4-methyl-N-(1-{[(3-nitroanilino)carbothioyl]amino}ethyl)benzamide

Example 29C and 3-nitrophenyl isothiocyanate were processed as described in Example 22E to provide the desired product.

mp 172–175° C.;

MS (APCI+) m/z 359 (M+H)$^+$;

$^1$H NMR (DMSO-d$_6$) δ 10.32 (s, 1H), 8.75 (s, 1H), 8.31 (br s, 1H), 7.98 (m, 3H), 7.81 (d, 2H, J=9 Hz), 7.62 (t, 1H, J=9 Hz), 7.28 (d, 2H, J=9 Hz), 6.15 (br s, 1H), 2.53 (d, 3H, J=6 Hz), 2.37 (s, 3H);

Anal. calcd for $C_{17}H_{18}N_4O_3S \cdot 0.5\ CH_2Cl_2$: C, 52.43; H, 4.78; N, 13.98. Found: C, 52.43; H, 4.60; N, 13.85.

EXAMPLE 30

4-methyl-N-(1-{[(3-nitroanilino)carbothioyl]amino}-2-phenylethyl)benzamide

EXAMPLE 30A

N-(4-methylbenzoyl)phenylalanine

Racemic phenylalanine and p-toluoyl chloride were processed as described in Example 26A to provide the desired product.

MS (APCI+) m/z 284 (M+H)$^+$.

EXAMPLE 30B

N-(2-amino-1-benzyl-2-oxoethyl)-4-methylbenzamide

Example 30A, isobutyl chloroformate, and ammonium hydroxide were processed as described in Example 26B to provide the desired product.

MS (APCI+) m/z 283 (M+H)$^+$.

EXAMPLE 30C

N-(1-amino-2-phenylethyl)-4-methylbenzamide Hydrochloride

Example 30B and iodobenzene diacetate were processed as described in Example 22E to provide the desired product.

MS (APCI+) m/z 255 (M+H)$^+$.

EXAMPLE 30D

4-methyl-N-(1-{[(3-nitroanilino)carbothioyl]amino}-2-phenylethyl)benzamide

Example 30C and 3-nitrophenyl isothiocyanate were processed as described in Example 22E to provide the desired product.

mp 170–171° C.;

MS (APCI+) m/z 435 (M+H)$^+$;

$^1$H NMR (DMSO-d$_6$) δ 10.16 (s, 1H), 8.75 (s, 1H), 8.40 (br s, 1H), 7.99–7.88 (m, 3H), 7.75 (d, 2H, J=9 Hz), 7.60 (t, 1H, J=9 Hz), 7.42–7.27 (m, 5H), 7.20 (d, 2H, J=9 Hz), 6.20 (br s, 1H), 3.25 (m, 2H), 2.35 (s, 3H);

Anal. calcd for $C_{23}H_{22}N_4O_3S$: C, 63.58; H, 5.10; N, 12.89. Found: C, 63.32; H, 5.09; N, 12.74.

EXAMPLE 31

N-((1R)-2-(tert-butoxy)-1-{[(3-nitroanilino)carbothioyl]amino}ethyl)-4-methylbenzamide

EXAMPLE 31A

Benzyl (1S)-2-amino-1-(tert-butoxymethyl)-2-oxoethylcarbamate

A stirred solution of racemic (2S)-2-(((benzyloxy)carbonyl)amino)-3-tert-butoxypropanoic acid (1.01 g, 3.43 mmol) in THF (10 mL) at −15° C. was treated with isobutyl chloroformate (0.440 mL, 3.43 mmol) followed by N-methylmorpholine (0.380 mL, 3.43 mmol). After 15 minutes, the milky white reaction mixture was treated dropwise with ammonium hydroxide (2.8 mL of 30% reagent, 5.0 mmol). The reaction flask was warmed to −15° C. and stirred for 45 minutes. The clear homogeneous mixture was treated with brine (20 mL) and extracted with ethyl acetate (2×40 mL). The organic portions were combined and washed with saturated aqueous NaHCO$_3$ solution (15 mL) and brine (15 mL), and dried (MgSO$_4$). Filtration and removal of solvent provided 928 mg of the desired product a white solid.

MS (APCI+) m/z 295 (M+H)$^+$.

EXAMPLE 31B

(2S)-2-amino-3-(tert-butoxy)propanamide Hydrochloride

A suspension of Example 31A (784 mg, 2.67 mmol) in methanol (9 mL) at ambient temperature was treated with 10% Pd/C (75 mg) and sufficient 1M HCl to solubilize the substrate (ca. 0.50 mL). The system was equipped with a hydrogen balloon and stirred for 4 hours at ambient temperature. The reaction mixture was purged with nitrogen, filtered through diatomaceous earth (Celite®), rinsed with methanol and water, and the aqueous filtrate was washed with diethyl ether (2×40 mL). The aqueous layer was lyophilized providing 467 mg of the desired product as a white solid.

MS (APCI+) m/z 161 (M+H)$^+$.

EXAMPLE 31C

N-((1S)-2-amino-1-(tert-butoxymethyl)-2-oxoethyl)-4-methylbenzamide

A solution of Example 31C (435 mg, 2.21 mmol) and p-toluoyl chloride (0.320 mL, 2.43 mmol) in CH$_2$Cl$_2$ (12 mL) at 0° C. was treated with triethylamine (0.310 mL, 2.21 mmol). After 3 hours, the mixture was diluted with ethyl acetate (25 mL) and washed sequentially with 1M HCl (10 mL), saturated aqueous NaHCO$_3$ solution (10 mL), water (15 mL), and brine (10 mL). The organic portion was dried (Na$_2$SO$_4$), filtered, and concentrated to provide 606 mg of the desired product as a white solid.

MS (APCI+) m/z 279 (M+H)$^+$.

EXAMPLE 31D

N-((1S)-1-amino-2-(tert-butoxy)ethyl)-4-methylbenzamide Hydrochloride

Example 31C and iodobenzene diacetate were processed as described in Example 22E to provide the desired product.

MS (APCI+) m/z 251 (M+H)$^+$.

EXAMPLE 31E

N-((1R)-2-(tert-butoxy)-1-{[(3-nitroanilino)carbothioyl]amino}ethyl)-4-methylbenzamide Example 31 D and 3-nitrophenyl isothiocyanate were processed as described in Example 22F to provide the desired product.

mp 169–171° C.;

MS (APCI+) m/z 431 (M+H)$^+$;

$^1$H NMR (DMSO-d$_6$) δ: 10.32 (s, 1H), 8.75 (s, 1H), 8.15 (br s, 1H), 7.99–7.88 (m, 3H), 7.78 (d, 2H, J=9 Hz), 7.62 (t, 1H, J=9 Hz),), 7.30 (d, 2H, J=9 Hz), 3.70–3.61 (m, 2H), 2.35 (s, 3H), 1.15 (s, 1H);

Anal. calcd for C$_{21}$H$_{26}$N$_4$O$_4$S: C, 58.59; H, 6.09; N, 13.01. Found: C, 58.56; H, 5.99; N, 12.94.

EXAMPLE 32

N-(2-fluoro-1-{[(3-nitroanilino)carbothioyl]amino}ethyl)-4-methylbenzamide

EXAMPLE 32A 3-fluoro-N-(4-methylbenzoyl)alanine

Racemic fluoromethyl glycine and p-toluoyl chloride were processed as described in Example 26A to provide the desired product.

MS (APCI+) m/z 226 (M+H)$^+$.

EXAMPLE 32B

N-(2-amino-1-(fluoromethyl)-2-oxoethyl)-4-methylbenzamide

Example 32B, isobutyl chloroformate, and ammonium hydroxide were processed as described in Example 26B to provide the desired product.

MS (APCI+) m/z 225 (M+H)$^+$.

EXAMPLE 32C

N-(1-amino-2-fluoroethyl)-4-methylbenzamide Hydrochloride

Example 32B and iodobenzene diacetate were processed as described in Example 22E to provide the desired product.

MS (APCI+) m/z 197 (M+H)$^+$.

EXAMPLE 32D

N-(2-fluoro-1-{[(3-nitroanilino)carbothioyl]amino}ethyl)-4-methylbenzamide

Example 32C and 3-nitrophenyl isothiocyanate were processed as described in Example 22F to provide the desired product.

mp 148–155° C.;

MS (APCI+) m/z 377 (M+H)$^+$;

$^1$H NMR (DMSO-d$_6$) δ 10.35 (s, 1H), 9.06 (s, 1H), 8.70 (d, 1H, J=9 Hz), 8.81 (br s, 1H), 7.96 (d, 2H, J=9 Hz), 7.90–7.78 (m, 3H), 7.60 (t, 1H, J=9 Hz),), 7.31 (d, H, J=9 Hz), 6.35 (m, 2H), 4.76 (d, 1H, J=7 Hz), 4.60 (d, 1H, J=7 Hz), 2.38 (s, 3H);

Anal. calcd for C$_{17}$H$_{17}$FN$_4$O$_3$S: C, 54.25; H, 4.55; N, 14.88. Found: C, 54.36; H, 4.59; N, 14.57.

EXAMPLE 33

4-methyl-N-[{[(3-nitroanilino)carbothioyl]amino}(phenyl)methyl]benzamide

EXAMPLE 33A 2-((4-methylbenzoyl)amino)-2-phenylacetic Acid

Racemic phenylglycine and p-toluoyl chloride were processed as described in Example 26A to provide the desired product.

MS (APCI+) m/z 270 (M+H)$^+$.

EXAMPLE 33B

N-(2-amino-2-oxo-1-phenylethyl)-4-methylbenzamide

Example 33A, isobutyl chloroformate, and ammonium hydroxide were processed as described in Example 26B to provide the desired product.

MS (APCI+) m/z 269 (M+H)$^+$.

EXAMPLE 33C

N-(amino(phenyl)methyl)-4-methylbenzamide Hydrochloride

Example 33B and iodobenzene diacetate were processed as described in Example 22E to provide the desired product.

MS (APCI+) m/z 241 (M+H)$^+$.

EXAMPLE 33D 4-methyl-N-[{[(3-nitroanilino)carbothioyl]amino}(phenyl)methyl]benzamide Example 33C and 3-nitrophenyl isothiocyanate were processed as described in Example 22F to provide the desired product.

mp 170–172° C.;

MS (APCI+) m/z 421 (M+H)$^+$;

$^1$H NMR (DMSO-d$_6$) δ 10.44 (s, 1H), 9.45 (d, 1H, J=8 Hz), 8.80 (s, 1H), 8.67 (d, 1H, J=8 Hz), 7.96 (dd, J=8, 4, 1H), 7.90 (dd, J=8, 4, 1H), 7.83 (d, 2H, J=8 Hz), 7.62 (t, 1H, J=8 Hz), 7.48–7.36 (m, 4H), 7.35–7.25 (m, 4H), 2.38 (s, 3H);

Anal. calcd for C$_{22}$H$_{20}$N$_4$O$_3$S.0.4 H$_2$O: C, 61.78; H, 4.90; N, 13.10. Found: C, 61.49; H, 4.72; N, 13.21.

EXAMPLE 34

4-methyl-N-(phenyl{[(3-pyridinylamino)carbothioyl]amino}methyl)benzamide

Example 33C and 3-pyridyl isothiocyanate were processed as described in Example 22F to provide the desired product.

mp 156–158° C.;

MS (ESI+) m/z 357 (M+H)$^+$;

$^1$H NMR (DMSO-d$_6$) δ 8.04 (m, 2H), 7.84–7.73 (m, 3H), 7.50 (br s, 1H), 7.43–7.39 (m, 1H), 7.29–7.21 (m, 3H), 7.22–7.13 (m, 5H), 7.05 (br s, 1H), 4.63 (t, 1H, J=9 Hz), 2.38 (s, 3H);

Anal. calcd for C$_{21}$H$_{20}$N$_4$OS: C, 67.00; H, 5.35; N, 14.88. Found: C, 66.87; H, 5.38; N, 14.81.

EXAMPLE 35

4-methyl-N-(2-methyl-1-{[(3-pyridinylamino)carbothioyl]amino}propyl)benzamide

EXAMPLE 35A

N-(4-methylbenzoyl)valine

Racemic valine and p-toluoyl chloride were processed as described in Example 26A to provide the desired product.

MS (APCI+) m/z 236 (M+H)$^+$.

EXAMPLE 35B

N-(1-(aminocarbonyl)-2-methylpropyl)-4-methylbenzamide

Example 35A, isobutyl chloroformate, and ammonium hydroxide were processed as described in Example 26B to provide the desired product.

MS (APCI+) m/z 235 (M+H)$^+$.

EXAMPLE 35C

N-(1-amino-2-methylpropyl)-4-methylbenzamide Hydrochloride

Example 35B and iodobenzene diacetate were processed as described in Example 22E to provide the desired product.

MS (APCI+) m/z 207 (M+H)$^+$.

EXAMPLE 35D 4-methyl-N-(2-methyl-1-{[(3-pyridinylamino)carbothioyl]amino}propyl)benzamide Example 35C and 3-pyridyl isothiocyanate were processed as described in Example 22F to provide the desired product.

mp 184–186° C.;

MS (ESI+) m/z 343 (M+H)$^+$;

$^1$H NMR (DMSO-d$_6$) δ 8.05 (m, 2H), 7.86–7.74 (m, 3H), 7.48 (br s, 1H), 7.43–7.36 (m, 1H), 7.30–7.22 (m, 3H), 7.05 (br s, 1H), 4.25 (t, 1H, J=9 Hz), 2.38 (s, 3H), 2.17–2.08 (m, 1H), 1.04–0.91 (m, 6H);

Anal. calcd for C$_{18}$H$_{22}$N$_4$OS: C, 63.13; H, 6.48; N, 16.36. Found: C, 63.35; H, 6.38; N, 16.47.

EXAMPLE 36

4-methyl-N-((1R,2S)-2-methyl-1-{[(3-pyridinylamino)carbothioyl]amino}butyl)benzamide

EXAMPLE 36A (2R,3R)-3-methyl-2-((4-methylbenzoyl)amino)pentanoic Acid (L)-Isoleucine and p-toluoyl chloride were processed as described in Example 26A to provide the desired product.

MS (APCI+) m/z 250 (M+H)$^+$.

EXAMPLE 36B

N-((1R,2R)-1-(aminocarbonyl)-2-methylbutyl)-4-methylbenzamide

Example 36B, isobutyl chloroformate, and ammonium hydroxide were processed as described in Example 26B to provide the desired product.

MS (APCI+) m/z 249 (M+H)$^+$.

EXAMPLE 36C

N-((1R,2R)-1-amino-2-methylbutyl)-4-methylbenzamide Hydrochloride

Example 36B and iodobenzene diacetate were processed as described in Example 22E to provide the desired product.

MS (APCI+) m/z 221 (M+H)$^+$.

EXAMPLE 36D 4-methyl-N-((1R,2S)-2-methyl-1-{[(3-pyridinylamino)carbothioyl]amino}butyl)benzamide Example 36C and 3-pyridyl isothiocyanate were processed as described in Example 22F to provide the desired product.

mp 102–104° C.;

MS (ESI+) m/z 357 (M+H)$^+$;

$^1$H NMR (DMSO-d$_6$) δ 10.05 (s, 1H), 8.62 (s, 1H), 8.30 (d, 1H, J=3 Hz), 8.11–8.07 (m, 2H), 7.88 (br s, 1H), 7.75 (d, 2H, J=9 Hz), 7.39–7.33 (m, 1H), 7.25 (d, 2H, J=9 Hz), 6.10 (br s, 1H), 2.38 (s, 3H), 2.15–2.10 (m, 1H), 1.55–1.51 (m, 1H), 1.26–1.18 (m, 1H), 0.96–0.89 (m, 6H);

Anal. calcd for C$_{19}$H$_{24}$N$_4$OS: C, 64.02; H, 6.79; N, 15.72. Found: C, 64.24; H, 6.74; N, 15.41.

EXAMPLE 37

4-methyl-N-{2,2,2-trichloro-1-[3-(3-fluorophenyl)-2-thioxo-1-imidazolidinyl]ethyl}benzamide

EXAMPLE 37A

N-(3-fluorophenyl)-1,2-ethanediamine Monohydrochloride

Equimolar quantities (45.7 mmol) of 2-oxazolidinone and 3-fluoroaniline hydrochloride were combined, heated to 165° C., and stirred for 18 hours. The dark-colored mixture was allowed to cool to ambient temperature and treated with ethanol (125 mL). The suspension was heated to reflux for 1 hour, allowed to cool to ambient temperature, treated with diethyl ether (125 mL), and the suspension was cooled to 0° C. for 2 hours. Filtration provided 5.53 g of the desired product as colorless crystals which were used without further purification.

MS (ESI+) m/z 155 (M+H)$^+$.

EXAMPLE 37B

N-(3-fluorophenyl)-2-imidazolinethione

A suspension of Example 37A (3.70 g, 19.5 mmol), in CH$_2$Cl$_2$ (50 mL) at ambient temperature was treated with triethylamine (4.5 mL). The reaction was treated with 1,1'-thiocarbonyldiimidazole (3.86 g, 19.5 mmol) and allowed to proceed for 1 hour at ambient temperature. The reaction mixture was poured into 2 N HCl (100 mL), and the aqueous phase was extracted with $CH_2Cl_2$ (2×25 mL). The combined organic extracts were washed with brine (25 mL), dried over anhydrous $Na_2SO_4$, filtered, and the solvent was removed in vacuo. Trituration with ether provided 3.14 g of the pure desired product as colorless crystals.

MS (ESI+) m/z 197 (M+H)$^+$.

EXAMPLE 37C 4-methyl-N-(2,2,2-trichloro-1-hydroxyethyl) benzamide

A mixture of p-toluamide (11.0 g, 81.3 mmol) and 2,2,2-trichloro-1,1-ethanediol (16.6 g, 100 mmol) in benzene (175 mL) was stirred at reflux in a Soxhlet extraction device charged with molecular sieves (20 g). After 12 hours, the extraction thimble of molecular sieves was replaced with a fresh portion of molecular sieves (20 g), and the reaction was allowed to heat at reflux for an additional 12 hours. Concentration in vacuo provided a heavy syrup which was dissolved in ethyl acetate (15 mL) and diluted with hexanes (175 mL). Refrigeration at 8° C. facilitated precipitation of a white solid that was collected by filtration and washed with hexanes to provide 20.2 g of the desired product.

MS (APCI+) m/z 264 (M–$H_2O$)$^+$.

EXAMPLE 37D 4-methyl-N-(1,2,2,2-tetrachloroethyl)benzamide

A stirred solution of Example 37C (20.0 g, 70.8 mmol) in $CH_2Cl_2$ (300 mL) at 0° C. was treated with pyridine (10 mL). The reaction mixture was treated dropwise with thionyl chloride (10.4 mL, 141 mmol), and the reaction flask was equipped with a calcium chloride drying tube. The reaction mixture was warmed to ambient temperature and stirred for 4 hours. Concentration of the reaction mixture to a reduced volume and addition of diethyl ether (100 mL) resulted in a precipitate which was filtered off, and the filtrate was concentrated and dried under reduced pressure to provide 19.0 g of the desired product as a white solid.

MS (APCI+) m/z 300 (M+H)$^+$.

EXAMPLE 37E 4-methyl-N-{2,2,2-trichloro-1-[3-(3-fluorophenyl)-2-thioxo-1-imidazolidinyl]ethyl}benzamide A solution of Example 37B (0.460 g, 2.35 mmol) in DMF (10 mL) was treated with solid potassium bis(trimethylsilyl) amide (0.470 g, 2.35 mmol). The reaction was stirred at ambient temperature for 15 minutes, treated with Example 37D (0.710 g, 2.35 mmol), allowed to proceed for 16 hours, diluted with ethyl acetate (30 mL), and poured into 2 N HCl (15 mL). The aqueous phase was extracted with ethyl acetate (2×5 mL), and the combined organic extracts were washed with brine (25 mL), dried ($Na_2SO_4$), filtered, and evaporated in vacuo. Purification by flash chromatography (elution with 50% ethyl acetate/hexanes) provided 460 mg of the desired product as a white powder.

mp 184–186° C.;

MS (ESI+) m/z 460 (M+H)$^+$;

$^1$H NMR (DMSO-$d_6$) δ 9.30 (d, 1H, J=10 Hz), 7.95 (d, 1H, J=10 Hz), 7.81 (d, 2H, J=8 Hz), 7.64–7.57 (m, 1H), 7.50–7.40 (m, 3H), 7.35 (d, 2H, J=8 Hz), 7.13–7.06 (m, 1H), 4.28–4.01 (m, 4H), 2.39 (s, 3H);

Anal. calcd for $C_{19}H_{17}Cl_3FN_3OS$: C, 49.53; H, 3.72; N, 9.12. Found: C, 49.21; H, 3.88; N, 8.97.

EXAMPLE 38

4-methyl-N-(2,2,2-trichloro-1-{[(3-pyridinylamino) carbonyl]amino}ethyl)benzamide

EXAMPLE 38A

N-(1-amino-2,2,2-trichloroethyl)-4-methylbenzamide

Diethyl ether (250 mL) was placed in a 500 mL three-necked round-bottom flask fitted with a gas dispersion tube, dropping funnel, and stirrer. The solvent was cooled to 0° C., and dry ammonia was passed into the solution for 10 minutes. While the ammonia was allowed to continue to pass through the solution, it was treated dropwise with Example 37D (9.50 g, 31.6 mmol) in diethyl ether (50 mL) for 30 minutes. The white solid that formed was removed by filtration and washed with diethyl ether. The combined filtrates were concentrated to provide 9.18 g of the desired product as a white solid.

MS (APCI+) m/z 281 (M+H)$^+$.

EXAMPLE 38B 4-methyl-N-(2,2,2-trichloro-1-(((3-pyridinylamino) carbothioyl)amino)ethyl)benzamide Example 38A (500 mg, 2.79 mmol) and 3-pyridyl isothiocyanate (335 mg, 2.79 mmol) were dissolved in $CH_2Cl_2$ (15 mL) and heated at 60° C. for 10 hours. The reaction was cooled and concentrated to provide a residue that was purified by flash chromatography (elution with 20% ethyl acetate/hexanes) to provide 396 mg of the desired product as an off-white solid.

MS (APCI+) m/z 417 (M+H)$^+$.

EXAMPLE 38C 4-methyl-N-(2,2,2-trichloro-1-{[(3-pyridinylamino) carbonyl]amino}ethyl)benzamide A solution of Example 38B (250 mg, 0.200 mmol) in glacial acetic acid (4 mL) at ambient temperature was treated slowly with acetic acid (6 mL) containing 30% hydrogen peroxide (4 mL), and the reaction was stirred for 30 minutes. The precipitate which formed was filtered off, washed with water, and crystallized from ethanol. The salt was dissolved in ethyl acetate and neutralized with saturated aqueous sodium carbonate solution. The organic solution was washed with brine (5 mL), dried ($Na_2SO_4$), and concentrated to provide a white solid. Recrystallization from ethanol/diethyl ether provided 71 mg of the desired product as a white solid.

mp 162–163° C.;

MS (ESI+) m/z 401 (M)$^+$;

$^1$H NMR (DMSO-$d_6$) δ 9.60 (s, 1H), 9.20 (d, 1H, J=9 Hz), 8.68 (s, 1H), 8.22 (d, 1H, J=6 Hz), 7.98 (d, 1H, J=9 Hz), 7.78 (d, 2H, J=9 Hz), 7.38 (q, 1H, J=3 Hz), 7.32 (d, 2H, J=9 Hz), 7.12 (d, 1H, J=9 Hz), 6.75 (t, 1H, J=9 Hz), 2.38 (s, 3H);

Anal. calcd for $C_{16}H_{15}Cl_3N_4O_2$: C, 47.84; H, 3.76; N, 13.95. Found: C, 47.81; H, 3.67; N, 13.62.

EXAMPLE 39

2-methyl-N-(2,2,2-trichloro-1-{[(3-pyridinylamino) carbonyl]amino}ethyl)benzamide

EXAMPLE 39A 2-methyl-N-(2,2,2-trichloro-1-hydroxyethyl) benzamide 2,2,2-Trichloro-1,1-ethanediol and o-toluamide were processed as described in Example 37C to provide the desired product.

MS (APCI+) m/z 263 (M–$H_2O$)$^+$.

EXAMPLE 39B 2-methyl-N-(1,2,2,2-tetrachloroethyl)benzamide

Example 39A and thionyl chloride were processed as described in Example 37D to provide the desired product.
MS (APCI+) m/z 300 (M+H)+.

EXAMPLE 39C

N-(1-amino-2,2,2-trichloroethyl)-2-methylbenzamide

Example 39B and ammonia were processed as described in Example 38A to provide the desired product.
MS (APCI+) m/z 281 (M+H)+.

EXAMPLE 39D 2-methyl-N-(2,2,2-trichloro-1-(((3-pyridinylamino)carbothioyl)amino)ethyl)benzamide Example 39C and 3-pyridyl isothiocyanate were processed as described in Example 38B to provide the desired product.
MS (APCI+) m/z 417 (M+H)+.

EXAMPLE 39E 2-methyl-N-(2,2,2-trichloro-1-{[(3-pyridinylamino)carbonyl]amino}ethyl)benzamide Example 39D and hydrogen peroxide were processed as described in Example 38C to provide the desired product.
mp 182–184° C.;
MS (APCI+) m/z 402 (M+H)+;
$^1$H NMR (DMSO-$d_6$) δ 9.38 (s, 1H), 8.95 (s, 1H), 8.55 (s, 1H), 8.20 (d, 1H, J=6 Hz), 7.93–7.88 (m, 1H), 7.68 (d, 2H, J=3 Hz), 7.44–7.28 (m, 4H), 6.72 (t, 1H, J=9 Hz), 2.37 (s, 3H);
Anal. calcd for $C_{16}H_{15}Cl_3N_4O_2$: C, 47.84; H, 3.76; N, 13.95. Found: C, 47.68; H, 3.52; N, 13.59.

EXAMPLE 40

N-(2,2,2-trichloro-1-{[(3-pyridinylamino)carbonyl]amino}ethyl)benzamide

EXAMPLE 40A

N-(2,2,2-trichloro-1-hydroxyethyl)benzamide 2,2,2-Trichloro-1,1-ethanediol and benzamide were processed as described in Example 37C to provide the desired product.
MS (APCI+) m/z 245 (M–H$_2$O)+.

EXAMPLE 40B

N-(1,2,2,2-tetrachloroethyl)benzamide

Example 40A and thionyl chloride were processed as described in Example 37D to provide the desired product.
MS (APCI+) m/z 286 (M+H)+.

EXAMPLE 40C

N-(1-amino-2,2,2-trichloroethyl)benzamide

Example 40B and ammonia were processed as described in Example 38A to provide the desired product.
MS (APCI+) m/z 267 (M+H)+.

EXAMPLE 40D

N-(2,2,2-trichloro-1-(((3-pyridinylamino)carbothioyl)amino)ethyl)benzamide

Example 40C and 3-pyridyl isothiocyanate were processed as described in Example 38B to provide the desired product.
MS (APCI+) m/z 403 (M+H)+.

EXAMPLE 40E

N-(2,2,2-trichloro-1-{[(3-pyridinylamino)carbonyl]amino}ethyl)benzamide

Example 40D and hydrogen peroxide were processed as described in Example 38C to provide the desired product.
mp 214–215° C.;
MS (ESI+) m/z 388 (M+H)+;
$^1$H NMR (DMSO-$d_6$) δ 9.48 (s, 1H), 9.32 (d, 1H, J=9 Hz), 8.55 (d, 1H, J=3 Hz), 8.20 (dd, 1H, J=6, 3 Hz), 7.95–7.89 (m, 1H), 7.85 (d, 2H, J=9 Hz), 7.64–7.59 (m, 1H), 7.52 (t, 2H, J=9 Hz), 7.32 (q, 1H, J=3 Hz), 7.10 (d, 1H, J=9 Hz), 6.75 (t, 1H, J=9 Hz);
Anal. calcd for $C_{15}H_{13}Cl_3N_4O_2$: C, 46.48; H, 3.38; N, 14.45. Found: C, 46.24; H, 3.41; N, 14.41.

EXAMPLE 41

4-chloro-N-(2,2,2-trichloro-1-{[(3-pyridinylamino)carbonyl]amino}ethyl)benzamide

EXAMPLE 41A 4-chloro-N-(2,2,2-trichloro-1-hydroxyethyl)benzamide 2,2,2-Trichloro-1,1-ethanediol and 4-chlorobenzamide were processed as described in Example 37C to provide the desired product.
MS (APCI+) m/z 283 (M–H$_2$O)+.

EXAMPLE 41B 4-chloro-N-(1,2,2,2-tetrachloroethyl)benzamide

Example 41A and thionyl chloride were processed as described in Example 37D to provide the desired product.
MS (APCI+) m/z 320 (M+H)+.

EXAMPLE 41C

N-(1-amino-2,2,2-trichloroethyl)-4-chlorobenzamide

Example 41B and ammonia were processed as described in Example 38A to provide the desired product.
MS (APCI+) m/z 301 (M+H)+.

EXAMPLE 41D 4-chloro-N-(2,2,2-trichloro-1-(((3-pyridinylamino)carbothioyl)amino)ethyl)benzamide Example 41C and 3-pyridyl isothiocyanate were processed as described in Example 38B to provide the desired product.
MS (APCI+) m/z 437 (M+H)+.

EXAMPLE 41E 4-chloro-N-(2,2,2-trichloro-1-{[(3-pyridinylamino)carbonyl]amino}ethyl)benzamide Example 41D and hydrogen peroxide were processed as described in Example 38C to provide the desired product.

mp 166–168° C.;

MS (ESI+) m/z 423 (M+H)$^+$;

$^1$H NMR (DMSO-d$_6$) δ 9.45 (s, 1H), 8.62 (s, 1H), 8.20 (d, 1H, J=6 Hz), 7.98–7.80 (m, 4H), 7.65–7.59 (m, 2H), 7.52 (d, 1H, J=9 Hz), 7.30 (q, 1H, J=3 Hz), 7.10 (d, 1H, J=9 Hz), 6.75 (t, 1H, J=9 Hz);

Anal. calcd for $C_{15}H_{12}Cl_4N_4O_2$: C, 42.68; H, 2.87; N, 13.27. Found: C, 42.56; H, 2.67; N, 13.25.

EXAMPLE 42

N-{1-[(anilinocarbonyl)amino]-2,2,2-trichloroethyl}-4-methylbenzamide

A solution of Example 38A (183 mg, 0.650 mmol) and phenyl isocyanate (77 mg, 0.65 mmol) in THF (4 mL) at ambient temperature was treated with triethylamine (0.93 mL, 0.66 mmol). The mixture was stirred for 10 hours, diluted with ethyl acetate (20 mL), and washed with aqueous NH$_4$Cl (10 mL), water (10 mL), and brine (5 mL). The organic portion was dried (MgSO$_4$), filtered, and concentrated to provide an oily residue which was purified by flash chromatography (elution with 5% methanol/CH$_2$Cl$_2$) to provide 151 mg of the desired product as an off-white solid.

mp 230–233° C.;

MS (ESI+) m/z 400 (M)$^+$;

$^1$H NMR(DMSO-d$_6$) δ 9.35 (s, 1H), 9.25 (d, 1H, J=9 Hz), 7.80 (d, 2H, J=9 Hz), 7.45 (d, 2H, J=9 Hz), 7.32 (d, 2H, J=9 Hz), 7.25 (q, 3H, J=7 Hz), 6.95 (t, 1H, J=7 Hz), 6.75 (t, 1H, J=9 Hz), 2.45 (s, 3H);

Anal. calcd for $C_{17}H_{16}Cl_3N_3O_2$: C, 50.96; H, 4.02; N, 10.49. Found: C, 50.66; H, 3.99; N, 10.38.

EXAMPLE 43

4-methyl-N-(2,2,2-trichloro-1-{[(2-fluoroanilino)carbonyl]amino}ethyl)benzamide

EXAMPLE 43A 4-methyl-N-(2,2,2-trichloro-1-isocyanatoethyl)benzamide

A stirred solution of Example 37D (1.00 g, 3.32.00 mmol) in acetone (20 mL) at ambient temperature was treated with potassium cyanate (1.60 g, 16.0 mmol). The reaction mixture was stirred for 12 hours, concentrated, and the crude residue was purified by flash chromatography (elution with 50% ethyl acetate/hexanes) to provide 620 mg of the desired product as an off-white solid.

MS (APCI+) m/z 307 (M+H)$^+$.

EXAMPLE 43B 4-methyl-N-(2,2,2-trichloro-1-{[(2-fluoroanilino)carbonyl]amino}ethyl)benzamide A solution of 2-fluoroaniline (132 mg, 1.40 mmol) in THF (8 mL) at ambient temperature was treated with a solution of Example 43A (386 mg, 1.26 mmol) in THF (1.5 mL). The reaction mixture was stirred for 2 hours and concentrated to a nominal volume. The white solids which precipitated from solution were collected by filtration and washed with diethyl ether. Recrystallization from 25% ethyl acetate/hexanes provided the desired product as a white solid.

mp 257–259° C.;

MS (APCI+) m/z 418 (M+H)$^+$;

$^1$H NMR (DMSO-d$_6$) δ 9.32–9.29 (d, 1H, J=9 Hz), 9.14 (br s, 1H), 8.12–8.06 (t, 1H, J=8 Hz), 7.81 (d, 2H, J=8 Hz), 7.55 (d, 1H, J=10 Hz), 7.30 (d, 2H, J=8 Hz), 7.25–7.18 (m, 1H), 7.11 (t, 1H, J=7 Hz), 7.03–6.96 (m, 1H), 6.78 (t, 1H, J=9 Hz), 2.37 (s, 3H);

Anal. calcd for $C_{17}H_{15}Cl_3FN_3O_2$: C, 48.77; H, 3.61; N, 10.04. Found: C, 48.76; H, 3.53; N, 9.97.

EXAMPLE 44

4-methyl-N-(2,2,2-trichloro-1-{[(cyanoimino)(3-pyridinylamino)methyl]amino}ethyl)benzamide

EXAMPLE 44A

N-cyano-N'-(3-pyridinyl)thiourea

A solution of cyanamide (352 mg, 8.40 mmol) in THF (20 mL) at 0° C. was treated with sodium hydride (211 mg of 95% reagent, 8.80 mmol). The slurry was stirred for 30 minutes at 0° C. and treated with a solution of 3-pyridyl isothiocyanate (1.12 g, 8.20 mmol) in THF (8 mL). The cooling bath was removed, and the reaction mixture was stirred for 30 minutes. The reaction was quenched with water (15 mL), poured into ethyl acetate (40 mL), and partitioned. The organic phase was washed with brine (10 mL), dried (Na$_2$SO$_4$), filtered, and concentrated. The residue was dissolved in diethyl ether, treated with HCl (2M solution in diethyl ether), and the resulting precipitate was collected providing 1.06 g of the desired product as an off-white solid.

MS (APCI+) m/z 179 (M+H)$^+$.

EXAMPLE 44B 4-methyl-N-(2,2,2-trichloro-1-{[(cyanoimino)(3-pyridinylamino)methyl]amino}ethyl)benzamide A solution of Example 44A (200 mg, 0.932 mmol) in DMF (7 mL) at 23° C. was treated with EDCI (250 mg, 1.30 mmol) followed by diisopropyethylamine (0.180 mL, 1.03 mmol). The mixture was stirred for 30 minutes, then treated with a solution of Example 38A (262 mg, 0.932 mmol) as a solution in DMF (2 mL) along with additonal diisopropyethylamine (0.360 mL, 2.06 mmol). The solution was stirred for 10 hours, poured into ethyl acetate (25 mL), and washed with water (25 mL). The aqueous layer was extracted with ethyl acetate (20 mL), and the combined organic portions were washed with water (3×20 mL) and brine (20 mL). The organic portion was dried (Na$_2$SO$_4$), filtered, and concentrated. Purification of the residue by flash chromatography (elution with 5% ethanol/hexanes) provided 146 mg of the desired product as an off-white solid.

mp 165–166° C.;

MS (ESI+) m/z 425 (M)$^+$;

$^1$H NMR (DMSO-d$_6$) δ 10.15 (s, 1H), 8.70 (d, 1H, J=9 Hz), 8.52 (d, 1H, J=3 Hz), 8.48–8.43 (m, 1H), 7.72 (d, 1H, J=9 Hz), 7.70–7.66 (m, 1H), 7.50 (q, 1H, J=4 Hz), 7.45 (d, 2H, J=9 Hz), 7.35 (d, 1H, J=9 Hz), 6.90 (t, 1H, J=9 Hz), 2.38 (s, 3H);

Anal. calcd for $C_{17}H_{15}N_6Cl_3O$: C, 47.96; H, 3.55; N, 19.74. Found: C, 47.72; H, 3.82; N, 19.71.

EXAMPLE 45

4-chloro-N-(2,2,2-trichloro-1-{[(cyanoimino)(3-pyridinylamino)methyl]amino}ethyl)benzamide

EXAMPLE 45A 4-chloro-N-(2,2,2-trichloro-1-isothiocyanatoethyl)benzamide

A solution of Example 41B (1.91 g, 6.31 mmol) in acetone (30 mL) at ambient temperature was treated with potassium thiocyanate (1.38 g, 14.1 mmol). The mixture was stirred for 6 hours and solids were removed by filtration. The filtrate was concentrated to provide a yellow residue. The residue was treated with diethyl ether, and the suspension was sonicated and filtered. Concentration of the residue and purification by recrystallization (25% ethyl acetate/hexanes) provided 1.85 mg of the desired product as a yellow solid.

MS (APCI+) m/z 343 (M+H)$^+$.

EXAMPLE 45B 4-chloro-N-(2,2,2-trichloro-1-(((3-pyridinylamino)carbothioyl)amino)ethyl)benzamide A solution of Example 45A (239mg, 0.695 mmol) and 3-aminopyridine (65 mg, 0.69 mmol) in THF (4 mL) at ambient temperature was treated with triethylamine (1.66 mL, 1.18 mmol). The mixture was stirred for 3 hours, diluted with ethyl acetate (20 mL), and washed with water (2×10 mL) and brine (10 mL). The organic portion was dried (MgSO$_4$), filtered, and concentrated to provide an oily residue which was purified by flash chromatography (elution with 5% ethanol/hexanes) to provide 158 mg of the desired product as an off-white solid.

MS (APCI+) m/z 437 (M+H)$^+$.

EXAMPLE 45C 4-chloro-N-(2,2,2-trichloro-1-{[(cyanoimino)(3-pyridinylamino)methyl]amino}ethyl)benzamide A stirred solution of Example 45B (500 mg, 1.14 mmol) and EDCI (656 mg, 3.42 mmol) in CH$_2$Cl$_2$ (10 ml) was heated at reflux for 10 hours. The mixture was cooled and was diluted with ethyl acetate (20 mL). The solution was washed with aqueous NaHCO$_3$ solution (10 mL) and brine (10 mL), dried (MgSO$_4$), filtered, and concentrated. The residue was dissolved in 5% ethanol/ethyl acetate and filtered through a short plug of silica gel. Concentration provided 440 mg of a pale yellow solid that was used without further purification.

The solid prepared above was dissolved in CH$_2$Cl$_2$ (10 mL), then treated with 2,6-lutidine (0.120 mL, 1.00 mmol), 3 A molecular sieves (200 mg), and cyanamide (208 mg, 4.99 mmol). This stirred suspension was treated with titanium isopropoxide (0.300 mL, 1.00 mmol), and the resulting mixture was heated at reflux for 8 hours. The mixture was cooled, diluted with CH$_2$Cl$_2$ (20 mL), and washed with water (10 mL) and brine (10 mL). The solution was dried (Na$_2$SO$_4$), filtered, and concentrated. The resulting residue was purified by flash chromatography (elution with 10% methanol/CH$_2$Cl$_2$) to provide 229 mg of the desired product as a white solid.

mp 126–128° C.;

MS (ESI+) m/z 426 (M+H)$^+$;

$^1$H NMR (DMSO-d$_6$) δ 10.12 (s, 1H), 8.72 (d, 1H, J=9 Hz), 8.50 (dd, 1H, J=12, 3 Hz), 7.70–7.67 (m, 1H), 7.51 (q, 1H, J=6 Hz), 7.45–7.38 (m, 1H), 7.30 (d, 1H, J=9 Hz), 6.82 (t, 1H, J=9 Hz), 2.38 (s, 3H);

Anal. calcd for C$_{17}$H$_{15}$Cl$_3$N$_6$O: C, 47.96; H, 3.55; N, 19.74. Found: C, 47.62; H, 3.25; N, 19.84.

EXAMPLE 46

N-(1-{[anilino(cyanoimino)methyl]amino}-2,2,2-trichloroethyl)-4-methylbenzamide

EXAMPLE 46A 4-methyl-N-(2,2,2-trichloro-1-isothiocyanatoethyl)benzamide

Example 37D and potassium thiocyanate were processed as described in Example 45A to provide the desired product.

MS (APCI+) m/z 323 (M+H)$^+$.

EXAMPLE 46B 4-methyl-N-(2,2,2-trichloro-1-(((3-pyridinylamino)carbothioyl)amino)ethyl)benzamide Example 46A and 3-aminopyridine were processed as described in Example 45B to provide the desired product.

MS (APCI+) m/z 417 (M+H)$^+$.

EXAMPLE 46C

N-(1-{[anilino(cyanoimino)methyl]amino}-2,2,2-trichloroethyl)-4-methylbenzamide

Example 46B, cyanamide, and titanium isopropoxide were processed as described in Example 45C to provide the desired product.

mp 197–199° C.;

MS (ESI+) m/z 424 (M)$^+$;

$^1$H NMR (DMSO-d$_6$) δ 9.86 (s, 1H), 8.77–8.74 (d, 1H, J=8 Hz), 7.72–7.70 (d, 2H, J=8 Hz), 7.49–7.44 (m, 2H), 7.34–7.26 (m, 5H), 6.94–6.88 (t, 1H, J=9 Hz), 2.36 (s, 3H);

Anal. calcd for C$_{18}$H$_{16}$Cl$_3$N$_5$O: C, 50.90; H, 3.80; N, 16.49. Found: C, 50.87; H, 3.78; N, 16.51.

EXAMPLE 47

4-methyl-N-(2,2,2-trichloro-1-{[(cyanoimino)(2-fluoroanilino)methyl]amino}ethyl)benzamide

EXAMPLE 47A 4-methyl-N-(2,2,2-trichloro-1-(((2-fluoroanilino)carbothioyl)amino)ethyl)benzamide Example 46A and 3-fluoroaniline were processed as described in Example 45B to provide the desired product.

MS (APCI+) m/z 434 (M+H)$^+$.

EXAMPLE 47B 4-methyl-N-(2,2,2-trichloro-1-{[(cyanoimino)(2-fluoroanilino)methyl]amino}ethyl)benzamide Example 47A, cyanamide, and titanium isopropoxide were processed as described in Example 45C to provide the desired product.

mp 220–222° C.;

MS (APCI+) m/z 442 (M+H)$^+$;

$^1$H NMR (DMSO-d$_6$) δ 9.85 (s, 1H), 8.83 (d, 1H, J=8 Hz), 7.73 (d, 2H, J=8 Hz), 7.25–7.40 (m, 6H), 7.1 (br d, 1H), 6.88 (t, 1H, J=8 Hz), 2.37 (s, 3H);

Anal. calcd for $C_{18}H_{15}Cl_3FN_5O$: C, 48.83; H, 3.41; N, 15.81. Found: C, 48.63; H, 3.44; N, 15.77.

EXAMPLE 48

4-methyl-N-(2,2,2-trichloro-1-{[(cyanoimino)(5-pyrimidinylamino)methyl]amino}ethyl)benzamide

EXAMPLE 48A 4-methyl-N-(2,2,2-trichloro-1-(((5-pyrimidinylamino)carbothioyl)amino)ethyl)benzamide Example 46A and 5-aminopyrimidine were processed as described in Example 45B to provide the desired product.
MS (APCI+) m/z 418 (M+H)+.

EXAMPLE 48B 4-methyl-N-(2,2,2-trichloro-1-{[(cyanoimino)(5-pyrimidinylamino)methyl]amino}ethyl)benzamide Example 48A, cyanamide, and titanium isopropoxide were processed as described in Example 45C to provide the desired product.
mp 186–188° C.;
MS (APCI+) m/z 426 (M+H)+;
$^1$H NMR (DMSO-$d_6$) δ 10.22 (s, 1H), 9.08 (s, 1H), 8.77–8.73 (m, 2H), 7.81–7.75 (m, 3H), 7.73–7.68 (m, 1H), 7.38 (d, 2H, J=6 Hz), 6.90 (t, 1H, J=6 Hz), 2.38 (s, 3H);
Anal. calcd for $C_{16}H_{14}Cl_3N_7O$: C, 45.03; H, 3.31; N, 22.98. Found: C, 44.66; H, 3.55; N, 22.66.

EXAMPLE 49

N-(2,2,2-trichloro-1-{[(cyanoimino)(3-pyridinylamino)methyl]amino}ethyl)benzamide

EXAMPLE 49A

N-(2,2,2-trichloro-1-isothiocyanatoethyl)benzamide

Example 40B and potassium thiocyanate were processed as described in Example 45A to provide the desired product.
MS (APCI+) m/z 308 (M+H)+.

EXAMPLE 49B

N-(2,2,2-trichloro-1-(((3-pyridinylamino)carbothioyl)amino)ethyl)benzamide

Example 49A and 3-aminopyridine were processed as described in Example 45B to provide the desired product.
MS (APCI+) m/z 403 (M+H)+.

EXAMPLE 49C

N-(2,2,2-trichloro-1-{[(cyanoimino)(3-pyridinylamino)methyl]amino}ethyl)benzamide Example 49B, cyanamide, and titanium isopropoxide were processed as described in Example 45C to provide the desired product.
mp 133–135° C.;
MS (ESI+) m/z 412 (M+H)+;
$^1$H NMR (DMSO-$d_6$) δ 10.15 (s, 1H), 8.82 (d, 1H, J=9 Hz), 8.53–8.48 (m, 2H), 7.82 (d, 2H, J=9 Hz), 7.72 (d, 1H, J=6 Hz), 7.62 (d, 1H, J=6 Hz), 7.58–7.51 (m, 3H), 7.45 (d, 1H, J=6 Hz), 6.90 (t, 1H, J=9 Hz);
Anal. calcd for $C_{16}H_{13}Cl_3N_6O$: C, 46.68; H, 3.18; N, 20.41. Found: C, 46.88; H, 3.41; N, 20.43.

EXAMPLE 50

2-methyl-N-(2,2,2-trichloro-1-{[(cyanoimino)(3-pyridinylamino)methyl]amino}ethyl)benzamide

EXAMPLE 50A 2-methyl-N-(2,2,2-trichloro-1-isothiocyanatoethyl)benzamide

Example 39B and potassium thiocyanate were processed as described in Example 45A to provide the desired product.
MS (APCI+) m/z 323 (M+H)+.

EXAMPLE 50B 2-methyl-N-(2,2,2-trichloro-1-(((3-pyridinylamino)carbothioyl)amino)ethyl)benzamide Example 50A and 3-aminopyridine were processed as described in Example 45B to provide the desired product.
MS (APCI+) m/z 417 (M+H)+.

EXAMPLE 50C 2-methyl-N-(2,2,2-trichloro-1-{[(cyanoimino)(3-pyridinylamino)methyl]amino}ethyl)benzamide Example 50B, cyanamide, and titanium isopropoxide were processed as described in Example 45C to provide the desired product.
mp 126–128° C.;
MS (ESI+) m/z 426 (M+H)+;
$^1$H NMR (DMSO-$d_6$) δ 10.12 (s, 1H), 8.72 (d, 1H, J=9 Hz), 8.50 (dd, 2H, J=3; 12 Hz), 7.69–7.65 (m, 1H), ), 7.51 (q, 1H, J=6 Hz), 7.43–7.38 (m, 3H), 7.30 (d, 2H, J=9 Hz), 6.82 (t, 1H, J=9 Hz), 2.38 (s, 3H);
Anal. calcd for $C_{17}H_{15}Cl_3N_6O$: C, 47.96; H, 3.55; N, 19.74. Found: C, 47.62; H, 3.25; N, 19.84.

EXAMPLE 51

N-(1-{[(cyanoimino)(3-pyridinylamino)methyl]amino}-2,2-dimethylpropyl)-4-methylbenzamide Example 44A, Example 22E, and EDCI were processed as described in Example 44B to provide the desired product.
mp 187–188° C.;
MS (APCI+) m/z 365 (M+H)+;
$^1$H NMR (DMSO-$d_6$) δ 9.58 (s, 1H), 8.48 (d, 1H, J=3 Hz), 8.42 (d, 1H, J=3 Hz), 8.25 (d, 1H, J=9 Hz), 7.75 (d, 2H, J=9 Hz), 7.73–7.69 (m, 1H), 7.47–7.43 (m, 1H), 7.30 (d, 2H, J=9 Hz), 6.85 (d, 1H, J=9 Hz), 5.85 (t, 1H, J=9 Hz), 2.37 (s, 3H), 0.97 (s, 9H);
Anal. calcd for $C_{20}H_{24}N_6O$: C, 65.91; H, 6.64; N, 23.06. Found: C, 65.95; H, 6.59; N, 23.20.

EXAMPLE 52

4-chloro-N-(1-{[(cyanoimino)(3-pyridinylamino)methyl]amino}-2,2-dimethylpropyl)benzamide

EXAMPLE 52A

N-(1-(aminocarbonyl)-2,2-dimethylpropyl)-4-chlorobenzamide

Example 22C and 4-chlorobenzoyl chloride were processed as described in Example 22D to provide the desired product.
MS (APCI+) m/z 269 (M+H)+.

EXAMPLE 52B

N-(1-amino-2,2-dimethylpropyl)-4-chlorobenzamide Hydrochloride

Example 52A and iodobenzene diacetate were processed as described in Example 22E to provide the desired product.

MS (APCI+) m/z 241 (M+H)$^+$.

EXAMPLE 52C 4-chloro-N-(1-{[(cyanoimino)(3-pyridinylamino)methyl]amino}-2,2-dimethylpropyl)benzamide Example 52B, Example 44A, and EDCI were processed as described in Example 44B to provide the desired product.

mp 194–195° C.;

MS (APCI+) m/z 393 (M+H)$^+$;

$^1$H NMR (DMSO-d$_6$) δ 9.55 (s, 1H), 8.48 (d, 1H, J=3 Hz), 8.47–7.38 (m, 2H), 7.85 (d, 2H, J=9 Hz), 7.71–7.68 (m, 1H), 7.58 (d, 2H, J=9 Hz), 7.42 (dd, 1H, J=9, 3 Hz), 6.85 (d, 1H, J=9 Hz), 5.84 (t, 1H, J=9 Hz), 0.97 (s, 9H);

Anal. calcd for $C_{19}H_{21}ClN_6O$: C, 59.29; H, 5.50; N, 21.84. Found: C, 59.16; H, 5.53; N, 21.90.

EXAMPLE 53

N-(1-{[(cyanoimino)(3-fluoroanilino)methyl]amino}-2,2-dimethylpropyl)-4-methylbenzamide

EXAMPLE 53A

N-(1-(1H-1,2,3-benzotriazol-1-yl)-2,2-dimethylpropyl)-4-methylbenzamide

A suspension of p-toluamide (4.11 g, 30.4 mmol), pivaldehyde (2.62 g, 30.4 mmol), and benzotriazole (3.62 g, 30.4 mmol) in toluene (200 mL) were treated with p-toluenesulfonic acid (286 mg, 1.52 mmol). The solution was heated at reflux under Dean-Stark conditions for 10 hours, cooled gradually to ambient temperature, and further cooled at 5° C. The white precipitate which formed was collected by filtration and was washed with 50% ether/hexanes (100 mL) to provide 6.67 g of the desired product as a white solid.

MS (DCI/NH$_3$) m/z 323 (M+H)$^+$.

EXAMPLE 53B

N-(1-amino-2,2-dimethylpropyl)-4-methylbenzamide hydrochloride

A stirred suspension of Example 53A (13.3 g, 38.8 mmol) in methanol (50 mL) was treated with finely powdered K$_2$CO$_3$ (11.8 g, 85.4 mmol) followed by ammonia (200 mL of a 2M solution in methanol). The mixture was stirred at ambient temperature for 3.5 hours, the solid was removed by filtration, and the filtrate was concentrated. The resulting solid was suspended in diethyl ether (200 mL) and stirred for 45 minutes at ambient temperature. The mixture was again filtered, and the filtrate was concentrated to a volume of 75 mL. This solution was treated with 1N HCl (200 mL of a 1N solution in diethyl ether), and the resulting suspension was sonicated to promote salt formation. The solid was isolated by filtration and washed with ethyl acetate (2×75 mL) to provide 8.88 g of the desired product as a white solid.

MS (DCI/NH$_3$) m/z 220 (M+H)$^+$.

EXAMPLE 53C

N-cyano-N'-(3-fluorophenyl)thiourea

Cyanamide and 3-fluoroaniline were processed as described in Example 44A to provide the desired product.

MS (DCI/NH$_3$) m/z 196 (M+H)$^+$.

EXAMPLE 53D

N-(1-{[(cyanoimino)(3-fluoroanilino)methyl]amino}-2,2-dimethylpropyl)-4-methylbenzamide Example 53B, Example 53C, and EDCI were processed as described in Example 44B to provide the desired product.

mp 193–194° C.;

MS (FAB+) m/z 382 (M+H)$^+$;

$^1$H NMR (DMSO-d$_6$) δ 9.57 (s, 1H); 8.26 (d, 1H, J=9 Hz); 7.72 (d, 2H, J=8 Hz); 7.41 (dd, 1H, J=8, 4 Hz); 7.29 (d, 2H, J=8 Hz); 7.11 (t, 2H, J=7 Hz); 7.01 (t, 1H, J=8 Hz); 6.85 (d, 1H, J=4); 5.82 (t, 1H, J=5 Hz); 2.36 (s, 3H); 0.98 (s, 9H);

Anal. calcd for $C_{21}H_{24}FN_5O$·$0.25 H_2O$: C, 65.35; H, 6.40; N, 18.15. Found: C, 65.33; H, 6.40; N, 18.20.

EXAMPLE 54

4-chloro-N-[{[(cyanoimino)(3-pyridinylamino)methyl]amino}(cyclopropyl)methyl]benzamide

EXAMPLE 54A

N-(1H-1,2,3-benzotriazol-1-yl(cyclopropyl)methyl)-4-chlorobenzamide

Benzotriazole, 4-chlorobenzamide, cyclopropanecarboxaldehyde, and p-toluenesulfonic acid were processed as described in Example 53A to provide the desired product.

MS (ESI+) m/z 327 (M+H)$^+$.

EXAMPLE 54B

Methyl N'-cyano-N-(3-pyridinyl)carbamimidothioate

A suspension of 3-aminopyridine (5.16 g, 54.8 mmol) and dimethyl N-cyanodithioiminocarbonate (8.02 g, 54.8 mmol) in acetonitrile (200 mL) was heated at reflux for 6 days. The solution was cooled and concentrated to a volume of 75 mL where upon a white solid precipitated from solution. The solid was collected by filtration and washed with 50% ether/hexanes (500 mL) to provide 7.79 g of the desired product as a pale yellow solid.

MS (ESI+) m/z 193 (M+H)$^+$.

EXAMPLE 54C

N"-cyano-N-(3-pyridinyl)guanidine

Example 54B (510 mg, 2.44 mmol) was dissolved in a 2M solution of ammonia in methanol (7 mL) and heated in a sealed tube at 80° C. for 12 hours. The reaction mixture was cooled to ambient temperature and further cooled to −5° C. where upon a white solid precipitated from solution. The solid was filtered and the filter cake washed with cold ethanol to provide 310 mg of the desired product as a white solid.

MS (ESI+) m/z 162 (M+H)$^+$.

EXAMPLE 54D 4-chloro-N-[{[(cyanoimino)(3-pyridinylamino)methyl]amino}(cyclopropyl)methyl]benzamide A solution of Example 54C (50 mg, 0.27 mmol) and Example 54A (55 mg, 0.18 mmol) in DMF (2 mL) at 23° C.

was treated with finely powdered $K_2CO_3$ (62 g, 0.45 mmol). The reaction mixture was stirred for 4 hours, then partitioned between ethyl acetate (15 mL) and water (10 mL). The aqueous layer was extracted with ethyl acetate (10 mL), and the combined organics were washed with water (2×5 mL) and brine (5 mL). The organic portions were dried ($Na_2SO_4$), filtered, and concentrated. Purification by flash chromatography (elution with 5% methanol/$CH_2Cl$) provided 21 mg of the desired product as a white solid.

mp 137–139° C.;

MS (ESI+) m/z 369 (M+H)$^+$;

$^1$H NMR (DMSO-$d_6$) δ 9.57 (s, 1H), 9.16 (d, 1H, J=7 Hz), 8.47 (d, 1H, J=3 Hz), 8.31 (dd, 1H, J=4, 1 Hz), 7.92 (d, 2H, J=8 Hz), 7.79–7.73 (m, 1H), 7.69 (d, 1H, J=8 Hz), 7.59 (d, 2H, J=8 Hz), 7.37 (dd, 1H, J=8, 5 Hz), 5.16 (dd, 1H, J=16, 8 Hz), 1.56–1.50 (m, 1H), 0.57–0.50 (m, 2H), 0.44–0.38 (m, 1H);

Anal. calcd for $C_{18}H_{17}ClN_6O$: C, 58.62; H, 4.65; N, 22.79. Found: C, 58.41; H, 4.88; N, 22.44.

EXAMPLE 55

N-(1-{[[(6-chloro-3-pyridinyl)amino](cyanoimino)methyl]amino}-2,2-dimethylpropyl)-4-methylbenzamide

EXAMPLE 55A 2-chloro-5-isothiocyanatopyridine

A solution of thiophosgene (3.21 mL, 42.1 mmol) in chloroform (10 mL) was heated at reflux and treated with a solution of 5amino-2-chloropyridine (3.61 g, 28.1 mmol) in chloroform (25 mL) for 40 minutes. The solution was heated an additional 2 hours, the reaction mixture was cooled, and the solids formed were removed by filtration. Concentration of the filtrate provided 2.73 g of the desired product as a white solid.

MS (DCI/$NH_3$) m/z 188 (M+$NH_4$)$^+$.

EXAMPLE 55B

Methyl N-(6-chloro-3-pyridinyl)-N'-cyanocarbamimidothioate

A solution of cyanamide (705 mg, 16.8 mmol) in THF (40 mL) at 0° C. was treated with sodium hydride (422 mg of 95% reagent, 17.6 mmol). The slurry was stirred for 30 minutes at 0° C., then treated with Example 55A (2.72 g, 16.0 mmol) as a solution in THF (20 mL) for 10 minutes. The cooling bath was removed, the reaction mixture was stirred for 30 minutes, and treated with methyl iodide (2.00 mL, 32.0 mmol). The reaction mixture was stirred for 15 minutes, quenched with water (50 mL), poured into ethyl acetate (150 mL), and partitioned. The organic phase was washed with brine (20 mL), dried ($Na_2SO_4$), filtered, and concentrated. The resulting precipitate was collected providing 3.24 g of the desired product as an off-white solid.

MS (DCI/$NH_3$) m/z 227 (M+H)$^+$.

EXAMPLE 55C

N-(6-chloro-3-pyridinyl)-N''-cyanoguanidine

Example 55B (2.08 mg, 9.18 mmol) was dissolved in a 2M solution of ammonia in methanol (45 mL) and heated in a sealed Pyrex vessel at 80° C. for 6 hours. The reaction mixture was cooled to ambient temperature and concentrated to provide an off-white solid. Recrystallization of this material from hot ethanol provided 1.51 g of the desired product as a white solid.

MS (DCI/$NH_3$) m/z 213 (M+NH)$^+$.

EXAMPLE 55D

N-(1-{[[(6-chloro-3-pyridinyl)amino](cyanoimino)methyl]amino}-2,2-dimethylpropyl)-4-methylbenzamide Example 55C and Example 53A were processed as described in Example 54D to provide the desired product.

mp 194–196° C.;

MS (DCI/$NH_3$) m/z 399 (M+H)$^+$;

$^1$H NMR (DMSO-$d_6$) δ 9.63 (s, 1H), 8.33 (d, 1H, J=2 Hz), 8.23 (br d, 1H, J=5 Hz), 7.79–7.61 (m, 2H), 7.75 (d, 1H, J=7 Hz), 7.56 (d, 1H, J=8 Hz), 7.30 (d, 1H, J=7 Hz), 6.98 (br d, 1H, J=6 Hz), 5.83 (t, 1H, J=6 Hz), 2.37 (s, 3H), 0.97 (s, 9H);

Anal. calcd for $C_{20}H_{23}ClN_6O$: C, 60.22; H, 5.81; N, 21.07. Found: C, 60.82; H, 5.95; N, 20.74.

EXAMPLE 56

4-chloro-N-[{[(cyanoimino)(3-fluoroanilino)methyl]amino}(3-thienyl)methyl]benzamide

EXAMPLE 56A

N-(1H-1,2,3-benzotriazol-1-yl(3-thienyl)methyl)-4-chlorobenzamide

Benzotriazole, 4-chlorobenzamide, 3-thiophenecarboxaldhehyde, and p-toluenesulfonic acid were processed as described in Example 53A to provide the desired product.

MS (DCI/$NH_3$) m/z 369 (M+H)$^+$.

EXAMPLE 56B 1-fluoro-3-isothiocyanatobenzene

A solution of thiophosgene and 3-fluoroaniline were processed as described in Example 55A to provide the desired product.

MS (DCI/$NH_3$) m/z 154 (M+H)$^+$;

EXAMPLE 56C

Methyl N'-cyano-N-(3-fluorophenyl)carbamimidothioate

Example 56B, cyanamide, and methyl iodide were processed as described in Example 55B to provide the desired product.

MS (DCI/$NH_3$) m/z 210 (M+H)$^+$.

EXAMPLE 56D

N''-cyano-N-(3-fluorophenyl)guanidine

Example 56C and ammonia were processed as described in Example 54C to provide the desired product.

MS (DCI/$NH_3$) m/z 196 (M+$NH_4$)$^+$.

EXAMPLE 56E 4-chloro-N-[{[(cyanoimino)(3-fluoroanilino)methyl]amino}(3-thienyl)methyl]benzamide Example 56A and Example 56D were processed as described in Example 54D to provide the desired product.

mp 166–168° C.;

MS (ESI+) m/z 428 (M+H)+;

$^1$H NMR (DMSO-d$_6$) δ 9.65 (s, 1H), 9.24 (d, 1H, J=8 Hz), 7.92 (d, 2H, J=7 Hz), 7.82–7.76 (m, 1H), 7.59 (d, 2H, J=7 Hz), 7.59–7.57 (m, 2H), 7.40–7.34 (m, 1H), 7.20–7.18 (m, 1H), 7.15–7.06 (m, 2H), 6.99–6.94 (m, 1H), 6.91 (dd, 1H, J=8, 7 Hz);

Anal. calcd for C$_{20}$H$_{15}$ClFN$_5$O.0.75 H$_2$O: C, 54.42; H, 3.77; N, 15.87. Found: C, 54.41; H, 3.83; N, 15.86.

EXAMPLE 57

(−) N-(1-{[(cyanoimino)(3-pyridinylamino)methyl]amino}-2,2-dimethylpropyl)-4-methylbenzamide Example 51 (161 mg) was chromatographed over a Daicel Chiral Technologies Chiralcel OD chiral column (2.0 cm×25 cm) eluting with 5% ethanol/hexanes (flow rate=10 mL/minutes) to provide 51 mg (retention time=15 minutes) of the desired product as the faster enantiomer.

mp 187–188° C.;

[α]$_D^{23}$ −38° (c 0.4, DMSO);

MS (APCI+) m/z 365 (M+H)+;

$^1$H NMR (DMSO-d$_6$) δ 9.58 (s, 1H), 8.48 (d, 1H, J=3 Hz), 8.42 (d, 1H, J=3 Hz), 8.25 (d, 1H, J=9 Hz), 7.75 (d, 2H, J=9 Hz), 7.73–7.69 (m, 1H), 7.47–7.43 (m, 1H), 7.30 (d, 2H, J=9 Hz), 6.85 (d, 1H, J=9 Hz), 5.85 (t, 1H, J=9 Hz), 2.37 (s, 3H), 0.97 (s, 9H);

Anal calcd for C$_{20}$H$_{24}$N$_6$O: C, 65.91; H, 6.64; N, 23.06. Found: C, 66.00; H, 6.63; N, 23.15.

EXAMPLE 58

(+) N-(1-{[(cyanoimino)(3-pyridinylamino)methyl]amino}-2,2-dimethylpropyl)-4-methylbenzamide Example 51 (161 mg) was chromatographed over a Daicel Chiral Technologies Chiralcel OD chiral column (2.0 cm×25 cm) eluting with 5% ethanol/hexanes (flow rate=10 mL/minutes) to provide 36 mg (retention time=25 minutes) of the desired product as the slower enantiomer.

mp 188–189° C.;

[α]$_D^{23}$ +51° (c 0.3, DMSO);

MS (APCI+) m/z 365 (M+H)+;

$^1$H NMR (DMSO-d$_6$) δ 9.58 (s, 1H), 8.48 (d, 1H, J=3 Hz), 8.42 (d, 1H, J=3 Hz), 8.25 (d, 1H, J=9 Hz), 7.75 (d, 2H, J=9 Hz), 7.73–7.69 (m, 1H), 7.47–7.43 (m, 1H), 7.30 (d, 2H, J=9 Hz), 6.85 (d, 1H, J=9 Hz), 5.85 (t, 1H, J=9 Hz), 2.37 (s, 3H), 0.97 (s, 9H);

Anal calcd for C$_{20}$H$_{24}$N$_6$O: C, 65.91; H, 6.64; N, 23.06. Found: C, 65.99; H, 6.60; N, 23.20.

EXAMPLE 59

4-chloro-N-(1-{[(cyanoimino)(3-pyridinylamino)methyl]amino}-2-ethylbutyl)benzamide

EXAMPLE 59A

N-[1-(1H-1,2,3-benzotriazol-1-yl)-2-ethylbutyl]-4-chlorobenzamide

Benzotriazole, 4-chlorobenzamide, 2-ethylbutanal, and p-toluenesulfonic acid were processed as in Example 53A to provide the desired product.

MS (ESI+) m/z 357 (M+H)+.

EXAMPLE 59B 4-chloro-N-(1-{[(cyanoimino)(3-pyridinylamino)methyl]amino}-2-ethylbutyl)benzamide Example 54C and Example 59A were processed as in Example 54D to provide the desired product.

mp 185–187° C.;

MS (ESI+) m/z 399 (M+H)+;

$^1$H NMR (DMSO-d$_6$) δ 9.68 (s, 1H), 8.88 (br s, 1H), 8.47 (d, 1H, J=2 Hz), 8.33 (dd, 1H, J=5, 1 Hz), 7.90 (d, 2H, J=8 Hz), 7.69 (d, 1H, J=8 Hz), 7.45 (br s, 1H), 7.38 (dd, 1H, J=9, 5 Hz), 5.57 (dd, 1H, J=17, 9 Hz), 1.90 (m, 1H), 1.541.32 (m, 4H), 0.87 (t, 3H, J=8 Hz), 0.84 (t, 4H, J=8 Hz;

Anal calcd for C$_{20}$H$_{23}$ClN$_6$O.0.15 C$_4$H$_8$O$_2$: C, 60.04; H, 5.92; N, 20.39, Cl, 8.61. Found: C, 59.75; H, 5.77; N, 20.22; Cl, 8.93.

EXAMPLE 60

4-chloro-N-(1-{[(cyanoimino)(3-pyridinylamino)methyl]amino}-3-methylbutyl)benzamide

EXAMPLE 60A

N-[1-(1H-1,2,3-benzotriazol-1-yl)-3-methylbutyl]-4-chlorobenzamide

Benzotriazole, 4-chlorobenzamide, 3-methylbutanal, and p-toluenesulfonic acid were processed as in Example 53A to provide the desired product.

MS (ESI+) m/z 343 (M+H)+.

EXAMPLE 60B 4-chloro-N-(1-{[(cyanoimino)(3-pyridinylamino)methyl]amino}-3-methylbutyl)benzamide Example 54C and Example 60A were processed as in Example 54D to provide the desired product.

mp 193–194° C.;

MS (ESI+) m/z 385 (M+H)+;

$^1$H NMR (DMSO-d$_6$) δ 9.77 (br s, 1H), 9.00 (d, 1H, J=6 Hz), 8.49 (s, 1H), 8.31 (d, 1H, J=5 Hz), 7.92 (d, 2H, J=8 Hz), 7.71 (d, 1H, J=8 Hz), 7.64 (d, 1H, J=7 Hz), 7.57 (d, 2H, J=8 Hz), 7.36 (dd, 1H, J=8, 5 Hz), 5.69 (m, 1H), 3.32 (m, 2H), 1.68 (m, 1H), 0.92 (t, 6H, J=6 Hz);

Anal calcd for C$_{19}$H$_{21}$ClN$_6$O: C, 59.30; H, 5.50; N, 9.21; Cl, 21.84. Found: C, 59.16; H, 5.50; N, 9.08; Cl, 21.50.

EXAMPLE 61

4-chloro-N-[{[(cyanoimino)(3-pyridinylamino)methyl]amino}(cyclohexyl)methyl]benzamide

EXAMPLE 61A

N-[1H-1,2,3-benzotriazol-1-yl(cyclohexyl)methyl]-4-chlorobenzamide

Benzotriazole, 4-chlorobenzamide, cyclohexanecarboxaldehyde, and p-toluenesulfonic acid were processed as in Example 53A to provide the desired product.

MS (ESI+) m/z 369 (M+H)+.

EXAMPLE 61B 4-chloro-N-[{[(cyanoimino)(3-pyridinylamino)methyl]amino}(cyclohexyl)methyl]benzamide Example 54C and Example 61A were processed as in Example 54D to provide the desired product.

mp 190–192° C.;

MS (ESI+) m/z 411 (M+H)+;

¹H NMR (DMSO-d₆) δ 9.69 (s, 1H), 8.92 (br s, 1H), 8.49 (s, 1H), 8.31 (d, 1H, J=4 Hz), 7.91 (d, 2H, J=8 Hz), 7.71 (d, 1H, J=7 Hz), 7.57 (d, 2H, J=8 Hz), 7.37 (dd, 1H, J=5, 7.62 Hz), 5.43 (m, 1H), 1.97–1.62 (m, 5H), 1.16–0.97 (m, 6H);

Anal calcd for $C_{21}H_{23}ClN_6O \cdot 0.25\ C_4H_6O_2$: C, 61.64; H, 5.82; N, 19.41; Cl, 8.19. Found: C, 61.33; H, 6.01; N, 19.17; Cl, 8.14.

EXAMPLE 62

4-chloro-N-(1-{[(cyanoimino)(3-pyridinylamino) methyl]amino}-3,3-dimethylbutyl)benzamide

EXAMPLE 62A

N-[1-(1H-1,2,3-benzotriazol-1-yl)-3,3-dimethylbutyl]-4-chlorobenzamide

Benzotriazole, 4-chlorobenzamide, 3,3-dimethylbutanal, and p-toluenesulfonic acid were processed as in Example 53A to provide the desired product.

MS (ESI+) m/z 357 (M+H)⁺.

EXAMPLE 62B 4-chloro-N-(1-{[(cyanoimino)(3-pyridinylamino) methyl]amino}-3,3-dimethylbutyl)benzamide Example 54C and Example 62A were processed as in Example 54D to provide the desired product.

mp 181–183° C.;

MS (ESI+) m/z 399 (M+H)⁺;

¹H NMR (DMSO-d₆) δ 9.69 (s, 1H), 9.00 (d, 1H, J=5 Hz), 5.01 (d, 1H, J=3 Hz), 8.33 (dd, 1H, J=5, 2 Hz), 7.92 (d, 2H, J=9 Hz), 7.70 (d, 1H, J=8 Hz), 7.58 (d, 2H, J=8 Hz), 7.56 (m, 1H), 7.38 (dd, 1H, J=8, 5 Hz), 5.73 (m, 1H), 1.87 (m, 2H), 0.96 (s, 9H);

Anal calcd for $C_{20}H_{23}ClN_6O$: C, 60.22; H, 5.81; N, 21.07; Cl, 8.89. Found: C, 60.04; H, 6.01; N, 20.75; Cl, 8.74.

EXAMPLE 63

4-chloro-N-(1-{[(cyanoimino)(3-pyridinylamino) methyl]amino}-2-methylpropyl)benzamide

EXAMPLE 63A

N-[1-(1H-1,2,3-benzotriazol-1-yl)-2-methylpropyl]-4-chlorobenzamide

Benzotriazole, 4-chlorobenzamide, isobutyraldehyde, and p-toluenesulfonic acid were processed as in Example 53A to provide the desired product.

MS (ESI+) m/z 329 (M+H)⁺.

EXAMPLE 63B 4-chloro-N-(1-{[(cyanoimino)(3-pyridinylamino) methyl]amino}-2-methylpropyl)benzamide Example 54C and Example 63A were processed as in Example 54D to provide the desired product.

mp 182–184° C.;

MS (ESI+) m/z 371 (M+H)⁺;

¹H NMR (DMSO-d₆) δ 9.72 (s, 1H), 8.25 (d, 1H, J=6 Hz), 8.50 (d, 1H, J=Hz), 8.33 (d, 1H, J=4 Hz), 7.92 (d, 2H, J=9 Hz), 7.72 (d, 1H, J=9 Hz), 7.60 (d, 2H, J=8 Hz), 7.53 (m, 1H), 7.38 (dd, 1H, J=8, 5 Hz), 5.42 (q, 1H, J=8 Hz), 2.22 (m, 1H), 1.00 (d, 3H, J=7 Hz), 0.97 (d, 3H, J=7 Hz);

Anal calcd for $C_{18}H_{19}ClN_6O$: C, 58.30; H, 5.16; N, 22.66. Found: C, 58.37; H, 5.02; N, 22.76.

EXAMPLE 64

4-chloro-N-(1-{[(cyanoimino)(3-pyridinylamino) methyl]amino}-2,2,2-trifluoroethyl)benzamide

EXAMPLE 64A 4-chloro-N-(2,2,2-trifluoro-1-hydroxyethyl) benzamide

Trifluoroacetaldehyde ethyl hemiacetal and 4-chlorobenzamide were processed as in Example 1A to provide the desired product.

MS (ESI+) m/z 235 (M–H₂O)⁺.

EXAMPLE 64B

N-(1-chloro-2,2,2-trifluoroethyl)-4-chlorobenzamide

Example 64A and thionyl chloride were processed as in Example 1B to provide the desired product.

MS (ESI+) m/z 272 (M+H)⁺.

EXAMPLE 64C 4-chloro-N-(1-{[(cyanoimino)(3-pyridinylamino) methyl]amino}-2,2,2-trifluoroethyl)benzamide Example 54C and Example 64B were processed as in Example 54D to provide the desired product.

mp 136–138° C.;

MS (ESI+) m/z 397 (M+H)⁺;

¹H NMR (DMSO-d₆) δ 9.98 (s, 1H), 9.12 (d, 1H, J=8 Hz), 8.48 (m, 2H), 7.86 (d, 2H, J=8 Hz), 7.65 (m, 1H), 7.63 (d, 2H, J=8 Hz), 7.51 (m, 1H), 7.46 (m, 1H), 6.67 (m, 1H);

Anal calcd for $C_{16}H_{12}ClF_3N_6O \cdot 0.6\ CHCl_3$: C, 48.44; H, 3.05; N, 21.18. Found: C, 24.27; H, 3.00; N, 18.08.

EXAMPLE 65

4-chloro-N-(4-cyano-1-{[(cyanoimino)(3-pyridinylamino)methyl]amino}-2,2-diethylbutyl) benzamide

EXAMPLE 65A

N-[1-(1H-1,2,3-benzotriazol-1-yl)-4-cyano-2,2-diethylbutyl]-4-chlorobenzamide

Benzotriazole, 4-chlorobenzamide, 4-cyano-2,2-diethylbutanal, and p-toluenesulfonic acid were processed as in Example 53A to provide the desired product.

MS (ESI+) m/z 410 (M+H)⁺.

EXAMPLE 65B 4-chloro-N-(4-cyano-1-{[(cyanoimino)(3-pyridinylamino)methyl]amino}-2,2-diethylbutyl) benzamide Example 54C and Example 65A were processed as in Example 54D to provide the desired product.

mp 187–188° C.;

MS (ESI+) m/z 452 (M+H)⁺;

¹H NMR (DMSO-d₆) δ 9.54 (s, 1H), 8.45 (d, 1H, J=2 Hz), 8.40 (d, 1H, J=5 Hz), 8.33 (d, 1H, J=8 Hz), 7.83 (d, 2H, J=8

Hz), 7.65 (d, 1H, J=8 Hz), 7.60 (d, 2H, J=9 Hz), 7.43 (dd, 1H, J=8, 5 Hz), 6.72 (d, 1H, J=9 Hz), 5.94 (t, 1H, J=9 Hz), 2.54 (m, 2H), 1.72 (t, 2H, J=8 Hz), 1.39 (m, 4H), 0.85 (t, 3H, J=7 Hz), 0.81 (t, 3H, J=7 Hz);

Anal calcd for $C_{23}H_{26}ClN_7O \cdot 0.3\ H_2O$: C, 61.12; H, 5.80; N, 21.69; Cl, 7.84. Found: C, 60.41; H, 5.77; N, 21.45; Cl, 7.58.

EXAMPLE 66

4-chloro-N-[1-{[(cyanoimino)(3-pyridinylamino) methyl]amino}-2-(2,6,6-trimethyl-1-cyclohexen-1-yl)ethyl]benzamide

EXAMPLE 66A

N-[1-(1H-1,2,3-benzotriazol-1-yl)-2-(2,6,6-trimethyl-1-cyclohexen-1-yl)ethyl]-4-chlorobenzamide Benzotriazole, 4-chlorobenzamide, (2,6,6-trimethyl-1-cyclohexenyl)acetaldehyde, and p-toluenesulfonic acid were processed as in Example 53A to provide the desired product.

MS (ESI+) m/z 423 (M+H)$^+$.

EXAMPLE 66B 4-chloro-N-[1-{[(cyanoimino)(3-pyridinylamino) methyl]amino}-2-(2,6,6-trimethyl-1-cyclohexen-1-yl)ethyl]benzamide Example 54C and Example 66A were processed as in Example 54D to provide the desired product.

mp 199–201° C.;

MS (ESI+) m/z 465 (M+H)$^+$;

$^1$H NMR (DMSO-$d_6$) δ 9.65 (br s, 1H), 8.80 (m, 1H), 8.46 (d, 1H, J=2 Hz), 8.37 (d, 1H, J=5 Hz), 7.86 (d, 2H, J=9 Hz), 7.66 (dt, 1H, J=8, 2 Hz), 7.60 (d, 2H, J=8 Hz), 7.41 (dd, 1H, J=8, 5 Hz), 7.12 (m, 1H), 5.85 (m, 1H), 2.60 (m, 2H), 1.87 (m, 2H), 1.63 (s, 3H), 1.53 (m, 2H), 1.38 (m, 2H), 1.02 (d, 3H, J=7 Hz);

Anal calcd for $C_{25}H_{29}ClN_6O$: C, 64.58; H, 6.29; N, 18.07. Found: C, 64.18; H, 6.14; N, 18.04.

EXAMPLE 67

4-chloro-N-(1-{[(cyanoimino)(3-pyridinylamino) methyl]amino}-2,2-dimethyl-4-pentenyl)benzamide

EXAMPLE 67A

N-[1-(1H-1,2,3-benzotriazol-1-yl)-2,2-dimethyl-4-pentenyl]-4-chlorobenzamide

Benzotriazole, 4-chlorobenzamide, 2,2-dimethyl-4-pentenal, and p-toluenesulfonic acid were processed as in Example 53A to provide Example 67A.

MS (ESI+) m/z 369 (M+H)$^+$.

EXAMPLE 67B 4-chloro-N-(1-{[(cyanoimino)(3-pyridinylamino) methyl]amino}-2,2-dimethyl-4-pentenyl)benzamide Example 54C and Example 67A were processed as in Example 54D to provide the desired product.

mp 174–175° C.;

MS (ESI+) m/z 411 (M+H)$^+$;

$^1$H NMR (DMSO-$d_6$) δ 9.54 (s, 1H), 8.47 (d, 1H, J=3 Hz), 8.39 (m, 2H), 7.84 (d, 2H, J=9 Hz), 7.68 (m, 1H), 7.57 (d, 2H, J=8 Hz), 7.43 (dd, 1H, J=8, 5 Hz), 6.84 (d, 1H, J=9 Hz), 5.91 (m, 1H), 5.84 (t, 1H, J=9 Hz), 5.05 (d, 2H, J=5 Hz), 2.09 (m, 2H), 0.93 (s, 6H);

Anal calcd for $C_{21}H_{23}ClN_6O \cdot 0.25\ H_2O$: C, 61.38; H, 5.64; N, 20.45. Found: C, 60.49; H, 5.43; N, 20.39.

EXAMPLE 68

4-chloro-N-(2-ethyl-1-{[2-nitro-1-(3-pyridinylamino)ethenyl]amino}butyl)benzamide

EXAMPLE 68A

N-[1-(methylsulfanyl)-2-nitroethenyl]-3-pyridinamine

3-Aminopyridine and 1,1-bis(methylthio)-2-nitroethylene were processed as in Example 54B to provide the desired product.

MS (ESI+) m/z 212 (M+H)$^+$.

EXAMPLE 68B 2-nitro-N-(3-pyridinyl)-1,1-ethenediamine

Example 68A and ammonia were processed as in Example 54C to provide the desired product.

MS (ESI+) m/z 181 (M+H)$^+$.

EXAMPLE 68C 4-chloro-N-(2-ethyl-1-{[2-nitro-1-(3-pyridinylamino)ethenyl]amino}butyl)benzamide Example 68B and 59A were processed as in Example 54D to provide the desired product.

mp 192–193° C.;

MS (ESI+) m/z 418 (M+H)$^+$;

$^1$H NMR (DMSO-$d_6$) δ 9.83 (m, 1H), 9.32 (d, 1H, J=7 Hz), 8.50 (d, 1H, J=5 Hz), 8.47 (d, 1H, J=2 Hz), 7.94 (d, 2H, J=8 Hz), 7.71 (d, 1H, J=8 Hz), 7.62 (d, 2H, J=8 Hz), 7.49 (dd, 1H, J=8, 5 Hz), 6.20 (s, 1H), 5.64 (q, 1H, J=8 Hz), 1.96 (m, 1H), 1.63 (m, 1H), 1.49 (m, 3H), 0.93 (t, 3H, J=7 Hz), 0.90 (t, 3H, J=8 Hz);

Anal calcd for $C_{20}H_{24}ClN_5O_3$: C, 57.48; H, 5.79; N, 16.76. Found: C, 57.39; H, 5.69; N, 16.82.

EXAMPLE 69

4-chloro-N-(1-{[(cyanoimino)(2-fluoroanilino) methyl]amino}-2,2-dimethylpropyl)benzamide

EXAMPLE 69A

N-cyano-N'-(2-fluorophenyl)thiourea

Cyanamide and 2-fluorophenyl isothiocyanate were processed as described in Example 44A to provide the desired product which was used without further purification.

EXAMPLE 69B

N-(1-(1H-1,2,3-benzotriazol-1-yl)-2,2-dimethylpropyl)-4-chlorobenzamide

A suspension of 4-chlorobenzamide, pivaldehyde, benzotriazole, and p-toluenesulfonic acid were processed as described in Example 53A to provide the desired product.

MS (DCI/NH$_3$) m/z 343 (M+H)$^+$.

EXAMPLE 69C

N-(1-amino-2,2-dimethylpropyl)-4-chlorobenzamide hydrochloride

A suspension of Example 69B, $K_2CO_3$, and ammonia were processed as described in Example 53B to provide the desired compound.

MS (DCI/NH$_3$) m/z 241 (M+H−HCl)$^+$.

EXAMPLE 69D 4-chloro-N-(1-{[(cyanoimino)(2-fluoroanilino) methyl]amino}-2,2-dimethylpropyl)benzamide Example 69A, Example 69C, and EDCI were processed as described in Example 44B to provide the desired product.

mp 208–209° C.;
MS (DCI/NH$_3$) m/z 402 (M+H)$^+$;
$^1$H NMR (DMSO-d$_6$) δ 9.37 (s, 1H), 8.47 (d, 1H, J=8.6 Hz), 7.93 (d, 2H, J=8.6 Hz), 7.68 (d, 2H, J=8.5 Hz), 7.45 (m, 3H), 7.35 (m, 1H), 6.69 (d, 1H, J=86 Hz), 5.93 (t, 1H, J=8.5 Hz), 1.05 (s, 9H);
Anal. calcd for $C_{20}H_{21}ClFN_5O$ 0.2$C_7H_7FN_4$: C, 59.07; H, 5.19; N, 18.67. Found: C, 59.21; H, 4.91; N, 18.58.

EXAMPLE 70

4-chloro-N-(1-{[(cyanoimino)(3-fluoroanilino) methyl]amino}-2,2-dimethylpropyl)benzamide Example 56D and Example 69B were processed as described in Example 54D to provide the desired product.

mp 167–170° C.;
MS (ESI+) m/z 402 (M+H)$^+$;
$^1$H NMR (DMSO-d$_6$) δ 9.53 (br s, 1H), 8.35 (d, 1H, J=8.5 Hz), 7.80 (d, 2H, J=8.6 Hz), 7.53 (d, 2H, J=8.6 Hz), 7.42–7.33 (m, 1H), 7.1 i6.93 (m, 3H), 6.84 (br d, 1H, J=9.2 Hz), 5.78 (t, 1H, J=8.8 Hz), 0.95 (s, 9H);
HRMS (FAB) calcd m/z for $C_{20}H_{21}ClFN_5O$ (M$^+$): 401.1419. Found 401.1429.

EXAMPLE 71

4-chloro-N-[1-({(cyanoimino)[3-(trifluoromethyl) anilino]methyl}amino)-2,2-dimethylpropyl] benzamide

EXAMPLE 71A

N''-cyano-N-[3-(trifluoromethyl)phenyl]guanidine

3-Trifluoromethylaniline (10 g, 62.1 mmol) was dissolved in 6N HCl (10.35 mmol, 62.1 mmol) and 50 ml of water. Sodium dicyanamide (5.53 g, 62.1 mmol) was added and the mixture was stirred for 12 hours at ambient temperature. The mixture was then cooled to 0° C. and stirred for 1 hour resulting in the formation of a precipitate. Filtration provided 12.22 g of the desired product as a white solid.

MS (ESI−) m/z 227 (M−H)$^-$.

EXAMPLE 71B 4-chloro-N-[1-({(cyanoimino)[3-(trifluoromethyl) anilino]methyl}amino)-2,2-dimethylpropyl] benzamide Example 71 A and Example 69B were processed as described in Example 54D to provide the desired product.

mp 184–186° C.;
MS (ESI+) m/z 452 (M+H)$^+$;
$^1$H NMR (DMSO-d$_6$) δ 9.65 (s, 1H), 8.39 (d, 1H, J=8.8 Hz), 7.84 (d, 2H, J=8.8 Hz), 7.59 (m, 4H), 7.57 (d, 2H, J=8.8 Hz), 6.96 (d, 1H, J=9.8 Hz), 5.83 (t, 1H, J=8.8 Hz), 0.99 (s, 3H);
Anal. calcd for $C_{21}H_{21}ClF_3N_5O$: C, 55.82; H, 4.68; N, 15.50. Found: C, 55.85; H, 4.77; N, 15.40.

EXAMPLE 72

4-chloro-N-(1-{[(cyanoimino)(3,5-difluoroanilino) methyl]amino}-2,2-dimethylpropyl)benzamide

EXAMPLE 72A

N''-cyano-N-(3,5-difluorophenyl)guanidine 3,5-Difluoroaniline and sodium dicyanamide were processed as described in Example 71A to provide the desired compound.

MS (ESI−) m/z 195 (M−H)$^-$.

EXAMPLE 72B 4-chloro-N-(1-{[(cyanoimino)(3,5-difluoroanilino) methyl]amino}-2,2-dimethylpropyl)benzamide Example 72A and Example 69B were processed as described in Example 54D to provide the desired product.

mp 196–198° C.;
MS (ESI+) m/z 420 (M+H)$^+$;
$^1$H NMR (DMSO-d$_6$) δ 9.67 (s, 1H), 8.41 (d, 1H, J=9.2 Hz), 7.85 (d, 2H, J=8.5 Hz), 7.57 (d, 2H, J=8.5 Hz), 7.12 (d, 1H, J=9.5 Hz), 6.98 (m, 3H), 5.78 (t, 1H, J=9.3 Hz), 1.00 (s, 3H);
Anal. calcd for $C_{20}H_{20}ClF_2N_5O$: C, 57.21; H, 4.80; N, 16.68. Found: C, 56.98; H, 4.78; N, 16.78.

EXAMPLE 73

4-chloro-N-(1-{[(cyanoimino)(2,5-difluoroanilino) methyl]amino}-2,2-dimethylpropyl)benzamide

EXAMPLE 73A

N''-cyano-N-(2,5-difluorophenyl)guanidine 2,5-Difluoroaniline and sodium dicyanamide were processed as described in Example 71A to provide the desired compound.

MS (ESI−) m/z 195 (M−H)$^-$.

EXAMPLE 73B 4-chloro-N-(1-{[(cyanoimino)(2,5-difluoroanilino) methyl]amino}-2,2-dimethylpropyl)benzamide Example 73A and Example 69B were processed as described in Example 54D to provide the desired product.

mp 196–198° C.;
MS (ESI+) m/z 420 (M+H)$^+$;
$^1$H NMR (DMSO-d$_6$) δ 9.67 (s, 1H), 8.41 (d, 1H, J=9.2 Hz), 7.85 (d, 2H, J=8.5 Hz), 7.57 (d, 2H, J=8.5 Hz), 7.12 (d, 1H, J=9.5 Hz), 6.98 (m, 3H), 5.78 (t, 1H, J=9.3 Hz), 1.00 (s, 3H);
Anal. calcd for $C_{20}H_{20}ClF_2N_5O$: C, 57.21; H, 4.80; N, 16.68. Found: C, 56.98; H, 4.78; N, 16.78.

EXAMPLE 74

4-chloro-N-(1-{[(cyanoimino)(2,6-difluoroanilino)methyl]amino}-2,2-dimethylpropyl)benzamide

EXAMPLE 74A

N"-cyano-N-(2,6-difluorophenyl)guanidine 2,6-Difluoroaniline and sodium dicyanamide were procesed as described in Example 71A to provide the desired compound.

MS (ESI−) m/z 195 (M−H)⁻.

EXAMPLE 74B 4-chloro-N-(1-{[(cyanoimino)(2,6-difluoroanilino)methyl]amino}-2,2-dimethylpropyl)benzamide Example 74A and Example 69B were processed as described in Example 54D to provide the desired product.
mp 211–213° C.;
MS (ESI+) m/z 420 (M+H)⁺;
$^1$H NMR (DMSO-$d_6$) δ 9.23 (s, 1H), 8.40 (d, 1H, J=8.5 Hz), 7.84 (d, 2H, J=8.5 Hz), 7.58 (d, 2H, J=8.5 Hz), 7.43 (m, 1H), 7.21 (dd, 2H, J=8.5, 8.0 Hz), 6.89 (m, 1H), 5.80 (t, 1H, J=8.9 Hz), 0.95 (s, 3H);
Anal. calcd for $C_{20}H_{20}ClF_2N_5O$: C, 57.20; H, 4.80; N, 16.68. Found: C, 57.05; H, 4.68; N, 16.55.

EXAMPLE 75

4-chloro-N-(1-{[(cyanoimino)(3-chloroanilino)methyl]amino}-2,2-dimethylpropyl)benzamide

EXAMPLE 75A

N"-cyano-N-(3-chlorophenyl)guanidine

3-Chloroaniline and sodium dicyanamide were processed as described in Example 71A to provide the desired compound.

MS (ESI−) m/z 193 (M−H)⁻.

EXAMPLE 75B 4-chloro-N-(1-{[(cyanoimino)(3-chloroanilino)methyl]amino}-2,2-dimethylpropyl)benzamide Example 75A and Example 69B were processed as described in Example 54D to provide the desired product.
mp 158–160° C.;
MS (ESI+) m/z 418 (M+H)⁺;
$^1$H NMR (DMSO-$d_6$) δ 9.52 (s, 1H), 8.87 (d, 1H, J=8.5 Hz), 7.84 (d, 2H, J=8.5 Hz), 7.57 (d, 2H, J=8.5 Hz), 7.41 (t, 1H, J=8.1 Hz), 7.32 (m, 1H), 7.23 (m, 2H), 6.84 (d, 1H, J=9.0 Hz), 5.81 (t, 1H, J=8.8 Hz), 0.98 (s, 3H);
Anal. calcd for $C_{20}H_{21}Cl_2N_5O$ 0.9$C_3H_8O$: C, 56.32; H, 5.68; N, 17.07. Found: C, 56.07; H, 5.79; N, 17.12.

EXAMPLE 76

4-chloro-N-(1-{[(cyanoimino)(3-methoxyanilino)methyl]amino}-2,2-dimethylpropyl)benzamide

EXAMPLE 76A

N"-cyano-N-(3-methoxyphenyl)guanidine

3-Methoxyaniline and sodium dicyanamide were procesed as described in Example 71A to provide the desired compound.

MS (ESI−) m/z 191 (M−H)⁻.

EXAMPLE 76B 4-chloro-N-(1-{[(cyanoimino)(3-methoxyanilino)methyl]amino}-2,2-dimethylpropyl)benzamide Example 76A and Example 69B were processed as described in Example 54D to provide the desired product.
mp 173–175° C.;
MS (ESI+) m/z 414 (M+H)⁺;
$^1$H NMR (DMSO-$d_6$) δ 9.39 (s, 1H), 8.37 (d, 1H, J=8.8 Hz), 7.81 (d, 2H, J=8.5 Hz), 7.57 (d, 2H, J=8.5 Hz), 7.32 (t, 1H, J=8.1 Hz), 6.82 (m, 3H), 6.63 (d, 1H, J=9.1 Hz), 5.84 (t, 1H, J=8.8 Hz), 3.74 (s, 3H), 0.95 (s, 3H);
Anal. calcd for $C_{21}H_{24}ClN_5O_2$: C, 60.94; H, 5.84; N, 16.92. Found: C, 60.98; H, 5.77; N, 17.03.

EXAMPLE 77

4-chloro-N-(1-{[[(2-chlorobenzyl)amino](cyanoimino)methyl]amino}-2,2-dimethylpropyl)benzamide

EXAMPLE 77A

Methyl N-(2-chlorobenzyl)-N'-cyanoimidothiocarbamate

2-Chlorobenzylamine and dimethyl N-cyanodithioiminocarbonate were processed as described in Example 54B to give the desired product.

MS (ESI+) m/z 240 (M+H)⁺.

EXAMPLE 77B

N-(2-chlorobenzyl)-N"-cyanoguanidine

Example 77A and ammonia were processed as described in Example 54C to give the desired product.

MS (ESI+) m/z 209 (M+H)⁺.

EXAMPLE 77C 4-chloro-N-(1-{[[(2-chlorobenzyl)amino](cyanoimino)methyl]amino}-2,2-dimethylpropyl)benzamide Example 77B and Example 69B were processed as described in Example 54D to provide the desired product.
mp 180–182° C.;
MS (DCI/NH₃) m/z 432 (M+H)⁺;
$^1$H NMR (DMSO-$d_6$) δ 8.49 (br d, 1H, J=5.1 Hz), 7.90–7.82 (m, 3H), 7.83 (d, 1H, J=8.5 Hz), 7.67 (d, 1H, J=8.6 Hz), 7.46–7.41 (m, 1H), 7.33–7.25 (m, 3H), 6.44 (d, 1H, J=8.6 Hz), 5.71 (t, 1H, J=8.1 Hz), 4.46–4.38 (m, 2H), 0.97 (s, 9H);
Anal. calcd for $C_{21}H_{23}Cl_2N_5O$: C, 58.34; H, 5.36; N, 16.20. Found: C, 58.00; H, 5.20; N, 16.65.

EXAMPLE 78

4-chloro-N-(1-{[[(3-chlorobenzyl)amino](cyanoimino)methyl]amino}-2,2-dimethylpropyl)benzamide

EXAMPLE 78A

Methyl N-(3-chlorobenzyl)-N'-cyanoimidothiocarbamate

3-Chlorobenzylamine and dimethyl N-cyano-dithioiminocarbonate were processed as described in Example 54B to give the desired product.

MS (ESI+) m/z 240 (M+H)⁺.

EXAMPLE 78B

N-(3-chlorobenzyl)-N''-cyanoguanidine

Example 78A and ammonia were processed as described in Example 54C to give the desired product.
MS (ESI+) m/z 209 (M+H)+.

EXAMPLE 78C 4-chloro-N-(1-{[[(3-chlorobenzyl)amino](cyanoimino)methyl]amino}-2,2-dimethylpropyl)benzamide Example 78B and Example 69B were processed as described in Example 54D to provide the desired product.
mp 178–180° C.;
MS (DCI/NH$_3$) m/z 432 (M+H)+;
$^1$H NMR (DMSO-d$_6$) δ 8.33 (br d, 1H, J=5.2 Hz), 7.95–7.85 (m, 2H), 7.83 (d, 1H, J=8.5 Hz), 7.79–7.73 (m, 1H), 7.67 (d, 1H, J=8.5 Hz), 7.46–7.41 (m, 1H), 7.33–7.25 (m, 3H), 6.41 (d, 1H, J=8.7 Hz), 5.66 (t, 1H, J=8.1 Hz), 4.46–4.38 (m, 2H), 0.98 (s, 9H);
Anal. calcd for C$_{21}$H$_{23}$Cl$_2$N$_5$O: C, 58.34; H, 5.36; N, 16.20. Found: C, 57.87; H, 5.22; N, 16.02.

EXAMPLE 79

4-chloro-N-(1-{[[(4-chlorobenzyl)amino](cyanoimino)methyl]amino}-2,2-dimethylpropyl)benzamide

EXAMPLE 79A

Methyl N-(4-chlorobenzyl)-N'-cyanoimidothiocarbamate

4-Chlorobenzylamine and dimethyl N-cyanodithioiminocarbonate were processed as described in Example 54B to give the desired product.
MS (ESI+) m/z 240 (M+H)+.

EXAMPLE 79B

N-(4-chlorobenzyl)-N''-cyanoguanidine

Example 79A and ammonia were processed as described in Example 54C to give the desired product.
MS (ESI+) m/z 209 (M+H)+.

EXAMPLE 79C 4-chloro-N-(1-{[[(4-chlorobenzyl)amino](cyanoimino)methyl]amino}-2,2-dimethylpropyl)benzamide Example 79B and Example 69B were processed as described in Example 54D to provide the desired product.
mp 173–175° C.;
MS (DCI/NH$_3$) m/z 432 (M+H)+;
$^1$H NMR (DMSO-d$_6$) δ 8.62 (br d, 1H, J=5.5 Hz), 7.91–7.84 (m, 2H), 7.83 (d, 1H, J=8.6 Hz), 7.83–7.77 (m, 1H), 7.79 (d, 1H, J=8.2 Hz), 7.56–7.50 (m, 1H), 7.39–7.32 (m, 2H), 7.27–7.22 (m, 1H), 6.50 (d, 1H, J=8.4 Hz), 5.70 (t, 1H, J=8.5 Hz), 4.31 (d, 2H, J=6.0 Hz), 0.97 (s, 9H);
Anal. calcd for C$_{21}$H$_{23}$Cl$_2$N$_5$O: C, 58.34; H, 5.36; N, 16.20. Found: C, 57.12; H, 5.18; N, 16.04.

EXAMPLE 80

4-chloro-N-[1-({(cyanoimino)[(3-pyridinylmethyl)amino]methyl}amino)-2,2-dimethylpropyl]benzamide

EXAMPLE 80A

Methyl N'-cyano-N-(3-pyridinylmethyl)imidothiocarbamate 3-(Aminomethyl)pyridine and dimethyl N-cyanodithioiminocarbonate were processed as described in Example 54B to give the desired product.
MS (ESI+) m/z 207 (M+H)+.

EXAMPLE 80B

N''-cyano-N-(3-pyridinylmethyl)guanidine

Example 80A and ammonia were processed as described in Example 54C to give the desired product.
MS (ESI+) m/z 176 (M+H)+.

EXAMPLE 80C 4-chloro-N-[1-({(cyanoimino)[(3-pyridinylmethyl)amino]methyl}amino)-2,2-dimethylpropyl]benzamide Example 80B and Example 69B were processed as described in Example 54D to provide the desired product.
mp 188–189° C.;
MS (ESI+) m/z 399 (M+H)+;
$^1$H NMR (DMSO-d$_6$)) δ 8.49 (d, 1H, J=1.8 Hz), 8.45 (dd, 1H, J=5.3, 1.5 Hz), 7.86 (m, 1H), 7.84 (d, 2H, J=8.5 Hz), 7.65 (m, 1H), 7.60 (d, 2H, J=8.5 Hz), 7.33 (dd, 1H, J=10.4, 5.5 Hz), 6.50 (d, 1H, J=9.6 Hz), 6.68 (t, 1H, J=9.2 Hz), 4.41 (m, 2H), 0.90 (s, 3H);
Anal. calcd for C$_{20}$H$_{23}$ClN$_6$O 0.15H$_2$O: C, 59.81; H, 5.85; N, 20.93. Found: C, 59.71; H, 5.77; N, 20.66.

EXAMPLE 81

4-chloro-N-[1-({(cyanoimino)[(4-pyridinylmethyl)amino]methyl}amino)-2,2-dimethylpropyl]benzamide

EXAMPLE 81A

Methyl N'-cyano-N-(4-pyridinylmethyl)imidothiocarbamate 4-(Aminomethyl)pyridine and dimethyl N-cyanodithioiminocarbonate were processed as described in Example 54B to provide the desired product.
MS (ESI+) m/z 207 (M+H)+.

EXAMPLE 81B

N''-cyano-N-(3-pyridinylmethyl)guanidine

Example 81A and ammonia were processed as described in Example 54C to give the desired product.
MS (ESI+) m/z 176 (M+H)+.

EXAMPLE 81C 4-chloro-N-[1-({(cyanoimino)[(4-pyridinylmethyl)amino]methyl}amino)-2,2-dimethylpropyl]benzamide Example 81B and Example 69B were processed as described in Example 54D to provide the desired product.

mp 189–191° C.;

MS (ESI+) m/z 399 (M+H)$^+$;

$^1$H NMR (DMSO-d$_6$) δ 8.62 (d, 1H, J=8.1 Hz), 8.47 (d, 2H, J=6.5 Hz), 8.08 (t, 1H, J=5.9 Hz), 7.87 (d, 2H, J=8.5 Hz), 7.59 (d, 2H, J=8.5 Hz), 7.24 (d, 2H, J=5.9 Hz), 6.50 (d, 1H, J=9.9 Hz), 5.70 (t, 1H, J=8.8 Hz), 4.44 (dd, 1H, J=16.7, 6.3 Hz), 4.36 (dd, 1H, J=16.6, 5.9 Hz), 0.92 (s, 3H);

Anal. calcd for C$_{20}$H$_{23}$ClN$_6$O: C, 60.22; H, 5.81; N, 21.07. Found: C, 60.03; H, 6.01; N, 21.23.

EXAMPLE 82

4-chloro-N-[1-({(cyanoimino)[(2-pyridinylmethyl)amino]methyl}amino)-2,2-dimethylpropyl]benzamide

EXAMPLE 82A

Methyl N'-cyano-N-(2-pyridinylmethyl)imidothiocarbamate 2-(Aminomethyl)pyridine and dimethyl N-cyanodithioiminocarbonate were processed as described in Example 54B to give the desired product.

MS (ESI+) m/z 207 (M+H)$^+$.

EXAMPLE 82B

N"-cyano-N-(2-pyridinylmethyl)guanidine

Example 82A and ammonia were processed as described in Example 54C to give the desired product.

MS (ESI+) m/z 176 (M+H)$^+$.

EXAMPLE 82C 4-chloro-N-[1-({(cyanoimino)[(2-pyridinylmethyl)amino]methyl}amino)-2,2-dimethylpropyl]benzamide Example 82B and Example 69B were processed as described in Example 54D to provide the desired product.

mp 184–185° C.;

MS (EST+) m/z 399 (M+H)$^+$;

$^1$H NMR (DMSO-d$_6$) δ 8.52 (dd, 1H, J=5.3, 2.2 Hz), 8.45 (d, 1H, J=8.1 Hz), 7.93 (t, 1H, J=5.5 Hz), 7.86 (d, 2H, J=8.8 Hz), 7.82 (m, 1H), 7.58 (d, 2H, J=8.8 Hz), 7.35 (m, 2H), 7.05 (m, 1H), 5.72 (t, 1H, J=9.2 Hz), 4.46 (d, 2H, J=5.9 Hz), 0.90 (s, 9H);

Anal. Calcd for C$_{20}$H$_{23}$ClN$_6$O: C, 60.22; H, 5.81; N, 21.07. Found: C, 60.09; H, 5.90; N, 21.29.

EXAMPLE 83

4-chloro-N-(1-{[(cyanoimino)(3-guinolinylamino)methyl]amino}-2,2-dimethylpropyl)benzamide

EXAMPLE 83A

Methyl N'-cyano-N-(2-guinolinylmethyl)imidothiocarbamate

3-Aminoquinoline and dimethyl N-cyanodithioiminocarbonate were processed as described in Example 54B to provide the desired product.

MS (ESI+) m/z 243 (M+H)$^+$.

EXAMPLE 83B

N"-cyano-N-(2-guinolinylmethyl)guanidine

Example 83A and ammonia were processed as described in Example 54C to provide the desired product.

MS (ESI+) m/z 212 (M+H)$^+$.

EXAMPLE 83C 4-chloro-N-(1-{[(cyanoimino)(3-guinolinylamino)methyl]amino}-2,2-dimethylpropyl)benzamide Example 83B and Example 69B were processed as described in Example 54D to provide the desired product.

mp 218–219° C.;

MS (DCI/NH$_3$) m/z 435 (M+H)$^+$;

$^1$H NMR (DMSO-d$_6$) δ 9.75 (s, 1H), 8.80 (d, 1H, J=1.9 Hz), 8.35 (d, 1H, J=8.4 Hz), 8.18 (d, 1H, J=3.5 Hz), 8.02 (d, 1H, J=8.6 Hz), 7.94 (dd, 1H, J=8.5, 1.5 Hz), 7.85 (d, 2H, J=8.7 Hz), 7.73 (ddd, 1H, J=8.4, 7.8, 2.3 Hz), 7.62 (ddd, 1H, J=8.4, 7.3, 1.8 Hz), 7.57 (d, 2H, J=8.6 Hz), 6.94 (d, 1H, J=8.8 Hz), 5.88 (t, 1H, J=8.6 Hz), 1.01 (s, 9H);

Anal. calcd for C$_{23}$H$_{23}$ClN6O: C, 63.52; H, 5.33; N, 19.32. Found: C, 63.31; H, 5.42; N, 18.98.

EXAMPLE 84

4-chloro-N-(1-{[(cyanoimino)(3-pyridinylamino)methyl]amino}propyl)benzamide

EXAMPLE 84A

N-[1-(1H-1,2,3-benzotriazol-1-yl)propyl]-4-chlorobenzamide

A suspension of 4-chlorobenzamide (1.50 g, 9.6 mmol), propionaldehyde diethyl acetal (1.53 g, 11.6 mmol), and benzotriazole (1.15 g, 9.6 mmol) in toluene (35 mL) was treated with p-toluenesulfonic acid (100 mg, 0.53 mmol). The mixture was heated at reflux under Dean-Stark conditions for 16 hours, cooled to ambient temperature, and concentrated to dryness. The crude material was purified by flash chromatography (elution with 40% ethyl acetate/hexanes) to provide 0.860 g of the desired product as a white solid.

MS (DCI/NH$_3$) m/z 315 (M+H)$^+$.

EXAMPLE 84B 4-chloro-N-(1-{[(cyanoimino)(3-pyridinylamino)methyl]amino}propyl)benzamide Example 54C and Example 84A were processed as described in Example 54D to provide the desired product.

mp 181–183° C.;

MS (DCI/NH$_3$) m/z 357 (M+H)$^+$;

$^1$H NMR (DMSO-d$_6$) δ 9.76 (s, 1H), 8.99 (d, 1H, J=6.9 Hz), 8.50 (d, 1H, J=2.4 Hz), 8.32 (dd, 1H, J=4.5, 2.2 Hz), 7.93 (d, 2H, J=8.6 Hz), 7.37 (dd, 1H, J=7.6, 3.3 Hz), 5.58 (m, 1H), 1.88 (m, 2H), 0.94 (t, 3H, J=7.3 Hz);

Anal. calcd for C$_{17}$H$_{17}$ClN$_6$O: C, 57.22; H, 4.80; N, 23.55. Found: C, 56.92; H, 4.99; N, 23.27.

EXAMPLE 85

4-chloro-N-({[(cyanoimino)(3-pyridinylamino)methyl]amino}methyl)benzamide

EXAMPLE 85A

N-(1H-1,2,3-benzotriazol-1-ylmethyl)-4-chlorobenzamide

A suspension of 4-chlorobenzamide (2.61 g, 16.8 mmol), paraformaldehyde (0.50 g, 16.8 mmol), benzotriazole (2.00 g, 16.8mmol), and MgSO$_4$ (2.00 g, 16.6 mmol) in toluene (50 mL) was treated with p-toluenesulfonic acid (168 mg, 0.88 mmol). The mixture was heated at reflux for 4 hours, cooled to ambient temperature, filtered and concentrated to dryness. The crude material was purified by trituration with diethyl ether to provide 2.11 g of the desired product as a white solid.

MS (DCI/NH$_3$) m/z 287 (M+H)$^+$.

EXAMPLE 85B 4-chloro-N-({[(cyanoimino)(3-pyridinylamino)methyl]amino}methyl)benzamide Example 54C and Example 85A were processed as described in Example 54D to provide the desired product.

mp 196–197° C.;

MS (DCI/NH$_3$) m/z 329 (M+H)$^+$;

$^1$H NMR (DMSO-d$_6$) δ 9.81 (s, 1H), 9.42 (s, 1H), 8.55 (d, 1H, J=1.4 Hz), 8.34 (dd, 1H, J=4.8, 2.2 Hz), 8.09 (s, 1H), 7.95 (d, 2H, J=8.5 Hz), 7.79 (ddd, 1H, J=8.5, 3.1, 2.2 Hz), 7.58 (d, 2H, J=7.6 Hz), 7.38 (dd, 1H, J=7.6, 4.4 Hz), 4.82 (s, 2H);

Anal. calcd for C$_{15}$H$_{13}$ClN$_6$O: C, 54.80; H, 3.99; N, 25.56. Found: C, 54.44; H, 4.04; N, 25.29.

EXAMPLE 86

(−) 4-chloro-N-(4-cyano-1-{[(cyanoimino)(3-pyridinylamino)methyl]amino}-2,2-diethylbutyl)benzamide Example 65B was chromatographed over a Daicel Chiral Technologies Chiralcel AS chiral column (2.0 cm×25 cm) eluting with 5% ethanol/hexanes (flow rate=10 mL/minutes) to provide the desired product as the levorotatory enantiomer.

$[\alpha]_D^{23}$=−23° (c 0.5, DMSO);

mp 150–152° C.;

MS (ESI+) m/z 452 (M+H)$^+$;

$^1$H NMR (DMSO-d$_6$) δ 9.56 (s, 1H), 8.45 (d, 1H, J=2.2 Hz), 8.41 (d, 1H, J4.4 Hz), 8.34 (d, 1H, J=8.8 Hz), 7.83 (d, 2H, J=8.8 Hz), 7.64 (m, 1H), 7.60 (d, 2H, J=8.5 Hz), 7.43 (dd, 1H, J=8.1, 4.8 Hz), 6.75 (m, 1H), 5.95 (dd, 1H, J=8.8, 8.0 Hz), 2.54 (m, 2H), 1.71 (t, 2H, J=8.1 Hz), 1.39 (m, 4H), 0.85 (m, 6H);

Anal. calcd for C$_{23}$H$_{26}$ClN$_7$O: C, 60.52; H, 5.85; N, 21.48. Found: C, 60.64; H, 5.86; N, 21.57.

EXAMPLE 87

(+) 4-chloro-N-(4-cyano-1-{[(cyanoimino)(3-pyridinylamino)methyl]amino}-2,2-diethylbutyl)benzamide Example 65B was chromatographed over a Daicel Chiral Technologies Chiralcel AS chiral column (2.0 cm×25 cm) eluting with 5% ethanol/hexanes (flow rate=10 mL/minutes) to provide the desired product as the dextrorotatory enantiomer.

$[\alpha]_D^{23}$=+21° (c 0.48, DMSO);

mp 146–148° C.;

MS (ESI+) m/z 452 (M+H)$^+$;

$^1$H NMR (DMSO-d$_6$) δ 9.55 (s, 1H), 8.45 (d, 1H, J=2.2 Hz), 8.41 (d, 1H, J=4.4 Hz), 8.34 (d, 1H, J=8.8 Hz), 7.83 (d, 2H, J=8.5 Hz), 7.64 (m, 1H), 7.60 (d, 2H, J=8.5 Hz), 7.43 (dd, 1H, J=4.8, 8.1 Hz), 6.75 (m, 1H), 5.94 (dd, 1H, J=8.8, 7.8 Hz), 2.54 (m, 2H), 1.72 (t, 2H, J=8.1 Hz), 1.39 (m, 4H), 0.85 (m, 6H);

Anal. calcd for C$_{23}$H$_{26}$ClN$_7$O: C, 60.52; H, 5.85; N, 21.48. Found: C, 60.64; H, 5.84; N, 21.29.

EXAMPLE 88

(+) 4-chloro-N-[1-{[(cyanoimino)(3-pyridinylamino)methyl]amino}-2-(2,6,6-trimethyl-1-cyclohexen-1-yl)ethyl]benzamide Example 66B was chromatographed over a Daicel Chiral Technologies Chiralcel OJ chiral column (2.0 cm×25 cm) eluting with 5% ethanol/hexanes (flow rate=10 mL/minutes) to provide the desired product as the dextrorotatory enantiomer.

$[\alpha]_D^{23}$=+12.2° (c 0.24, DMSO);

mp 95–96° C.;

MS (ESI+) m/z 465 (M+H)$^+$;

$^1$H NMR (DMSO-d$_6$) δ 9.65 (br s, 1H), 8.80 (m, 1H), 8.46 (d, 1H, J=2.4 Hz), 8.37 (d, 1H, J=4.8 Hz), 7.86 (d, 2H, J=8.5 Hz), 7.66 (dt, 1H, J=7.8, 1.5 Hz), 7.60 (d, 2H, J=8.5 Hz), 7.41 (dd, 1H, J=8.5, 4.8 Hz), 7.12 (m, 1H), 5.85 (m, 1H), 2.60 (m, 2H), 1.87 (m, 2H), 1.63 (s, 3H), 1.53 (m, 2H), 1.38 (m, 2H), 1.02 (d, 3H, J=7.5 Hz);

Anal. calcd for C$_{25}$H$_{29}$ClN$_6$O 0.2CH$_2$Cl$_2$ 0.1C$_6$H$_{14}$: C, 63.16; H, 6.33; N, 17.13. Found: C, 63.30; H, 6.39; N, 16.92.

EXAMPLE 89

(−) 4-chloro-N-[1-{[(cyanoimino)(3-pyridinylamino)methyl]amino}-2-(2,6,6-trimethyl-1-cyclohexen-1-yl)ethyl]benzamide Example 66B was chromatographed over a Daicel Chiral Technologies Chiralcel OJ chiral column (2.0 cm×25 cm) eluting with 5% ethanol/hexanes (flow rate=10 mL/minutes) to provide the desired product as the levorotatory enantiomer.

$[\alpha]_D^{23}$=−13.5° (c 0.25, DMSO);

mp 94–96° C.;

MS (ESI+) m/z 465 (M+H)$^+$;

$^1$H NMR (DMSO-d$_6$) δ 9.65 (br s, 1H), 8.80 (m, 1H), 8.46 (d, 1H, J=2.4 Hz), 8.37 (d, 1H, J=4.8 Hz), 7.86 (d, 2H, J=8.5 Hz), 7.66 (dt, 1H, J=7.8, 1.5 Hz), 7.60 (d, 2H, J=8.5 Hz), 7.41 (dd, 1H, J=8.5, 4.8 Hz), 7.12 (m, 1H), 5.85 (m, 1H), 2.60 (m, 2H,) 1.87 (m, 2H), 1.63 (s, 3H), 1.53 (m, 2H), 1.38 (m, 2H), 1.02 (d, 3H, J=7.5 Hz);

Anal. calcd for C$_{25}$H$_{29}$ClN$_6$O 0.15CH$_2$Cl$_2$ 0.07C$_6$H$_{14}$: C, 63.48; H, 6.31; N, 17.37. Found: C, 63.74; H, 6.33; N, 17.13.

EXAMPLE 90

(−) 4-chloro-N-(1-{[(cyanoimino)(3-pyridinylamino)methyl]amino}-2,2-dimethyl-4-pentenyl)benzamide Example 67B was chromatographed over a Daicel Chiral Technologies Chiralcel AS chiral column (2.0 cm×25 cm) eluting with 5% ethanol/hexanes (flow rate=10 mL/minutes) to provide the desired product as the levorotatory enantiomer.

$[\alpha]_D^{23}$=−18.3° (c 0.23, DMSO);

mp 97–98° C.;

MS (ESI+) m/z 411 (M+H)$^+$;

¹H NMR (DMSO-d₆) δ 9.54 (br s, 1H), 8.47 (d, 1H, J=2.5 Hz), 8.39 (m, 2H), 7.84 (d, 2H, J=8.9 Hz), 7.68 (m, 1H), 7.57 (d, 2H, J=8.5 Hz), 7.43 (dd, 1H, J=8.1, 4.7 Hz), 6.84 (m, 1H), 5.88 (m, 2H), 5.09 (s, 1H), 5.05 (m, 1H) 2.09 (m, 2H), 0.94 (s, 3H), 0.92 (s, 3H);

Anal. calcd for $C_{21}H_{23}ClN_6O$ 0.35$H_2O$: C, 60.46; H, 5.73; N, 20.14. Found: C, 60.20; H, 5.65; N, 20.21.

EXAMPLE 91

(+) 4-chloro-N-(1-{[(cyanoimino)(3-pyridinylamino)methyl]amino}-2,2-dimethyl-4-pentenyl)benzamide Example 67B was chromatographed over a Daicel Chiral Technologies Chiralcel AS chiral column (2.0 cm×25 cm) eluting with 5% ethanol/hexanes (flow rate=10 mL/minutes) to provide the desired product as the dextrorotatory enantiomer.

$[\alpha]_D^{23}$=+17.5° (c 0.24, DMSO);
mp 98–99° C.;
MS (ESI+) m/z 411 (M+H)⁺;
¹H NMR (DMSO-d₆) δ 9.54 (br s, 1H), 8.47 (d, 1H, J=2.5 Hz), 8.39 (m, 2H), 7.84 (d, 2H, J=8.9 Hz), 7.68 (m, 1H), 7.57 (d, 2H, J=8.5 Hz), 7.43 (dd, 1H, J=8.1, 4.7 Hz), 6.84 (m, 1H), 5.88 (m, 2H), 5.09 (s, 1H), 5.05 (m, 1H) 2.09 (m, 2H), 0.94 (s, 3H), 0.92 (s, 3H);

Anal. calcd for $C_{21}H_{23}ClN_6O$ 0.3$H_2O$: C, 60.59; H, 5.71; N, 20.19. Found: C, 60.53; H, 5.71;N, 19.97.

EXAMPLE 92

4-chloro-N(1-{[(cyanoimino)(3-pyridinylamino) methyl]amino}-3,3-dimethyl-4-pentenyl)benzamide

EXAMPLE 92A 3,3-dimethyl-4-pentenal

Prepared according to the method of Buchi, et. al. J.Org.Chem. (1983) 48, 5406–5408.

MS (DCI/NH₃) 113 (M+H)⁺.

EXAMPLE 92B

N-[1-(1H-1,2,3-benzotriazol-1-yl)-3,3-dimethyl-4-pentenyl]-4-chlorobenzamide

A suspension of 4-chlorobenzamide (1.32 g, 8.5 mmol), Example 92A (0.96 g, 8.5 mmol), benzotriazole (1.01 g, 8.5 mmol), and MgSO₄ (2.00 g, 16.6 mmol) in toluene (50 mL) was treated with p-toluenesulfonic acid (100 mg, 0.53 mmol). The solution was heated at reflux for 48 hours, cooled to ambient temperature, filtered and concentrated to dryness. The crude material was purified by recrystallization from EtOAc/hexanes to provide 1.301 g of the desired product as a white solid.

MS (DCI/NH₃) 369 (M+H)⁺;
¹H NMR (DMSO-d₆) δ 9.80 (d, 1H, J=8.5 Hz), 8.03 (dd, 2H, J=8.6, 2.7 Hz), 7.88 (d, 2H, J=8.6 Hz), 7.61–7.54 (m, 3H), 7.43–7.38 (m, 1H), 6.84 (q, 1H, J=7.4 Hz), 5.75 (dd, 1H, J=17.3, 10.7 Hz), 4.84–4.75 (m, 2H), 2.65–2.43 (m, 2H), 1.05 (s, 3H), 0.93 (s, 3H).

EXAMPLE 92C 4-chloro-N-(1-{[(cyanoimino)(3-pyridinylamino) methyl]amino}-3,3-dimethyl-4-pentenyl)benzamide Example 54C and Example 92B were processed as described in Example 54D to provide the desired product.

mp 171–172° C.;
MS (DCI/NH₃) m/z 411 (M+H)⁺;
¹H NMR (DMSO-d₆) δ 9.73 (s, 1H), 9.00 (s, 1H), 8.49 (d, 1H, J=2.4 Hz), 8.33 (dd, 1H, J=5.3, 1.9 Hz), 7.90 (m, 3H), 7.70 (m, 1H), 7.58 (d, 2H, J=8.6 Hz), 7.40–7.36 (m, 1H), 5.89 (dd, 1H, J=17.2, 11.5 Hz), 5.60 (pentet, 1H, J=7.4 Hz), 4.93–4.86 (m, 2H), 2.00 (d, 2H, J=6.3 Hz), 1.06 (s, 3H), 1.05 (s, 3H);

Anal. calcd for $C_{21}H_{23}ClN_6O$: C, 61.38; H, 5.64; N, 20.45. Found: C, 61.24; H, 5.76; N, 20.33.

EXAMPLE 93

4-chloro-N-(1-{[(cyanoimino)(3-pyridinylamino) methyl]amino}-2-cyclohexyl-2-methylpropyl) benzamide

EXAMPLE 93A

N-[1-(1H-1,2,3-benzotriazol-1-yl)-2-cyclohexyl-2-methylpropyl]-4-chlorobenzamide Oxalyl chloride (7.8 g, 61.42 mmol) in methylene chloride (60 mL) at −78° C. was treated with dimethylsufoxide (8.4 g, 107.5 mmol). After stirring at −78° C. for 10 minutes, the mixture was treated with 2-cyclohexyl-2-methylpropanol (4.8 g, 36.86 mmol) in 15 ml of methylene chloride. The mixture was allowed to stir at −78° C. for 30 minutes and then treated with triethylamine (15.54 g, 153.6 mmol). The reaction mixture was stirred for 10 minutes and then stirred an additional 5 minutes at 0° C. The mixture was quenched with saturated aqueous ammonium (10 mL) chloride and extracted with diethyl ether (2×50 mL). The organic layer was washed with brine (15 mL), dried over anhydrous sodium sulfate and concentrated under vacuo. The crude product was redissolved in diethyl ether and the resulting precipitate was filtered through a pad of Celite. The solution was concentrated under reduced pressure to provide 4.5 g of 2-cyclohexyl-2-methylpropanal as an oil.

A suspension of p-chlorobenzamide (5.31 g, 35.10 mmol), 2-cyclohexyl-2-methylpropanal (4.5 g, 35.10 mmol), and benzotriazole (4.18 g, 35.10 mmol) in toluene (100 mL) was treated with p-toluenesulfonic acid (334 mg, 1.76 mmol). The solution was heated at reflux under Dean-Stark conditions for 10 hours, then cooled gradually to ambient temperature. The solvent was removed under reduced pressure and the residue was purified by flash chromatography (elution with 10% EtOAc/hexane) to provide 5.3 g of the desired product as a white solid.

MS (ESI+) m/z 383 (M+H)⁺.

EXAMPLE 93B 4-chloro-N-(1-{[(cyanoimino)(3-pyridinylamino) methyl]amino}-2-cyclohexyl-2-methylpropyl) benzamide Example 54C and Example 93A were processed as described in Example 54D to provide the desired compound.

mp 181–183° C.;
MS (ESI+) m/z 453 (M+H)⁺;
¹H NMR (DMSO-d₆) δ 9.54 (s, 1H), 8.45 (d, 1H, J=2.2 Hz), 8.39 (d, 1H, J=5.8 Hz), 8.29 (d, 1H, J=8.8 Hz), 7.83 (d, 2H, J=8.8 Hz), 7.62 (m, 1H), 7.58 (d, 2H, J=8.8 Hz), 7.43 (dd, 1H, J=8.5, 4.8 Hz), 6.78 (d, 1H, J=9.1 Hz), 6.02 (t, 1H, J=8.8 Hz), 1.78 (m, 4H), 1.62 (m, 1H), 1.28–0.96 (m, 6H), 0.87 (s, 3H), 0.83 (s, 3H);

Anal. calcd for $C_{24}H_{29}ClN_6O$: C, 66.63; H, 6.45;N, 18.55. Found: C, 63.74; H, 6.39; N, 18.57.

EXAMPLE 94

4-chloro-N-(1-{[(cyanoimino)(3-pyridinylamino)methyl]amino}-2,2-dimethylhexyl)benzamide

EXAMPLE 94A

N-[1-(1H-1,2,3-benzotriazol-1-yl)-2,2-dimethylhexyl]-4-chlorobenzamide 2,2-Dimethylhexanol was processed as described in Example 93A to provide the desired product.
MS (ESI+) m/z 383 (M+H)$^+$.

EXAMPLE 94B 4-chloro-N-(1-{[(cyanoimino)(3-pyridinylamino)methyl]amino}-2,2-dimethylhexyl)benzamide Example 54C and Example 94A were processed as described in Example 54D to provide the desired product.
mp 168–170° C.;
MS (ESI+) m/z 427 (M+H)$^+$;
$^1$H NMR (DMSO-d$_6$) δ 9.53 (s, 1H), 8.46 (d, 1H, J=2.4 Hz), 8.38 (d, 1H, J=4.7 Hz), 8.34 (m, 1H), 7.83 (d, 2H, J=8.5 Hz), 7.65 (m, 1H), 7.57 (d, 2H, J=8.5 Hz), 7.43 (dd, 1H, J=4.4, 8.1 Hz), 6.79 (m, 1H), 5.86 (dd, 1H, J=8.9 Hz), 1.28 (m, 6H), 0.94 (s, 3H), 0.92 (s, 3H), 0.87 (t, 3H, J=13 Hz);
Anal. calcd for $C_{22}H_{27}ClN_6O$: C, 61.89; H, 6.37; N, 19.68. Found: C, 62.22; H, 6.37; N, 19.62.

EXAMPLE 95

N-(2-(1-adamantyl)-1-{[(cyanoimino)(3-pyridinylamino)methyl]amino}ethyl)-4-chlorobenzamide

EXAMPLE 95A

N-[2-(1-adamantyl)-1-(1H-1,2,3-benzotriazol-1-yl)ethyl]-4-chlorobenzamide 2-(1-Adamantyl)ethanol was processed as described in Example 93A to provide the desired product.
MS (ESI+) m/z 435 (M+H)$^+$.

EXAMPLE 95B

N-(2-(1-adamantyl)-1-{[(cyanoimino)(3-pyridinylamino)methyl]amino}ethyl)-4-chlorobenzamide Example 54C and Example 95A were processed as described in Example 54D to provide the desired product.
mp 202–203° C.;
MS (ESI+) m/z 477 (M+H)$^+$;
$^1$H NMR (DMSO-d$_6$) δ 9.70 (s, 1H), 9.00 (m, 1H), 8.46 (d, 1H, J=2.2 Hz), 8.33 (dd, 1H, J=4.8, 1.5 Hz), 7.91 (d, 2H, J=8.5 Hz), 7.66 (m, 2H), 7.58 (d, 2H, J=8.5 Hz), 7.38 (dd, 1H, J=8.1, 4.8 Hz), 5.76 (m, 1H), 4.11 (dd, 1H, J=6.6, 5.2 Hz), 3.17 (d, 1H, J=5.2 Hz), 1.91 (m, 3H), 1.82–1.51 (m, 12H);
Anal. calcd for $C_{26}H_{29}ClN_6O$: C, 65.47; H, 6.13; N, 17.62. Found: C, 65.30; H, 6.13; N, 17.69.

EXAMPLE 96

N-(2,2-bis[(allyloxy)methyl]-1-{[(cyanoimino)(3-pyridinylamino)methyl]amino}butyl)-4-chlorobenzamide

EXAMPLE 96A

N-[2,2-bis[(allyloxy)methyl]-1-(1H-1,2,3-benzotriazol-1-yl)butyl]-4-chlorobenzamide 2,2-Bis(allyloxymethyl)-1-butanol was processed as described in Example 93A to provide the desired product.
MS (ESI+) m/z 469 (M+H)$^+$.

EXAMPLE 96B

N-(2,2-bis[(allyloxy)methyl]-1-{[(cyanoimino)(3-pyridinylamino)methyl]amino}butyl)-4-chlorobenzamide Example 54C and Example 96A were processed as described in Example 54D to provide the desired product.
MS (ESI+) m/z 511 (M+H)$^+$;
$^1$H NMR (DMSO-d$_6$) δ 9.63 (s, 1H), 8.88 (m, 1H), 8.54 (d, 1H, J=2.7 Hz), 8.39 (dd, 1H, J=4.5, 1.4 Hz), 7.84 (d, 2H, J=8.5 Hz), 7.80 (m, 1H), 7.60 (d, 2H, J=8.5 Hz), 7.42 (dd, 1H, J=8.1, 4.8 Hz), 5.93–5.74 (m, 3H), 5.27–5.08 (m, 4H), 4.03–3.08 (m, 4H), 3.60 (d, 1H, J=9.5 Hz), 3.47–3.32 (m, 3H), 1.43 (m, 2H), 0.86 (t, 3H, J=7.4 Hz);
Anal. calcd for $C_{26}H_{31}ClN_6O_3$ 0.35 $C_3H_7NO$: C, 60.55; H, 6.28; N, 16.58. Found: C, 60.84; H, 6.08; N, 16.96.

EXAMPLE 97

4-chloro-N-[1-{[(cyanoimino)(3-pyridinylamino)methyl]amino}-3-(dimethylamino)-2,2-dimethylpropyl]benzamide

EXAMPLE 97A

N-[1-(1H-1,2,3-benzotriazol-1-yl)-3-dimethylamino)-2,2-dimethylpropyl]-4-chlorobenzamide 3-(Dimethylamino)-2,2-dimethyl-1-propanol was processed as described in Example 93A to provide the desired product.
MS (ESI+) m/z 386 (M+H)$^+$.

EXAMPLE 97B 4-chloro-N-[1-{[(cyanoimino)(3-pyridinylamino)methyl]amino}-3-(dimethylamino)-2,2-dimethylpropyl]benzamide Example 54C and Example 97A were processed as described in Example 54D to provide the desired product.
mp 101–103° C.;
MS (ESI+) m/z 428 (M+H)$^+$;
$^1$H NMR (DMSO-d$_6$) δ 9.52 (s, 1H), 8.81 (m, 1H), 8.56 (m, 1H), 8.38 (m, 1H), 7.81 (d, 2H, J=8.5 Hz), 7.80 (m, 1H), 7.59 (d, 2H, J=8.5 Hz), 7.43 (dd, 1H, J=8.1, 4.1 Hz), 5.57 (t, 1H, J=8.4 Hz), 2.09 (m, 8H), 1.12 (s, 3H), 0.83 (s, 3H);
Anal. calcd for $C_{21}H_{26}ClN_7O$: C, 58.94; H, 6.12; N, 22.91. Found: C, 58.72; H, 5.97; N, 22.76.

EXAMPLE 98

Tert-butyl (2R)-2-((R)-[(4-chlorobenzoyl)amino]{[(cyanoimino)(3-pyridinylamino)methyl]amino}methyl)-1-pyrrolidinecarboxylate

EXAMPLE 98A

Tert-butyl (2R)-2-{1H-1,2,3-benzotriazol-1-yl[(4-chlorobenzoyl)amino]methyl}-1-pyrrolidinecarboxylate 4-Chlorobenzamide, tert-butyl (2R)-formyl-1-pyrrolidinecarboxylate, benzotriazole, and p-toluenesulfonic acid were processed as described in Example 53A to provide the desired product.
MS (ESI+) m/z 456 (M+H)$^+$.

EXAMPLE 98B

Tert-butyl (2R)-2-((R)-[(4-chlorobenzoyl)amino]{
[(cyanoimino)(3-pyridinylamino)methyl]
amino}methyl)-1-pyrrolidinecarboxylate Example 54C and Example 98A were processed as described in Example 54D to provide the desired product.

mp 184–185° C.;

MS (ESI+) m/z 498 (M+H)+;

$^1$H NMR (DMSO-$d_6$) δ 9.61 (s, 1H), 8.78 (m, 1H), 8.45 (d, 1H, J=2.2 Hz), 8.36 (m, 1H), 7.83 (d, 2H, J=8.5 Hz), 7.65 (m, 1H), 7.60 (d, 2H, J=8.5 Hz), 7.38 (m, 1H), 5.65 (m, 1H), 4.21 (m, 1H), 1.90 (m, 6H), 1.31 (s, 9H);

Anal. calcd for $C_{24}H_{28}ClN_7O_7$: C, 57.89; H, 5.67; N, 19.69. Found: C, 57.94; H, 5.59; N, 19.72.

EXAMPLE 99

4-chloro-N-[1-{[(cyanoimino)(3-pyridinylamino)
methyl]amino}-3-(methylsulfanyl)propyl]benzamide

EXAMPLE 99A

N-[1-(1H-1,2,3-benzotriazol-1-yl)-(methylsulfanyl)
propyl]-4-chlorobenzamide

4-Chlorobenzamide, 3-methylthio-1-propanal, benzotriazole, and p-toluenesulfonic acid were processed as described in Example 53A to provide the desired product.

MS (ESI+) m/z 361 (M+H)+.

EXAMPLE 99B 4-chloro-N-[1-{[(cyanoimino)(3-pyridinylamino)
methyl]amino}-3-(methylsulfanyl)propyl]benzamide Example 54C and Example 99A were processed as described in Example 54D to provide the desired product.

mp 104–105° C.; (ESI+) m/z 403 (M+H)+;

$^1$H NMR (DMSO-$d_6$) δ 9.82 (br s, 1H), 9.09 (m, 1H), 8.49 (d, 1H, J=2.6 Hz), 8.32 (d, 1H, J=4.9 Hz), 7.94 (d, 2H, J=8.5 Hz), 7.85 (m, 1H), 7.70 (m, 1H), 7.59 (d, 2H, J=8.5 Hz), 7.38 (dd, 1H, J=8.3, 4.4 Hz), 5.73 (m, 1H), 2.58 (m, 2H), 2.16 (m, 2H), 2.08 (s, 3H);

Anal. calcd for $C_{18}H_{19}ClN_6OS$ 0.1$CH_2Cl_2$: C, 52.84; H, 4.70; N, 20.43. Found: C, 53.04; H, 4.89; N, 20.08.

EXAMPLE 100

N-(1-adamantyl{[(cyanoimino)(3-pyridinylamino)
methyl]amino}methyl)-4-chlorobenzamide

EXAMPLE 100A

N-[1-adamantyl(1H-1,2,3-benzotriazol-1-yl)methyl]-
4-chlorobenzamide

1-Adamantylmethanol was processed as described in Example 93A to provide the desired product.

MS (ESI+) m/z 421 (M+H)+.

EXAMPLE 100B

N-(1-adamantyl{[(cyanoimino)(3-pyridinylamino)
methyl]amino}methyl)-4-chlorobenzamide Example 54C and Example 100A were processed as described in Example 54D to provide the desired product.

mp 209–210° C.;

MS (ESI+) m/z 463 (M+H)+;

$^1$H NMR (DMSO-$d_6$) δ 9.52 (s, 1H), 8.49 (d, 1H, J=2.6 Hz), 8.38 (m, 2H), 7.84 (d, 2H, J=8.5 Hz), 7.69 (m, 1H), 7.59 (d, 2H, J=8.5 Hz), 7.42 (dd, 1H, J=8.0, 4.8 Hz), 6.82 (m, 1H), 5.69 (t, 1H, J=8.8, 8.8 Hz), 1.72–1.51 (m, 15H);

Anal. calcd for $C_{25}H_{27}ClN_6O$ 0.2 $CH_2Cl_2$ 0.4 $C_4H_8O_2$: C, 62.48; H, 5.99; N, 16.31. Found: C, 62.68; H, 6.26; N, 16.37.

EXAMPLE 101

4-chloro-N-[{[(cyanoimino)(3-pyridinylamino)
methyl]amino}(5-ethyl-1,3-dioxan-5-yl)methyl]
benzamide

EXAMPLE 101A

N-[1H-1,2,3-benzotriazol-1-yl(5-ethyl-1,3-dioxan-5-
yl)methyl]-4-chlorobenzamide 5-Ethyl-1,3-dioxan-5-ol was processed as described in Example 93A to provide the desired product.

MS (ESI+) m/z 399 (M+H)+.

EXAMPLE 101B 4-chloro-N-[{[(cyanoimino)(3-pyridinylamino)
methyl]amino}(5ethyl-1,3-dioxan-5-yl)methyl]
benzamide Example 54C and Example 101A were processed as described in Example 54D to provide the desired product.

mp 194–195° C.;

MS (ESI+) m/z 443 (M+H)+;

$^1$H NMR (DMSO-$d_6$) δ 9.55 (s, 1H), 8.74 (m, 1H), 8.52 (d, 1H, J=2.2 Hz), 8.40 (d, 1H, J=4.1 Hz), 7.88 (d, 2H, J=8.8 Hz), 7.75 (m, 1H), 7.58 (d, 2H, J=8.8 Hz), 7.42 (dd, 1H, J=8.3, 4.4 Hz), 7.32 (m, 1H), 6.07 (t, 1H, J=8.5 Hz), 4.78 (d, 1H, J=5.9 Hz), 4.70 (d, 1H, J=5.9 Hz), 4.15 (m, 1H), 4.03 (m, 1H), 3.68 (d, 1H, J=12.1 Hz), 3.64 (d, 1H, J=12.1 Hz), 1.35 (m, 2H), 0.85 (t, 3H, J=7.4 Hz);

Anal. calcd for $C_{21}H_{23}ClN_6O_3$: C, 56.95; H, 5.23; N, 18.98. Found: C, 56.69; H, 5.20; N, 19.02.

EXAMPLE 102

4-chloro-N-(1-{[(cyanoimino)(3-pyridinylamino)
methyl]amino}-2,2-dimethyl-3-phenylpropyl)
benzamide

EXAMPLE 102A

N-[1-(1H-1,2,3-benzotriazol-1-yl)-2,2dimethyl-3-
phenylpropyl]-4-chlorobenzamide 2,2-Dimethyl-3-phenyl-1-propanol was processed as described in Example 93A to provide the desired product.

MS (ESI+) m/z 419 (M+H)+.

EXAMPLE 102B 4-chloro-N-(1-{[(cyanoimino)(3-pyridinylamino)
methyl]amino}-2,2-dimethyl-3-phenylpropyl)
benzamide Example 54C and Example 102A were processed as described in Example 54D to provide the desired product.

mp 182–183° C.;

MS (ESI+) m/z 461 (M+H)+;

1H NMR (DMSO-d6) δ 9.59 (s, 1H), 8.50 (d, 1H, J=2.2 Hz), 8.47 (m, 1H), 8.39 (d, 1H, J=4.4 Hz), 7.86 (d, 2H, J=8.5 Hz), 7.70 (m, 1H), 7.59 (d, 2H, J=8.5 Hz), 7.43 (dd, 1H, J=7.7, 4.8 Hz), 7.29 (m, 2H), 7.21 (m, 3H), 6.98 (m, 1H), 5.91 (t, 1H, J=8.8 Hz), 2.72 (d, 1H, J=12.9 Hz), 2.60 (d, 1H, J=12.9 Hz), 0.87 (s, 3H), 0.86 (s, 3H);

Anal. calcd for $C_{25}H_{25}ClN_6O$: C, 65.14; H, 5.47; N, 18.23. Found: C, 65.07; H, 5.48; N, 18.36.

EXAMPLE 103

N-(1-{[(cyanoimino)(3-pyridinylamino)methyl]amino}-1–2,2-dimethylpropyl)-4-iodobenzamide

EXAMPLE 103A 4-iodobenzamide

A suspension of 4-iodobenzoic acid (20.0 g, 80.6 mL) in $CH_2Cl_2$ (350 mL) at 0° C. was treated with oxalyl chloride (42.3 mL of a 2.0 M solution in $CH_2Cl_2$, 81.7 mmol). Dimethylformamide was added (0.5 mL) until a homogeneous solution was achieved and then the cooling bath was removed. The reaction mixture was stirred at ambient temperature for 3 hours and then concentrated to provide crude 4iodobenzoyl chloride as a waxy oil that was used without further purification.

Crude 4-iodobenzoyl chloride (11.4 g, 42.7 mmol) in THF (75 mL), prepared above, was treated with ammonium hydroxide (5 mL) followed by water (40 mL) at ambient temperature. The reaction mixture was stirred for 3 hours and then partitioned between EtOAc (50 mL) and brine (50 mL). The phases were separated and the organic phase was washed with 10% aqueous $NaHCO_3$ solution (30 mL) and brine (30 mL), dried over $Na_2SO_4$, and filtered. The filtrate volume was reduced until a white solid precipitated from solution. The white solid was collected by filtration and washed with diethyl ether to provide the desired product (10.2 g, 41.4 mmol, 97%).

MS (DCI/NH3) m/z 265 (M+NH)+.

EXAMPLE 103B

N-[1-(1H-1,2,3-benzotriazol-1-yl)-2,2-dimethylpropyl]-4-iodobenzamide

Example 103A, pivaldehyde, benzotriazole, and p-toluenesulfonic acid were processed as described in Example 53A to provide the desired product.

MS (ESI+) m/z 435 (M+H)+.

EXAMPLE 103C

N-(1-{[(cyanoimino)(3-pyridinylamino)methyl]amino}-2,2-dimethylpropyl)-4-iodobenzamide Example 54C and Example 103B were processed as described in Example 54D to provide the desired product.

mp 180–183° C.;

MS (ESI+) m/z 477 (M+H)+;

1H NMR (DMSO-d6) δ 9.52 (br s, 1H), 8.48 (d, 1H, J=2.4 Hz), 8.41–8.35 (m, 2H), 7.49 (d, 2H, J=8.5 Hz), 7.68 (br d, 1H, J=8.3 Hz), 7.60 (d, 2H, J=8.5 Hz), 7.42 (dd, 1H, J=8.1, 2.7 Hz), 6.83 (br d, 1H, J=9.2 Hz), 5.83 (t, 1H, J=8.8 Hz), 0.98 (s, 9H);

Anal. calcd for $C_{19}H_{21}IN_6O$: C, 47.91; H, 4.44; N, 17.64. Found: C, 47.80; H, 4.71; N, 17.30.

EXAMPLE 104

N-(1-{[(cyanoimino)(3-pyridinylamino)methyl]amino}-2,2-dimethylpropyl)-4-(2-furyl)benzamide Example 103C (0.230 g, 0.48 mmol), triphenylarsenine (0.04 g, 0.12 mmol), and 2-(tributylstannyl)furan (0.28 g, 0.77 mmol) in N-methylpyrrolidinone (3.5 mL) were treated with tris(dibenzylidineacetone)dipalladium(0) (0.02 g, 0.02 mmol) and stirred at ambient temperature for 6 hours. The reaction mixture was diluted with 100 mL EtOAc and filtered through a pad of celite and the solvent removed under reduced pressure. The crude material was purified by flash chromatography (elution with 80% ethyl acetate/hexanes) to provide 0.088 g of the desired product as a white solid.

mp 181–182° C.;

MS (ESI+) m/z 417 (M+H)+;

1H NMR (DMSO-d6) δ 9.57 (s, 1H), 8.50 (d, 1H, J=8.4 Hz), 8.40 (dd, 1H, J=5.3, 1.2 Hz), 8.36 (d, 1H, J=8.5 Hz), 7.89 (d, 2H, J=8.6 Hz), 7.83 (s, 1H), 7.82 (d, 2H, J=8.6 Hz), 7.71 (d, 1H, J=8.7 Hz), 7.44 (dd, 1H, J=8.7, 5.9 Hz), 7.12 (d, 1H, J=3.6 Hz), 6.87 (d, 1H, J=11.2 Hz), 6.65 (dd, 1H, J=3.6, 1.7 Hz), 5.87 (t, 1H, J=9 Hz), 1.00 (s, 9H);

Anal. calcd for $C_{23}H_{24}N_6O_2$ 0.2 $H_2O$: C, 65.76; H, 5.85; N, 20.01. Found: C, 65.73; H, 5.76; N, 20.15.

EXAMPLE 105

4-bromo-N-(1-{[(cyanoimino)(3-pyridinylamino)methyl]amino}-2,2-dimethylpropyl)benzamide

EXAMPLE 105A

N-[1-(1H-1,2,3-benzotriazol-1-yl)-2,2-dimethylpropyl]-4-bromobenzamide

4-Bromobenzamide, pivaldehyde, benzotriazole, and p-toluenesulfonic acid were processed as described in Example 53A to provide the desired product.

MS (DCI/NH3) m/z 387 (M+H)+.

EXAMPLE 105B 4-bromo-N-(1-{[(cyanoimino)(3-pyridinylamino)methyl]amino}-2,2-dimethylpropyl)benzamide Example 54C and Example 104A were processed as described in Example 54D to provide the desired product.

mp 180–181° C.;

MS (ESI+) m/z 429 (M+H)+;

1H NMR (DMSO-d6) δ 9.50 (br s, 1H), 8.48 (d, 1H, J=2.4 Hz), 8.42–8.36 (m, 2H), 7.8–7.65 (m, 5H), 7.44 (dd, 1H, J=8.1, 2.8 Hz), 6.84 (br d, 1H, J=9.1 Hz), 5.83 (t, 1H, J=8.8 Hz), 0.98 (s, 9H);

HRMS (FAB) calcd m/z for $C_{19}H_{21}N_6O$ (M+): (428.0960). Found: 428.0966.

EXAMPLE 106

4-chloro-N-(1-{[(cyanoimino)(3-pyridinylamino)methyl]amino}-2,2-dimethylpropyl)-2-fluorobenzamide

EXAMPLE 106A

N-[1-(1H-1,2,3benzotriazol-1-yl)-2,2-dimethylpropyl]-4-chloro-2-fluorobenzamide

4-Chloro-2-fluorobenzamide, pivaldehyde, benzotriazole and p-toluenesulfonic acid were processed as described in Example 53A to provide the desired product.

MS (DCI/NH3) m/z 361 (M+H)+.

EXAMPLE 106B 4-chloro-N-(1-{[(cyanoimino)(3-pyridinylamino)methyl]amino}-2,2-dimethylpropyl)-2-fluorobenzamide Example 54C and Example 106A were processed as described in Example 54D to provide the desired product.

mp 183–184° C.;

MS (DCI/NH$_3$) m/z 403 (M+H)$^+$;

$^1$H NMR (DMSO-d$_6$) δ 9.48 (s, 1H), 8.47 (d, 1H, J=2.4 Hz), 8.40 (d, 1H, J=8.4 Hz), 8.37 (dd, 1H, J=5.8, 1.6 Hz), 7.71–7.65 (m, 2H), 7.58 (dd, 1H, J=11.3, 1.8 Hz), 7.43–7.40 (m, 2H), 6.95 (d, 1H, J=8.7 Hz), 5.80 (t, 1H, J=8.6 Hz), 0.98 (s, 9H);

Anal. calcd for C$_{19}$H$_{20}$ClFN$_6$O: C, 56.65; H, 5.00; N, 20.86. Found: C, 56.58; H, 5.18; N, 20.86.

EXAMPLE 107

N-(1-{[(cyanoimino)(3-pyridinylamino)methyl]amino}-2,2-dimethylpropyl)-4-fluorobenzamide

EXAMPLE 107A

N-[1-(1H-1,2,3-benzotriazol-1-yl)-2,2-dimethylpropyl]-4-fluorobenzamide

4-Fluorobenzamide, pivaldehyde, benzotriazole and p-toluenesulfonic acid were processed as described in Example 53A to provide the desired product.

MS (ESI+) m/z 327 (M+H)$^+$.

EXAMPLE 107B

N-(1-{[(cyanoimino)(3-pyridinylamino)methyl]amino}-2,2-dimethylpropyl)-4-fluorobenzamide Example 54C and Example 107A were processed as described in Example 54D to provide the desired product.

mp 195–196° C.;

MS (ESI+) m/z 369 (M+H)$^+$;

$^1$H NMR (DMSO-d$_6$) δ 9.53 (s, 1H), 8.48 (d, 1H, J=2 Hz), 8.39 (dd, 1H, J=5, 1 Hz), 8.34 (d, 1H, J=8 Hz), 7.90 (m, 2H), 7.69 (ddd, 1H, J=8, 3, 1 Hz), 7.42 (dd, 1H, J=8, 5 Hz), 7.33 (m, 2H), 6.82 (d, 1H, J=9 Hz), 5.83 (t, 1H, J=9 Hz), 0.98 (s, 9H);

Anal. calcd for C$_{19}$H$_{21}$FN$_6$O: C, 61.94; H, 5.75; N, 22.81. Found: C, 61.75; H, 5.80; N, 22.78.

EXAMPLE 108

N-(1-{[(cyanoimino)(3-pyridinylamino)methyl]amino}-1-2,2-dimethylpropyl)-3-methylbenzamide

EXAMPLE 108A

N-[1-(1H-1,2,3-benzotriazol-1-yl)-2,2-dimethylpropyl]-3-methylbenzamide meta-Toluamide, pivaldehyde, benzotriazole and p-toluenesulfonic acid were processed as described in Example 53A to provide the desired product.

MS (ESI+) m/z 323 (M+H)$^+$.

EXAMPLE 108B

N-(1-{[(cyanoimino)(3-pyridinylamino)methyl]amino}-2,2-dimethylpropyl)-3-methylbenzamide Example 54C and Example 108A were processed as described in Example 54D to provide the desired product.

MS (ESI+) m/z 365 (M+H)$^+$;

$^1$H NMR (DMSO-d$_6$) δ 9.67 (s, 1H), 8.85 (br s, 1H), 8.58 (m, 1H), 8.44 (m, 1H), 7.83 (m, 1H), 7.68–7.61(m, 2H), 7.55 (m, 1H), 7.38 (m, 2H), 7.00 (d, 1H), 5.84 (t, 1H), 2.38 (s, 3H), 1.01 (s, 9H).

EXAMPLE 109

N-(1-{[(cyanoimino)(3-pyridinylamino)methyl]amino}-2,2-dimethylpropyl)-2-methylbenzamide

EXAMPLE 109A

N-[1-(1H-1,2,3-benzotriazol-1-yl)-2,2-dimethylpropyl]-2-methylbenzamide ortho-Toluamide, pivaldehyde, benzotriazole and p-toluenesulfonic acid were processed as described in Example 53A to provide the desired product.

MS (ESI+) m/z 323 (M+H)$^+$.

EXAMPLE 109B

N-(1-{[(cyanoimino)(3-pyridinylamino)methyl]amino}-2,2-dimethylpropyl)-2-methylbenzamide Example 54C and Example 109A were processed as described in Example 54D to provide the desired product.

MS (ESI+) m/z 365 (M+H)$^+$;

$^1$H NMR (DMSO-d$_6$) δ 9.68 (s, 1H), 9.02 (br s, 1H), 8.57 (m, 1H), 8.41 (m, 1H), 7.82 (m, 1H), 7.53(m, 1H), 7.39–7.33 (m, 2H), 7.26 (m, 2H), 7.00 (d, 1H), 5.72 (t, 1H), 2.32 (s, 3H), 1.01 (s, 9H).

EXAMPLE 110

N-(1-{[(cyanoimino)(3-pyridinylamino)methyl]amino}-2,2-dimethylpropyl)-3,5-difluorobenzamide

EXAMPLE 110A

N-[1-(1H-1,2,3-benzotriazol-1-yl)-2,2-dimethylpropyl]-3,5-difluorobenzamide 3,5-Difluorobenzamide, pivaldehyde, benzotriazole and p-toluenesulfonic acid were processed as described in Example 53A to provide the desired product.

MS (ESI+) m/z 345 (M+H)$^+$.

EXAMPLE 110B

N-(1-{[(cyanoimino)(3-pyridinylamino)methyl]amino}-1-2,2-dimethylpropyl)-3,5-difluorobenzamide Example 54C (161 mg, 1.00 mmol), Example 110A (344 mg, 1.00 mmol) and cesium carbonate (757 mg, 2.33 mmol) in anhydrous DMF (5 mL) were stirred at ambient temperature for 12 hours. The reaction mixture was acidified with 10% HCl and extracted with methylene chloride (3×20 mL). The organic extracts were combined, dried (sodium sulfate), filtered, and concentrated. The residue was purified by flash column chromatography (elution with 5% MeOH/methylene chloride) to provide the desired product (86 mg, 43%) as a white solid.

MS (ESI+) m/z 387 (M+H)$^+$;

$^1$H NMR (DMSO-d$_6$) δ 9.50 (s, 1H), 8.45 (m, 3H), 7.54 (m, 5H), 6.82 (d, 1H), 5.82 (t, 1H), 0.98 (s, 9H);

Anal. calcd for C$_{19}$H$_{20}$F$_2$N$_6$O: C, 59.06; H, 5.22; N, 21.75. Found: C, 58.73; H, 5.40; N, 21.98.

EXAMPLE 111

4-chloro-N-{1-[[(cyanoimino)(3-pyridinylamino)methyl](methyl)amino]-2,2-dimethylpropyl}benzamide

EXAMPLE 111A

N''-cyano-N-methyl-N'-(3-pyridinyl)guanidine

Example 54B and methylamine were processed as described as in Example 54C to give the desired product.
MS (ESI+) m/z 176 (M+H)$^+$.

EXAMPLE 111B 4-chloro-N-{1-[[(cyanoimino)(3-pyridinylamino)methyl](methyl)amino]-2,2-dimethylpropyl}benzamide Example 111A and Example 69B were processed as described in Example 54D to provide the desired product.
mp 127–129° C.;
MS (ESI+) m/z 399 (M+H)$^+$;
$^1$H NMR (DMSO-d$_6$) δ 9.36 (s, 1H), 8.78 (m, 1H), 8.35 (d, 1H, J=2.0 Hz), 8.28 (d, 1H, J=3.7 Hz), 7.92 (d, 2H, J=8.1 Hz), 7.60 (d, 2H, J=8.1 Hz), 7.49 (m, 1H), 7.37 (dd, 1H, J=8.1, 4.4 Hz), 6.04 (m, 1H), 2.97 (s, 3H), 1.08 (s, 3H);
Anal. calcd for C$_{20}$H$_{23}$ClN$_6$O: C, 60.22; H, 5.81; N, 21.07. Found: C, 59.88; H, 6.09; N, 21.06.

EXAMPLE 112

(−) 4-chloro-N-(2,2,2-trichloro-1-{[(cyanoimino)(3-pyridinylamino)methyl]amino}ethyl)benzamide Example 45C was chromatographed over a Daicel Chiral Technologies Chiralcel AS chiral column (2.0 cm×25 cm) eluting with 5% ethanol/hexanes (flow rate=10 mL/minutes) to provide the desired product as the levorotatory enantiomer.
[α]$_D^{23}$=−19.2° (c 0.04, DMSO);
mp 126–128° C.;
MS (ESI+) m/z 426 (M+H)$^+$;
$^1$H NMR (DMSO-d$_6$) δ 10.12 (s, 1H), 8.72 (d, 1H, J=9 Hz), 8.50 (dd, 1H, J=12, 3 Hz), 7.70–7.67 (m, 1H), 7.51 (q, 1H, J=6 Hz), 7.45–7.38 (m, 1H), 7.30 (d, 1H, J=9 Hz), 6.82 (t, H, J=9 Hz), 2.38 (s, 3H);
Anal. calcd for C$_{17}$H$_{15}$Cl$_3$N$_6$O: C, 47.96; H, 3.55; N, 19.74. Found: C, 47.62; H, 3.25; N, 19.84.

EXAMPLE 113

(+) 4-chloro-N-(2,2,2-trichloro-1-{[(cyanoimino)(3-pyridinylamino)methyl]amino}ethyl)benzamide Example 45C was chromatographed over a Daicel Chiral Technologies Chiralcel AS chiral column (2.0 cm×25 cm) eluting with 5% ethanol/hexanes (flow rate=10 mL/minutes) to provide the desired product as the dextrorotatory enantiomer.
[α]$_D^{23}$=+14.8° (c 0.03, DMSO);
mp 126–128° C.;
MS (ESI+) m/z 426 (M+H)$^+$;
$^1$H NMR (DMSO-d$_6$) δ 10.12 (s, 1H), 8.72 (d, 1H, J=9 Hz), 8.50 (dd, 1H, J=12, 3 Hz), 7.70–7.67 (m, 1H), 7.51 (q, 1H, J=6 Hz), 7.45–7.38 (m, 1H), 7.30 (d, 1H, J=9 Hz), 6.82 (t, 1H, J=9 Hz), 2.38 (s, 3H);
Anal. calcd for C$_{17}$H$_{15}$Cl$_3$N$_6$O: C, 47.96; H, 3.55; N, 19.74. Found: C, 47.73; H, 3.31; N, 19.59.

EXAMPLE 114

4-iodo-N-(2,2,2-trichloro-1-{[(cyanoimino)(3-pyridinylamino)methyl]amino}ethyl)benzamide

EXAMPLE 114A 4-iodo-N-(2,2,2-trichloro-1-hydroxyethyl)benzamide

Example 103A was processed as described in Example 37C to provide the desired compound.
MS (ESI+) m/z 394 (M+H)$^+$.

EXAMPLE 114B 4-iodo-N-(1,2,2,2-tetrachloroethyl)benzamide

Example 114A was processed as described in Example 37D to provide the desired compound. MS (ESI+) m/z 412 (M+H)$^+$.

EXAMPLE 114C 4-iodo-N-(2,2,2-trichloro-1-isothiocyanatoethyl)benzamide

Example 114B was processed as described in Example 45A to provide the desired compound.
MS (ESI+) m/z 435 (M+H)$^+$.

EXAMPLE 114D 4-iodo-N-(2,2,2-trichloro-1-{[(3-pyridinylamino)carbothioyl]amino}ethyl)benzamide Example 114C and 3-aminopyridine were processed as described in Example 45B to provide the desired compound.
MS (ESI+) m/z 545 (M+H)$^+$.

EXAMPLE 114E 4-iodo-N-(2,2,2-trichloro-1-{[(cyanoimino)(3-pyridinylamino)methyl]amino}ethyl)benzamide Example 114D was processed as described in Example 45C to provide the desired compound.
mp 208–210° C.;
MS (DCI/NH$_3$) m/z 553 (M+NH)$^+$;
$^1$H NMR (DMSO-d$_6$) δ 10.33 (br s, 1H), 9.25 (d, 1H, J=8.20 Hz), 8.62 (d, 1H, J=2.5 Hz), 8.38 (dd, 1H, J=5.4, 1.6 Hz), 8.18 (d, 1H, J=9.5 Hz), 8.04 (dt, 1H, J=8.65, 1.6 Hz), 7.92 (d, 2H, J=8.6 Hz), 7.62 (d, 2H, J=8.6 Hz), 7.48 (t, 1H, J=8.3 Hz), 7.44 (dd, 1H, J=8.8, 5.6 Hz);
Anal. calcd for C$_{16}$H$_{12}$Cl$_3$IN$_6$O: C, 35.75; H, 2.40; N, 15.47. Found: C, 35.55; H, 2.40; N, 15.47.

EXAMPLE 115

4-chloro-N-(2,2-dichloro-1-{[(cyanoimino)(3-pyridinylamino)methyl]amino}pentyl)benzamide

EXAMPLE 115A

N-[1-(1H-1,2,3-benzotriazol-1-yl)-2,2-dichloropentyl]-4-chlorobenzamide

4-Chlorobenzamide, 2,2-dichloropentanal, benzotriazole, and p-toluenesulfonic acid were processed as described in Example 53A to provide the desired product.
MS (ESI−) m/z 409 (M−H)$^-$.

EXAMPLE 115B 4-chloro-N-(2,2-dichloro-1-{[(cyanoimino)(3-pyridinylamino)methyl]amino}pentyl)benzamide Example 54C and Example 115A were processed as described in Example 54D to provide the desired product.

mp 192–193° C.;

MS (ESI+) m/z 453 (M+H)$^+$;

$^1$H NMR (DMSO-d$_6$) δ 9.92 (s, 1H), 8.70 (d, 1H, J=8.1 Hz), 8.52 (d, 1H, J=2.0 Hz), 8.46 (d, 1H, J=4.1 Hz), 7.85 (d, 2H, J=8.5 Hz), 7.69 (m, 1H), 7.60 (d, 2H, J=8.5 Hz), 7.48 (dd, 1H, J=8.0, 4.4 Hz), 7.15 (d, 1H, J=8.8 Hz), 6.58 (t, 1H, J=8.6 Hz), 2.12 (m, 2H), 1.72 (m, 2H), 0.96 (t, 3H, J=7.1 Hz);

Anal. calcd for C$_{19}$H$_{19}$Cl$_3$N$_6$O: C, 50.29; H, 4.22; N, 18.52. Found: C, 50.54; H, 4.34; N, 18.70.

EXAMPLE 116

4-chloro-N-(2,2-dichloro-1-{[(cyanoimino)(3-pyridinylamino)methyl]amino}propyl)benzamide

EXAMPLE 116A 2,2-dichloropropionaldehyde

Chlorine gas was bubbled through dimethylformamide (14.7 g, 0.202 mmol) for 5 minutes. The solution was heated to 45–55° C. and propionaldehyde (11.7, 0.202 mmol) in dimethylformamide (29.5 g, 0.404 mmol) was added slowly, maintaining the reaction temperature at 45–55° C. (a cooling bath was necessary to control the temperature). During the addition, Cl$_2$ was bubbled through the reaction mixture to maintain a yellow color. After complete addition, the reaction mixture was heated at 45–55° C. for 30 minutes. The solution was cooled to 0° C. and diethyl ether (100 mL) was added followed by cold water (100 mL). The phases were separated and the organic phase was washed with aqueous sodium bicarbonate (20 mL), brine (20 mL), dried (sodium sulfate), and concentrated under reduced pressure to provide 21.1 g of crude 2,2-dichloropropionaldehyde as an oil.

EXAMPLE 116B

N-[1-(1H-1,2,3-benzotriazol-1-yl)-2,2-dichloropropyl]-4-chlorobenzamide

4-Chlorobenzamide, Example 116A, benzotriazole, and p-toluenesulfonic acid were processed as described in Example 53A to provide the desired product.

MS (ESI−) m/z 381 (M−H)$^-$.

EXAMPLE 116C 4-chloro-N-(2,2-dichloro-1-{[(cyanoimino)(3-pyridinylamino)methyl]amino}propyl)benzamide Example 54C and Example 116B were processed as described in Example 110B to provide the desired product.

mp 185–187° C.;

MS (ESI+) m/z 425 (M+H)$^+$;

$^1$H NMR (DMSO-d$_6$) δ 9.95 (s, 1H), 8.75 (d, 1H, J=8.8 Hz), 8.52 (d, 1H, J=2.4 Hz), 8.46 (d, 1H, J=4.8 Hz), 7.85 (d, 2H, J=8.8 Hz), 7.69 (m, 1H), 7.60 (d, 2H, J=8.8 Hz), 7.47 (dd, =H, J=8.3, 4.8 Hz), 7.16 (d, 1H, J=8.5 Hz), 6.55 (t, 1H, J=8.5 Hz), 2.17 (s, 3H);

Anal. calcd for C$_{17}$H$_{15}$Cl$_3$N$_6$O: C, 47.96; H, 3.55; N, 19.74. Found: C, 48.21; H, 3.75; N, 19.81.

EXAMPLE 117

(−) 4-chloro-N-(2,2-dichloro-1-{[(cyanoimino)(3-pyridinylamino)methyl]amino}propyl)benzamide Example 116C was chromatographed over a Daicel Chiral Technologies Chiralcel AS chiral column (2.0 cm×25 cm) eluting with 5% ethanol/hexanes (flow rate=10 mL/minutes) to provide the desired product as the levorotatory enantiomer.

[α]$_D^{23}$=−22° (c 0.19, DMSO);

mp 188–190° C.;

MS (ESI+) m/z 425 (M+H)$^+$;

$^1$H NMR (DMSO-d$_6$) δ 9.93 (s, 1H), 8.75 (d, 1H, J=8.1 Hz), 8.52 (d, 1H, J=2.0 Hz), 8.46 (d, 1H, J=4.4 Hz), 7.85 (d, 2H, J=8.5 Hz), 7.69 (m, 1H), 7.60 (d, 2H, J=8.5 Hz), 7.47 (dd, 1H, J=8.0, 4.4 Hz), 7.16 (d, 1H, J=8.5 Hz), 6.55 (t, 1H, J=8.5 Hz), 2.17 (s, 3H);

Anal. calcd for C$_{17}$H$_{15}$Cl$_3$N$_6$O: C, 47.96; H, 3.55; N, 19.74. Found: C, 48.14; H, 3.64; N, 19.47.

EXAMPLE 118

(+) 4-chloro-N-(2,2-dichloro-1-{[(cyanoimino)(3-pyridinylamino)methyl]amino}propyl)benzamide Example 116C was chromatographed over a Daicel Chiral Technologies Chiralcel AS chiral column (2.0 cm×25 cm) eluting with 5% ethanol/hexanes (flow rate=10 mL/minutes) to provide the desired product as the dextrorotatory enantiomer.

[α]$_D^{23}$=+21° (c 0.19, DMSO);

mp 187–189° C.;

MS (ESI+) m/z 425 (M+H)$^+$;

$^1$H NMR (DMSO-d$_6$) δ 9.93 (s, 1H), 8.75 (d, 1H, J=8.1 Hz), 8.52 (d, 1H, J=2.0 Hz), 8.46 (d, 1H, J=4.4 Hz), 7.85 (d, 2H, J=8.5 Hz), 7.69 (m, 1H), 7.60 (d, 2H, J=8.5 Hz), 7.47 (dd, 1H, J=8.0, 4.4 Hz), 7.16 (d, 1H, J=8.5 Hz), 6.55 (t, 1H, J=8.5 Hz), 2.17 (s, 3H);

Anal. calcd for C$_{17}$H$_{15}$Cl$_3$N$_6$O: C, 47.96; H, 3.55; N, 19.74. Found: C, 48.12; H, 3.73; N, 19.34.

EXAMPLE 119

3-chloro-N-(2,2-dichloro-1-{[(cyanoimino)(3-pyridinylamino)methyl]amino}propyl)benzamide

EXAMPLE 119A

N-[1-(1H-1,2,3-benzotriazol-1-yl)-2,2-dichloropropyl]-3-chlorobenzamide

3-Chlorobenzamide, Example 116A, benzotriazole, and p-toluenesulfonic acid were processed as described in Example 53A to provide the desired product.

MS (ESI−) m/z 381 (M−H)$^-$.

EXAMPLE 119B 3-chloro-N-(2,2-dichloro-1-{[(cyanoimino)(3-pyridinylamino)methyl]amino}propyl)benzamide Example 54C and Example 119A were processed as described in Example 110B to provide the desired product.

mp 142–143° C.;

MS (ESI+) m/z 425 (M+H)⁺;
¹H NMR (DMSO-d₆) δ 9.93 (s, 1H), 8.81 (d, 1H, J=8.5 Hz), 8.52 (d, 1H, J=2.4 Hz), 8.46 (d, 1H, J=4.4 Hz), 7.85 (m, 1H), 7.70 (m, 2H), 7.56 (t, 1H, J=8.0 Hz), 7.49 9 (dd, 1H, J=8.2, 4.8 Hz), 7.14 (d, 1H, J=8.5 Hz), 6.55 (t, 1H, J=8.8 Hz), 2.18 (s, 3H);

Anal. calcd for $C_{17}H_{15}Cl_3N_6O$: C, 47.96; H, 3.55; N, 19.74. Found: C, 47.82; H, 3.62; N, 19.76.

EXAMPLE 120

N-(2,2-dichloro-1-{[(cyanoimino)(3-pyridinylamino)methyl]amino}propyl)-3,5-difluorobenzamide

EXAMPLE 120A

N-[1-(1H-1,2,3-benzotriazol-1-yl)-2,2-dichloropropyl]-3,5-difluorobenzamide 3,5-Difluorobenzamide, Example 116A, benzotriazole, and p-toluenesulfonic acid were processed as described in Example 53A to provide the desired product.
MS (ESI+) m/z385 (M+H)⁺.

EXAMPLE 120B

N-(2,2-dichloro-1-{[(cyanoimino)(3-pyridinylamino)methyl]amino}propyl)-3,5-difluorobenzamide Example 54C and Example 120A were processed as described in Example 110B to provide the desired product.
mp 191–193° C.;
MS (ESI+) m/z427 (M+H)⁺;
¹H NMR (DMSO-d₆) δ 9.93 (s, 1H), 8.87 (d, 1H, J=8.1 Hz), 8.52 (d, 1H, J=2.0 Hz), 8.46 (dd, 1H, J=4.8, 1.0 Hz), 7.70 (m, 1H), 7.52 (m, 3H), 7.48 (dd, 1H, J=8.1, 4.7 Hz), 7.12 (d, 1H, J=8.5 Hz), 6.53 (t, 1H, J=8.6 Hz), 2.18 (s, 3H);
Anal. calcd for $C_{17}H_{14}Cl_2F_2N_6O$: C, 47.79; H, 3.30; N, 19.67. Found: C, 47.85; H, 3.38; N, 19.55.

EXAMPLE 121

4-chloro-N-(1-{[(cyanoimino)(3-pyridinylamino)methyl]amino}-2,2,3,3,3-pentafluoropropyl)benzamide

EXAMPLE 121A

N-[1-(1H-1,2,3-benzotriazol-1-yl)-2,2,3,3,3-pentafluoropropyl]-4-chlorobenzamide 4-Chlorobenzamide, pentafluoropropanal, benzotriazole, and p-toluenesulfonic acid were processed as described in Example 53A to provide the desired product.
MS (ESI–) m/z 403 (M–H)⁻.

EXAMPLE 121B 4-chloro-N-(1-{[(cyanoimino)(3-pyridinylamino)methyl]amino}-2,2,3,3,3-pentafluoropropyl)benzamide Example 54C and Example 121A were processed as described in Example 110B to provide the desired product.
mp 177–178° C.;
MS (ESI+) m/z 447 (M+H)⁺;
¹H NMR (DMSO-d₆) δ 10.05 (s, 1H), 9.04 (d, 1H, J=8.8 Hz), 8.46 (m, 2H), 7.83 (d, 2H, J=8.5 Hz), 7.66 (m, 1H), 7.64 (d, 2H, J=8.5 Hz), 7.48 (dd, 1H, J=8.0, 4.6 Hz), 7.41 (m, 1H), 6.86 (m, 1H);
Anal. calcd for $C_{17}H_{12}ClF_5N_6O$: C, 45.70; H, 2.71; N, 18.81. Found: C, 45.79; H, 2.50; N, 19.05.

EXAMPLE 122

3-chloro-N-(1-{[(cyanoimino)(3-pyridinylamino)methyl]amino}-2,2,3,3,3-pentafluoropropyl)benzamide

EXAMPLE 122A

N-[1-(1H-1,2,3-benzotriazol-1-yl)-2,2,3,3,3-pentafluoropropyl]-3-chlorobenzamide 3-Chlorobenzamide, pentafluoropropanal, benzotriazole, and p-toluenesulfonic acid were processed as described in Example 53A to provide the desired product.
MS (ESI–) m/z 403 (M–H)⁻.

EXAMPLE 122B 3-chloro-N-(1-{[(cyanoimino)(3-pyridinylamino)methyl]amino}-2,2,3,3,3-pentafluoropropyl)benzamide Example 54C and Example 122A were processed as described in Example 110B to provide the desired product.
mp 183–185° C.;
MS (ESI+) m/z 447 (M+H)⁺;
¹H NMR (DMSO-d₆) δ 10.05 (br s, 1H), 9.13 (d, 1H, J=8.8 Hz), 8.47 (m, 2H), 7.84 (m, 1H), 7.78 (m, 1H), 7.70 (m, 1H), 7.65 (m, 1H), 7.58 (t, 1H, J=8.1 Hz), 7.48 (m, 2H), 6.86 (m, 1H);
Anal. calcd for $C_{17}H_{12}ClF_5N_6O$: C, 45.70; H, 2.71; N, 18.81. Found: C, 45.77; H, 2.83; N, 18.90.

EXAMPLE 123

4-chloro-N-(1-{[(nitroimino)(3-pyridinylamino)methyl]amino}-2,2-dimethylpropyl)benzamide

EXAMPLE 123A

N-(3-pyridinyl)guanidine dihydrochloride

3-Aminopyridine (38.96 g, 413.96 mmol) and cyanamide (21.40 g, 509.2 mmol) in 12N hydrochloric acid (271 mL) were stirred at 140–150° C. for 4 hours. Concentration under reduced pressure provided a heavy syrup which was purified by recrystalization from 1:1 isopropanol:diethyl ether (500 mL) to provide 60.2 g of the desired product as a white solid.
MS (ESI+) m/z 137 (M+H)⁺.

EXAMPLE 123B

N″-nitro-N-(3-pyridinyl)guanidinium nitrate

Example 123A (20.0 g, 146.0 mmol) was added in small portions to concentrated sulfuric acid (122.8 ml, 2.19 mol) at –10° C. Concentrated nitric acid was added dropwise at 0° C. for a period of 10 minutes. The mixture was stirred at 0° C. for 1 hour and then dripped slowly into 700 g of crushed ice. The resulting precipitate was collected by filtration providing 17.5 g of the desired product as a white solid.
MS (ESI+) m/z 182 (M+H)⁺.

EXAMPLE 123C 4-chloro-N-(1-{[(nitroimino)(3-pyridinylamino)methyl]amino}-2,2-dimethylpropyl)benzamide Example 123B and Example 69B were processed as described in Example 110B to provide the desired product.

mp 203–204° C.;

MS (ESI+) m/z 405 (M+H)$^+$;

$^1$H NMR (DMSO-d$_6$) δ 9.81 (s, 9H), 9.50–9.10 (br s, 1H), 8.90 (d, 1H, J=8 Hz), 8.52 (d, 1H, J=2 Hz), 8.40 (dd, 1H, J=5, 2 Hz), 7.91–7.88 (m, 2H), 7.75 (ddd, 1H J=8, 3, 2 Hz), 7.59 (d, 2H, J=9 Hz), 7.52 (d, 1H, J=8 Hz), 7.43 (dd, 1H, J=8, 5 Hz), 5.90 (t, 1H, J=9 Hz), 1.08 (s, 9H);

Anal. calcd for C$_{18}$H$_{21}$ClN$_6$O$_3$: C, 53.40; H, 5.23; N, 20.76. Found: C, 53.41; H, 5.30; N, 20.76.

EXAMPLE 124

4-chloro-N-(1-{[(nitroimino)(3-pyridinylamino)methyl]amino}-3,3-dimethylbutyl)benzamide Example 62A and Example 123B were processed as described in Example 110B to provide the desired product.

mp 195–197° C.;

MS (ESI+) m/z 419 (M+H)$^+$;

$^1$H NMR (DMSO-d$_6$) δ 9.30 (br s, 1H), 8.51 (d, 1H), 8.39 (d, 1H), 7.94 (d, 2H), 7.73 (d, 2H), 7.62 (d, 2H), 7.42 (dd, 1H), 5.83–5.78 (m, 1H), 2.01 (dd, 1H), 1.87 (dd, 1H), 0.98 (s, 9H);

Anal. calcd for C$_{19}$H$_{23}$ClN$_6$O$_3$: C, 54.48; H, 5.53; N, 20.06. Found: C, 54.42; H, 5.54; N, 20.27.

EXAMPLE 125

(+) 4-chloro-N-(1-{[(nitroimino)(3-pyridinylamino)methyl]amino}-3,3-dimethylbutyl)benzamide Example 124 was chromatographed over a Daicel Chiral Technologies Chiralcel OJ chiral column (2.0 cm×25 cm) eluting with 5% ethanol/hexanes (flow rate=10 mL/minutes) to provide the desired product as the dextrorotatory enantiomer.

[α]$_D^{23}$=+64.2° (c 0.308, DMSO);

mp 184–185° C.;

MS (ESI+) m/z 419 (M+H)$^+$;

$^1$H NMR (DMSO-d$_6$) δ 9.30 (br s, 1H), 8.52 (d, 1H, J=2.0 Hz), 8.38 (d, 1H, J=4.8 Hz), 7.93 (d, 2H, J=8.5 Hz), 7.75 (m, 1H), 7.62 (d, 2H, J=8.5 Hz), 7.40 (dd, 1H, J=8.0, 5.1 Hz), 5.80 (m, 1H), 2.03 (dd, 1H, J=14.1, 7.1 Hz), 1.86 (dd, 1H, J=14.1, 5.4 Hz), 0.98 (s, 3H);

Anal. calcd for C$_{19}$H$_{23}$ClN$_6$O$_3$: C, 54.48; H, 5.53; N, 20.06. Found: C, 54.69; H, 5.41; N, 20.05.

EXAMPLE 126

(−) 4-chloro-N-(1-{[(nitroimino)(3-pyridinylamino)methyl]amino}-3,3-dimethylbutyl)benzamide Example 124 was chromatographed over a Daicel Chiral Technologies Chiralcel OJ chiral column (2.0 cm×25 cm) eluting with 5% ethanol/hexanes (flow rate=10 mL/minutes) to provide the desired product as the levorotatory enantiomer.

[α]$_D^{23}$=−58.9° (c, 0.292, DMSO);

mp 185–186° C.;

MS (ESI+) m/z 419 (M+H)$^+$;

$^1$H NMR (DMSO-d$_6$) δ 9.30 (br s, 1H), 8.52 (d, 1H, J=2.0 Hz), 8.38 (d, 1H, J=4.8 Hz), 7.93 (d, 2H, J=8.5 Hz), 7.75 (m, 1H), 7.62 (d, 2H, J=8.5 Hz), 7.40 (dd, 1H, J=8.0, 5.1 Hz), 5.80 (m, 1H), 2.03 (dd, 1H, J=14.1, 7.1 Hz), 1.86 (dd, 1H, J=14.1, 5.4 Hz), 0.98 (s, 3H);

Anal. calcd for C$_{19}$H$_{23}$ClN$_6$O$_3$: C, 54.48; H, 5.53; N, 20.06. Found: C, 54.63; H, 5.53; N, 20.18.

EXAMPLE 127

4-chloro-N-(1-{[(nitroimino)(3-pyridinylamino)methyl]amino}-2,2-dimethyl-4-pentenyl)benzamide Example 123B and Example 67A were processed as described in Example 110B to provide the desired product.

mp 200–203° C.;

MS (ESI+) m/z 431 (M+H)$^+$;

$^1$H NMR (DMSO-d$_6$) δ 9.88 (br s, 1H), 8.95 (br s, 1H), 8.51 (d, 1H, J=2.5 Hz), 8.40 (dd, 1H, J=8.6, 4.7 Hz), 7.90 (d, 2H, J=8.6 Hz), 7.74 (d, 1H, J=4.7 Hz), 7.60 (d, 2H, J=8.6 Hz), 7.43 (dd, 1H, J=4.8, 2.8 Hz), 5.96–5.82 (m, 2H), 5.10 (s, 1H), 5.11–5.08 (dd, J=8.7, 7.6 Hz, 1H), 2.25–2.10 (m, 2H), 1.06 (s, 3H), 1.04 (s, 3H);

Anal. calcd for C$_{20}$H$_{23}$ClN$_6$O$_3$: C, 55.75; H, 5.38; N, 19.50. Found: C, 55.84; H, 5.37; N, 19.48.

EXAMPLE 128

4-chloro-N-(1-{[(nitroimino)(3-pyridinylamino)methyl]amino}-2,2-dimethyl-3-phenylpropyl)benzamide Example 123B and Example 102A were processed as described in Example 110B to provide the desired product.

mp 205–207° C.;

MS (ESI+) m/z 481 (M+H)$^+$;

$^1$H NMR (DMSO-d$_6$) δ 9.89 (s, 1H); 8.99 (br s, 1H), 8.520 (s, 1H), 8.41 (d, 1H), 7.92 (d, 2H), 7.75 (d, 1H), 7.60 (d, 2H), 7.44 (dd, 2H), 7.30–7.19 (m, 5H), 5.90 (t, 1H), 2.78 (d, 1H), 2.70 (d, 1H), 1.00 (s, 3H), 0.97 (s, 3H);

Anal. calcd for C$_{24}$H$_{25}$ClN$_6$O3: C, 59.94; H, 5.24, N, 17.47. Found: C, 60.19; H, 5.24; N, 17.58.

EXAMPLE 129

4-chloro-N-[1-{[(nitroimino)(3-pyridinylamino)methyl]amino}-2-(2,6,6-trimethyl-1-cyclohexen-1-yl)ethyl]benzamide Example 123B and Example 66A were processed as described in Example 110B to provide the desired product.

mp 217–218° C.;

MS (ESI+) m/z 485 (M+H)$^+$;

$^1$H NMR (DMSO-d$_6$) δ 8.50 (d, 1H), 8.41 (d, 1H), 7.91 (d, 2H), 7.73 (d, 1H), 7.63 (d, 2H), 7.44 (dd, 1H), 1.96–1.88 (m, 2H), 1.69 (s, 3H), 1.58–1.48 (m, 2H), 1.57–1.47 (m, 2H), 1.04 (s. 3H), 1.02 (s, 3H);

Anal. calcd for C$_{24}$H$_{29}$ClN$_6$O$_3$: C, 59.44; H, 6.03; N, 17.33. Found: C, 59.55; H, 6.07; N, 17.48.

EXAMPLE 130

4-chloro-N-(1-{[(nitroimino)(3-pyridinylamino)methyl]amino}-2-cyclohexyl-2-methylpropyl)benzamide Example 123B and Example 93A were processed as described in Example 110B to provide the desired product.

mp 201–203° C.;

MS (ESI+) m/z 473 (M+H)$^+$;

$^1$H NMR (DMSO-d$_6$) δ 9.85 (br s, 1H), 8.89 (br s, 1H), 8.50 (d, 1H), 8.40 (dd, 1H), 7.88 (d, 2H), 7.73 (d, 1H), 7.59 (d, 2H), 7.43 (dd, 1H), 5.93 (t, 1H), 1.83–1.03 (m, 11H), 0.99 (s, 3H), 0.98 (s, 3H);

Anal. calcd for C$_{23}$H$_{29}$ClN$_6$O$_3$: C, 58.41; H, 6.18; N, 17.77. Found: C, 58.19; H, 6.07; N, 17.71.

EXAMPLE 131

N-(2,2-bis[(allyloxy)methyl]-1-{[(nitroimino)(3-pyridinylamino)methyl]amino}butyl)-4-chlorobenzamide Example 123B and Example 96A were processed as described in Example 110B to provide the desired product.
mp 175–180° C.;
MS (ESI+) m/z 531 (M+H)$^+$;
$^1$H NMR (DMSO-d$_6$) δ 9.87 (br s, 1H), 9.31 (br s, 1H), 8.56 (d, 1H), 8.40 (d, 1H), 7.89 (d, 2H), 7.80 (d, 1H), 7.61 (d, 2H), 7.44 (dd, 2H), 5.94–5.78 (m, 3H), 5.26 (dd, 1H), 5.20 (dd, 1H), 5.15 (dd, 1H), 5.12 (dd, 1H), 4.04–3.86 (m, 4H), 3.70 (d, 1H), 3.59 (d, 1H), 3.48 (d, 1H), 3.39 (d, 1H), 1.49 (q, 2H), 0.88 (t, 3H);
Anal. calcd for C$_{25}$H$_{31}$ClN$_6$O$_5$: C, 56.55; H, 5.88; N, 15.83. Found: C, 56.42; H, 5.94; N, 15.55.

EXAMPLE 132

4-chloro-N-(4-cyano-1-{[(nitroimino)(3-pyridinylamino)methyl]amino}-2,2-diethylbutyl)benzamide Example 123B and Example 65A were processed as described in Example 110B to provide the desired product.
mp 100–110° C.;
MS (ESI+) m/z 472 (M+H)$^+$;
$^1$H NMR (DMSO-d$_6$) δ 9.81 (br s, 1H), 8.86 (br s, 1H), 8.49 (d, 1H), 7.87 (d, 2H), 7.71 (d, 1H), 7.60 (d, 2H), 7.44 (dd, 1H), 5.92 (t, 1H), 2.61–2.54 (m, 2H), 1.82 (t, 2H), 1.51 (q, 4H), 0.89 (t, 3H);
Anal. calcd for C$_{22}$H$_{26}$ClN$_7$O$_3$: C, 55.89; H, 5.80; N, 19.33. Found: C, 55.50; H, 5.61; N, 19.55.

EXAMPLE 133

4-chloro-N-(1-{[(nitroimino)(3-pyridinylamino)methyl]amino}-3,3-dimethyl-4-pentenyl)benzamide Example 123B and Example 92B were processed as described in Example 110B to provide the desired product.
mp 186–186° C.;
MS (DCI/NH$_3$) m/z 431 (M+H)$^+$;
$^1$H NMR (DMSO-d$_6$) δ 10.12 (s, 1H), 9.30 (s, 1H), 8.51 (d, 1H, J=3.3 Hz), 8.39 (dd, 1H, J=5.6, 1.5 Hz), 7.93 (d, 2H, J=8.2 Hz), 7.73 (d, 1H, J=8.3 Hz), 7.61 (d, 2H, J=8.3 Hz), 7.42 (dd, 1H, J=18.1, 11.7 Hz), 5.68 (m, 1H), 4.91 (d, 1H, J=18.2 Hz), 4.87 (dd, 1H, J=11.6, 1.5 Hz), 2.07 (AB of ABX, 2H, J=46.4 Hz, 14.0, 7.0 Hz), 1.07 (s, 9H);
Anal. calcd for C$_{20}$H$_{23}$ClN$_6$O$_3$: C, 55.75; H, 5.38; N, 19.50. Found: C, 55.71; H, 5.42; N, 19.70.

EXAMPLE 134

N-(2-(1-adamantyl)-1-{[(nitroimino)(3-pyridinylamino)methyl]amino}ethyl)-4-chlorobenzamide Example 123B and Example 95A were processed as described in Example 110B to provide the desired product.
mp 219–220° C.;
MS (ESI+) m/z 497 (M+H)$^+$;
$^1$H NMR (DMSO-d$_6$) δ 10.09 (br s, 1H), 9.83 (br s, 1H), 8.39 (d, 1H), 8.52 (d, 1H), 7.93 (d, 2H), 7.74 (d, 1H), 7.62 (d, 2H), 7.42 (dd, 1H), 5.82 (t, 1H), 1.92–1.58 (m, 17H);
Anal. calcd for C$_{25}$H$_{29}$ClN$_6$O$_3$: C, 60.42; H, 5.88; N, 16.91. Found: C, 60.44; H, 5.80; N, 16.72.

EXAMPLE 135

N-(1-{[(nitroimino)(3-pyridinylamino)methyl]amino}-2,2-dimethylpropyl)-4-phenylbenzamide

EXAMPLE 135A

N-[1-(1H-1,2,3-benzotriazol-1-yl)-2,2-dimethylpropyl]-4-phenylbenzamide

4-Phenylbenzamide, pivaldehyde, benzotriazole, and p-toluenesulfonic acid were processed as described in Example 53A to provide the desired product.
MS (ESI+) m/z 385 (M+H)$^+$.

EXAMPLE 135B

N-(1-{[(nitroimino)(3-pyridinylamino)methyl]amino}-2,2-dimethylpropyl)-4-phenylbenzamide Example 123B and Example 135A were processed as described in Example 110B to provide the desired product.
MS (ESI+) m/z 447 (M+H)$^+$;
$^1$H NMR (DMSO-d$_6$) δ 9.89 (br, s, 1H), 8.92 (br s, 1H), 8.58 (d, 1H), 8.43 (m, 1H), 7.99 (d, 2H), 7.83 (m, 3H), 7.73 (d, 2H), 7.51 (m, 4H), 6.98 (m, 1H), 5.92 (t, 1H), 1.06 (s, 9H).

EXAMPLE 136

4-chloro-N-(2,2-dichloro-1-{[(nitroimino)(3-pyridinylamino)methyl]amino}pentyl)benzamide Example 123B and Example 115A were processed as described in Example 110B to provide the desired product.
mp 198–200° C.;
MS (ESI+) m/z 473 (M+H)$^+$;
$^1$H NMR (DMSO-d$_6$) δ 9.16 (br s, 1H), 8.52 (d, 1H, J=1.4 Hz), 8.47 (d, 1H, J=3.4 Hz), 7.87 (d, 2H, J=8.5 Hz), 7.73 (m, 1H), 7.60 (d, 2H, J=8.5 Hz), 7.48 (dd, 1H, J=8.0, 3.7 Hz), 6.69 (t, 1H, J=8.8 Hz), 2.24 (m, 2H), 1.76 (m, 2H), 0.96 (t, 3H, J=7.1 Hz);
Anal. calcd for C$_{18}$H$_{19}$Cl$_3$N$_6$O$_3$: C, 45.64; H, 4.04; N, 17.74. Found: C, 45.85; H, 4.07; N, 17.91.

EXAMPLE 137

4-chloro-N-(2,2-dichloro-1-{[(nitroimino)(3-pyridinylamino)methyl]amino}propyl)benzamide Example 123B and Example 116B were processed as described in Example 110B to provide the desired product.
mp 170–172° C.;
MS (ESI+) m/z 445 (M+H)$^+$;
$^1$H NMR (DMSO-d$_6$) δ 10.30 (m, 1H), 9.10 (br s, 1H), 8.53 (d, 1H, J=2.0 Hz), 8.48 (m, 1H), 7.89 (d, 2H, J=8.8 Hz), 7.74 (m, 1H), 7.61 (d, 2H, J=8.8 Hz), 7.47 (m, 1H), 6.68 (t, 1H, J=8.5 Hz), 2.21 (s, 3H);
Anal. calcd for C$_{16}$H$_{15}$Cl$_3$N$_6$O$_3$ 0.2C$_4$H$_8$O$_2$: C, 43.55; H, 3.61; N, 18.14. Found: C, 43.98; H, 3.50; N, 18.53.

EXAMPLE 138

3-chloro-N-(2,2-dichloro-1-{[(nitroimino)(3-pyridinylamino)methyl]amino}propyl)benzamide Example 123B and Example 119A were processed as described in Example 110B to provide the desired product.

mp 160–161° C.;

MS (ESI+) m/z 445 (M+H)+;

$^1$H NMR (DMSO-d$_6$) δ 9.18 (m, 1H), 8.53 (d, 1H, J=1.0 Hz), 8.48 (d, 1H, J=4.1 Hz), 7.89 (s, 1H), 7.83 (d, 1H, J=7.5 Hz), 7.68 (m, 2H), 7.57 (dd, 1H, J=8.1, 7.8 Hz), 7.48 (dd, 1H, J=8.1, 4.8 Hz), 6.68 (t, 1H, J=8.8 Hz), 2.23 (s, 3H);

Anal. calcd for C$_{16}$H$_{15}$ClN$_6$O$_3$: C, 43.12; H, 3.39; N, 18.86. Found: C, 43.34; H, 3.38; N, 18.99.

EXAMPLE 139

4-chloro-N-(2,2-dimethyl-1-{[[(phenylsulfonyl)imino](3-pyridinylamino)methyl]amino}propyl)benzamide

EXAMPLE 139A

N"-phenylsulfonyl-N-(3-pyridinyl)guanidine

Phenylsulfonamide (1.49 g, 10 mmol) in anhydrous DMF (20 mL) at ambient temperature was treated with sodium hydride (400 mg of 60% reagent, 10.0 mmol). After 30 minutes, the reaction mixture was treated with 3-pyridyl isothiocyanate (1.36 g, 10.0 mmol), stirred for an additional 30 minutes, then treated with methyl iodide (1.42 g, 10.0 mmol). The resulting suspension was stirred for 1.5 hours and then water was added until a clear solution was formed. The solution was extracted with methylene chloride (3×50 mL) and the extracts were combined, dried (sodium sulfate), filtered, and concentrated to provide a yellow oil that was used without further purification.

The crude material obtained above was dissolved in methanol (50 mL) and treated with ammonia (150 mL of a 2.0 M solution in methanol). The reaction mixture was then heated at 80° C. in a sealed high-pressure flask for 24 hours. The solvent was removed and the residue was purified by flash chromatography (elution with 5% MeOH/methylene chloride) to provide the desired product (2.10 g) as a white solid.

MS (ESI+) m/z 277 (M+H)+.

EXAMPLE 139B 4-chloro-N-(2,2-dimethyl-1-{[[(phenylsulfonyl)imino](3-pyridinylamino)methyl]amino}propyl)benzamide Example 139A and Example 69B were processed as described in Example 54D to provide the desired product.

mp 196–197° C.;

MS (DCI/NH$_3$) m/z 500 (M+)+;

$^1$H NMR (DMSO-d$_6$) δ 9.44 (br s, 1H), 9.03 (br s, 1H), 8.49 (d, 1H, J=2.5 Hz), 8.34 (dd, H, J=4.8, 1.1 Hz), 7.92 (s, 1H), 7.90 (d, 2H, J=8.4 Hz), 7.80 (d, 2H, J=7.7 Hz), 7.75–7.70 (m, 1H), 7.61–7.49 (m, 5H), 7.39 (dd, 1H, J=8.4, 4.8 Hz), 5.67 (t, 1H, J=8.8 Hz), 1.02 (s, 9H);

Anal. calcd for C$_{24}$H$_{26}$ClN$_5$O$_3$S: C, 57.65, H, 5.24, N, 14.01. Found: C, 57.34, H, 5.38, N, 14.22.

EXAMPLE 140

4-chloro-N-(3,3-dimethyl-1-{[[(phenylsulfonyl)imino](3-pyridinylamino)methyl]amino}butyl)benzamide Example 139A and Example 62A were processed as described in Example 54D to provide the desired product.

mp 199–200° C.;

MS (ESI+) m/z 514 (M+H)+;

$^1$H NMR (DMSO-d$_6$) δ 9.68–9.51 (br s, 1H), 9.49–9.20 (br s, 1H), 8.49 (s, 1H), 8.33 (dd, 1H, J=5, 1 Hz), 7.92 (d, 2H, J=8 Hz), 7.81 (d, 2H, J=8 Hz), 7.80 (s, 1H overlapped), 7.71 (d, 1H, J=8 Hz), 7.63–7.43 (m, 5H), 7.37 (ddd, 1H, J=8, 5, 1 Hz), 5.72 (m, 1H), 1.99 (s, 1H), 1.70 (dd, 1H, J=14, 5 Hz), 0.92 (s, 9H);

Anal. calcd for C$_{25}$H$_{28}$ClN$_5$O$_3$S: C, 58.41; H, 5.49; N, 13.62. Found: C, 58.31; H, 5.56; N, 13.65.

EXAMPLE 141

4-chloro-N-{2,2-dimethyl-1-[((3-pyridinylamino){[(trifluoromethyl)sulfonyl]imino}methyl)amino]propyl}benzamide

EXAMPLE 141A

N-(3-pyridinyl)-N"-[(trifluoromethyl)sulfonyl]guanidine

Trifluoromethanesulfonamide was processed as described in Example 139A to provide the desired product.

MS (APCI) m/z 269 (M+H)+.

EXAMPLE 141B 4-chloro-N-{2,2-dimethyl-1-[((3-pyridinylamino){[(trifluoromethyl)sulfonyl]imino}methyl)amino]propyl}benzamide Example 141A and Example 69B were processed as described in Example 110B to provide the desired product.

MS (ESI+) m/z 492 (M+H)+;

$^1$H NMR (DMSO-d$_6$) δ 10.23 (br s, 1H), 8.90 (br s, 1H), 8.54 (m, 2H), 7.87 (m, 4H), 7.60 (m, 3H), 5.88 (t, 1H), 1.06 (s, 9H);

Anal. calcd for C$_{19}$H$_{21}$ClF$_3$N$_5$O$_3$S: C, 46.39; H, 4.30; N, 14.24. Found: C, 46.29; H, 4.56; N, 14.27.

EXAMPLE 142

4-chloro-N-{3,3-dimethyl-1-[((3-pyridinylamino){[(trifluoromethyl)sulfonyl]imino}methyl)amino]butyl}benzamide Example 141A and Example 62A were processed as described in Example 110B to provide the desired product.

MS (ESI+) m/z 506 (M+H)+;

$^1$H NMR (DMSO-d$_6$) δ 10.19 (br s, 1H), 9.21 (br s, 1H), 8.49 (m, 2H), 7.92 (m, 3H), 7.71 (d, 1H), 7.61 (d, 2H), 7.44 (m, 1H), 5.83 (m, 1H), 1.88 (m, 2H), 0.97 (s, 9H);

Anal. calcd for C$_{20}$H$_{23}$ClF$_3$N$_5$O$_3$S: C, 47.48; H, 4.58; N, 13.84. Found: C, 47.44; H, 4.80; N, 13.56.

EXAMPLE 143

N-(1-{[[(aminosulfonyl)imino](3-pyridinylamino)methyl]amino}-2,2-dimethylpropyl)-4-chlorobenzamide

EXAMPLE 143A

N"-(aminosulfonyl)-N-(3-pyridinyl)guanidine

Sulfamide was processed as described in Example 139A to provide the desired product.

MS (APCI+) m/z 216 (M+H)+.

EXAMPLE 143B

N-(1-{[[(aminosulfonyl)imino](3-pyridinylamino)methyl]amino}-2,2-dimethylpropyl)-4-chlorobenzamide Example 143A and Example 69B were processed as described in Example 110B to provide the desired product.

MS (ESI+) m/z 439 (M+H)+.

$^1$H NMR (DMSO-d$_6$) δ 9.25 (s, 1H), 8.99 (s, 1H), 8.67 (s, 1H), 8.29 (d, 1H), 7.90 (d, 3H), 7.77 (br s, 1H), 7.59 (d, 1H), 7.35 (m, 1H), 6.57 (s, 2H), 5.67 (t, 1H), 1.09 (s, 9H).

EXAMPLE 144

N-(1-{[[(aminosulfonyl)imino](3-pyridinylamino)methyl]amino}-3,3-dimethylbutyl)-4-chlorobenzamide Example 143A and Example 62A were processed as described in Example 110B to provide the desired product.

MS (ESI+) m/z 453 (M+H)+;

$^1$H NMR (DMSO-d$_6$) δ 9.48 (br s, 2H), 8.68 (s, 1H), 8.28 (n, 1H), 7.94 (m, 3H), 7.64 (d, 3H), 7.36 (m, 1H), 6.57 (s, 2H), 5.70 (m 1H), 2.03 (m, 1H), 1.81 (m, 1H), 0.98 (s, 9H).

EXAMPLE 145

4-chloro-N-(1-{[{[(dimethylamino)sulfonyl]imino}(3-pyridinylamino)methyl]amino}-2,2-dimethylpropyl)benzamide

EXAMPLE 145A

N,N-dimethylsulfamide

Dimethylsulfamoyl chloride (3.70 g) was treated with ammonia (200 mL of a 2 M in solution in methanol) in a sealed high-pressure flask and heated at 60° C. for 12 h. Solvent was removed by rotary evaporation to furnish a white solid. This material was washed with methylene chloride and dried at 50° C. under reduced pressure to provide the desired product (3.10 g) as a white solid.

MS (APCI+) m/z 124 (M+H)+.

EXAMPLE 145B

N"-(dimethylaminosulfonyl)N-(3-pyridinyl)guanidine

Example 145A was processed as described in Example 139A to provide the desired product.

MS (ESI+) m/z 244 (M+H)+.

EXAMPLE 145C 4-chloro-N-(1-{[{[(dimethylamino)sulfonyl]imino}(3-pyridinylamino)methyl]amino}-2,2-dimethylpropyl)benzamide Example 145B and Example 69B were processed as described in Example 110B to provide the desired product.

MS (ESI+) m/z 467 (M+H)+;

$^1$H NMR (DMSO-d$_6$) δ 9.50 (br s, 1H), 9.05 (br s, 1H), 8.75 (d, 1H), 8.41 dd, 1H), 8.02 (dd, 1H), 7.91 (d, 2H), 7.73 (br s, 1H), 7.59 (m 3H), 5.69 (t, 1H), 2.55 (s, 6H), 1.08 (s, 9H).

EXAMPLE 146

4-chloro-N-(1-{[{[(dimethylamino)sulfonyl]imino}(3-pyridinylamino)methyl]amino}-3,3-dimethylbutyl)benzamide Example 145A and Example 62A were processed as described in Example 110B to provide the desired product.

MS (ESI+) m/z 481 (M+H)+;

$^1$H NMR (DMSO-d$_6$) δ 9.69 (br s, 1H), 9.39 (br s, 1H), 8.73 (s, 1H), 8.41 (d, 1H), 8.02 (d, 1H), 7.93 (d, 2H), 7,56 (m, 4H), 5.78 (m, 1H), 2.59 (s, 6H), 1.99 (dd, 1H), 1.79 (dd, 1H), 0.98 (s, 9H).

EXAMPLE 147

4-chloro-N-(1-{[(2-fluoroanilino)carbonyl]amino}-2,2-dimethylpropyl)benzamide

3-Pyridyl isocyanate and Example 69C were processed as described in Example 42 to provide the desired product.

mp 229–230° C.;

MS (ESI+) m/z 378 (M+H)+;

$^1$H NMR (DMSO-d$_6$) δ 8.63 (d, 1H, J=2.0 Hz), 8.52 (d, 1H, J=8.5 Hz), 8.12 (dt, 1H, J=8.1, 1.7 Hz), 7.87 (d, 2H, J=8.8 Hz), 7.53 (d, 2H, J=8.8 Hz), 7.17 (m, 1H), 7.06 (m, 2H), 6.91 (m, 1H), 5.62 (t, 1H, J=8.5 Hz), 0.96 (s, 9H);

Anal. Calcd for $C_{19}H_{21}ClFN_3O_2$: C, 60.40; H, 5.60; N, 11.12. Found: C, 60.36; H, 5.62; N, 11.08.

EXAMPLE 148

4-iodo-N-(2,2,2-trichloro-1-{[(3-pyridinylamino)carbothioyl]amino}ethyl)benzamide Example 114C and 3-aminopyridine were processed as described in Example 45B to provide the desired product.

mp 197–199° C.;

MS (DCI/NH$_3$) m/z 469 (M+H)+;

$^1$H NMR (DMSO-d$_6$) δ 10.57 (s, 1H), 9.23 (d, 1H, J=8.0 Hz), 8.60 (d, 1H, J=2.5 Hz), 8.35 (dd, 1H, J=5.3, 1.7 Hz), 8.27 (d, 1H, J=9.4 Hz), 8.03 (dt, 1H, J=8.5, 1.8 Hz), 7.91 (d, 2H, J=8.5 Hz), 7.63 (d, 2H, J=8.5 Hz), 7.48 (t, 1H, J=8.3 Hz), 7.39 (dd, 1H, J=8.6, 5.1 Hz);

Anal. calcd for $C_{15}H_{12}Cl_3IN_5OS$: C, 34.02; H, 2.24; N, 10.81. Found: C, 33.91; H, 2.24; N, 10.81.

EXAMPLE 149

3-phenyl-N-(2,2,2-trichloro-1-{[(3-nitroanilino)carbothioyl]amino}ethyl)propanamide

EXAMPLE 149A 3-phenyl-N-(2,2,2-trichloro-1-hydroxyethyl)propanamide

3-Phenylpropionamide was processed as described in Example 37C to provide the desired compound.

MS (ESI+) m/z 296 (M+H)+.

EXAMPLE 149B 3-phenyl-N-(1,2,2,2-tetrachloroethyl)propanamide

Example 149A was processed as described in Example 37D to provide the desired compound.

MS (ESI+) m/z 314 (M+H)+.

EXAMPLE 149C 3-phenyl-N-(2,2,2-trichloro-1-isothiocyanatoethyl)propanamide

Example 149B was processed as described in Example 45A to provide the desired compound.

MS (ESI+) m/z 337 (M+H)+.

EXAMPLE 149D 3-phenyl-N-(2,2,2-trichloro-1-{[(3-nitroanilino)carbothioyl]amino}ethyl)propanamide Example 149C and 3-nitroaniline were processed as described in Example 45B to provide the desired compound.

mp 171–173° C.;

MS (ESI+) m/z 477 (M+H)$^+$;

$^1$H NMR (DMSO-d$_6$) δ 10.71 (s, 1H), 8.82 (d, 1H, J=8.2 Hz), 8.72 (t, 1H, J=1.1 Hz), 8.37 (d, 1H, J=8.6 Hz), 7.96 (dd, 1H, J=8.2, 1.2 Hz), 7.87 (dd, 1H, J=8.5, 1.2 Hz), 7.61 (t, 1H, J=8.1 Hz), 7.30–7.09 (m, 8H), 2.81 (t, 2H, J=8.0 Hz);

Anal. calcd for C$_{19}$H$_{17}$Cl$_3$N$_5$O: C, 52.13; H, 3.91; N, 16.00. Found: C, 52.42; H, 4.10; N, 15.82.

EXAMPLE 150

4-chloro-N-(2,2-dimethyl-1-{[2-nitro-1-(3-pyridinylamino)ethenyl]amino}propyl)benzamide Example 68B and Example 69B were processed as described in Example 54D to provide the desired product.

mp 195–196° C.;

MS (ESI+) m/z 404 (M+H)$^+$;

$^1$H NMR (DMSO-d$_6$) δ 9.61 (br s, 1H), 9.07 (d, 1H, J=8.8 Hz), 8.49 (dd, 1H, J=4.7, 0.7 Hz), 8.45 (d, 1H, J=2.0 Hz), 7.90 (d, 2H, J=8.8 Hz), 7.67 (m, 1H), 7.59 (d, 2H, J=8.8 Hz), 7.54 (m, 1H), 7.47 (dd, 1H, J=8.3, 4.8 Hz), 6.15 (s, 1H), 5.79 (dd, 1H, J=9.2, 8.8 Hz), 1.1 (s, 3H);

Anal. calcd for C$_{19}$H$_{22}$ClN$_5$O$_3$: C, 56.51; H, 5.49; N, 17.34. Found: C, 56.47; H, 5.55; N, 17.53.

EXAMPLE 151

4-chloro-N-(2,2-dichloro-1-{[2-nitro-1-(3-pyridinylamino)ethenyl]amino}pentyl)benzamide Example 68B and Example 115A were processed as described in Example 54D to provide the desired product.

mp 185–186° C.;

MS (ESI+) m/z 472 (M+H)$^+$;

$^1$H NMR (DMSO-d$_6$) δ 9.75 (br s, 1H), 9.58 (m, 1H), 8.48 (m, 1H), 8.44 (m, 1H), 7.92 (d, 2H, J=8.5 Hz), 7.67 (m, 1H), 7.60 (d, 2H, J=8.5 Hz), 7.47 (m, 1H), 6.59 (br s, 1H), 6.19 (m, 1H), 2.27 (m, 2H), 1.24 (m, 1H), 0.97 (t, 3H, J=6.8 Hz);

Anal. calcd for C$_{19}$H$_{20}$Cl$_3$N$_5$O$_3$: C, 48.27; H, 4.26; N, 14.81. Found: C, 48.32; H, 4.16; N, 14.76.

EXAMPLE 152

4-chloro-N-(1-{[2,2-dicyano-1-(3-pyridinylamino)vinyl]amino}-2,2-dimethylpropyl)benzamide

EXAMPLE 152A

2-[(methylsulfanyl)(3-pyridinylamino)methylene]malononitrile

3-Aminopyridine (2.76 g, 29.4 mmol) and 2-[bis(methylsulfanyl)methylene]malononitrile (5.00 g, 29.4 mmol) in isopropanol (50 mL) were heated at reflux for 12 hours. The solution was concentrated to a volume of 15 ml and cooled to 0° C. for 2 hours. The solid was colleted by filtration to provide the desired product (4.40 g) as a yellow solid.

MS (ESI–) m/z 215 (M–H)$^-$.

EXAMPLE 152B

2-[amino(3-pyridinylamino)methylene]malononitrile

Example 152A (4.40 g, 20.3 mmol) was dissolved in a 2M solution of ammonia in isopropanol (60 mL) and heated in a sealed tube at 60° C. for 8 hours. The reaction mixture was cooled to ambient temperature and then further cooled to 0° C., whereupon a solid precipitated from solution. The solid was filtered and the filter cake washed with cold isopropanol to provide the desired product (1.80 g) as a light brown solid.

MS (ESI–) m/z 184 (M–H)$^-$.

EXAMPLE 152C 4-chloro-N-(1-{[2,2-dicyano-1-(3-pyridinylamino)vinyl]amino}-2,2-dimethylpropyl)benzamide Example 152B and Example 69B were processed as described in Example 110B to provide the desired product.

mp 213–214° C.;

MS (ESI+) m/z 409 (M+H)$^+$;

$^1$H NMR (DMSO-d$_6$) δ 9.84 (s, 1H), 8.69 (d, 1H, J=8.1 Hz), 8.35 (d, 1H, J=2.4 Hz), 8.33 (dd, 1H, J=4.8, 1.4 Hz), 7.85 (d, 2H, J=8.8 Hz), 7.82 (m, 1H), 7.60 (d, 2H, J=8.8 Hz), 7.51 (m, 1H), 7.40 (dd, 1H, J=8.2, 4.8 Hz), 5.56 (dd, 1H, J=8.6, 8.2 Hz), 1.04 (s, 9H);

Anal. calcd for C$_{21}$H$_{21}$ClN$_6$O: C, 61.68; H, 5.17; N, 20.55. Found: C, 61.47; H, 5.33; N, 20.32.

EXAMPLE 153

3-chloro-N-(2,2-dichloro-1-{[[(6-chloro-3-pyridinyl)amino](cyanoimino)methyl]amino}propyl)benzamide A suspension of Example 55C, Example 119A, and Cs$_2$CO$_3$ was processed as described in Example 110B to provide the desired product.

mp 138–140° C.;

MS (ESI+) m/z 460 (M+H)$^+$;

$^1$H NMR (DMSO-d$_6$) δ 9.98 (s, 1H); 8.80 (d, 1H, J=8.1 Hz); 8.35 (d, 1H, J=2.4 Hz); 7.85 (m, 1H); 7.78 (m, 2H); 7.68 (m, 1H); 7.61 (d, 1H, J=5.8 Hz); 7.54 (d, 1H, J=5.8 Hz); 7.32 (d, 1H, J=9.2 Hz); 6.54 (dd, 1H, J=8.8, 8.8 Hz); 2.19 (s, 3H);

Anal. calcd for C$_{17}$H$_{14}$Cl4N$_6$O: C, 44.37; H, 3.07; N, 18.26. Found: C, 44.36; H, 3.08; N, 18.29.

EXAMPLE 154

N-(2,2-dichloro-1-{[[(6-chloro-3-pyridinyl)amino](cyanoimino)methyl]amino}propyl)-4-methylbenzamide

EXAMPLE 154A

N-[1-(1H-1,2,3-benzotriazol-1-yl)-2,2-dichloropropyl]-4-methylbenzamide

A suspension of p-toluamide, 2,2-dichloropropionaldehyde, benzotriazole, and p-toluenesulfonic acid was processed as described in Example 53A to provide the desired product.

MS (ESI+) m/z 363 (M+H)$^+$.

EXAMPLE 154B

N-(2,2-dichloro-1-{[[(6-chloro-3-pyridinyl)amino](cyanoimino)methyl]amino}propyl)-4-methylbenzamide A suspension of Example 55C, Example 154A, and Cs$_2$CO$_3$ was processed as described in Example 110B to provide the desired product.

mp 198–200° C.;

MS (ESI+) m/z 439 (M+H)+;

$^1$H NMR (DMSO-d$_6$) δ 9.99 (s, 1H); 8.52 (d, 1H, J=8.47 Hz); 8.35 (d, 1H, J=2.4 Hz); 7.77 (dd, 1H, J=2.7, 8.5 Hz); 7.74 (d, 2H, J=8.5 Hz); 7.60 (d, 1H, J=8.5 Hz); 7.35 (d, 3H, J=7.8 Hz); 6.55 (dd, 1H, J=8.8, 8.8 Hz); 2.37 (s, 3H); 2.17 (s, 3H);

Anal. calcd for C$_{18}$H$_{17}$Cl$_3$N$_6$O: C, 49.17; H, 3.90; N, 19.11. Found: C, 48.98; H, 3.85; N, 19.14.

EXAMPLE 155

N-{2,2-dichloro-1-[((cyanoimino){[6-(trifluoromethyl)-3-pyridinyl]amino}methyl)amino]propyl}-3,5-difluorobenzamide

EXAMPLE 155A

N"-cyano-N-[6-(trifluoromethyl)-3-pyridinyl]guanidine

A solution of 5-amino-2-(trifluoromethyl)pyridine and sodium dicyanamide was processed as described in Example 71A to provide the desired product.

MS (ESI+) m/z 439 (M+H)+.

EXAMPLE 155B

N-{2,2-dichloro-1-[((cyanoimino){[6-(trifluoromethyl)-3-pyridinyl]amino}methyl)amino]propyl}-3,5-difluorobenzamide A suspension of Example 155A, Example 120A, and Cs$_2$CO$_3$ was processed as described in Example 110B to provide the desired product.

mp 202–203° C.;

MS (ESI+) m/z 495 (M+H)+;

$^1$H NMR (DMSO-d$_6$) δ 10.24 (s, 1H); 8.89 (d, 1H, J=8 Hz); 8.68 (s, 1H); 7.98–7.90 (m, 2H); 7.65 (d, 1H, 9 Hz); 7.60–7.52 (m, 3H); 6.57 (t, 1H, J=8 Hz); 2.22 (s, 3H);

Anal. calcd for C$_{18}$H$_{13}$Cl$_2$F$_5$N$_6$O: C, 43.65; H, 2.65; N, 16.97. Found: C, 43.88; H, 2.90; N, 16.70.

EXAMPLE 156

N-(2,2-dichloro-1-{[[(6-chloro-3-pyridinyl)amino](cyanoimino)methyl]amino}propyl)-3-fluorobenzamide

EXAMPLE 156A

N-[1-(1H-1,2,3-benzotriazol-1-yl)-2,2-dichloropropyl]-3-fluorobenzamide

A suspension of 3-fluorobenzamide, 2,2-dichloropropionaldehyde, benzotriazole, and p-toluenesulfonic acid was processed as described in Example 53A to provide the desired product.

MS (ESI+) m/z 367 (M+H)+.

EXAMPLE 156B

N-(2,2-dichloro-1-{[[(6-chloro-3-pyridinyl)amino](cyanoimino)methyl]amino}propyl)-3-fluorobenzamide A suspension of Example 55C, Example 156A, and Cs$_2$CO$_3$ was processed as described in Example 110B to provide the desired product.

mp 191–192° C.;

MS (ESI+) m/z 443 (M+H)+;

$^1$H NMR (DMSO-d$_6$) δ 9.98 (s, 1H); 8.76 (d, 1H, J=8.1 Hz); 8.35 (d, 1H, J=2.7 Hz); 7.77 (dd, 1H, J=8.5, 2.7 Hz); 7.69–7.44 (m, 5H); 7.30 (d, 3H, J=8.8 Hz); 6.54 (dd, 1H, J=8.8, 8.5 Hz); 2.19 (s, 3H);

Anal. calcd for C$_{17}$H$_{14}$Cl$_3$FN$_6$O: C, 46.02; H, 3.18; N, 18.94. Found: C, 45.95; H, 3.16; N, 19.02.

EXAMPLE 157

N-[2,2-dichloro-1-({(cyanoimino)[(2-methoxy-3-pyridinyl)amino]methyl}amino)propyl]-3,5-difluorobenzamide

EXAMPLE 157A

N"-cyano-N-(2-methoxy-3-pyridinyl)guanidine

A solution of 3-amino-2-methoxypyridine and sodium dicyanamide was processed as described in Example 71A to provide the desired product.

MS (ESI–) m/z 190 (M–H)−.

EXAMPLE 157B

N-[2,2-dichloro-1-({(cyanoimino)[(2-methoxy-3-pyridinyl)amino]methyl}amino)propyl]-3,5-difluorobenzamide A suspension of Example 157A, Example 120A, and Cs$_2$CO$_3$ was processed as described in Example 110B to provide the desired product.

mp 125–126° C.;

MS (ESI+) m/z 457 (M+H)+;

$^1$H NMR (DMSO-d$_6$) δ 8.90 (d, 1H, J=7 Hz); 8.12 (d, 1H, J=4 Hz); 7.64 (br s, 1H); 7.58–7.52 (m, 4H); 7.06 (dd, 1H, J=7, 5 Hz); 6.80 (br s, 1H); 6.47 (d, 1H, J=7 Hz); 3.87 (s, 3H); 2.16 (s, 3H);

Anal. calcd for C$_{18}$H$_{16}$Cl$_2$F$_2$N$_6$O$_2$: C, 47.28; H, 3.53; N, 18.38. Found: C, 47.22; H, 3.62; N, 18.35.

EXAMPLE 158

4-chloro-N-{2,2-dichloro-1-[((cyanoimino){[6-(trifluoromethyl)-3-pyridinyl]amino}methyl)amino]propyl}benzamide A suspension of Example 155A, Example 116B, and Cs$_2$CO$_3$ was processed as described in Example 110B to provide the desired product.

mp 204–205° C.;

MS (ESI+) m/z 493 (M+H)+;

$^1$H NMR (DMSO-d$_6$) δ 10.25 (s, 1H); 8.73 (d, 1H, J=8 Hz); 8.68 (s, 1H); 7.99–7.91 (m, 2H); 7.86 (d, 2H, J=9 Hz); 7.65 (d, 1H, J=10 Hz); 7.61 (d, 2H, J=8 Hz); 6.58 (t, 1H, J=9 Hz); 2.20 (s, 3H);

Anal. calcd for C$_{18}$H$_{14}$Cl$_3$F$_3$N$_6$O: C, 43.79; H, 2.86; N, 17.02. Found: C, 43.79; H, 2.74; N, 17.10.

EXAMPLE 159

3-chloro-N-{2,2-dichloro-1-[((cyanoimino){[6-(trifluoromethyl)-3-pyridinyl]amino}methyl)amino]propyl}benzamide A suspension of Example 155A, Example 119A, and Cs$_2$CO$_3$ was processed as described in Example 110B to provide the desired product.

mp 191–192° C.;

MS (ESI+) m/z 493 (M+H)+;

¹H NMR (DMSO-d₆) δ 10.25 (s, 1H); 8.84 (d, 1H, J=8 Hz); 8.68 (s, 1H); 7.98–7.92 (m, 2H); 7.87 (t, 1H, J=2 Hz); 7.81 (d, 1H, J=8 Hz); 7.76–7.65 (m, 2H); 7.57 (t, 1H, J=8 Hz); 6.58 (t, 1H, J=8 Hz); 2.21 (s, 3H);

Anal. calcd for $C_{18}H_{14}Cl_3F_3N_6O$: C, 43.79; H, 2.86; N, 17.02. Found: C, 44.12; H, 3.04; N, 16.81.

EXAMPLE 160

4-chloro-N-(2,2-dichloro-1-{[[(6-chloro-3-pyridinyl)amino](cyanoimino)methyl]amino}propyl)benzamide A suspension of Example 55C, Example 116B, and $Cs_2CO_3$ was processed as described in Example 110B to provide the desired product.

mp 199–200° C.;

MS (ESI+) m/z 460 (M+H)+;

¹H NMR (DMSO-d₆) δ 9.98 (s, 1H); 8.73 (d, 1H, J=8.5 Hz); 8.35 (d, 1H, J=2.7 Hz); 7.84 (d, 2H, J=8.8 Hz); 7.76 (dd, 1H, J=8.5, 2.7 Hz); 7.61 (d, 2H, J=8.8 Hz); 7.59 (d, 1H, J=8.5 Hz); 7.29 (d, 1H, J=9.1 Hz); 6.54 (dd, 1H, J=8.8, 8.5 Hz); 2.18 (s, 3H);

Anal. calcd for $C_{17}H_{14}Cl_4N_6O$: C, 44.37; H, 3.07; N, 18.26. Found: C, 44.70; H, 3.08; N, 18.34.

EXAMPLE 161

(−) 4-chloro-N-(2,2-dichloro-1-{[[(6-chloro-3-pyridinyl)amino](cyanoimino)methyl]amino}propyl)benzamide Example 160 was chromatographed over a Daicel Chiral Technologies Chiralcel OD chiral column (2.0 cm×25 cm) eluting with 5% ethanol/hexanes (flow rate=10 mL/minutes) to provide the desired product as the levorotatory enantiomer.

$[\alpha]_D^{23}$ −31° (c=0.19, DMSO);

mp 199–201° C.;

MS (ESI+) m/z 460 (M+H)+;

¹H NMR (DMSO-d₆) δ 9.98 (s, 1H); 8.73 (d, 1H, J=8.5 Hz); 8.35 (d, 1H, J=2.7 Hz); 7.84 (d, 2H, J=8.8 Hz); 7.76 (dd, 1H, J=8.5, 2.7 Hz); 7.61 (d, 2H, J=8.8 Hz); 7.59 (d, 1H, J=8.5 Hz); 7.29 (d, 1H, J=9.1 Hz); 6.54 (dd, 1H, J=8.8, 8.5 Hz); 2.18 (s, 3H);

Anal. calcd for $C_{17}H_{14}Cl_4N_6O$: C, 44.37; H, 3.07; N, 18.26. Found: C, 44.64; H, 3.11; N, 18.11.

EXAMPLE 162

(+) 4-chloro-N-(2,2-dichloro-1-{[[(6-chloro-3-pyridinyl)amino](cyanoimino)methyl]amino}propyl)benzamide Example 160 was chromatographed over a Daicel Chiral Technologies Chiralcel OD chiral column (2.0 cm×25 cm) eluting with 5% ethanol/hexanes (flow rate=10 mL/minutes) to provide the desired product as the dextrotatory enantiomer.

$[\alpha]_D^{23}$ +30° (c=0.20, DMSO);

mp 197–199° C.;

MS (ESI+) m/z 460 (M+H)+;

¹H NMR (DMSO-d₆) δ 9.98 (s, 1H); 8.73 (d, 1H, J=8.5 Hz); 8.35 (d, 1H, J=2.7 Hz); 7.84 (d, 2H, J=8.8 Hz); 7.76 (dd, 1H, J=2.7, 8.5 Hz); 7.63 (d, 2H, J=8.8 Hz); 7.60 (d, 1H, J=8.5 Hz); 7.29 (d, 1H, J=9.1 Hz); 6.54 (dd, 1H, J=8.8, 8.5 Hz); 2.18 (s, 3H);

Anal. calcd for $C_{17}H_{14}Cl_4N_6O \cdot 0.04C_6HI_4$ (hexane): C, 44.67; H, 3.17; N, 18.13. Found: C, 44.99; H, 3.16; N, 17.93.

EXAMPLE 163

4-bromo-N-(2,2-dichloro-1-{[[(6-chloro-3-pyridinyl)amino](cyanoimino)methyl]amino}propyl)benzamide

EXAMPLE 163A

N-[1-(1H-1,2,3-benzotriazol-1-yl)-2,2-dichloropropyl]-4-bromobenzamide

A suspension of 4-bromobenzamide, 2,2-dichloropropionaldehyde, benzotriazole, and p-toluenesulfonic acid was processed as described in Example 53A to provide the desired product.

MS (ESI+) m/z 427 (M+H)+.

EXAMPLE 163B 4-bromo-N-(2,2-dichloro-1-{[[(6-chloro-3-pyridinyl)amino](cyanoimino)methyl]amino}propyl)benzamide A suspension of Example 55C, Example 163A, and $Cs_2CO_3$ was processed as described in Example 110B to provide the desired product.

mp 215–216° C.;

MS (ESI+) m/z 503 (M+H)+;

¹H NMR (DMSO-d₆) δ 9.98 (br s, 1H); 8.72 (d, 1H, J=8.3 Hz); 8.36 (d, 1H, J=2.4 Hz), 7.81–7.75 (m, 1H), 7.77 (s, 4H), 7.61 (d, 1H, J=8.6 Hz); 7.32 (d, 1H, J=8.3 Hz); 6.55 (t, 1H, J=8.5 Hz); 2.20 (s, 3H);

Anal. calcd for $C_{17}H_{14}BrCl_3N_6O$: C, 40.46; H, 2.80; N, 16.66. Found: C, 40.53; H, 2.74; N, 16.61.

EXAMPLE 164

3,5-dichloro-N-[2,2-dichloro-1-({(cyanoimino)[(2-methoxy-3-pyridinyl)amino]methyl}amino)propyl]benzamide

EXAMPLE 164A

N-[1-(1H-1,2,3-benzotriazol-1-yl)-2,2-dichloropropyl]-3,5-dichlorobenzamide

A suspension of 3,5-dichlorobenzamide, 2,2-dichloropropionaldehyde, benzotriazole, and p-toluenesulfonic acid was processed as described in Example 53A to provide the desired product.

MS (ESI+) m/z 418 (M+H)+.

EXAMPLE 164B 3,5-dichloro-N-[2,2-dichloro-1-({(cyanoimino)[(2-methoxy-3-pyridinyl)amino]methyl}amino)propyl]benzamide A suspension of Example 157A, Example 164A, and $Cs_2CO_3$ was processed as described in Example 110B to provide the desired product.

mp 149–150° C.;

MS (ESI+) m/z 490 (M+H)+;

¹H NMR (DMSO-d₆) δ 9.44 (s, 1H); 8.97 (d, 1H, J=8.2 Hz); 8.12 (dd, 1H, J=1.7, 5.1 Hz);

7.88 (t, 1H, J=2.0 Hz); 7.82 (d, 2H, J=2.0 Hz); 7.62 (dd, 1H, J=1.7, 7.8 Hz); 7.05 (dd, 1H, J=5.1, 7.4 Hz); 6.82 (d, 1H, J=8.8 Hz); 6.45 (dd, 1H, J=8.5, 8.5 Hz); 3.85 (s, 3H); 2.15 (s, 3H);

Anal. calcd for $C_{18}H_{16}Cl_4N_6O_2$ 0.4H₂O: C, 43.47; H, 3.40; N, 16.90. Found: C, 43.15; H, 3.34; N, 16.88.

EXAMPLE 165

3,5-dichloro-N-(2,2-dichloro-1-{[[(6chloro-3-pyridinyl)amino](cyanoimino)methyl]amino}propyl)benzamide A suspension of Example 55C, Example 164A, and Cs₂CO₃ was processed as described in Example 110B to provide the desired product.

mp 138–140° C.;

MS (ESI+) m/z 492 (M+H)⁺;

¹H NMR (DMSO-d₆) δ 9.97 (br s, 1H); 8.90 (d, 1H, J=8.6 Hz); 8.35 (d, 1H, J=3.1 Hz), 7.92–7.87 (m, 1H), 7.83 (app d, 2H, J=1.7 Hz), 7.77 (dd, 1H, J=8.5, 2.9 Hz), 7.60 (d, 1H, J=8.5 Hz), 7.31 (d, 1H, J=8.7 Hz); 6.52 (t, 1H, J=8.6 Hz); 2.20 (s, 3H);

Anal. calcd for $C_{17}H_{13}Cl_5N_6O$: C, 41.28; H, 2.65; N, 16.99. Found: C, 41.65; H, 2.62; N, 16.98.

EXAMPLE 166

N-(2,2-dichloro-1-{[[(6-chloro-3-pyridinyl)amino](cyanoimino)methyl]amino}propyl)-3,5-difluorobenzamide A suspension of Example 55C, Example 120A, and Cs₂CO₃ was processed as described in Example 110B to provide the desired product.

mp 195–196° C.;

MS (ESI+) m/z 461 (M+H)⁺;

¹H NMR (DMSO-d₆) δ 10.00 (br s, 1H); 8.88 (d, 1H, J=7.8 Hz); 8.35 (d, 1H, J=2.5 Hz), 7.77 (dd, 1H, J=8.5, 2.7 Hz), 7.63–7.52 (m, 4H); 7.30 (d, 1H, J=8.5 Hz); 6.52 (t, 1H, J=8.6 Hz); 2.19 (s, 3H);

Anal. calcd for $C_{17}H_{13}Cl_3F_2N_6O$: C, 44.23; H, 2.84; N, 18.20. Found: C, 44.43; H, 2.90; N, 18.16.

EXAMPLE 167

4-bromo-N-(2,2-dichloro-1-{[[(6-chloro-3-pyridinyl)amino](cyanoimino)methyl]amino}propyl)benzamide A suspension of Example 55C, Example 163A, and Cs₂CO₃ was processed as described in Example 110B to provide the desired product.

mp 215–216° C.;

MS (ESI+) m/z 503 (M+H)⁺;

¹H NMR (DMSO-d₆) δ 9.98 (br s, 1H); 8.72 (d, 1H, J=8.3 Hz); 8.36 (d, 1H, J=2.4 Hz), 7.81–7.75 (m, 1H), 7.77 (app s, 4H), 7.61 (d, 1H, J=8.6 Hz); 7.32 (d, 1H, J=8.3 Hz); 6.55 (t, 1H, J=8.5 Hz); 2.20 (s, 3H);

Anal. calcd for $C_{17}H_{14}BrCl_3N_6O$: C, 40.46; H, 2.80; N, 16.66. Found: C, 40.53; H, 2.74; N, 16.61.

EXAMPLE 168

4-chloro-N-(2,2-dichloro-1-{[[(2-chloro-3-pyridinyl)amino](cyanoimino)methyl]amino}propyl)benzamide

EXAMPLE 168A

N-(2-chloro-3-pyridinyl)-N"-cyanoguamidine

A solution of 3-amino-2-chloropyridine and sodium dicyanamide was processed as described in Example 71 A to provide the desired product.

MS (ESI–) m/z 194 (M–H)⁻.

EXAMPLE 168B 4-chloro-N-(2,2-dichloro-1-{[[(2-chloro-3-pyridinyl)amino](cyanoimino)methyl]amino}propyl)benzamide A suspension of Example 168A, Example 116B, and Cs₂CO₃ was processed as described in Example 110B to provide the desired product.

mp 200–201° C.;

MS (ESI+) m/z 461 (M+H)⁺;

¹H NMR (DMSO-d₆) δ 9.86 (s, 1H); 8.90 (d, 1H, J=8 Hz); 8.66 (dd, 1H, J=4, 2 Hz);

7.90–7.85 (m, 3H); 7.63 (d, 2H, J=9 Hz); 7.52 (dd, 1H, J=8, 5 Hz); 7.16 (d, 1H, J=8 Hz); 6.50 (t, 1H, J=8 Hz); 2.17 (s, 3H);

Anal. calcd for $C_{17}H_{14}Cl_4N_6O$: C, 44.37; H, 3.07; N, 18.26. Found: C, 44.44; H, 2.99; N, 18.19.

EXAMPLE 169

3-chloro-N-(2,2-dichloro-1-{[(cyanoimino)(3-fluoroanilino)methyl]amino}propyl)benzamide

EXAMPLE 169A

N"-cyano-N-(3-fluorophenyl)guanidine

A solution of 3-fluoroaniline and sodium dicyanamide was processed as described in Example 71A to provide the desired product.

MS (ESI–) m/z 177 (M–H)⁻.

EXAMPLE 169B 3-chloro-N-(2,2-dichloro-1-{[(cyanoimino)(3-fluoroanilino)methyl]amino}propyl)benzamide A suspension of Example 169A, Example 119A, and Cs₂CO₃ was processed as described in Example 110B to provide the desired product.

mp 179–181° C.;

MS (ESI+) m/z 442 (M+H)⁺;

¹H NMR (DMSO-d₆) δ 9.93 (s, 1H); 8.48 (d, 1H, J=8 Hz); 7.84 (m, 1H); 7.80 (m, 1H);

7.67 (m, 1H); 7.56 (dd, 1H, J=7.8, 7.9 Hz); 7.47 (m, 1H); 7.18–7.09 (m, 4H); 6.54 (dd, 1H, J=8.8, 8.7 Hz); 2.18 (s, 3H);

Anal. calcd for $C_{17}H_{14}C_{14}N_6O$ 0.41$C_2H_3N$ (CH₃CN): C, 49.19; H, 3.56; N, 16.49. Found: C, 49.59; H, 3.50; N, 16.09.

EXAMPLE 170

N-(2,2-dichloro-1-{[[(6-chloro-3-pyridinyl)amino](cyanoimino)methyl]amino}propyl)-3-methylbenzamide

EXAMPLE 170A

N-[-(1H-1,2,3-benzotriazol-1-yl)-2,2-dichloropropyl]-3-methylbenzamide

A suspension of m-toluamide, 2,2-dichloropropionaldehyde, benzotriazole, and p-toluenesulfonic acid was processed as described in Example 53A to provide the desired product.

MS (ESI+) m/z 363 (M+H)⁺.

EXAMPLE 170B

N-(2,2-dichloro-1-{[[(6-chloro-3-pyridinyl)amino]
(cyanoimino)methyl]amino}propyl)-3-
methylbenzamide A suspension of Example 55C, Example 170A, and Cs$_2$CO$_3$ was processed as described in Example 110B to provide the desired product.

mp 145–146° C.;

MS (ESI+) m/z 439 (M+H)$^+$;

$^1$H NMR (DMSO-d$_6$) δ 10.0 (s, 1H); 8.59 (d, 1H, J=8.5 Hz); 8.36 (d, 1H, J=2.7 Hz); 7.78 (dd, 1H, J=2.7, 8.5 Hz); 7.64–7.50 (m, 3H); 7.42 (m, 2H) 7.35 (d, 1H, J=9.2 Hz); 6.56 (dd, 1H, J=8.5, 8.8 Hz); 2.38 (s, 3H); 2.17 (s, 3H);

Anal. calcd for C$_{18}$H$_{17}$Cl$_3$F$_3$N$_6$O: C, 49.17; H, 3.90; N, 19.11. Found: C, 49.15; H, 3.93; N, 19.05.

EXAMPLE 171

N-(2,2-dichloro-1-{[[(6-chloro-3-pyridinyl)amino]
(cyanoimino)methyl]amino}propyl)-4-
(trifluoromethyl)benzamide

EXAMPLE 171A

N-[1-(1H-1,2,3-benzotriazol-1-yl)-2,2-
dichloropropyl]-4-(trifluoromethyl)benzamide A suspension of 4-(trifluoromethyl)benzamide, 2,2-dichloropropionaldehyde, benzotriazole, and p-toluenesulfonic acid was processed as described in Example 53A to provide the desired product.

MS (ESI+) m/z 417 (M+H)$^+$.

EXAMPLE 171B

N-(2,2-dichloro-1-{[[(6-chloro-3-pyridinyl)amino]
(cyanoimino)methyl]amino}propyl)-4-
(trifluoromethyl)benzamide A suspension of Example 55C, Example 171A, and Cs$_2$CO$_3$ was processed as described in Example 110B to provide the desired product.

mp 210–211° C.;

MS (ESI+) m/z 493 (M+H)$^+$;

$^1$H NMR (DMSO-d$_6$) δ 9.97 (br s, 1H); 8.88 (d, 1H, J=7.8 Hz); 8.35 (d, 1H, J=2.5 Hz), 8.03 (d, 2H, J=8.9 Hz), 7.92 (d, 2H, J=8.9 Hz); 7.78 (dd, 1H, J=8.5, 2.7 Hz), 7.59 (d, 1H, J=8.7 Hz); 7.32 (d, 1H, J=8.1 Hz); 6.56(t, 1H, J=8.6 Hz); 2.10 (s, 3H);

Anal. calcd for C$_{18}$H$_{14}$Cl$_3$F$_3$N$_6$O: C, 43.79; H, 2.86; N, 17.02. Found: C, 43.58; H, 2.73; N, 16.93.

EXAMPLE 172

3-chloro-N-(2,2-dichloro-1-{[(cyanoimino)(2-
fluoroanilino)methyl]amino}propyl)benzamide

EXAMPLE 172A

N"-cyano-N-(2-fluorophenyl)guanidine

A solution of 2-fluoroaniline and sodium dicyanamide was processed as described in Example 71A to provide the desired product.

MS (ESI–) m/z 177 (M–H)$^-$.

EXAMPLE 172B 3-chloro-N-(2,2-dichloro-1-{[(cyanoimino)(2-
fluoroanilino)methyl]amino}propyl)benzamide A suspension of Example 172A, Example 119A, and Cs$_2$CO$_3$ was processed as described in Example 110B to provide the desired product.

mp 136–138° C.;

MS (ESI+) m/z 442 (M+H)$^+$;

$^1$H NMR (DMSO-d$_6$) δ 9.69 (s, 1H); 8.48 (d, 1H, J=8 Hz); 7.85 (m, 1H); 7.80 (m, 1H);

7.68 (m, 1H); 7.57 (dd, 1H, J=7.8, 7.9 Hz); 7.43–7.24 (m, 4H); 6.87 (d, 1H, J=8.5 Hz); 6.52 (dd, 1H, J=8.6, 8.7 Hz); 2.15 (s, 3H);

Anal. calcd for C$_{17}$H$_{14}$Cl$_4$N$_6$O: C, 48.83; H, 3.42; N, 15.82. Found: C, 48.94; H, 3.49; N, 15.81.

EXAMPLE 173

N-(2,2-dichloro-1-{[[(6-chloro-3-pyridinyl)amino]
(cyanoimino)methyl]amino}propyl)-4-
fluorobenzamide

EXAMPLE 173A

N-[1-(1H-1,2,3-benzotriazol-1-yl)-2,2-
dichloropropyl]-4-fluorobenzamide

A suspension of 4-fluorobenzamide, 2,2-dichloropropionaldehyde, benzotriazole, and p-toluenesulfonic acid was processed as described in Example 53A to provide the desired product.

MS (ESI+) m/z 367 (M+H)$^+$.

EXAMPLE 173B

N-(2,2-dichloro-1-{[[(6-chloro-3-pyridinyl)amino]
(cyanoimino)methyl]amino}propyl)-4-
fluorobenzamide A suspension of Example 55C, Example 173A, and Cs$_2$CO$_3$ was processed as described in Example 110B to provide the desired product.

mp 197–198° C.;

MS (ESI+) m/z 443 (M+H)$^+$;

$^1$H NMR (DMSO-d$_6$) δ 9.96 (s, 1H); 8.66 (d, 1H, J=7.8 Hz); 8.34 (d, 1H, J=2.5 Hz), 7.91 (dd, 2H, J=8.7, 5.3 Hz), 7.77 (dd, 1H, J=8.5, 2.7 Hz), 7.59 (d, 1H, 8.8 Hz), 7.37 (d, 2H, J=8.8 Hz); 7.27 (br d, 1H, J=8.0 Hz); 6.54 (t, 1H, J=8.6 Hz); 2.18 (s, 3H);

Anal. calcd for C$_{17}$H$_{14}$Cl$_3$FN$_6$O: C, 46.02; H, 3.18; N, 18.94. Found: C, 46.32; H, 3.37; N, 18.67.

EXAMPLE 174

3-chloro-N-[2,2-dichloro-1-({(cyanoimino)[(2-
methoxy-3-pyridinyl)amino]methyl}amino)propyl]
benzamide A suspension of Example 157A, Example 119A, and Cs$_2$CO$_3$ was processed as described in Example 110B to provide the desired product.

mp 115–116° C.;

MS (ESI+) m/z 456 (M+H)$^+$ $^1$H NMR (DMSO-d$_6$) δ 9.46 (s, 1H); 8.86 (d, 1H, J=8.5 Hz); 8.15 (dd, 1H, J=1.7, 5.1 Hz);

7.85 (m, 1H); 7.78 (m, 1H); 7.68 (m, 1H); 7.62 (dd, 1H, J=1.7, 7.5 Hz); (dd, 1H, J=7.8, 8.1 Hz); 7.08 (dd, 1H, J=5.1, 7.5 Hz); 6.83 (d, 1H, J=8.8 Hz); 6.52 (dd, 1H, J=8.5, 8.8 Hz); 3.86 (s, 3H); 2.16 (s, 3H);

Anal. calcd for $C_{18}H_{17}Cl_3N_6O_2$ 0.05$C_2H_3N$ (CH$_3$CN): C, 47 49; H, 3.78; N, 18.51. Found: C, 47.79; H, 3.67; N, 18.90.

EXAMPLE 175

4-chloro-N-(2,2-dichloro-1-{[(cyanoimino)(2-fluoroanilino)methyl]amino}propyl)benzamide A suspension of Example 172A, Example 116B, and Cs$_2$CO$_3$ was processed as described in Example 110B to provide the desired product.

mp 216–217° C.;

MS (ESI+) m/z 442 (M+H)$^+$;

$^1$H NMR (DMSO-d$_6$) δ 9.68 (s, 1H); 8.84 (d, 1H, J=8 Hz); 7.85 (d, 1H, J=8 Hz); 7.61 (d, 2H, J=8 Hz); 7.43–7.22 (m, 2H); 6.88 (d, 1H, J=8 Hz); 6.52 (t, 1H, J=8 Hz); 2.14 (s, 3H);

Anal. calcd for $C_{18}H_{15}Cl_3FN_5O$: C, 48.83; H, 3.42; N, 15.82. Found: C, 49.05; H, 3.42; N, 15.70.

EXAMPLE 176

4-chloro-N-[2,2-dichloro-1-({(cyanoimino)[(2-methoxy-3-pyridinyl)amino]methyl}amino)propyl]benzamide A suspension of Example 157A, Example 116B, and Cs$_2$CO$_3$ was processed as described in Example 110B to provide the desired product.

mp 155–156° C.;

MS (ESI+) m/z 455 (M+H)$^+$;

$^1$H NMR (DMSO-d$_6$) δ 9.45 (s, 1H); 8.77 (d, 1H, J=8 Hz); 8.14 (dd, 1H, J=5, 2 Hz); 7.84 (d, 2H, J=8 Hz); 7.64–7.60 (m, 3H); 7.07 (dd, 1H, J=7, 5 Hz); 6.82 (d, 1H, J=9 Hz); 6.50 (t, 1H, J=8 Hz); 3.86 (s, 3H); 2.16 (s, 3H);

Anal. calcd for $C_{18}H_{17}Cl_3N_6O_2$: C, 47.44; H, 3.76; N, 18.44. Found: C, 47.44; H, 3.93; N, 18.38.

EXAMPLE 177

3-chloro-N-[2,2-dichloro-1-({(cyanoimino)[(6-fluoro-3-pyridinyl)amino]methyl}amino)propyl]benzamide

EXAMPLE 177A

N"-cyano-N-(6-fluoro-3-pyridinyl)guanidine

A solution of 5-amino-2-fluoropyridine and sodium dicyanamide was processed as described in Example 71A to provide the desired product.

MS (ESI–) m/z 178 (M–H)$^-$;

EXAMPLE 177B 3-chloro-N-[2,2-dichloro-1-({(cyanoimino)[(6-fluoro-3-pyridinyl)amino]methyl}amino)propyl]benzamide A suspension of Example 177A, Example 119A, and Cs$_2$CO$_3$ was processed as described in Example 110B to provide the desired product.

mp 124–125° C.;

MS (ESI+) m/z 443 (M+H)$^+$;

$^1$H NMR (DMSO-d$_6$) δ 9.88 (s, 1H); 8.79 (br d, 1H, J=8.3 Hz), 8.18 (d, 1H, J=1.4 Hz), 7.94–7.89 (m, 1H), 7.85 (t, 1H, J=1.1 Hz); 7.80 (br d, 1H, J=7.8 Hz), 7.73–7.66 (m, 1H), 7.57 (t, 1H, 8.1 Hz), 7.29 (dd, 1H, J=8.2, 2.6 Hz), 7.13 (br d, 1H, J=8.7 Hz); 6.53 (t, 1H, J=8.5 Hz); 2.18 (s, 3H);

Anal. calcd for $C_{17}H_{14}Cl_3FN_6O$: C, 46.02; H, 3.18; N, 18.94. Found: C, 46.00; H, 3.12; N, 18.89.

EXAMPLE 178

N-(2,2-dichloro 1-{[[(6-chloro-3-pyridinyl)amino](cyanoimino)methyl]amino}propyl)-3,5-dimethoxybenzamide

EXAMPLE 178A

N-[1-(1H-1,2,3-benzotriazol-1-yl)-2,2-dichloropropyl]-3,5-dimethoxybenzamide

A suspension of 3,5-dimethoxybenzamide, 2,2-dichloropropionaldehyde, benzotriazole, and p-toluenesulfonic acid was processed as described in Example 53A to provide the desired product.

MS (ESI+) m/z 409 (M+H)$^+$;

EXAMPLE 178B

N-(2,2-dichloro-1-{[[(6-chloro-3-pyridinyl)amino](cyanoimino)methyl]amino}propyl)-3,5-dimethoxybenzamide A suspension of Example 55C, Example 178A, and Cs$_2$CO$_3$ was processed as described in Example 110B to provide the desired product.

mp 193–195° C.;

MS (ESI+) m/z 485 (M+H)$^+$;

$^1$H NMR (DMSO-d$_6$) δ 9.96 (br s, 1H); 8.59 (d, 1H, J=8.6 Hz); 8.36 (d, 1H, J=5.5 Hz), 7.78 (dd, 1H, J=8.5, 2.7 Hz), 7.60 (d, 1H, J=8.5 Hz), 7.27 (d, 1H, J=8.8 Hz); 6.95 (d, 2H, J=2.1 Hz); 6.75 (d, 1H, J=1.3 Hz); 6.52 (t, 1H, J=8.7 Hz); 3.80 (s, 6H), 2.17 (s, 3H);

Anal. calcd for $C_{19}H_{19}Cl_3N_6O_3$: C, 46.98; H, 3.94; N, 17.30. Found: C, 47.18; H, 3.81; N, 17.38.

EXAMPLE 179

N-(2,2-dichloro-1-{[(cyanoimino)(3-pyridinylamino)methyl]amino}propyl)-3-methylbenzamide A suspension of Example 54C, Example 170A, and Cs$_2$CO$_3$ was processed as described in Example 110B to provide the desired product.

mp 171–172° C.;

MS (ESI+) m/z 405 (M+H)$^+$;

$^1$H NMR (DMSO-d$_6$) δ 9.93 (s, 1H); 8.63 (d, 1H, J=8.5 Hz); 8.53 (d, 1H, J=2.4 Hz); 8.47 (dd, 1H, J=1.4, 4.8 Hz); 7.72 (m, 1H); 7.62 (m, 2H); 7.49 (dd, 1H, J=4.8, 8.3);. 7.42 (m, 2H); 7.21 (d, 1H, J=9.2 Hz); 6.57 (dd, 1H, J=8.8, 8.8 Hz); 2.37 (s, 3H); 2.17 (s, 3H);

Anal. calcd for $C_{18}H_{18}Cl_2N_6O$: C, 53.34; H; 4.48; N, 20.74. Found: C, 53.52; H, 4.67; N, 21.02.

EXAMPLE 180

4-chloro-N-[2,2-dichloro-1-({(cyanoimino)[(6-fluoro-3-pyridinyl)amino]methyl}amino)propyl]benzamide A suspension of Example 177A, Example 116B, and Cs$_2$CO$_3$ was processed as described in Example 110B to provide the desired product.

mp 206–207° C.;

MS (ESI+) m/z 443 (M+H)⁺;

¹H NMR (DMSO-d₆) δ 9.87 (s, 1H); 8.70 (br d, 1H, J=8.5 Hz), 8.15 (d, 1H, J=1.0 Hz), 7.92–7.84 (m, 1H), 7.83 (d, 2H, J=8.7 Hz), 7.60 (d, 2H, J=8.7 Hz), 7.28 (dd, 1H, J=8.2, 2.3 Hz), 7.12 (br d, 1H, J=8.6 Hz); 6.52 (t, 1H, J=8.5 Hz); 2.15 (s, 3H);

Anal. calcd for $C_{17}H_{14}Cl_3FN_6O$: C, 46.02; H, 3.18; N, 18.94. Found: C, 46.00; H, 3.12; N, 18.89.

EXAMPLE 181

4-chloro-N-(2,2-dichloro-1-{[(cyanoimino)(2-methoxyanilino)methyl]amino}propyl)benzamide

EXAMPLE 181A

N″-cyano-N-(2-methoxyphenyl)guanidine

A solution of 2-methoxyaniline and sodium dicyanamide was processed as described in Example 71A to provide the desired product.

MS (ESI−) m/z 189 (M−H)⁻.

EXAMPLE 181B 4-chloro-N-(2,2-dichloro-1-{[(cyanoimino)(2-methoxyanilino)methyl]amino}propyl)benzamide A suspension of Example 181A, Example 116B, and $Cs_2CO_3$ was processed as described in Example 110B to provide the desired product.

mp 185–186° C.;

MS (ESI+) m/z 454 (M+H)⁺;

¹H NMR (DMSO-d₆) δ 9.29 (s, 1H); 8.75 (m, 1H); 7.85 (m, 1H); 7.82 (d, 2H, J=8.5 Hz);

7.62 (d, 2H, J=8.5 Hz); 7.35 (m, 1H); 7.22 (dd, 1H, J=1.4, 7.7 Hz); 7.13 (dd, 1H, J=1.0, 7.7 Hz); 7.01 (m, 1H); 6.50 (d, 2H, J=4.4 Hz); 3.77 (s, 3H); 2.14 (s, 3H);

Anal. calcd for $C_{19}H_{18}Cl_3N_5O_2 \cdot 0.3CH_2Cl_2$: C, 48.27; H, 3.90; N, 14.58. Found: C, 48.03; H, 3.83; N, 14.28.

EXAMPLE 182

3-chloro-N-[2,2-dichloro-1-({(cyanoimino)[(6-methoxy-3-pyridinyl)amino]methyl}amino)propyl]benzamide

EXAMPLE 182A

N-(6-methoxy-3-pyridinyl)-N″-cyanoguanidine

A solution of 5-amino-2-methoxypyridine and sodium dicyanamide was processed as described in Example 71A to provide the desired product.

MS (ESI−) m/z 190 (M−H)⁻.

EXAMPLE 182B 3-chloro-N-[2,2-dichloro-1-({(cyanoimino)[(6-methoxy-3-pyridinyl)amino]methyl}amino)propyl]benzamide A suspension of Example 182A, Example 119A, and $Cs_2CO_3$ was processed as described in Example 110B to provide the desired product.

mp 189–190° C.;

MS (ESI+) m/z 455 (M+H)⁺;

¹H NMR (DMSO-d₆) δ 9.65 (s, 1H); 8.76 (d, 1H, J=8.1 Hz); 8.09 (d, 1H, J=2.4 Hz); 7.81 (m, 1H); 7.75 (m, 1H); 7.65 (m, 1H); 7.62 (dd, 1H, J=2.7, 8.7 Hz); 7.54 (dd, 1H, J=7.8, 7.8 Hz); 6.92 (dd, 1H, J=2.7, 9.3 Hz); 6.79 (d, 1H, J=9.0 Hz); 6.49 (dd, 1H, J=8.4, 8.4 Hz); 3.85 (s, 3H); 2.13 (s, 3H).

EXAMPLE 183

N-{2,2-dichloro-1-[((cyanoimino){[6-(trifluoromethyl)-3-pyridinyl]amino}methyl)amino]propyl}-3,5-dimethoxybenzamide A suspension of Example 155A, Example 178A, and $Cs_2CO_3$ was processed as described in Example 110B to provide the desired product.

mp 187–189° C.;

MS (ESI+) m/z 519 (M+H)⁺;

¹H NMR (DMSO-d₆) δ 10.24 (s, 1H); 8.69 (s, 1H); 8.63 (d, 1H, J=8 Hz); 7.97–7.94 (m, 2H); 7.60 (d, 1H, J=8 Hz); 6.97 (d, 2H, J=2 Hz); 6.57 (t, 1H, J=9 Hz); 3.80 (s, 6H); 2.20 (s, 3H);

Anal. calcd for $C_{20}H_{19}Cl_2F_3N_6O_3$: C, 46.26; H, 3.69; N, 16.18. Found: C, 46.53; H, 3.56; N, 16.26.

EXAMPLE 184

4-chloro-N-{2,2-dichloro-1-[((cyanoimino){[2-methyl-6-(trifluoromethyl)-3-pyridinyl]amino}methyl)amino]propyl}benzamide

EXAMPLE 184A

N-(2-methyl-6-trifluoromethyl)-N″-cyanoguanidine

A solution of 3-amino-2-methyl-6-(trifluoromethyl)pyridine and sodium dicyanamide was processed as described in Example 71A to provide the desired product.

MS (ESI−) m/z 242 (M−H)⁻.

EXAMPLE 184B 4-chloro-N-{2,2-dichloro-1-[((cyanoimino){[2-methyl-6-(trifluoromethyl)-3-pyridinyl]amino}methyl)amino]propyl}benzamide A suspension of Example 184A, Example 116B, and $Cs_2CO_3$ was processed as described in Example 110B to provide the desired product.

mp 115–116° C.;

MS (ESI+) m/z 507 (M+H)⁺;

¹H NMR (DMSO-d₆) o 9.79 (s, 1H); 8.80 (d, 1H, J=8 Hz); 7.90–7.81 (m, 2H); 7.86 (d, 2H, J=9 Hz); 7.62 (d, 2H, J=8 Hz); 7.13 (d, 1H, J=8 Hz); 6.16 (t, 1H, J=8 Hz); 3.31 (s, 3H, obscured); 2.17 (s, 3H);

Anal. calcd for $C_{19}H_{16}Cl_3F_3N_6O$: C, 44.95; H, 3.18; N, 16.55. Found: C, 44.89; H, 3.10; N, 16.55.

EXAMPLE 185

N-(1-{[(cyanoimino)(3-pyridinylamino)methyl]amino}-2,2-dimethylpropyl)-4-fluoro-3-(trifluoromethyl)benzamide

EXAMPLE 185A

N-(1-(1H-1,2,3-benzotriazol-1-yl)-2,2-dimethylpropyl)-4-fluoro-3-(trifluoromethyl)benzamide A suspension of 4-fluoro-3-(trifluoromethyl)benzamide, pivaldehyde, benzotriazole, and p-toluenesulfonic acid was processed as described in Example 53A to provide the desired product.

MS (ESI+) m/z 395 (M+H)+;

EXAMPLE 185B

N-(1-{[(cyanoimino)(3-pyridinylamino)methyl]amino}-2,2-dimethylpropyl)-4-fluoro-3-(trifluoromethyl)benzamide A suspension of Example 54C, Example 185A, and $Cs_2CO_3$ was processed as described in Example 110B to provide the desired product.

MS (ESI+) m/z 437 (M+H)+;
$^1$H NMR (DMSO-$d_6$) δ 9.48 (br s, 1H); 8.54 (d, 1H, J=8.5 Hz); 8.46 (d, 1H, J=2.3 Hz);
8.37 (dd, 1H, J=4.7, 1.4 Hz); 8.23–8.14 (m, 2H), 7.70–7.62 (m, 3H), 7.40 (dd, 1H, J=8.1, 4.8 Hz); 5.80 (t, 1H, J=8.6 Hz); 1.20 (s, 9H);
Anal. calcd for $C_{20}H_{20}F_4N_6O$: C, 55.04; H, 4.62; N, 19.26. Found: C, 54.91; H, 4.66; N, 19.41.

EXAMPLE 186

(+) 4-chloro-N-{3,3-dimethyl-1-[((3-pyridinylamino){[(trifluoromethyl)sulfonyl]imino}methyl)amino]butyl}benzamide Example 142 was chromatographed over a Daicel Chiral Technologies Chiralcel OJ chiral column (2.0 cm×25 cm) eluting with 8% ethanol/hexanes (flow rate=10 mL/minutes) to provide the desired product as the dextrorotatory enantiomer.

$[\alpha]_D^{23}$ +24° (c=0.20, DMSO);
MS (ESI-) m/z 506 (M-H)+;
$^1$H NMR (DMSO-$d_6$) δ 10.16 (br s, 1H), 9.21 (br s, 1H), 8.50 (s, 1H), 8.43 (s, 1H), 7.91 (d, 3H, J=8.1 Hz), 7.68 (s, 1H), 7.60 (d, 2H, J=8.3 Hz), 7.44 (t, 1H, J=6.8 Hz), 5.82 (t, 1H, J=8.1 Hz), 1.97–1.76 (m, 2H), 0.97 (s, 9H).

EXAMPLE 187

(−) 4-chloro-N-{3,3-dimethyl-1-[((3-pyridinylamino){[(trifluoromethyl)sulfonyl]imino}methyl)amino]butyl}benzamide Example 142 was chromatographed over a Daicel Chiral Technologies Chiralcel OJ chiral column (2.0 cm×25 cm) eluting with 8% ethanol/hexanes (flow rate=10 mL/minutes) to provide the desired product as the levorotatory enantiomer.

$[\alpha]_D^{23}$ −26° (c=0.20, DMSO);
MS (ESI-) m/z 506 (M-H)+;
$^1$H NMR (DMSO-$d_6$) δ 10.15 (br s, 1H), 9.21 (br s, 1H), 8.50 (s, 1H), 8.43 (s, 1H), 7.91 (d, 3H, J=8.1 Hz), 7.68 (s, 1H), 7.60 (d, 2H, J=8.3 Hz), 7.44 (t, 1H, J=6.8 Hz), 5.82 (t, 1H, J=8.1 Hz), 1.97–1.76 (m 2H), 0.97 (s, 9H).

EXAMPLE 188

4-bromo-N-{3,3-dimethyl-1-[((3-pyridinylamino){[(trifluoromethyl)sulfonyl]imino}methyl)amino]butyl}benzamide

EXAMPLE 188A

N-[1-(1H-1,2,3-benzotriazol-1-yl)-3,3-dimethylbutyl]-4-bromobenzamide

A suspension of 4-bromobenzamide, 3,3-dimethylbutanal, benzotriazole, and p-toluenesulfonic acid was processed as described in Example 53A to provide the desired product.

MS (ESI+) m/z 401 (M+H)+.

EXAMPLE 188B 4-bromo-N-{3,3-dimethyl-1-[((3-pyridinylamino){[(trifluoromethyl)sulfonyl]imino}methyl)amino]butyl}benzamide A suspension of Example 141A, Example 188A, and $Cs_2CO_3$ was processed as described in Example 110B to provide the desired product.

mp 185–186° C.;
MS (ESI-) m/z 552 (M+H)+;
$^1$H NMR (DMSO-$d_6$) δ 10.21 (br s, 1H), 9.25 (br s, 1H), 8.54 (s, 1H), 8.47 (d, 2H, J=8.1 Hz), 8.02 (d, 1H, J=8.3 Hz), 7.85–7.73 (m, 5H), 5.80 (m, 1H), 2.05–1.76 (m, 2H), 0.97 (s, 9H);
Anal. Calcd for $C_{20}H_{23}BrF_3N_5O_3S$: C, 43.64; H, 4.21; N, 12.72. Found: C, 46.63; H, 4.10; N, 12.57.

EXAMPLE 189

N-{3,3-dimethyl-1-[((3-pyridinylamino){[(trifluoromethyl)sulfonyl]imino}methyl)amino]butyl}-4-(trifluoromethyl)benzamide

EXAMPLE 189A

N-[1-(1H-1,2,3-benzotriazol-1-yl)-3,3-dimethylbutyl]-4-bromobenzamide

A suspension of 4-(trifluoromethyl)benzamide, 3,3-dimethylbutanal, benzotriazole, and p-toluenesulfonic acid was processed as described in Example 53A to provide the desired product.

MS (ESI+) m/z 391 (M+H)+.

EXAMPLE 189B

N-{3,3-dimethyl-1-[((3-pyridinylamino){[(trifluoromethyl)sulfonyl]imino}methyl)amino]butyl}-4-(trifluoromethyl)benzamide A suspension of Example 141A, Example 189A, and $Cs_2CO_3$ was processed as described in Example 110B to provide the desired product.

mp 192–193° C.;
MS (ESI-) m/z 540 (M+H)+;
$^1$H NMR (DMSO-$d_6$) δ 10.05 (br s, 1H), 9.29 (br s, 1H), 8.50 (d, 1H, J=4.3 Hz), 8.43 (d, 1H, J=2.2 Hz), 8.07 (d, 2H, J=8.1 Hz), 7.98 (d, 1H, J=4.9 Hz), 7.92 (d, 2H, J=8.1 Hz), 7.68 (d, 1H, J=2.3 Hz), 7.46 (dd, 1H, J=5.5, 2.4 Hz), 5.85 (m, 1H), 2.05–1.76 (m, 2H), 0.98 (s, 9H);
Anal. Calcd for $C_{21}H_{23}F_6N_5O_3S$: C, 46.75; H, 4.30; N, 12.98. Found: C, 47.02; H, 4.31; N, 13.00.

EXAMPLE 190

3,5-dichloro-N-{2,2-dichloro-1-[((3-pyridinylamino){[(trifluoromethyl)sulfonyl]imino}methyl)amino]propyl}benzamide A suspension of Example 141A, Example 164A, and $Cs_2CO_3$ was processed as described in Example 110B to provide the desired product.

mp 213–215° C.;

MS (ESI+) m/z 567 (M+H)$^+$;

$^1$H NMR (DMSO-d$_6$) δ 10.29 (br s, 1H), 9.35 (br s, 1H), 8.52 (s, 2H), 7.91 (dd, 3H, J=7.9, 3.1 Hz), 7.74 (d, 1H, J=2.7 Hz), 7.53 (d, 2H, J=2.9 Hz), 6.65 (m, 1H), 2.21 (s, 3H);

Anal. Calcd for C$_{17}$H$_{14}$Cl$_4$F$_3$N$_5$O$_3$S: C, 36.00; H, 2.49; N, 12.35. Found: C, 36.30; H, 2.63; N, 12.26.

EXAMPLE 191

N-{2,2-dichloro-1-[((3-pyridinylamino){[(trifluoromethyl)sulfonyl]imino}methyl)amino]propyl}-4-(trifluoromethyl)benzamide A suspension of Example 141A, Example 171A, and Cs$_2$CO$_3$ was processed as described in Example 110B to provide the desired product.

mp 214–215° C.;

MS (ESI+) m/z 566 (M+H)$^+$;

$^1$H NMR (DMSO-d$_6$) δ 10.30 (br s, 1H), 9.00 (br s, 1H), 8.53 (s, 2H), 8.05 (d, 2H, J=8.2 Hz), 7.91 (d, 2H, J=8.1 Hz), 7.73 (d, 2H, 2.5), 7.51 (t, 1H, J=2.6 Hz), 6.69 (m, 1H), 2.13 (s, 3H);

Anal. Calcd for C$_{18}$H$_{15}$Cl$_2$F$_5$N$_5$O$_3$S: C, 38.18; H, 2.67; N, 12.37. Found: C, 38.24; H, 2.60; N, 12.35.

EXAMPLE 192

N-(2,2-dichloro-1-{[[(6-chloro-3-pyridinyl)amino](cyanoimino)methyl]amino}propyl)-2-thiophenecarboxamide

EXAMPLE 192A

N-[1-(1H-1,2,3-benzotriazol-1-yl)-2,2-dichloropropyl]-2-thiophenecarboxamide

A suspension of 2-thiophenecarboxamide, 2,2-dichloropropionaldehyde, benzotriazole, and p-toluenesulfonic acid was processed as described in Example 53A to provide the desired product.

MS (ESI+) m/z 355 (M+H)$^+$.

EXAMPLE 192B

N-(2,2-dichloro-1-{[[(6-chloro-3-pyridinyl)amino](cyanoimino)methyl]amino}propyl)-2-thiophenecarboxamide A suspension of Example 55C, Example 192A, and Cs$_2$CO$_3$ was processed as described in Example 110B to provide the desired product.

mp 201–203° C.;

MS (ESI+) m/z 431 (M+H)$^+$;

$^1$H NMR (DMSO-d$_6$) δ 9.88 (s, 1H); 8.62 (br d, 1H, J=8.5 Hz), 8.35 (d, 1H, J=2.7 Hz), 7.89 (dd, 1H, J=4.8, 1.0 Hz), 7.80–7.74 (m, 2H), 7.60 (d, 2H, J=8.7 Hz), 7.60 (d, 1H, J=8.5 Hz), 7.30 (br d, 1H, J=8.5 Hz); 7.22 (dd, 1H, J=5.1, 3.9 Hz), 6.49 (t, 1H, J=8.5 Hz); 2.17 (s, 3H);

Anal. calcd for C$_{15}$H$_{13}$Cl$_3$N$_6$OS: C, 41.73; H, 3.04; N, 19.47. Found: C, 41.88; H, 2.77; N, 19.38.

EXAMPLE 193

N-(2,2-dichloro-1-{[[(6-chloro-3-pyridinyl)amino](cyanoimino)methyl]amino}propyl)nicotinamide

EXAMPLE 193A

N-[1-(1H-1,2,3-benzotriazol-1-yl)-2,2-dichloropropyl]nicotinamide

A suspension of nicotinamide, 2,2-dichloropropionaldehyde, benzotriazole, and p-toluenesulfonic acid was processed as described in Example 53A to provide the desired product.

MS (ESI+) m/z 350 (M+H)$^+$.

EXAMPLE 193B

N-(2,2-dichloro-1-{[[(6-chloro-3-pyridinyl)amino](cyanoimino)methyl]amino}propyl)nicotinamide A suspension of Example 55C, Example 193A, and Cs$_2$CO$_3$ was processed as described in Example 110B to provide the desired product.

mp 212–213° C.;

MS (ESI+) m/z 427 (M+H)$^+$;

$^1$H NMR (DMSO-d$_6$) δ 9.96 (br s, 1H); 8.97 (d, 1H, J=2.4 Hz); 8.88 (d, 1H, J=8.1 Hz);

8.76 (dd, 1H, J=4.9, 1.5 Hz); 8.33 (d, 1H, J=2.3 Hz), 8.17 (dt, 1H, J=8.3, 1.7 Hz), 7.76 (dd, 1H, J=8.4, 2.7 Hz), 7.60–7.53 (m, 2H); 7.31 (br d, 1H, J=8.8 Hz); 6.53 (t, 1H, J=8.7 Hz); 2.18 (s, 3H);

Anal. calcd for C$_{16}$H$_{14}$Cl$_3$N$_7$O: C, 45.04; H, 3.31; N, 22.98. Found: C, 45.00; H, 3.43; N, 22.72.

Determination of Potassium Channel Opening Activity Membrane Hyperpolarization Assays Compounds were evaluated for potassium channel opening activity using primary cultured guinea-pig urinary bladder (GPB) cells.

For the preparation of urinary bladder smooth muscle cells, urinary bladders were removed from male guinea-pigs (Hartley, Charles River, Wilmington, Mass.) weighing 300–400 g and placed in ice-cold Ca$^{2+}$-free Krebs solution (Composition, mM: KCl, 2.7; KH$_2$PO$_4$, 1.5; NaCl, 75; Na$_2$HPO$_4$, 9.6; Na$_2$HPO$_4$.7H$_2$O, 8; MgSO$_4$, 2; glucose, 5; HEPES, 10; pH 7.4). Cells were isolated by enzymatic dissociation as previously described with minor modifications (Klockner, U. and Isenberg, G., Pflugers Arch. (1985), 405, 329–339), hereby incorporated by reference. The bladder was cut into small sections and incubated in 5 mL of the Kreb's solution containing I mg/mL collagenase (Sigma, St. Louis, Mo.) and 0.2 mg/mL pronase (Calbiochem, La Jolla, Calif.) with continuous stirring in a cell incubator for 30 minutes. The mixture was then centrifuged at 1300×g for 5 minutes, and the pellet resuspended in Dulbecco's PBS (GIBCO, Gaithersburg, Md.) and recentrifuged to remove residual enzyme. The cell pellet was resuspended in 5 mL growth media (composition: Dulbecco's modified Eagle's medium supplemented with 10% fetal bovine serum, 100 units/mL penicillin, 100 units/mL streptomycin and 0.25 mg/mL amphotericin B) and further dissociated by pipetting the suspension through a flame-polished Pasteur pipette and passing it through a polypropylene mesh membrane (Spectrum, Houston, Tex.). The cell density was adjusted to 100,000 cells/mL by resuspension in growth media. Cells were plated in clear-bottomed black 96-well plates (Packard) for membrane potential studies at a density of 20,000 cells/well and maintained in a cell incubator with 90% air: 10% CO$_2$ until confluent. Cells were confirmed to be of smooth muscle type by cytoskeletal staining using a monoclonal mouse anti human-α-smooth muscle actin (Biomeda, Foster City, Calif.).

Functional activity at potassium channels was measured by evaluating changes in membrane potential using the bis-oxonol dye DiBAC(4) (Molecular Probes) in a 96-well cell-based kinetic assay system, Fluorescent Imaging Plate Reader (FLIPR) (K. S. Schroeder et al., J. Biomed. Screen., v. 1 pp. 75–81 (1996)), hereby incorporated by reference. DiBAC(4)$_3$ is an anionic potentiometric probe which partitions between cells and extracellular solution in a membrane potential-dependent manner. With increasing membrane potential (for example, K$^+$ depolarization), the probe further partitions into the cell; this is measured as an increase in fluorescence due to dye interaction with intracellular lipids and proteins. Conversely, decreasing membrane potential (hyperpolarization by potassium channel openers) evokes a decrease in fluorescence.

Confluent guinea-pig urinary bladder cells cultured in black clear-bottomed 96-well plates were rinsed twice with 200 mL assay buffer (composition, mM: HEPES, 20; NaCl, 120; KCl, 2; CaCl$_2$, 2; MgCl$_2$, 1; glucose, 5; pH 7.4 at 25° C.) containing 5 μM DiBAC(4)$_3$ and incubated with 180 mL of the buffer in a cell incubator for 30 minutes at 37° C. to ensure dye distribution across the membrane. After recording the baseline fluorescence for 5 minutes, the reference or test compounds, prepared at 10 times the concentration in the assay buffer, were added directly to the wells. Changes in fluorescence were monitored for an additional 25 minutes. Hyperpolarization responses were corrected for any background noise and were normalized to the response observed with 10 μM of the reference compound P1075 (assigned as 100%), a potent opener of smooth muscle K$_{ATP}$ channels (Quast et al., Mol. Pharmacol., v. 43 pp. 474–481 (1993)), hereby incorporated by reference.

Routinely, five concentrations of P1075 or test compounds (log or half-log dilutions) were evaluated and the maximal steady-state hyperpolarization values (expressed as % relative to P1075) plotted as a function of concentration. The EC$_{50}$ (concentration that elicites 50% of the maximal response for the test sample) values were calculated by non-linear regression analysis using a four parameter sigmoidal equation. The maximal response of each compound (expressed as % relative to P1075) is reported. Stock solutions of compounds were prepared in 100% DMSO and further dilutions were carried out in the assay buffer and added to a 96-well plate.

TABLE 1

Membrane Hyperpolarization (MHP) in Guinea-Pig Bladder (GPB) Cells

| Example # | Maximal Response (% P1075) | MHP GPB EC$_{50}$ (μM) |
|---|---|---|
| 1 | 116 | 0.07 |
| 3 | 79 | 0.89 |
| 4 | 133 | 0.30 |
| 5 | 106 | 1.08 |
| 6 | 107 | 1.55 |
| 7 | 101 | 0.45 |
| 8 | 10 | 10 |
| 9 | 104 | 0.08 |
| 10 | 65 | 0.70 |
| 11 | 109 | 0.51 |
| 12 | 4 | 10 |
| 13 | 91 | 0.35 |
| 14 | 110 | 0.30 |
| 15 | 70 | 0.55 |
| 16 | 65 | 0.370 |
| 17 | 109 | 0.09 |
| 18 | 123 | 0.09 |
| 19 | 117 | 0.06 |
| 20 | 85 | 0.09 |
| 21 | 96 | 0.09 |
| 22 | 100 | 0.22 |
| 23 | 66 | 3.96 |
| 24 | 93 | 0.08 |
| 25 | 103 | 0.07 |
| 26 | 80 | 0.99 |
| 27 | 80 | 0.10 |
| 28 | 77 | 0.50 |
| 29 | 28 | 1.0 |
| 30 | 22 | 3.2 |
| 32 | 15 | 1.0 |
| 33 | 102 | 0.22 |
| 34 | 80 | 0.50 |
| 35 | 40 | 13.1 |
| 36 | 50 | 25.5 |
| 37 | 85 | 0.78 |
| 38 | 100 | 0.10 |
| 39 | 101 | 0.46 |
| 40 | 100 | 0.12 |
| 41 | 98 | 0.14 |
| 42 | 66 | 2.14 |
| 43 | 80 | 1.21 |
| 44 | 103 | 0.04 |
| 45 | 92 | 0.04 |
| 46 | 105 | 0.04 |
| 47 | 98 | 0.06 |
| 48 | 96 | 0.20 |
| 49 | 92 | 0.04 |
| 50 | 92 | 0.10 |
| 51 | 88 | 0.57 |
| 52 | 72 | 0.27 |
| 57 | 80 | 4.6 |
| 58 | 87 | 0.65 |
| 59 | 73 | 0.31 |
| 60 | 62 | 1.0 |
| 61 | 36 | 0.33 |
| 62 | 81 | 0.33 |
| 63 | 73 | 4.4 |
| 64 | 89 | 0.40 |
| 65 | 89 | 0.130 |
| 66 | 79 | 0.082 |
| 68 | 99 | 0.43 |
| 70 | 74 | 0.32 |
| 84 | 69 | 6 |
| 85 | <20 | >10 |
| 86 | 83 | 0.086 |
| 87 | 85 | 0.52 |
| 88 | 87 | 0.22 |
| 89 | 88 | 0.1 |
| 90 | 55 | 0.17 |
| 91 | 68 | 2.9 |
| 92 | 71 | 0.25 |
| 93 | 75 | 0.14 |
| 94 | 82 | 0.16 |
| 95 | 97 | 0.84 |
| 96 | 93 | 0.24 |
| 97 | 74 | 1.6 |
| 98 | 62 | 1.1 |
| 99 | 84 | 3.5 |
| 100 | 87 | 0.18 |
| 101 | 59 | 6.1 |
| 102 | <20 | >10 |
| 103 | 103 | 0.05 |
| 105 | 106 | 0.053 |
| 106 | 85 | 0.63 |
| 123 | 90 | 0.85 |
| 124 | 98 | 0.11 |
| 127 | 65 | 1.2 |
| 128 | 116 | 0.47 |
| 129 | 132 | 0.12 |
| 130 | 147 | 0.53 |
| 131 | 53 | 2 |
| 132 | 124 | 0.13 |
| 133 | 106 | 0.039 |
| 134 | 86 | 2 |
| 148 | 61 | 0.096 |
| 149 | 129 | 0.084 |

In Vitro Functional Models

Compounds were evaluated for functional potassium channel opening activity using tissue strips obtained from Landrace pig bladders.

Landrace pig bladders were obtained from female Landrace pigs of 9–30 kg. Landrace pigs were euthanized with an intraperitoneal injection of pentobarbital solution, Somlethal®, J. A. Webster Inc., Sterling, Mass. The entire bladder was removed and immediately placed into Krebs Ringer bicarbonate solution (composition, mM: NaCl, 120; $NaHCO_3$, 20; dextrose, 11; KCl, 4.7; $CaCl_2$, 2.5; $MgSO_4$, 1.5; $KH_2PO_4$, 1.2; $K_2EDTA$, 0.01, equilibrated with 5% $CO_2$/95% $O_2$ pH 7.4 at 37° C.). Propranolol (0.004 mM) was included in all of the assays to block β-adrenoceptors. The trigonal and dome portions were discarded. Strips 3–5 mm wide and 20 mm long were prepared from the remaining tissue cut in a circular fashion. The mucosal layer was removed. One end was fixed to a stationary glass rod and the other to a Grass FT03 transducer at a basal preload of 1.0 gram. Two parallel platinum electrodes were included in the stationary glass rod to provide field stimulation of 0.05 Hz, 0.5 milli-seconds at 20 volts. This low frequency stimulation produced a stable twitch response of 100–500 centigrams. Tissues were allowed to equilibrate for at least 60 minutes and primed with 80 mM KCl. A control concentration response curve (cumulative) was generated for each tissue using the potassium channel opener P1075 as the control agonist. P1075 completely eliminated the stimulated twitch in a dose dependent fashion over a concentration range of $10^{-9}$ to $10^{-5}$ M dissolved in DMSO using ½ log increments. After a 60 minute rinsing period, a concentration response curve (cumulative) was generated for the test agonist in the same fashion as that used for the control agonist P1075. The maximal efficacy of each compound (expressed as % relative to P1075) is reported. The amount of agent necessary to cause 50% of the agent's maximal response ($ED_{50}$) was calculated using "ALLFIT" (DeLean et al., Am. J. Physiol., 235, E97 (1980)), hereby incorporated by reference. Agonist potencies were also expressed as an index relative to P1075. The index was calculated by dividing the $ED_{50}$ for P1075 by the $ED_{50}$ for the test agonist in a given tissue. Each tissue was used for only one test agonist, and the indices obtained from each tissue were averaged to provide an average index of potency. These data are shown in Table 2.

TABLE 2

Functional Potassium Channel Opening Activity in Isolated Bladder Stripes

| Example # | Landrace Pig Bladder Efficacy (% P1075) | $ED_{50}$ ($\mu$M) | Index |
|---|---|---|---|
| 1 | 100 | 9 | 0.009 |
| 3 | 97 | 9 | 0.012 |
| 4 | 89 | 18 | 0.015 |
| 9 | 91 | 17 | 0.011 |
| 11 | 100 | 19 | 0.011 |
| 13 | 95 | 10 | 0.022 |
| 14 | 96 | 14 | 0.027 |
| 15 | 97 | 28 | 0.005 |
| 17 | 100 | 12 | 0.006 |
| 18 | 97 | 8 | 0.020 |
| 20 | 84 | 28 | 0.011 |
| 21 | 86 | 21 | 0.014 |
| 22 | 100 | 5 | 0.017 |
| 23 | 100 | 16 | 0.009 |
| 24 | 100 | 17 | 0.007 |
| 25 | 100 | 1 | 0.078 |
| 27 | 94 | 25 | 0.009 |
| 28 | 100 | 42 | 0.004 |
| 33 | 80 | 12 | 0.027 |
| 34 | 99 | 23 | 0.003 |
| 38 | 98 | 7 | 0.015 |
| 40 | 100 | 15 | 0.007 |
| 44 | 95 | 2 | 0.040 |
| 46 | 84 | 5 | 0.015 |
| 47 | 67 | 36 | 0.019 |
| 49 | 100 | 3 | 0.031 |
| 50 | 90 | 17 | 0.007 |
| 51 | 100 | 17 | 0.006 |
| 52 | 72 | 19 | 0.012 |
| 57 | 85 | 14 | 0.007 |
| 58 | 59 | 12 | 0.008 |
| 83 | 62 | 2.8 | 0.031 |
| 86 | 19 | 30 | 0.01 |
| 87 | 67 | 7.6 | 0.02 |
| 88 | 36 | 10 | 0.074 |
| 89 | 41 | 3.4 | 0.120 |
| 90 | 44 | 0.42 | 0.420 |
| 91 | 46 | 0.83 | 0.360 |
| 92 | 76 | 1.8 | 0.047 |
| 98 | 30 | 33 | 0.004 |
| 103 | 83 | 2.4 | 0.450 |
| 106 | 69 | 12 | 0.010 |
| 110 | 61 | 6.2 | 0.017 |
| 116 | 94 | 3.3 | 0.028 |
| 117 | 79 | 5.8 | 0.030 |
| 118 | 69 | 22 | 0.006 |
| 119 | 78 | 3.4 | 0.939 |
| 120 | 84 | 7.5 | 0.017 |
| 121 | 89 | 4.8 | 0.044 |
| 123 | 63 | 10 | 0.028 |
| 124 | 47 | 9.3 | 0.012 |
| 125 | 92 | 9.2 | 0.030 |
| 126 | 94 | 3.8 | 0.096 |
| 133 | 58 | 8.4 | 0.039 |
| 142 | 44 | 0.60 | 0.270 |
| 148 | 78 | 1.1 | 0.082 |
| 149 | 95 | 2.4 | 0.076 |
| 153 | 93 | 4.9 | 0.014 |
| 155 | 95 | 2.5 | 0.022 |
| 156 | 93 | 4.0 | 0.048 |
| 158 | 92 | 4.8 | 0.061 |
| 159 | 92 | 7.9 | 0.013 |
| 160 | 98 | 0.69 | 0.221 |
| 161 | 93 | 4.0 | 0.108 |
| 162 | 87 | 9.0 | 0.025 |
| 168 | 92 | 0.89 | 0.064 |
| 169 | 75 | 5.0 | 0.231 |
| 170 | 100 | 4.2 | 0.012 |
| 172 | 53 | 0.49 | 0.507 |
| 174 | 34 | 1.2 | 2.2 |
| 175 | 54 | 1.5 | 0.148 |
| 180 | 98 | 2.3 | 0.040 |
| 186 | 66 | 1.2 | 2.1 |
| 187 | 52 | 7.8 | 0.077 |
| 188 | 87 | 10 | 0.020 |
| 189 | 66 | 0.93 | 0.078 |
| 192 | 99 | 3.1 | 0.019 |

As shown by the data in Tables 1 and 2, the compounds of this invention reduce stimulated contractions of the bladder by opening potassium channels and therefore have utility in the treatment of diseases prevented by or ameliorated with potassium channel openers.

In Vivo Data

The utility of compounds of the present invention for the treatment of urinary incontinence, bladder overactivity, and bladder instability is illustrated by the ability of compounds of the present invention to inhibit bladder contractions in vivo. The following method is illustrative of the in vivo bladder efficacy of compounds of the present invention.

In Vivo Bladder Efficacy Protocol (Isovolumetric Contractions Model)

Male CD rats (400–450 g) were anesthetized with urethane (0.6 g/kg ip+0.6 g/kg sc). The left femoral vein was cannulated with polyethylene (PE-50) tubing for the administration of test compound. A third polyethylene catheter (PE-60) was inserted 3–4 mm into the apex of the bladder dome and secured using a 5–0 silk purse string suture. The bladder was emptied via this catheter and additionally by applying slight manual pressure on the lower abdomen. The urinary catheter was connected using a Y-tube connector to both a pressure transducer and a syringe pump. The urethra was then ligated using 4–0 silk suture and the bladder was slowly filled using a constant infusion of room temperature saline at the rate of 0.1 mL/min until spontaneous rhythmic contractions were evident (1.0–1.3 mL). After the contractions stabilized to a consistent pattern, bladder pressure was monitored for 20 minutes before and after a dose of the vehicle (equal parts of β-cyclodextrin stock solution (100 g β-cyclodextrin dissolved in 200 mL) and sterile water) alone. Then three doses of a test compound were administered cumulatively intravenous (iv) at 20 minute intervals. Each dosing solution (1 mL/kg) was warmed to body temperature before dosing and was infused over 3 minutes to minimize dosing artifacts on the bladder pressure trace. Data were averaged over the last 10 minutes of each period and presented as percent change from control. Area under the curve of the bladder contractions was determined from the respective waveforms using a Modular Instruments, Inc. computerized data acquisition system and averaged over the last ten minutes of each twenty minute period. The doses required to reduce the area under the curve of the bladder contractions by 30% (AUC ED30%) relative to control were estimated using a customized Excel spreadsheet. Data for representative compounds of the present invention are shown in Table 3.

TABLE 3

Bladder Pressure Effects in the Rat Isovolumetric Contractions Model

| Example # | AUC $EC_{30}$ ($\mu$mol/kg) |
|---|---|
| 46 | 0.70 |
| 51 | 0.28 |
| 52 | 0.78 |
| 91 | >10 |
| 126 | 13.5 |
| 153 | 1 |
| 160 | 1.7 |

The data in Table 3 illustrates the ability of compounds of the present invention to inhibit bladder contractions in vivo.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The present invention provides pharmaceutical compositions which comprise compounds of the present invention formulated together with one or more nontoxic pharmaceutically acceptable carriers. The pharmaceutical compositions can be formulated for oral administration in solid or liquid form, for parenteral injection or for rectal administration.

Further included within the scope of the present invention are pharmaceutical compositions comprising one or more of the compounds of formula I–VII prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar—agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar—agar, calcium carbonate, potato or tapioca starch, alginic acid, certain silicates, and sodium carbonate; e) solution retarding agents such as paraffin); f) absorption accelerators such as quaternary ammonium compounds; g) wetting agents such as cetyl alcohol and glycerol monostearate;) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal or vaginal administration are preferably suppositories which can be prepared by mixing the compounds of this invention with suitable non+irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required.

Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the present invention may also be administered in the form of liposomes. As is known in the art, liposomes are generally derived from phospholipids or other lipid substances. Liposomes are formed by mono or multi-lamellar hydrated liquid crystals that are dispersed in an aqueous medium. Any nontoxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

The term "pharmaceutically acceptable cation," as used herein, refers to a positively-charged inorganic or organic ion that is generally considered suitable for human consumption. Examples of pharmaceutically acceptable cations are hydrogen, alkali metal (lithium, sodium and potassium), magnesium, calcium, ferrous, ferric, ammonium, alkylammonium, dialkylammonium, trialkylammonium, tetraalkylammonium, diethanolammmonium, and choline. Cations may be interchanged by methods known in the art, such as ion exchange.

The terms "pharmaceutically acceptable salts, esters and amides," as used herein, refer to carboxylate salts, amino acid addition salts, zwitterions, esters and amides of compounds of formula I–VII which are, within the scope of sound medical judgement, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt," as used herein, refers to salts that are well known in the art. For example, S. M Berge et al. describe pharmaceutically acceptable salts in detail in J. Pharmaceutical Sciences, 66:1–19 (1977). Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl sulfate, and the like, metal salts such as sodium, potassium, magnesium or calcium salts or amino salts such as ammonium, triethylamine salts, and the like, all of which may be prepared according to conventional methods.

The term "pharmaceutically acceptable ester," as used herein, refers to esters of compounds of the present invention which hydrolyze in vivo and include those that break down readily in the human body to leave the parent compound or a salt thereof. Examples of pharmaceutically acceptable, nontoxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula I–VII may be prepared according to conventional methods.

The term "pharmaceutically acceptable amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula I–VII my be prepared according to conventional methods. It is intended that amides of the present invention include amino acid and peptide derivatives of the compounds of formula I–VII, as well.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to the parent compound of the above formula, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration.

The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

The present invention contemplates pharmaceutically active metabolites formed by in vivo biotransformation of compounds of formula I–VII. The term pharmaceutically active metabolite, as used herein, refers to a compound formed by the in vivo biotransformation of compounds of formula I–VII. The present invention contemplates compounds of formula I–VII and metabolites thereof. A thorough discussion of biotransformation is provided in Goodman and Gilman's, The Pharmacological Basis of Therapeutics, seventh edition, hereby incorporated by reference.

The compounds of the invention, including but not limited to those specified in the examples, possess potassium channel opening activity in mammals (especially humans). As potassium channel openers, the compounds of the present invention may be useful for the treatment and prevention of diseases such as asthma, epilepsy, male sexual dysfunction, female sexual dysfunction, pain, bladder overactivity, stroke, diseases associated with decreased skeletal blood flow such as Raynaud's phenomenon and intermittent claudication, eating disorders, functional bowel disorders, neurodegeneration, benign prostatic hyperplasia (BPH), dysmenorrhea, premature labor, alopecia, cardioprotection, coronary artery disease, angina and ischemia.

The ability of the compounds of the present invention, including but not limited to those specified in the examples, to treat bladder overactivity, sensations of incontinence urgency, urinary incontinence, pollakiuria, bladder instability, nocturia, bladder hyerreflexia, and enuresis may be demonstrated by (Resnick, The Lancet (1995) 346, 94–99; Hampel, Urology (1997) 50 (Suppl 6A), 4–14; Bosch, BJU International (1999) 83 (Suppl 2), 7–9; Andersson, Urology (1997) 50 (Suppl 6A), 74–84; Lawson, Pharmacol. Ther., (1996) 70, 39–63; Nurse., Br.J. Urol., (1991) 68, 27–31; Howe, J. Pharmacol. Exp. Ther., (1995) 274, 884–890; Gopalakrishnan, Drug Development Research, (1993) 28, 95–127).

The ability of the compounds of the present invention, including but not limited to those specified in the examples, to treat male sexual dysfunction such as male erectile dysfunction, impotence and premature ejaculation may be demonstrated by (Andersson, Pharmacological Reviews (1993) 45, 253; Lee, Int. J. Impot. Res. (1999) 11(4), 179–188; Andersson, Pharmacological Reviews (1993) 45, 253; Lawson, Pharmacol. Ther., (1996) 70, 39–63, Vick, J. Urol. (2000) 163: 202).

The ability of the compounds of the present invention, including but not limited to those specified in the examples, to treat female sexual dysfunction such as clitoral erectile insufficiency, vaginismus and vaginal engorgement may be demonstrated by (Kim et al., J. Urol. (2000) 163 (4): 240; Goldstein and Berman, Int. J. Impotence Res. (1998) 10:S84–S90).

The ability of the compounds of the present invention, including but not limited to those specified in the examples, to treat benign prostatic hyperplasia (BPH) may be demonstrated by (Pandita, The J. of Urology (1999) 162, 943; Andersson; Prostate (1997) 30: 202–215).

The ability of the compounds of the present invention, including but not limited to those specified in the examples, to treat premature labor and dysmenorrhoea may be demonstrated by (Sanborn, Semin. Perinatol. (1995) 19, 31–40; Morrison, Am. J. Obstet. Gynecol. (1993) 169(5), 1277–85; Kostrzewska, Acta Obstet. Gynecol. Scand. (1996) 75(10), 886–91; Lawson, Pharmacol. Ther., (1996) 70, 39–63).

The ability of the compounds of the present invention, including but not limited to those specified in the examples, to treat functional bowel disorders such as irritable bowel syndrome may be demonstrated by (Lawson, Pharmacol. Ther., (1996) 70, 39–63).

The ability of the compounds of the present invention, including but not limited to those specified in the examples, to treat asthma and airways hyperreactivity may be demonstrated by (Lawson, Pharmacol. Ther., (1996) 70, 39–63; Buchheit, Pulmonary Pharmacology & Therapeutics (1999) 12, 103; Gopalakrishnan, Drug Development Research, (1993) 28, 95–127).

The ability of the compounds of the present invention, including but not limited to those specified in the examples, to treat various pain states including but not limited to migraine and dyspareunia may be demonstrated by (Rodrigues, Br. J. Pharmacol. (2000) 129(1), 110–4; Vergoni, Life Sci. (1992) 50(16), PL135–8; Asano, Anesth. Analg. (2000) 90(5), 1146–51; Lawson, Pharmacol. Ther., (1996) 70, 39–63; Gopalakrishnan, Drug Development Research, (1993) 28, 95–127; Gehlert, Prog. Neuro-Psychopharmacol. & Biol. Psychiat., (1994) 18, 1093–1102).

The ability of the compounds of the present invention, including but not limited to those specified in the examples, to treat epilepsy may be demonstrated by (Lawson, Pharmacol. Ther., (1996) 70, 39–63; Gopalakrishnan, Drug Development Research, (1993) 28, 95–127; Gehlert, Prog. Neuro-Psychopharmacol & Biol. Psychiat., (1994) 18, 1093–1102).

The ability of the compounds of the present invention, including but not limited to those specified in the examples, to treat neurodegenerative conditions and diseases such as cerebral ischemia, stroke, Alzheimer's disease and Parkinson's disease may be demonstrated by (Lawson, Pharmacol. Ther., (1996) 70, 39–63; Gopalakrishnan, Drug Development Research, (1993) 28, 95–127; Gehlert, Prog. Neuro-Psychopharmacol. & Biol. Psychiat., (1994) 18, 1093–1102; Freedman, The Neuroscientist (1996) 2, 145).

The ability of the compounds of the present invention, including but not limited to those specified in the examples, to treat diseases or conditions associated with decreased skeletal muscle blood flow such as Raynaud's syndrome and intermittent claudication may be demonstrated by (Lawson, Pharmacol. Ther., (1996) 70, 39–63; Gopalakrishnan, Drug Development Research, (1993) 28, 95–127; Dompeling Vasa. Supplementum (1992) 3434; WO9932495).

The ability of the compounds of the present invention, including but not limited to those specified in the examples, to treat eating disorders such as obesity may be demonstrated by (Spanswick, Nature, (1997) 390, 521–25; Freedman, The Neuroscientist (1996) 2, 145).

The ability of the compounds of the present invention, including but not limited to those specified in the examples, to treat alopecia may be demonstrated by (Lawson, Pharmacol. Ther., (1996) 70, 39–63; Gopalakrishnan, Drug Development Research, (1993) 28, 95–127).

The ability of the compounds of the present invention, including but not limited to those specified in the examples, to treat myocardial injury during ischemia and reperfusion may be demonstrated by (Garlid, Circ Res (1997) 81(6), 1072–82; Lawson, Pharmacol. Ther., (1996) 70, 39–63; Grover, J. Mol. Cell Cardiol. (2000) 32, 677).

The ability of the compounds of the present invention, including but not limited to those specified in the examples, to treat coronary artery disease may be demonstrated by (Lawson, Pharmacol. Ther., (1996) 70, 39–63, Gopalakrishnan, Drug Development Research, (1993) 28, 95–127).

Aqueous liquid compositions of the present invention are particularly useful for the treatment and prevention of asthma, epilepsy, hypertension, Raynaud's syndrome, male sexual dysfunction, female sexual dysfunction, migraine, pain, eating disorders, urinary incontinence, functional bowel disorders, neurodegeneration and stroke.

When used in the above or other treatments, a therapeutically effective amount of one of the compounds of the present invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 50 mg/kg/day. For purposes of oral administration, more preferable doses can be in the range of from about 0.01 to about 25 mg/kg/day. If desired, the effective daily dose can be divided into multiple doses for purposes of administration; consequently, single dose compositions may contain such amounts or submultiples thereof to make up the daily dose.

We claim:
1. A compound having formula I:

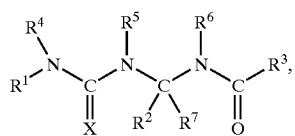

or a pharmaceutically acceptable salt thereof wherein,

X is selected from the group consisting of O, S, CHCN, $C(CN)_2$, $CHNO_2$, and $NR^8$;

$R^8$ is selected from the group consisting of hydrogen, alkoxy, alkyl, alkylsulfonyl, arylalkoxy, aryloxy, arylsulfonyl, cyano, haloalkylsulfonyl, heterocyclealkoxy, heterocycleoxy, hydroxy, nitro, and sulfamyl;

$R^1$ is selected from the group consisting of heterocycle, and heterocyclealkyl;

$R^2$ is selected from hydrogen, alkenyl, alkenyloxyalkyl, alkenyloxy(alkenyloxy)alkyl, alkoxyalkyl, alkoxycarbonyl, alkoxycarbonylalkyl, alkoxycarbonyl(halo)alkyl, alkoxy(halo)alkyl, alkyl, alkylcarbonyl, alkylcarbonylalkyl, alkylcarbonyl(halo)alkyl, alkylcarbonyloxyalkyl, alkylsulfinylalkyl, alkylsulfonylalkyl, alkylthioalkyl, alkynyl, amido, amidoalkyl, aryl, arylalkoxyalkyl, arylalkoxycarbonyl, arylalkoxycarbonylalkyl, arylalkyl, arylcarbonyl, arylcarbonylalkyl, arylcarbonyloxyalkyl, aryl(halo)alkyl, aryloxyalkyl, aryloxycarbonyl, aryloxycarbonylalkyl, arylalkylthioalkyl, arylsulfonylalkyl, carboxy, carboxyalkyl, carboxy(halo)alkyl, cyanoalkyl, cyano(halo)alkyl, cycloalkenyl, cycloalkenylalkyl, cycloalkyl, cycloalkylalkoxyalkyl, cycloalkylalkyl, cycloalkylcarbonyl, cycloalkyloxyalkyl, cycloalkylalkylthioalkyl, formyl, haloalkenyl, haloalkyl, haloalkylcarbonyl, haloalkynyl, heterocycle, heterocyclealkoxyalkyl, heterocyclealkyl, heterocyclecarbonyl, heterocycleoxyalkyl, heterocyclealkylthioalkyl, hydroxyalkyl, mercaptoalkyl, sulfamylalkyl, sulfamyl(halo)alkyl, and $(NR^9R^{10})$alkyl wherein $R^9$ and $R^{10}$ are independently selected from hydrogen, alkyl, alkylcarbonyl, aryl, arylalkyl, arylcarbonyl, formyl, and $S(O)_2R^{11}$, wherein $R^{11}$ is selected from alkyl, aryl, and arylalkyl;

$R^3$ is selected from the group consisting of alkyl, aryl, arylalkyl, heterocycle, and heterocyclealkyl;

$R^4$ is hydrogen; or $R^4$ and $R^1$ taken together with the nitrogen atom to which they are attached, together form a heterocycle selected from the group consisting of benzimidazolyl, benzotriazolyl, indazolyl, indolyl, isoindolyl, indolinyl and isoindolinyl wherein benzimidazolyl, benzotriazolyl, indazolyl, indolyl, isoindolyl, indolinyl and isoindolinyl are optionally substituted with 1, 2, or 3 substituents independently selected from the group consisting of alkenyl, alkoxy, alkoxycarbonyl, alkyl, alkylcarbonyl, alkylsulfinyl, alkylsulfonyl, alkynyl, arylalkoxycarbonyl, cyano, halogen, haloalkyl, haloalkoxy, nitro, sulfamyl, and —$NR^AR^B$ wherein $R^A$ and $R^B$ are independently selected from the group consisting of hydrogen, alkyl, alkylcarbonyl and formyl;

$R^5$ is selected from the group consisting of hydrogen, alkyl and $OR^{12}$;

$R^{12}$ is selected from the group consisting of hydrogen, alkyl and arylalkyl; or $R^5$ and $R^4$ taken together form an alkylene bridge of 2–3 carbons;

$R^6$ is hydrogen; or $R^6$ and $R^5$ taken together form an alkylene bridge of 2–3 carbons; or $R^6$ taken together with the nitrogen atom to which it is attached and $R^3$ taken together with the carbon atom to which it is attached, together form a heterocycle selected from the group consisting of 1-isoindolinonyl and 1-isoquinolinonyl wherein 1-isoindolinonyl and 1-isoquinolinonyl are optionally substituted with 1, 2, or 3 substituents selected from the group consisting of alkenyl, alkoxy, alkoxycarbonyl, alkyl, alkylcarbonyl, alkylsulfinyl, alkylsulfonyl, alkynyl, arylalkoxycarbonyl, cyano, halogen, haloalkyl, haloalkoxy, nitro, oxo, sulfamyl, and —$NR^AR^B$ wherein $R^A$ and $R^B$ are independently selected from the group consisting of hydrogen, alkyl, alkylcarbonyl and formyl; and $R^7$ is selected from the group consisting of hydrogen, haloalkyl, and lower alkyl; or $R^7$ and $R^2$ taken together with the carbon atom to which they are attached, together form a 5 or 6 membered carbocyclic ring wherein the 5 or 6 membered carbocyclic ring is optionally substituted with 1 or 2 substituents independently selected from the group consisting of alkenyl, alkoxy, alkyl, alkynyl, halogen, haloalkoxy, and haloalkyl;

provided that when X is O; $R^2$ is —$CCl_3$; $R^3$ is alkyl or phenyl; and $R^4$, $R^5$, $R^6$, and $R^7$ are hydrogen; then $R^1$ is other than phenyl.

2. A compound according to claim 1 wherein

X is selected from the group consisting of O, S, CHCN, $C(CN)_2$, $CHNO_2$, and $NR^8$;

$R^8$ is selected from the group consisting of alkoxy, alkylsulfonyl, arylalkoxy, arylsulfonyl, cyano, haloalkylsulfonyl, hydroxy, and nitro;

$R^1$ is selected from the group consisting of heterocycle, and heterocyclealkyl;

$R^2$ is selected from the group consisting of hydrogen, alkenyl, alkenyloxyalkyl, alkenyloxy(alkenyloxy)alkyl, alkoxyalkyl, alkoxycarbonylalkyl, alkyl, alkylcarbonyl, alkylsulfonylalkyl, alkylthioalkyl, aryl, arylalkyl, arylsulfonylalkyl, cyanoalkyl, cycloalkenyl, cycloalkenylalkyl, cycloalkyl, cycloalkylalkyl, haloalkyl, haloalkylcarbonyl, heterocycle, heterocyclealkyl, hydroxyalkyl, sulfamylalkyl, and ($NR^9R^{10}$)alkyl;

$R^3$ is selected from the group consisting of aryl, arylalkyl, and heterocycle;

$R^4$ is hydrogen; or $R^4$ and $R^1$ taken together with the nitrogen atom to which they are attached, together form a heterocycle selected from the group consisting of benzimidazolyl and indolyl wherein benzimidazolyl and indolyl are optionally substituted with 1 or 2 substituents independently selected from the group consisting of alkoxy, alkyl, halo, haloalkyl, and haloalkoxy;

$R^5$ is selected from the group consisting of hydrogen and alkyl; or $R^5$ and $R^4$ taken together form an alkylene bridge of 2–3 carbons;

$R^6$ is hydrogen; or $R^6$ and $R^5$ taken together form an alkylene bridge of 2–3 carbons; or $R^6$ taken together with the nitrogen atom to which it is attached and $R^3$ taken together with the carbon atom to which it is attached, together form a heterocycle selected from the group consisting of 1-isoindolinonyl and 1-isoquinolinonyl wherein 1-isoindolinonyl and 1-isoquinolinonyl are optionally substituted with 1 or 2 substituents selected from the group consisting of alkoxy, alkyl, halo, haloalkyl, and haloalkoxy; and $R^7$ is selected from the group consisting of hydrogen, haloalkyl, and lower alkyl; or $R^7$ and $R^2$ taken together with the carbon atom to which they are attached, together form a 5 or 6 membered carbocyclic ring wherein the 5 or 6 membered carbocyclic ring is optionally substituted with 1 or 2 substituents independently selected from the group consisting of alkyl, halo, haloalkoxy, and haloalkyl.

3. A compound according to claim 2 wherein

X is selected from the group consisting of O, S, CHCN, $C(CN)_2$, $CHNO_2$, and $NR^8$;

$R^8$ is selected from the group consisting of alkoxy, alkylsulfonyl, haloalkylsulfonyl, cyano, hydroxy, nitro, arylalkoxy wherein the aryl portion of arylalkoxy is phenyl, and arylsulfonyl wherein the aryl portion of arylsulfonyl is phenyl;

$R^1$ is heterocycle wherein heterocycle is selected from the group consisting of pyridinyl, pyrimidinyl and quinolinyl wherein pyridinyl, pyrimidinyl and quinolinyl are optionally substituted with 1, 2, or 3 substituents independently selected from the group consisting of alkoxy, alkyl, halo, haloalkyl, nitro, phenylsulfonyl and sulfamyl;

$R^2$ is selected from the group consisting of hydrogen, alkenyl, alkenyloxyalkyl, alkenyloxy(alkenyloxy)alkyl, alkoxyalkyl, alkoxycarbonylalkyl, alkyl, alkylcarbonyl, alkylsulfonylalkyl, aryl wherein aryl is phenyl, arylalkyl wherein the aryl portion of arylalkyl is phenyl, arylsulfonylalkyl wherein the aryl portion of arylsulfonylalkyl is phenyl, cyanoalkyl, cycloalkenylalkyl, cycloalkyl, haloalkyl, haloalkylcarbonyl, hydroxyalkyl, sulfamylalkyl, ($NR^9R^{10}$)alkyl and heterocycle wherein heterocycle is selected from the group consisting of 1,3-dioxanyl, pyrrolidinyl and thienyl; and $R^3$ is selected from the group consisting of aryl wherein aryl is phenyl and arylalkyl wherein the aryl portion of arylalkyl is phenyl.

4. A compound according to claim 1 wherein,

X is selected from the group consisting of O, S, $CHNO_2$, $C(CN)_2$, and $NR^8$;

$R^8$ is selected from the group consisting of arylsulfonyl, cyano, haloalkylsulfonyl, nitro and sulfamyl;

$R^1$ is selected from the group consisting of heterocycle and heterocyclalkyl;

$R^2$ is selected from the group consisting of hydrogen, alkenyl, alkenyloxyalkyl, alkenyloxy(alkenyloxy)alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and ($NR^9R^{10}$)alkyl;

$R^3$ is selected from the group consisting of aryl and arylalkyl;

$R^4$ is hydrogen;

$R^5$ is selected from the group consisting of hydrogen and alkyl; or $R^5$ and $R^4$ taken together form an alkylene bridge of 2–3 carbons;

$R^6$ is hydrogen; and $R^7$ is hydrogen.

5. A compound according to claim 1 wherein,

X is selected from the group consisting of O, S, $CHNO_2$, $C(CN)_2$, and $NR^8$;

$R^8$ is selected from the group consisting of arylsulfonyl wherein the aryl portion of arylsulfonyl is phenyl, cyano, haloalkylsulfonyl, nitro and sulfamyl;

$R^1$ is heterocycle wherein heterocycle is selected from the group consisting of quinolinyl, pyridinyl and pyrimidinyl, and heterocyclalkyl wherein the heterocycle portion of heterocyclealkyl is pyridinyl;

$R^2$ is selected from the group consisting of hydrogen, alkenyl, alkenyloxyalkyl, alkenyloxy(alkenyloxy) alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from the group consisting of 1,3-dioxanyl, pyrrolidinyl and thienyl;

$R^3$ is selected from the group consisting of aryl wherein aryl is phenyl and arylalkyl wherein the aryl portion of arylalkyl is phenyl;

$R^4$ hydrogen;

$R^5$ is selected from the group consisting of hydrogen and alkyl; or $R^5$ and $R^4$ taken together form an alkylene bridge of 2–3 carbons;

$R^6$ is hydrogen; and $R^7$ is hydrogen.

6. A compound according to claim 1 wherein,

X is $NR^8$;

$R^8$ is cyano;

$R^1$ is selected from the group consisting of heterocycle and heterocyclealkyl;

$R^3$ is selected from the group consisting of heterocycle and heterocyclealkyl;

$R^4$ hydrogen;

$R^5$ is hydrogen; and $R^6$ is hydrogen.

7. A compound according to claim 6 wherein, $R^2$ is selected from the group consisting of hydrogen, alkenyl, alkenyloxyalkyl, alkenyloxy(alkenyloxy) alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and $(NR^9R^{10})$alkyl; and $R^7$ hydrogen.

8. A compound according to claim 1 wherein,

X is $NR^8$;

$R^8$ is cyano;

$R^1$ is heterocycle wherein heterocycle is pyridinyl;

$R^2$ is selected from the group consisting of hydrogen, alkenyl, alkenyloxyalkyl, alkenyloxy(alkenyloxy) alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from the group consisting of 1,3-dioxanyl, pyrrolidinyl and thienyl;

$R^3$ is heterocycle wherein heterocycle is selected from the group consisting of furyl, pyrazinyl, pyridinyl, pyrimidinyl and quinolinyl;

$R^4$ hydrogen;

$R^5$ is hydrogen;

$R^6$ is hydrogen; and $R^7$ is hydrogen.

9. A compound according to claim 8 selected from the group consisting of

N-(2,2-dichloro-1-{[[(6-chloro-3-pyridinyl)amino] (cyanoimino)methyl]amino}propyl)-2-thiophenecarboxamide and N-(2,2-dichloro-1-{[[(6-chloro-3-pyridinyl)amino] (cyanoimino)methyl]amino}propyl)nicotiinamide.

10. A compound according to claim 1 wherein,

X is $NR^8$;

$R^8$ is cyano;

$R^1$ is selected from the group consisting of heterocycle and heterocyclealkyl;

$R^3$ is selected from the group consisting of aryl and arylalkyl;

$R^4$ is hydrogen;

$R^5$ is hydrogen; and $R^6$ is hydrogen.

11. A compound according to claim 10 wherein, $R^2$ is selected from the group consisting of hydrogen, alkenyl, alkenyloxyalkyl, alkenyloxy(alkenyloxy) alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and $(NR^9R^{10})$ alkyl; and $R^7$ is hydrogen.

12. A compound according to claim 1 wherein,

X is $NR^8$;

$R^8$ is cyano;

$R^1$ is heterocyclealkyl wherein the heterocycle portion of heterocyclealkyl is pyridinyl;

$R^2$ is selected from the group consisting of hydrogen, alkenyl, alkenyloxyalkyl, alkenyloxy(alkenyloxy) alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from the group consisting of 1,3-dioxanyl, pyrrolidinyl and thienyl;

$R^3$ is aryl wherein aryl is phenyl;

$R^4$ is hydrogen;

$R^5$ is hydrogen; and $R^6$ is hydrogen.

13. A compound according to claim 12 selected from the group consisting of 4-chloro-N-[1-({(cyanoimino)[(3-pyridinylmethyl)amino]methyl}amino)-2,2-dimethylpropyl]benzamide;

4-chloro-N-[1-({(cyanoimino)[(4-pyridinylmethyl) amino]methyl}amino)-2,2-dimethylpropyl]benzamide; and 4-chloro-N-[1-({(cyanoimino)[(2-pyridinylmethyl) amino]methyl}amino)-2,2-dimethylpropyl]benzamide.

14. A compound according to claim 1 wherein,

X is $NR^8$;

$R^8$ is cyano;

$R^1$ is heterocycle wherein heterocycle is selected from the group consisting of quinolinyl and pyrimidinyl;

$R^2$ is selected from the group consisting of hydrogen, alkenyl, alkenyloxyalkyl, alkenyloxy(alkenyloxy) alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from the group consisting of 1,3-dioxanyl, pyrrolidinyl and thienyl;

R³ is aryl wherein aryl is phenyl;
R⁴ hydrogen;
R⁵ is hydrogen;
R⁶ is hydrogen; and
R⁷ hydrogen.

15. A compound according to claim 14 that is selected from the group consisting of
4-methyl-N-(2,2,2-trichloro-1-{[(cyanoimino)(5-pyrimidinylamino)methyl]amino}ethyl)benzamide and
4-chloro-N-(1-{[(cyanoimino)(3-quinolinylamino)methyl]amino}-2,2-dimethylpropyl)benzamide.

16. A compound according to claim 1 wherein,
X is NR⁸;
R⁸ is cyano;
R¹ is heterocycle wherein heterocycle is pyridinyl;
R² is selected from the group consisting of hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, (NR⁹R¹⁰)alkyl and heterocycle wherein heterocycle is selected from the group consisting of 1,3-dioxanyl, pyrrolidinyl and thienyl;
R³ is aryl wherein aryl is phenyl;
R⁴ is hydrogen;
R⁵ is hydrogen;
R⁶ is hydrogen; and
R⁷ is hydrogen.

17. A compound according to claim 16 selected from the group consisting of
N-(1-{[(cyanoimino)(3-pyridinylamino)methyl]amino}-2,2-dimethylpropyl)-4-methylbenzamide;
4-chloro-N-(1-{[(cyanoimino)(3-pyridinylamino)methyl]amino}-2,2-dimethylpropyl)benzamide;
4-chloro-N-[{[(cyanoimino)(3-pyridinylamino)methyl]amino}(cyclopropyl)methyl]benzamide;
N-(1-{[[(6-chloro-3-pyridinyl)amino](cyanoimino)methyl]amino}-2,2-dimethylpropyl)-4-methylbenzamide;
(−) N-(1-{[(cyanoimino)(3-pyridinylamino)methyl]amino}-2,2-dimethylpropyl)-4-methylbenzamide;
(+) N-(1-{[(cyanoimino)(3-pyridinylamino)methyl]amino}-2,2-dimethylpropyl)-4-methylbenzamide;
4-chloro-N-(1-{[(cyanoimino)(3-pyridinylamino)methyl]amino}-2-ethylbutyl)benzamide;
4-chloro-N-(1-{[(cyanoimino)(3-pyridinylamino)methyl]amino}-3-methylbutyl)benzamide;
4-chloro-N-[{[(cyanoimino)(3-pyridinylamino)methyl]amino}(cyclohexyl)methyl]benzamide;
4-chloro-N-(1-{[(cyanoimino)(3-pyridinylamino)methyl]amino}-3,3-dimethylbutyl)benzamide;
4-chloro-N-(1-{[(cyanoimino)(3-pyridinylamino)methyl]amino}-2-methylpropyl)benzamide;
4-chloro-N-(4-cyano-1-{[(cyanoimino)(3-pyridinylamino)methyl]amino}-2,2-diethylbutyl)benzamide;
4-chloro-N-[1-{[(cyanoimino)(3-pyridinylamino)methyl]amino}-2-(2,6,6-trimethyl-1-cyclohexen-1-yl)ethyl]benzamide;
4-chloro-N-(1-{[(cyanoimino)(3-pyridinylamino)methyl]amino}-2,2-dimethyl-4-pentenyl)benzamide;
4-chloro-N-(1-{[(cyanoimino)(3-pyridinylamino)methyl]amino}propyl)benzamide;
4-chloro-N-({[(cyanoimino)(3-pyridinylamino)methyl]amino}methyl)benzamide;
(−) 4-chloro-N-(4-cyano-1-{[(cyanoimino)(3-pyridinylamino)methyl]amino}-2,2-diethylbutyl)benzamide;
(+) 4-chloro-N-(4-cyano-1-{[(cyanoimino)(3-pyridinylamino)methyl]amino}-2,2-diethylbutyl)benzamide;
(±) 4-chloro-N-[1-{[(cyanoimino)(3-pyridinylamino)methyl]amino}-2-(2,6,6-trimethyl-1-cyclohexen-1-yl)ethyl]benzamide;
(−) 4-chloro-N-[1-{[(cyanoimino)(3-pyridinylamino)methyl]amino}-2-(2,6,6-trimethyl-1-cyclohexen-1-yl)ethyl]benzamide;
(−) 4-chloro-N-(1-{[(cyanoimino)(3-pyridinylamino)methyl]amino}-2,2-dimethyl-4-pentenyl)benzamide;
(+) 4-chloro-N-(1-{[(cyanoimino)(3-pyridinylamino)methyl]amino}-2,2-dimethyl-4-pentenyl)benzamide;
4-chloro-N-(1-{[(cyanoimino)(3-pyridinylamino)methyl]amino}-3,3-dimethyl-4-pentenyl)benzamide;
4-chloro-N-(1-{[(cyanoimino)(3-pyridinylamino)methyl]amino}-2-cyclohexyl-2-methylpropyl)benzamide;
4-chloro-N-(1-{[(cyanoimino)(3-pyridinylamino)methyl]amino}-2,2-dimethylhexyl)benzamide;
N-(2-(1-adamantyl)-1-{[(cyanoimino)(3-pyridinylamino)methyl]amino}ethyl)-4-chlorobenzamide;
N-(2,2-bis[(allyloxy)methyl]-1-{[(cyanoimino)(3-pyridinylamino)methyl]amino}butyl)-4-chlorobenzamide;
4-chloro-N-[1-{[(cyanoimino)(3-pyridinylamino)methyl]amino}-3-(dimethylamino)-2,2-dimethylpropyl]benzamide;
tert-butyl (2R)-2-((R)-[(4-chlorobenzoyl)amino]{[(cyanoimino)(3-pyridinylamino)methyl]amino}methyl)-1-pyrrolidinecarboxylate;
4-chloro-N-[1-{[(cyanoimino)(3-pyridinylamino)methyl]amino}-3-(methylsulfanyl)propyl]benzamide;
N-(1-adamantyl {[(cyanoimino)(3-pyridinylamino)methyl]amino}methyl)-4-chlorobenzamide;
4-chloro-N-[{[(cyanoimino)(3-pyridinylamino)methyl]amino}(5-ethyl-1,3-dioxan-5-yl)methyl]benzamide;
4-chloro-N-(1-{[(cyanoimino)(3-pyridinylamino)methyl]amino}-2,2-dimethyl-3-phenylpropyl)benzamide;
N-(1-{[(cyanoimino)(3-pyridinylamino)methyl]amino}-2,2-dimethylpropyl)-4-iodobenzamide;
N-(1-{[(cyanoimino)(3-pyridinylamino)methyl]amino}-2,2-dimethylpropyl)-4-(2-furyl)benzamide;
4-bromo-N-(1-{[(cyanoimino)(3-pyridinylamino)methyl]amino}-2,2-dimethylpropyl)benzamide;
4-chloro-N-(1-{[(cyanoimino)(3-pyridinylamino)methyl]amino}-2,2-dimethylpropyl)-2-fluorobenzamide;
N-(1-{[(cyanoimino)(3-pyridinylamino)methyl]amino}-2,2-dimethylpropyl)-4-fluorobenzamide;
N-(1-{[(cyanoimino)(3-pyridinylamino)methyl]amino}-2,2-dimethylpropyl)-3-methylbenzamide;
N-(1-{[(cyanoimino)(3-pyridinylamino)methyl]amino}-2,2-dimethylpropyl)-2-methylbenzamide;
N-(1-{[(cyanoimino)(3-pyridinylamino)methyl]amino}-2,2-dimethylpropyl)-3,5-difluorobenzamide; and
N-(1-{[(cyanoimino)(3-pyridinylamino)methyl]amino}-2,2-dimethylpropyl)-4-fluoro-3-(trifluoromethyl)benzamide.

18. A compound according to claim 1 wherein,
X is $NR^8$;
$R^8$ is cyano;
$R^1$ is heterocycle;
$R^2$ is haloalkyl;
$R^3$ is aryl;
$R^4$ is hydrogen;
$R^5$ is hydrogen;
$R^6$ is hydrogen; and
$R^7$ is hydrogen.

19. A compound according to claim 1 wherein,
X is $NR^8$;
$R^8$ is cyano;
$R^1$ is heterocycle wherein heterocycle is pyridinyl;
$R^2$ is haloalkyl;
$R^3$ is aryl wherein aryl is phenyl;
$R^4$ is hydrogen;
$R^5$ hydrogen;
$R^6$ is hydrogen; and
$R^7$ is hydrogen.

20. A compound according to claim 19 selected from the group consisting of
  4-methyl-N-(2,2,2-trichloro-1-{[(cyanoimino)(3-pyridinylamino)methyl]amino}ethyl)benzamide;
  4-chloro-N-(2,2,2-trichloro-1-{[(cyanoimino)(3-pyridinylamino)methyl]amino}ethyl)benzamide;
  N-(2,2,2-trichloro-1-{[(cyanoimino)(3-pyridinylamino)methyl]amino}ethyl)benzamide;
  2-methyl-N-(2,2,2-trichloro-1-{[(cyanoimino)(3-pyridinylamino)methyl]amino}ethyl)benzamide;
  4-chloro-N-(1-{[(cyanoimino)(3-pyridinylamino)methyl]amino}-2,2,2-trifluoroethyl)benzamide;
  (−) 4-chloro-N-(2,2,2-trichloro-1-{[(cyanoimino)(3-pyridinylamino)methyl]amino}ethyl)benzamide;
  (+) 4-chloro-N-(2,2,2-trichloro-1-{[(cyanoimino)(3-pyridinylamino)methyl]amino}ethyl)benzamide;
  4-iodo-N-(2,2,2-trichloro-1-{[(cyanoimino)(3-pyridinylamino)methyl]amino}ethyl)benzamide;
  4-chloro-N-(2,2-dichloro-1-{[(cyanoimino)(3-pyridinylamino)methyl]amino}pentyl)benzamide;
  4-chloro-N-(2,2-dichloro-1-{[(cyanoimino)(3-pyridinylamino)methyl]amino}propyl)benzamide;
  (−) 4-chloro-N-(2,2-dichloro-1-{[(cyanoimino)(3-pyridinylamino)methyl]amino}propyl)benzamide;
  (+) 4-chloro-N-(2,2-dichloro-1-{[(cyanoimino)(3-pyridinylamino)methyl]amino}propyl)benzamide;
  3-chloro-N-(2,2-dichloro-1-{[(cyanoimino)(3-pyridinylamino)methyl]amino}propyl)benzamide;
  N-(2,2-dichloro-1-{[(cyanoimino)(3-pyridinylamino)methyl]amino}propyl)3,5-difluorobenzamide;
  4-chloro-N-(1-{[(cyanoimino)(3-pyridinylamino)methyl]amino}-2,2,3,3,3-pentafluoropropyl)benzamide;
  3-chloro-N-(1-{[(cyanoimino)(3-pyridinylamino)methyl]amino}-2,2,3,3,3-pentafluoropropyl)benzamide;
  3-chloro-N-(2,2-dichloro-1-{[[(6-chloro-3-pyridinyl)amino](cyanoimino)methyl]amino}propyl)benzamide;
  N-(2,2-dichloro-1-{[[(6-chloro-3-pyridinyl)amino](cyanoimino)methyl]amino}propyl)-4-methylbenzamide;
  N-{2,2-dichloro-1-[((cyanoimino){6-(trifluoromethyl)-3-pyridinyl]amino}methyl)amino]propyl}-3,5-difluorobenzamide;
  N-(2,2-dichloro-1-{[[(6-chloro-3-pyridinyl)amino](cyanoimino)methyl]amino}propyl)-3-fluorobenzamide;
  N-[2,2-dichloro-1-({(cyanoimino)[(2-methoxy-3-pyridinyl)amino]methyl}amino)propyl]-3,5-difluorobenzamide;
  4-chloro-N-{2,2-dichloro-1-[((cyanoimino){[6-(trifluoromethyl)-3-pyridinyl]amino}methyl)amino]propyl}benzamide;
  3-chloro-N-{2,2-dichloro-1-[((cyanoimino){[6-(trifluoromethyl)-3-pyridinyl]amino}methyl)amino]propyl}benzamide;
  4-chloro-N-(2,2-dichloro-1-{[[(6-chloro-3-pyridinyl)amino](cyanoimino)methyl]amino}propyl)benzamide;
  (−) 4-chloro-N-(2,2-dichloro-1-{[[(6-chloro-3-pyridinyl)amino](cyanoimino)methyl]amino}propyl)benzamide;
  (+) 4-chloro-N-(2,2-dichloro-1-{[[(6-chloro-3-pyridinyl)amino](cyanoimino)methyl]amino) propyl)benzamide;
  4-bromo-N-(2,2-dichloro-1-{[[(6-chloro-3-pyridinyl)amino](cyanoimino)methyl]amino) propyl)benzamide;
  3,5-dichloro-N-[2,2-dichloro-1-({(cyanoimino)[(2-methoxy-3-pyridinyl)amino]methyl}amino)propyl]benzamide;
  3,5-dichloro-N-(2,2-dichloro-1-{[[(6-chloro-3-pyridinyl)amino](cyanoimino)methyl]amino}propyl)benzamide;
  N-(2,2-dichloro-1-{[[(6-chloro-3-pyridinyl)amino](cyanoimino)methyl]amino}propyl)-3,5-difluorobenzamide;
  4-bromo-N-(2,2-dichloro-1-{[[(6-chloro-3-pyridinyl)amino](cyanoimino)methyl]amino}propyl)benzamide;
  4-chloro-N-(2,2-dichloro-1-{[[(2-chloro-3-pyridinyl)amino](cyanoimino)methyl]amino}propyl)benzamide;
  N-(2,2-dichloro-1-{[[(6-chloro-3-pyridinyl)amino](cyanoimino)methyl]amino}propyl)-3-methylbenzamide;
  N-(2,2-dichloro-1-{[[(6-chloro-3-pyridinyl)amino](cyanoimino)methyl]amino}propyl)-4-(trifluoromethyl)benzamide;
  N-(2,2-dichloro-1-{[[(6-chloro-3-pyridinyl)amino](cyanoimino)methyl]amino}propyl)-4-fluorobenzamide;
  3-chloro-N-[2,2-dichloro-1-({(cyanoimino)[(2-methoxy-3-pyridinyl)amino]methyl}amino)propyl]benzamide;
  4-chloro-N-[2,2-dichloro-1-({(cyanoimino)[(2-methoxy-3-pyridinyl)amino]methyl}amino)propyl]benzamide;
  3-chloro-N-[2,2-dichloro-1-({(cyanoimino)[(6-fluoro-3-pyridinyl)amino]methyl}amino)propyl]benzamide;
  N-(2,2-dichloro-1-{[[(6-chloro-3-pyridinyl)amino](cyanoimino)methyl]amino}propyl)-3,5-dimethoxybenzamide;
  N-(2,2-dichloro-1-{[(cyanoimino)(3-pyridinylamino)methyl]amino}propyl)-3-methylbenzamide;
  4-chloro-N-[2,2-dichloro-1-({(cyanoimino)[(6-fluoro-3-pyridinyl)amino]methyl}amino)propyl]benzamide;
  3-chloro-N-[2,2-dichloro-1-({(cyanoimino)[(6-methoxy-3-pyridinyl)amino]methyl}amino)propyl]benzamide;
  N-(2,2-dichloro-1-[((cyanoimino){6-(trifluoromethyl)-3-pyridinyl]amino}methyl)amino]propyl}-3,5-dimethoxybenzamide; and
  4-chloro-N-{2,2-dichloro-1-[((cyanoimino){[2-methyl-6-(trifluoromethyl)-3-pyridinyl]amino}methyl)amino]propyl}benzamide.

21. A compound according to claim 1 wherein,

X is $NR^8$;

$R^8$ is cyano;

$R^1$ is heterocycle wherein heterocycle is selected from the group consisting of quinolinyl, pyridinyl and pyrimidinyl;

$R^2$ is selected from the group consisting of hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from the group consisting of 1,3-dioxanyl, pyrrolidinyl and thienyl;

$R^3$ is aryl wherein aryl is phenyl;

$R^4$ hydrogen;

$R^5$ is alkyl;

$R^6$ is hydrogen; and $R^7$ is hydrogen.

22. A compound according to claim 21 that is 4-chloro-N-{1-[[(cyanoimino)(3-pyridinylamino)methyl](methyl)amino]-2,2-dimethylpropyl}benzamide.

23. A compound according to claim 1 wherein,

X is $NR^8$;

$R^8$ is cyano;

$R^1$ is selected from the group consisting of heterocycle and heterocyclealkyl;

$R^3$ is alkyl;

$R^4$ is hydrogen;

$R^5$ is hydrogen; and $R^6$ is hydrogen.

24. A compound according to claim 1 wherein,

X is $NR^8$;

$R^1$ is selected from the group consisting of heterocycle and heterocyclealkyl;

$R^8$ is selected from the group consisting of hydrogen, alkoxy, alkyl, alkylsulfonyl, arylalkoxy, aryloxy, arylsulfonyl, haloalkylsulfonyl, heterocyclealkoxy, heterocycleoxy, hydroxy, nitro, and sulfamyl;

$R^4$ is hydrogen;

$R^5$ is hydrogen; and $R^6$ is hydrogen.

25. A compound according to claim 1 wherein,

X is $NR^8$;

$R^1$ is selected from the group consisting of heterocycle and heterocyclealkyl;

$R^8$ is nitro;

$R^4$ is hydrogen;

$R^5$ is hydrogen; and $R^6$ is hydrogen.

26. A compound according to claim 1 wherein,

X is $NR^8$;

$R^8$ is nitro;

$R^1$ is heterocycle wherein heterocycle is selected from the group consisting of quinolinyl, pyridinyl and pyrimidinyl;

$R^2$ is selected from the group consisting of hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, $(NR^9R^{10})$alkyl and heterocycle wherein heterocycle is selected from the group consisting of 1,3-dioxanyl, pyrrolidinyl and thienyl;

$R^3$ is aryl wherein aryl is phenyl;

$R^4$ is hydrogen;

$R^5$ is hydrogen; and $R^6$ is hydrogen.

27. A compound according to claim 26 selected from the group consisting of 4-chloro-N-(1-{[(nitroimino)(3-pyridinylamino)methyl]amino}-2,2-dimethylpropyl)benzamide;

4-chloro-N-(1-{[(nitroimino)(3-pyridinylamino)methyl]amino}-3,3-dimethylbutyl)benzamide;

(+) 4-chloro-N-(1-{[(nitroimino)(3-pyridinylamino)methyl]amino}-3,3-dimethylbutyl)benzamide;

(−) 4-chloro-N-(1-{[(nitroimino)(3-pyridinylamino)methyl]amino}-3,3-dimethylbutyl)benzamide;

4-chloro-N-(1-{[(nitroimino)(3-pyridinylamino)methyl]amino}-2,2-dimethyl-4-pentenyl)benzamide;

4-chloro-N-(1-{[(nitroimino)(3-pyridinylamino)methyl]amino}-2,2-dimethyl-3-phenylpropyl)benzamide;

4-chloro-N-[1-{[(nitroimino)(3-pyridinylamino)methyl]amino}-2-(2,6,6-trimethyl-1-cyclohexen-1-yl)ethyl]benzamide;

4-chloro-N-(1-{[(nitroimino)(3-pyridinylamino)methyl]amino}-2-cyclohexyl-2-methylpropyl)benzamide;

N-(2,2-bis[(allyloxy)methyl]-1-{[(nitroimino)(3-pyridinylamino)methyl]amino}butyl)-4-chlorobenzamide;

4-chloro-N-(4-cyano-1-{[(nitroimino)(3-pyridinylamino)methyl]amino}-2,2-diethylbutyl)benzamide;

4-chloro-N-(1-{[(nitroimino)(3-pyridinylamino)methyl]amino}-3,3-dimethyl-4-pentenyl)benzamide;

N-(2-(1-adamantyl)-1-{[(nitroimino)(3-pyridinylamino)methyl]amino}ethyl)-4-chlorobenzamide;

N-(1-{[(nitroimino)(3-pyridinylamino)methyl]amino}-2,2-dimethylpropyl)-4-phenylbenzamide;

4-chloro-N-(2,2-dichloro-1-{[(nitroimino)(3-pyridinylamino)methyl]amino}pentyl)benzamide;

4-chloro-N-(2,2-dichloro-1-{[(nitroimino)(3-pyridinylamino)methyl]amino}propyl)benzamide; and 3-chloro-N-(2,2-dichloro-1-{[(nitroimino)(3-pyridinylamino)methyl]amino}propyl)benzamide.

28. A compound according to claim 1 wherein,

X is $NR^8$;

$R^1$ is selected from the group consisting of heterocycle and heterocyclealkyl;

$R^8$ is selected from the group consisting of arylsulfonyl, haloalkylsulfonyl and sulfamyl;

$R^4$ is hydrogen;

$R^5$ is hydrogen; and $R^6$ is hydrogen.

29. A compound according to claim 1 wherein,

X is $NR^8$, $R^8$ is selected from the group consisting of haloalkylsulfonyl, sulfamyl and arylsulfonyl wherein the aryl portion of arylsulfonyl is phenyl;

$R^1$ is heterocycle wherein heterocycle is selected from the group consisting of quinolinyl, pyridinyl and pyrimidinyl;

R² is selected from the group consisting of hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, (NR⁹R¹⁰)alkyl and heterocycle wherein heterocycle is selected from the group consisting of 1,3-dioxanyl, pyrrolidinyl and thienyl;

R³ is aryl wherein aryl is phenyl;

R⁴ is hydrogen;

R⁵ is hydrogen; and

R⁶ is hydrogen.

30. A compound according to claim 29 selected from the group consisting of 4-chloro-N-(2,2-dimethyl-1-{[[(phenylsulfonyl)imino](3-pyridinylamino)methyl]amino}propyl)benzamide;

4-chloro-N-(3,3-dimethyl-1-{[[(phenylsulfonyl)imino](3-pyridinylamino)methyl]amino}butyl)benzamide;

4-chloro-N-{2,2-dimethyl-1-[((3-pyridinylamino){[(trifluoromethyl)sulfonyl]imino}methyl)amino]propyl}benzamide;

4-chloro-N-{3,3-dimethyl-1-[((3-pyridinylamino){[(trifluoromethyl)sulfonyl]imino}methyl)amino]butyl}benzamide;

N-(1-{[[(aminosulfonyl)imino](3-pyridinylamino)methyl]amino}-2,2-dimethylpropyl)-4-chlorobenzamide;

N-(1-{[[(aminosulfonyl)imino](3-pyridinylamino)methyl]amino}-3,3-dimethylbutyl)-4-chlorobenzamide;

4-chloro-N-(1-{[{[(dimethylamino)sulfonyl]imino}(3-pyridinylamino)methyl]amino}-2,2-dimethylpropyl)benzamide;

4-chloro-N-(1-{[{[(dimethylamino)sulfonyl]imino}(3-pyridinylamino)methyl]amino}-3,3-dimethylbutyl)benzamide;

(+) 4-chloro-N-{3,3-dimethyl-1-[((3-pyridinylamino){[(trifluoromethyl)sulfonyl]imino}methyl)amino]butyl}benzamide;

(−) 4-chloro-N-{3,3-dimethyl-1-[((3-pyridinylamino){[(trifluoromethyl)sulfonyl]imino}methyl)amino]butyl}benzamide;

4-bromo-N-{3,3-dimethyl-1-[((3-pyridinylamino){[(trifluoromethyl)sulfonyl]imino}methyl)amino]butyl}benzamide;

N-{3,3-dimethyl-1-[((3-pyridinylamino){[(trifluoromethyl)sulfonyl]imino}methyl)amino]butyl}-4-(trifluoromethyl)benzamide;

3,5-dichloro-N-{2,2-dichloro-1-[((3-pyridinylamino){[(trifluoromethyl)sulfonyl]imino}methyl)amino]propyl}benzamide; and N-{2,2-dichloro-1-[((3-pyridinylamino){[(trifluoromethyl)sulfonyl]imino}methyl)amino]propyl}-4-(trifluoromethyl)benzamide.

31. A compound according to claim 1 wherein,

X is S;

R⁴ is hydrogen;

R⁵ is hydrogen; and

R⁶ is hydrogen.

32. A compound according to claim 1 wherein,

X is S;

R¹ is selected from the group consisting of heterocycle and heterocyclealkyl;

R³ is selected from the group consisting of aryl and arylalkyl;

R⁴ is hydrogen;

R⁵ is hydrogen; and

R⁶ is hydrogen.

33. A compound according to claim 32 wherein,

R² is selected from the group consisting of hydrogen, alkenyl, alkenyloxyalkyl, alkenyloxy(alkenyloxy)alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and (NR⁹R¹⁰)alkyl; and R⁷ is hydrogen.

34. A compound according to claim 1 wherein,

X is S;

R¹ is heterocycle wherein heterocycle is selected from the group consisting of quinolinyl, pyridinyl and pyrimidinyl;

R² is selected from the group consisting of hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, (NR⁹R¹⁰)alkyl and heterocycle wherein heterocycle is selected from the group consisting of 1,3-dioxanyl, pyrrolidinyl and thienyl;

R³ is aryl wherein aryl is phenyl;

R⁴ hydrogen;

R⁵ is hydrogen;

R⁶ is hydrogen; and

R⁷ is hydrogen.

35. A compound according to claim 34 that is selected from the group consisting of N-(2,2-dimethyl-1-{[(3-pyridinylamino)carbothioyl]amino}propyl)-4-methylbenzamide;

N-((1R)-2,2-dimethyl-1-([(3-pyridinylamino)carbothioyl]amino}propyl)-4-methylbenzamide;

N-((1S)-2,2-dimethyl-1-{[(3-pyridinylamino)carbothioyl]amino}propyl)-4-methylbenzamide;

N-(2,2-dimethyl-1-{[(3-pyridinylamino)carbothioyl]amino}propyl)-2-methylbenzamide;

4-chloro-N-(2,2-dimethyl-1-{[(3-pyridinylamino)carbothioyl]amino}propyl)benzamide;

N-(2,2-dimethyl-1-{[(3-pyridinylamino)carbothioyl]amino}propyl)benzamide;

4-methyl-N-(phenyl {[(3-pyridinylamino)carbothioyl]amino}methyl)benzamide;

4-methyl-N-(2-methyl-1-{[(3-pyridinylamino)carbothioyl]amino}propyl)benzamide; and 4-methyl-N-((1R,2S)-2-methyl-1-{[(3-pyridinylamino)carbothioyl]amino}butyl)benzamide.

36. A compound according to claim 1 wherein,

X is S;

R¹ is heterocycle;

R² is haloalkyl;

R³ is aryl;

R⁴ hydrogen;

R⁵ hydrogen;

R⁶ is hydrogen; and

R⁷ hydrogen.

37. A compound according to claim 1 wherein,
X is S;
$R^1$ is heterocycle wherein heterocycle is pyridinyl;
$R^2$ is haloalkyl;
$R^3$ is aryl wherein aryl is phenyl;
$R^4$ is hydrogen;
$R^5$ hydrogen;
$R^6$ is hydrogen; and
$R^7$ is hydrogen.

38. A compound according to claim 37 that is selected from the group consisting of
4-methyl-N-(2,2,2-trifluoro-1-{[(3-pyridinylamino) carbothioyl]amino}ethyl)benzamide;
N-[1-({[(6-chloro-3-pyridinyl)amino] carbothioyl}amino)-2,2,2-trifluoroethyl]-4-methylbenzamide;
4-chloro-N-(2,2,2-trifluoro-1-{[(3-pyridinylamino) carbothioyl]amino}ethyl)benzamide; and
4-iodo-N-(2,2,2-trichloro-1-{[(3-pyridinylamino) carbothioyl]amino}ethyl)benzamide.

39. A compound according to claim 1 wherein,
X is O;
$R^1$ is selected from the group consisting of heterocycle and heterocyclealkyl;
$R^3$ is selected from the group consisting of aryl and arylalkyl;
$R^4$ is hydrogen;
$R^5$ is hydrogen; and
$R^6$ is hydrogen.

40. A compound according to claim 39 wherein,
$R^2$ is selected from the group consisting of hydrogen, alkenyl, alkenyloxyalkyl, alkenyloxy(alkenyloxy) alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and $(NR^9R^{10})$ alkyl; and
$R^7$ hydrogen.

41. A compound according to claim 1 wherein,
X is O;
$R^1$ is heterocycle wherein heterocycle is selected from the group consisting of quinolinyl, pyridinyl and pyrimidinyl;
$R^2$ is selected from the group consisting of hydrogen, alkenyl, alkenyloxyalkyl, alkenyloxy(alkenyloxy) alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, $(NR^9R^{10})$alkyl and heterocycle wherein heterocycle is selected from the group consisting of 1,3-dioxanyl, pyrrolidinyl and thienyl;
$R^3$ is aryl wherein aryl is phenyl;
$R^4$ is hydrogen;
$R^5$ is hydrogen;
$R^6$ is hydrogen; and
$R^7$ is hydrogen.

42. A compound according to claim 1 wherein,
X is O;
$R^1$ is heterocycle;
$R^2$ is haloalkyl;
$R^3$ is aryl;
$R^4$ is hydrogen;
$R^5$ is hydrogen;
$R^6$ is hydrogen; and
$R^7$ is hydrogen.

43. A compound according to claim 1 wherein,
X is O;
$R^1$ is heterocycle wherein heterocycle is pyridinyl;
$R^2$ is haloalkyl;
$R^3$ is aryl wherein aryl is phenyl;
$R^4$ is hydrogen;
$R^5$ hydrogen;
$R^6$ is hydrogen; and
$R^7$ is hydrogen.

44. A compound according to claim 43 that is selected from the group consisting of
4-methyl-N-(2,2,2-trichloro-1-{[(3-pyridinylamino) carbonyl]amino}ethyl)benzamide;
2-methyl-N-(2,2,2-trichloro-1-{[(3-pyridinylamino) carbonyl]amino}ethyl)benzamide;
N-(2,2,2-trichloro-1-{[(3-pyridinylamino)carbonyl] amino}ethyl)benzamide; and
4-chloro-N-(2,2,2-trichloro-1-{[(3-pyridinylamino) carbonyl]amino}ethyl)benzamide.

45. A compound according to claim 1 wherein,
X is O;
$R^1$ is selected from the group consisting of heterocycle and heterocyclealkyl;
$R^3$ is selected from the group consisting of heterocycle, and heterocyclealkyl;
$R^4$ is hydrogen;
$R^5$ hydrogen; and
$R^6$ is hydrogen.

46. A compound according to claim 1 wherein,
X is selected from the group consisting of CHCN and $CHNO_2$;
$R^1$ is selected from the group consisting of heterocycle and heterocyclealkyl;
$R^3$ is selected from the group consisting of heterocycle and heterocyclealkyl;
$R^4$ hydrogen;
$R^5$ is hydrogen; and
$R^6$ is hydrogen.

47. A compound according to claim 1 wherein,
X is selected from the group consisting of CHCN and $CHNO_2$;
$R^1$ is selected from the group consisting of heterocycle and heterocyclealkyl;
$R^3$ is selected from the group consisting of aryl and arylalkyl;
$R^4$ hydrogen;
$R^5$ is hydrogen; and
$R^6$ is hydrogen.

48. A compound according to claim 47 wherein,
$R^2$ is selected from the group consisting of hydrogen, alkenyl, alkenyloxyalkyl, alkenyloxy(alkenyloxy) alkyl, alkoxyalkyl, alkyl, alkylthioalkyl, aryl, arylalkyl, cyanoalkyl, cycloalkenylalkyl, cycloalkyl, cycloalkylalkyl, haloalkyl, heterocycle and $(NR^9R^{10})$ alkyl; and
$R^7$ hydrogen.

49. A compound according to claim 1 wherein,
X is selected from the group consisting of CHCN and $CHNO_2$;

R[1] is heterocycle wherein heterocycle is selected from the group consisting of quinolinyl, pyridinyl and pyrimidinyl;

R[2] is selected from the group consisting of hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, (NR[9]R[10])alkyl and heterocycle wherein heterocycle is selected from the group consisting of 1,3-dioxanyl, pyrrolidinyl and thienyl;

R[3] is aryl wherein aryl is phenyl;

R[4] hydrogen;

R[5] is hydrogen;

R[6] is hydrogen; and

R[7] hydrogen.

50. A compound according to claim 49 selected from the group consisting of 4-chloro-N-(2-ethyl-1-{[2-nitro-1-(3-pyridinylamino)ethenyl]amino}butyl)benzamide; and 4-chloro-N-(2,2-dimethyl-1-{[2-nitro-1-(3-pyridinylamino)ethenyl]amino}propyl)benzamide.

51. A compound according to claim 1 wherein,

X is selected from the group consisting of CHCN and CHNO$_2$;

R[1] is heterocycle;

R[2] is haloalkyl;

R[3] is aryl;

R[4] hydrogen;

R[5] is hydrogen;

R[6] is hydrogen; and

R[7] is hydrogen.

52. A compound according to claim 1 wherein,

X is selected from the group consisting of CHCN and CHNO$_2$;

R[1] is heterocycle wherein heterocycle is pyridinyl;

R[2] is haloalkyl;

R[3] is aryl wherein aryl is phenyl;

R[4] is hydrogen;

R[5] hydrogen;

R[6] is hydrogen; and

R[7] is hydrogen.

53. A compound according to claim 52 that is 4-chloro-N-(2,2-dichloro-1-{[2-nitro-1-(3-pyridinylamino)ethenyl]amino}pentyl)benzamide.

54. A compound according to claim 1 wherein,

X is selected from the group consisting of CHCN and CHNO$_2$;

R[1] is selected from the group consisting of heterocycle and heterocyclealkyl;

R[3] is alkyl;

R[4] hydrogen;

R[5] hydrogen; and

R[6] is hydrogen.

55. A compound according to claim 1 wherein,

X is C(CN)$_2$;

R[1] is selected from the group consisting of heterocycle and heterocyclealkyl;

R[3] is selected from the group consisting of aryl and arylalkyl;

R[4] hydrogen;

R[5] hydrogen; and

R[6] is hydrogen.

56. A compound according to claim 1 wherein,

X is C(CN)$_2$;

R[1] is heterocycle wherein heterocycle is selected from the group consisting of quinolinyl, pyridinyl and pyrimidinyl;

R[2] is selected from the group consisting of hydrogen, alkenyl, alkenyloxyalkyl, alkenyloxy(alkenyloxy)alkyl, alkoxyalkyl, alkyl, alkylthioalkyl, aryl wherein aryl is phenyl, arylalkyl wherein the aryl portion of arylalkyl is phenyl, cyanoalkyl, cycloalkenylalkyl, cycloalkyl, cycloalkylalkyl, haloalkyl, (NR[9]R[10])alkyl and heterocycle wherein heterocycle is selected from the group consisting of 1,3-dioxanyl, pyrrolidinyl and thienyl;

R[3] is aryl wherein aryl is phenyl;

R[4] hydrogen;

R[5] is hydrogen; and

R[6] is hydrogen.

57. A compound according to claim 56 that is 4-chloro-N-(1-{[2,2-dicyano-1-(3-pyridinylamino)vinyl]amino}-2,2-dimethylpropyl)benzamide.

58. A compound according to claim 1 of formula VI:

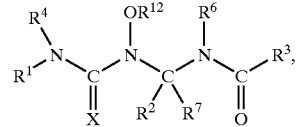

or a pharmaceutically acceptable salt thereof.

59. A compound according to claim 58 wherein,

X is NR[8];

R[1] is selected from the group consisting of heterocycle and heterocyclealkyl;

R[8] is cyano;

R[4] hydrogen; and

R[6] is hydrogen.

60. A compound according to claim 58 wherein,

X is NR[8];

R[1] is selected from the group consisting of heterocycle and heterocyclealkyl;

R[8] is selected from the group consisting of hydrogen, alkoxy, alkyl, alkylsulfonyl, arylalkoxy, aryloxy, arylsulfonyl, haloalkylsulfonyl, heterocyclealkoxy, hydroxy, nitro, and sulfamyl;

R[4] hydrogen; and

R[6] is hydrogen.

61. A compound according to claim 58 wherein,

X is S;

R[1] is selected from the group consisting of heterocycle and heterocyclealkyl;

R[4] is hydrogen; and

R[6] is hydrogen.

62. A compound according to claim 58 wherein,

X is O;

R[1] is selected from the group consisting of heterocycle and heterocyclealkyl;

R[4] hydrogen; and

R[6] is hydrogen.

63. A compound according to claim 58 wherein,
X is selected from the group consisting of CHCN and CHNO$_2$;
R$^1$ is selected from the group consisting of heterocycle and heterocyclealkyl;
R$^4$ hydrogen; and
R$^6$ is hydrogen.

64. A compound selected from the group consisting of
4-chloro-N-(1-{[(hydroxyimino)(3-pyridinylamino) methyl]amino}-2,2-dimethylpropyl)benzamide;
4-chloro-N-(1-{[(methoxyimino)(3-pyridinylamino) methyl]amino}-2,2-dimethylpropyl)benzamide;
4-chloro-N-(1-{[{[(4-fluorobenzyl)oxy]imino}(3-pyridinylamino)methyl]amino}-2,2-dimethylpropyl) benzamide;
4-chloro-N-(2,2-dimethyl-1-{[[(methylsulfonyl)imino] (3-pyridinylamino)methyl]amino}propyl)benzamide;
4-chloro-N-(1-{[(cyanoimino)(6-fluoro-1H-indol-1-yl) methyl]amino}-2,2-dimethylpropyl)benzamide;
4-chloro-N-(1-{[(cyanoimino)(6-fluoro-1H-benzimidazol-1-yl)methyl]amino}-2,2-dimethylpropyl)benzamide;
3-(4-chlorophenyl)-N-(1-{[(cyanoimino)(3-pyridinylamino)methyl]amino}-2,2-dimethylpropyl) propanamide;
N-(1-{[(cyanoimino)(3-pyridinylamino)methyl]amino}-2,2-dimethylpropyl)-3-phenylpropanamide;
N-(1-{[(cyanoimino)(3-pyridinylamino)methyl]amino}-2,2-dimethylpropyl)-2-phenylacetamide;
N-[1-(5-chloro-1-oxo-1,3-dihydro-2H-isoindol-2-yl)-2,2-dimethylpropyl]-N"-cyano-N'-(3-pyridinyl)guanidine;
4-(aminosulfonyl)-N-(1-{[(cyanoimino)(3-pyridinylamino)methyl]amino}-2,2-dimethylpropyl)-2-fluorobenzamide;
4-chloro-N-[1-({(cyanoimino) [(4-ethyl-3-pyridinyl) amino]methyl}amino)-2,2-dimethylpropyl]benzamide;
N-(1-{[(cyanoimino)(3-pyridinylamino)methyl]amino}-2,2-dimethylpropyl)-4-(trifluoromethoxy)benzamide;
4-chloro-N-[1-({(cyanoimino) [(4-ethyl-3-pyridinyl) amino]methyl}amino)-2,2-dimethylpropyl]-2-fluorobenzamide;
4-chloro-N-(1-{[(cyanoimino)(5-pyrimidinylamino) methyl]amino}-2,2-dimethylpropyl)benzamide;
4-chloro-N-(1-{[(cyanoimino)(5-pyrimidinylamino) methyl]amino}-2,2-dimethylpropyl)-2-fluorobenzamide;
N-(1-{[[(4-bromo-3-pyridinyl)amino](cyanoimino) methyl]amino}-2,2-dimethylpropyl)-4-chlorobenzamide;
4-chloro-2-fluoro-N-[2,2,2-trichloro-1-({(cyanoimino) [(4-ethyl-3-pyridinyl)amino]methyl}amino)ethyl] benzamide;
4-chloro-N-(2,2,2-trichloro-1-{[(cyanoimino)(5-pyrimidinylamino)methyl]amino}ethyl)benzamide;
4-chloro-2-fluoro-N-(2,2,2-trichloro-1-{[(cyanoimino) (5pyrimidinylamino)methyl]amino}ethyl)benzamide;
N-(1-{[[(4-bromo-3-pyridinyl)amino](cyanoimino) methyl]amino}-2,2,2-trichloroethyl)-4-chlorobenzamide;
N-(1-{[[(2-bromo-3-pyridinyl)amino](cyanoimino) methyl]amino}-2,2-dimethylpropyl)-4-chlorobenzamide;

4-chloro-N-[1-({(cyanoimino)[(2-ethyl-3-pyridinyl) amino]methyl}amino)-2,2-dimethylpropyl]benzamide;
N-(1-{[[(5-bromo-4-ethyl-3-pyridinyl)amino] (cyanoimino)methyl]amino}-2,2-dimethylpropyl)-4-chlorobenzamide;
4-chloro-N-[1-({(cyanoimino) [(4,5-dibromo-3-pyridinyl)amino]methyl}amino)-2,2-dimethylpropyl] benzamide;
4-chloro-N-(1-{[[(5-chloro-3-pyridinyl)amino] (cyanoimino)methyl]amino}-2,2-dimethylpropyl) benzamide;
N-(1-{[[(5-bromo-6-chloro-3-pyridinyl)amino] (cyanoimino)methyl]amino}-2,2-dimethylpropyl)-4-chlorobenzamide;
N-(1-{[[(5-bromo-3-pyridinyl)amino](cyanoimino) methyl]amino}-2,2-dimethyipropyl)-4-chlorobenzamide;
N-(1-{[[(6-bromo-3-pyridinyl)amino](cyanoimino) methyl]amino}-2,2-dimethyipropyl)-4-chlorobenzamide;
4-chloro-N-(1-{[(cyanoimino)({5-[(4-fluorophenyl) sulfonyl]-3-pyridinyl}amino)methyl]amino}-2,2-dimethylpropyl)benzamide;
N-(1-{[({5-[(aminoperoxy)sulfanyl]-3-pyridinyl}amino) (cyanoimino)methyl]amino}-2,2-dimethylpropyl)-4-chlorobenzamide;
N-(1-{[[(6-bromo-4-fluoro-3-pyridinyl)amino] (cyanoimino)methyl]amino}-2,2-dimethylpropyl)-4-chlorobenzamide;
4-chloro-N-[1-{[(cyanoimino)(3-pyridinylamino)methyl] amino}-2,2,2-trifluoro-1-(trifluoromethyl)ethyl] benzamide;
4-chloro-N-(1-{[(cyanoimino)(3-pyridinylamino)methyl] amino}cyclopentyl)benzamide;
4-chloro-N-(1-{[(cyanoimino)(3-pyridinylamino)methyl] amino}cyclohexyl)benzamide;
4-chloro-N-[{[(cyanoimino)(3-pyridinylamino)methyl] amino}(2,6-dimethylphenyl)methyl]benzamide;
4-chloro-N-[{[(cyanoimino)(3-pyridinylamino)methyl] amino}(3-pyridinyl)methyl]benzamide;
4-chloro-N-[{[(cyanoimino)(3-pyridinylamino)methyl] amino}(2-pyridinyl)methyl]benzamide;
4-chloro-N-(1-{[(cyanoimino)(3-pyridinylamino)methyl] amino}-2-methyl-2-phenylpropyl)benzamide;
4-chloro-N-(1-{[(cyanoimino)(3-pyridinylamino)methyl] amino}-3,3-dimethyl-2-oxobutyl)benzamide;
4-chloro-N-(1-{[(cyanoimino)(3-pyridinylamino)methyl] amino}-3,3,3-trifluoro-2-oxopropyl)benzamide;
4-chloro-N-[1-{[(cyanoimino)(3-pyridinylamino)methyl] amino}-3,3,3-trifluoro-2-methyl-2-(trifluoromethyl) propyl]benzamide;
methyl 4-[(4-chlorobenzoyl)amino]-4-{[(cyanoimino)(3-pyridinylamino)methyl]amino}-3,3-dimethylbutanoate;
4-chloro-N-[1-{[(cyanoimino)(3-pyridinylamino)methyl] amino}-4-(dimethylamino)-2,2-dimethylbutyl] benzamide;
4-chloro-N-(4-cyano-1-{[(cyanoimino)(3-pyridinylamino)methyl]amino}-2,2-dimethylbutyl) benzamide;
4-chloro-N-(1-{[(cyanoimino)(3-pyridinylamino)methyl] amino}-4-methoxy-2,2-dimethylbutyl)benzamide;
4-chloro-N-(1-{[(cyanoimino)(3-pyridinylamino)methyl] amino}-4-hydroxy-2,2-dimethylbutyl)benzamide;

N-(4-(aminosulfonyl)-1-{[(cyanoimino)(3-pyridinylamino)methyl]amino}-2,2-dimethylbutyl)-4-chlorobenzamide;

4-chloro-N-[1-{[(cyanoimino)(3-pyridinylamino)methyl]amino}-2,2-dimethyl-4-(phenylsulfonyl)butyl]benzamide;

4-chloro-N-(1-{[(cyanoimino)(3-pyridinylamino)methyl]amino}-3-hydroxy-2,2-dimethylpropyl)benzamide;

4-chloro-N-{2,2,2-trichloro-1-[2-(cyanoimino)-3-(3-pyridinyl)imidazolidinyl]ethyl}benzamide;

4-chloro-N-{1-[2-(cyanoimino)-3-(3-pyridinyl)imidazolidinyl]-2,2-dimethyipropyl}benzamide;

2-tert-butyl-3-(4-chlorobenzoyl)-N'-cyano-N-(3-pyridinyl)-1-imidazolidinecarboximidamide;

N-(4-(aminosulfonyl)-2,2-dichloro-1-{[(cyanoimino)(3-pyridinylamino)methyl]amino}butyl)-4-chlorobenzamide;

4-chloro-N-[4-cyano-1-{[(cyanoimino)(3-pyridinylamino)methyl]amino}-2,2-bis(trifluoromethyl)butyl]benzamide;

4-chloro-N-(1-{[(cyanoimino)(3-pyridinylamino)methyl]amino}-2,2-difluoro-4-oxopentyl)benzamide;

4-chloro-N-(1-{[2-cyano-1-(3-pyridinylamino)ethenyl]amino}-2,2-dimethylpropyl)benzamide;

4-chloro-N-{1-[[(cyanoimino)(3-pyridinylamino)methyl](hydroxy)amino]-2,2-dimethyipropyl}benzamide;

4-chloro-N-(2,2,2-trichloro-1-{[2-nitro-1-(3-pyridinylamino)ethenyl]amino}ethyl)benzamide; and 4-chloro-N-(2,2,2-trichloro-1-{[2-cyano-1-(3-pyridinylamino)ethenyl]amino}ethyl)benzamide.

65. A pharmaceutical composition comprising a therapeutically effective amount of a compound of claim 1 in combination with a pharmaceutically acceptable carrier.

66. A method of treating a disease or disorder in a host mammal in need of such treatment comprising administering a therapeutically effective amount of a compound of claim 1, wherein said disease or disorder is selected from the group consisting of asthma, epilepsy, Raynaud's syndrome, intermittent claudication, migraine, pain, pollakiuria, bladder instability, nocturia, bladder hyperreflexia, enuresis, alopecia, cardioprotection, ischemia, eating disorders, functional bowel disorders, and neurodegeneration.

67. The method of claim 66 wherein the disorder is bladder overactivity.

68. The method of claim 66 wherein the disorder is benign prostatic hyperplasia.

69. The method of claim 66 wherein the disorder is dysmenorrhea.

70. The method of claim 66 wherein the disorder is premature labor.

71. The method of claim 66 wherein the disorder is urinary incontinence.

72. The method of claim 66 wherein the disorder is selected from the group consisting of male erectile dysfunction and premature ejaculation.

73. The method of claim 66 wherein the disorder is female sexual dysfunction.

74. A compound of claim 1 having formula I wherein X is $NR^8$; $R^8$ is cyano; $R^1$ is heterocycle wherein the heterocycle is pyridinyl; $R^2$ is selected dichloroethyl; $R^3$ is aryl wherein aryl is phenyl; $R^4$ is hydrogen; $R^5$ is hydrogen; $R^6$ is hydrogen; and $R^7$ is hydrogen.

75. A compound of claim 1 having formula I wherein X is $NR^8$; $R^8$ is cyano; $R^1$ is heterocycle wherein the heterocycle pyridinyl which is optionally substituted with alkoxy, halo, and haloalkyl; $R^2$ is selected dichloroethyl; $R^3$ is aryl wherein aryl is phenyl which is optionally substituted with halo; $R^4$ is hydrogen; $R^5$ is hydrogen; $R^6$ is hydrogen; and $R^7$ is hydrogen.

76. A compound of claim 1 having formula I wherein X is $NR^8$; $R^8$ is cyano; $R^1$ is heterocycle wherein the heterocycle is pyridinyl; $R^2$ is selected alkyl and haloalkyl; $R^3$ is heterocycle wherein wherein the heterocycle is pyridinyl; $R^4$ is hydrogen; $R^5$ is hydrogen; $R^6$ is hydrogen; and $R^7$ is hydrogen.

77. A compound of claim 1 having formula I wherein X is $NR^8$; $R^8$ is cyano; $R^1$ is heterocycle wherein the heterocycle is pyridinyl; $R^2$ is selected dichloroethyl; $R^3$ is heterocycle wherein wherein the heterocycle is pyridinyl; $R^4$ is hydrogen; $R^5$ is hydrogen; $R^6$ is hydrogen; and $R^7$ is hydrogen.

78. A compound of claim 1 having formula I wherein X is $NR^8$; $R^8$ is cyano; $R^1$ is heterocycle wherein the heterocycle is pyridinyl which is optionally substituted with alkoxy, halo, and haloalkyl; $R^2$ is selected dichloroethyl; $R^3$ is heterocycle wherein wherein the heterocycle is pyridinyl which is optionally substituted with alkoxy, halo, and haloalkyl; $R^4$ is hydrogen; $R^5$ is hydrogen; $R^6$ is hydrogen; and $R^7$ is hydrogen.

* * * * *